(12) United States Patent
Chang

(10) Patent No.: US 11,554,179 B2
(45) Date of Patent: Jan. 17, 2023

(54) LYOPHILIZED PHARMACEUTICAL COMPOSITIONS FOR NAKED DNA GENE THERAPY

(71) Applicant: Helixmith Co., Ltd, Seoul (KR)

(72) Inventor: Byeong Seon Chang, Thousand Oaks, CA (US)

(73) Assignee: Helixmith Co., Ltd, Seoul (KR)

( * ) Notice: Subject to any disclaimer, the term of this patent is extended or adjusted under 35 U.S.C. 154(b) by 539 days.

(21) Appl. No.: 16/517,323

(22) Filed: Jul. 19, 2019

(65) Prior Publication Data

US 2020/0023075 A1     Jan. 23, 2020

Related U.S. Application Data

(60) Provisional application No. 62/700,655, filed on Jul. 19, 2018.

(51) Int. Cl.
*A61K 48/00* (2006.01)
*A61K 9/00* (2006.01)
(Continued)

(52) U.S. Cl.
CPC ........ *A61K 48/0016* (2013.01); *A61K 9/0095* (2013.01); *A61K 9/19* (2013.01);
(Continued)

(58) Field of Classification Search
CPC ......... A61P 43/00; A61P 35/00; A61P 29/00; A61P 35/02; A61P 11/00; A61P 9/10; A61P 37/00; A61P 21/00; A61P 9/00; A61P 27/02; A61P 37/06; A61P 3/10; A61P 19/02; A61P 1/18; A61P 25/00; A61P 25/16; A61P 25/28; A61P 21/04; A61P 37/02; A61P 3/04; A61P 13/12; A61P 15/00; A61P 19/08; A61P 31/04; A61P 37/04; A61P 5/00; A61P 7/00; A61P 17/06; A61P 25/14; A61P 37/08; A61P 11/06; A61P 17/00; A61P 19/06; A61P 1/04; A61P 21/02; A61P 31/18; A61P 11/02; A61P 15/08; A61P 17/04; A61P 17/08; A61P 1/16; A61P 25/06; A61P 25/08; A61P 27/16; A61P 31/00; A61P 31/12; A61P 33/00; A61P 33/06; A61P 33/10; A61P 33/12; A61P 5/14; A61P 7/04; A61P 7/06; A61P 9/06; A61P 9/08; A61P 19/00; A61P 19/04; A61P 19/10; A61P 3/14; A61P 7/08; A61P 35/04; A61P 7/10; A61P 17/02; A61P 27/04; A61P 27/10; A61P 27/14; A61P 31/10; A61P 31/22; A61P 3/00; A61P 3/02; A61P 3/06; A61P 9/14; A61P 17/10; A61P 9/04; A61P 31/20; A61P 39/06; A61P 9/02; A61K 2300/00; A61K 2039/505; A61K 47/6803; A61K 31/537; A61K 38/28; A61K 38/47; A61K 47/3849; A61K 47/6817; A61K 47/6851; A61K 9/19; A61K 38/486; A61K 38/195; A61K 39/39541; A61K 47/6809; A61K 39/39558; A61K 51/1027; A61K 31/337; A61K 38/05; A61K 39/3955; A61K 47/10; A61K 47/6811; A61K 47/6867; A61K 31/4025; A61K 31/4196; A61K 31/513; A61K 31/555; A61K 31/7068; A61K 31/7072; A61K 38/07; A61K 38/08; A61K 47/6835; A61K 9/0019; A61K 47/6813; A61K 47/6857; A61K 47/6869; A61K 31/704; A61K 47/64; A61K 9/0048; A61K 2039/507; A61K 31/13; A61K 31/428; A61K 31/4439; A61K 31/7056; A61K 38/1833; A61K 38/30; A61K 38/50; A61K 2039/6037; A61K 47/02; A61K 47/26; A61K 47/60;
(Continued)

(56) References Cited

U.S. PATENT DOCUMENTS 5,328,836 A   7/1994 Shima et al.
5,500,354 A   3/1996 Kitamura et al.
(Continued)

FOREIGN PATENT DOCUMENTS

CN     1358543 A    7/2002
EP     0 838 221 A1  4/1998
(Continued)

OTHER PUBLICATIONS

Allison, S.D. et al., "Mechanisms of protection of cationic lipid DNA complexes during lyophilization" Journal of Pharmaceutical Sciences, vol. 89, No. 5, May 2000, pp. 682-691.
(Continued)

*Primary Examiner* — Audrea B Coniglio
(74) *Attorney, Agent, or Firm* — Fenwick & West LLP

(57) ABSTRACT

The present invention provides a novel lyophilized pharmaceutical composition that maintains the stability of a DNA plasmid while forming a uniform and elegant cake during lyophilization. The novel lyophilization formulation further allows uniform reconstitution of the DNA plasmid in a pharmaceutically acceptable solution, enabling complete recover of the active ingredients, minimizing partial loss of potency and allowing administration of the active ingredients in an accurate and consistent manner. Additionally provided herein include methods of making the lyophilized pharmaceutical composition and methods of administering the composition for treatment of various diseases.

18 Claims, 52 Drawing Sheets

Figure 1:
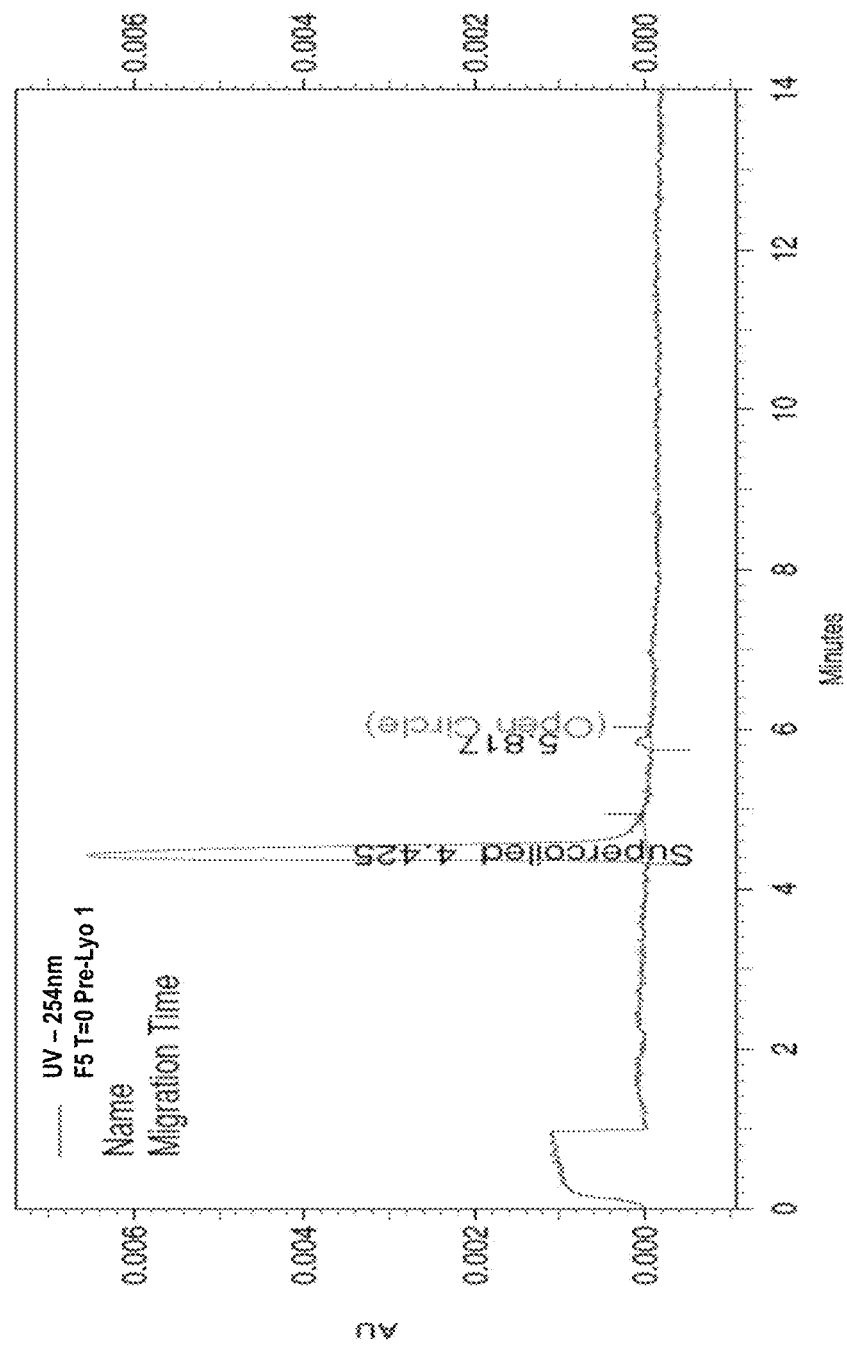

Specification includes a Sequence Listing.

(51) Int. Cl.
A61K 47/02 (2006.01)
A61K 47/26 (2006.01)
A61K 9/19 (2006.01)

(52) U.S. Cl.
CPC .............. *A61K 47/02* (2013.01); *A61K 47/26* (2013.01); *A61K 48/0091* (2013.01)

(58) Field of Classification Search
CPC ........ A61K 2039/522; A61K 2039/552; A61K 2039/55505; A61K 2039/55555; A61K 2039/55572; A61K 2039/55577; A61K 2039/6068; A61K 2039/627; A61K 2039/70; A61K 31/431; A61K 31/713; A61K 35/76; A61K 38/1767; A61K 38/22; A61K 39/085; A61K 39/092; A61K 39/12; A61K 39/245; A61K 39/385; A61K 47/46; A61K 47/6815; A61K 47/6843; A61K 47/6855; A61K 48/0016; A61K 51/1051; A61K 9/0095; A61K 9/08; A61K 9/1075; A61K 31/711; A61K 48/00; A61K 2039/53; A61K 38/00; A61K 48/0041; A61K 31/436; A61K 45/06; A61K 48/0091; A61K 47/183; A61K 31/519; A61K 31/53; A61K 38/1709; A61K 48/0025; A61K 48/005; A61K 2039/5156; A61K 2039/5158; A61K 2039/5256; A61K 31/7105; A61K 31/7115; A61K 31/712; A61K 31/7125; A61K 35/741; A61K 39/00; A61K 39/21; A61K 39/39; A61K 47/20; A61K 48/0083; A61K 9/127; A61K 9/1271; A61K 9/1272; A61K 2039/545; A61K 2039/55566; A61K 2039/57; A61K 2039/6093; A61K 31/136; A61K 31/155; A61K 31/164; A61K 31/167; A61K 31/196; A61K 31/454; A61K 31/4748; A61K 31/517; A61K 31/5415; A61K 31/7048; A61K 39/02; A61K 47/12; A61K 47/38; A61K 9/1617; A61K 9/1647; A61K 9/5123; A61K 2039/525; A61K 31/7088; A61K 35/17; A61K 35/761; A61K 39/0011; A61K 39/001112; A61K 39/135; A61K 39/145; A61K 47/32; A61K 47/42; A61K 47/6929; A61K 48/0075; A61K 49/005; A61K 9/1274; A61K 9/1694; A61K 9/501; A61K 9/5115; A61K 2039/5254; A61K 2039/55511; A61K 31/7052; A61K 35/747; A61K 38/465; A61K 39/0258; A61K 39/0266; A61K 39/155; A61K 39/175; A61K 39/235; A61K 47/18; A61K 47/186; A61K 47/24; A61K 47/36; A61K 48/0008; A61K 9/0075; C40B 40/02
See application file for complete search history.

(56) References Cited

U.S. PATENT DOCUMENTS

| | | | |
|---|---|---|---|
| 5,587,359 A | 12/1996 | Higashio et al. | |
| 6,121,246 A | 9/2000 | Isner | |
| 6,248,722 B1 | 6/2001 | Morishita et al. | |
| 6,258,787 B1 | 7/2001 | Isner | |
| 6,316,419 B1 | 11/2001 | Leiden et al. | |
| 6,387,695 B1 | 5/2002 | Evans et al. | |
| 7,276,359 B1 | 10/2007 | Musunuri et al. | |
| 7,285,540 B2 | 10/2007 | Morishita et al. | |
| 7,323,297 B1 | 1/2008 | Szoka et al. | |
| 7,745,174 B2 | 6/2010 | Kim et al. | |
| 7,812,146 B2 | 10/2010 | Kim et al. | |
| 7,875,446 B2* | 1/2011 | Kang ............... A61P 31/12 435/235.1 |
| 7,927,870 B2 | 4/2011 | Volkin et al. | |
| 8,389,492 B2 | 3/2013 | Kim et al. | |
| 2003/0148968 A1 | 8/2003 | Hammond et al. | |
| 2003/0171287 A1 | 9/2003 | Morishita et al. | |
| 2003/0176347 A1 | 9/2003 | Nakamura et al. | |
| 2004/0105882 A1 | 6/2004 | Morishita et al. | |
| 2004/0110714 A1 | 6/2004 | Adami et al. | |
| 2004/0228834 A1 | 11/2004 | Isner et al. | |
| 2005/0079581 A1 | 4/2005 | Kim et al. | |
| 2005/0164208 A1 | 7/2005 | Poulin | |
| 2006/0286072 A1 | 12/2006 | Giordano et al. | |
| 2008/0081366 A1 | 4/2008 | Musunuri et al. | |
| 2008/0268030 A1 | 10/2008 | Morishita et al. | |
| 2009/0004260 A1 | 1/2009 | Morishita et al. | |
| 2009/0082293 A1 | 3/2009 | Giordano et al. | |
| 2009/0130761 A1 | 5/2009 | Koyama et al. | |
| 2009/0131350 A1 | 5/2009 | Kirn et al. | |
| 2009/0202606 A1 | 8/2009 | Kirn et al. | |
| 2009/0258932 A1 | 10/2009 | Kim et al. | |
| 2012/0010273 A1 | 1/2012 | Kim et al. | |
| 2013/0034573 A1 | 2/2013 | Ahmed et al. | |
| 2016/0025749 A1 | 1/2016 | Park et al. | |

FOREIGN PATENT DOCUMENTS

| | | | | |
|---|---|---|---|---|
| EP | 1042347 A1 | 10/2000 | | |
| EP | 1061955 B1 | 5/2005 | | |
| EP | 1555033 A2 | 7/2005 | | |
| EP | 2281040 B1 | 11/2015 | | |
| JP | 2001526292 A | 12/2001 | | |
| JP | 2006-515855 A | 6/2006 | | |
| JP | 2011516545 A | 5/2011 | | |
| WO | WO 98/50079 A2 | 11/1998 | | |
| WO | WO 99/45775 A1 | 9/1999 | | |
| WO | WO 01/34208 A1 | 5/2001 | | |
| WO | WO 02/089856 A1 | 11/2002 | | |
| WO | WO 03/078568 A2 | 9/2003 | | |
| WO | WO 2004/060059 | 7/2004 | | |
| WO | WO 2007/132873 A1 | 11/2007 | | |
| WO | WO 2009/125986 A2 | 10/2009 | | |
| WO | WO2009/125986 A2 * | 10/2009 | ............. C12N 15/10 |

OTHER PUBLICATIONS

Anchordoquy, T., et al., "Low molecular weight dextrans stabilize nonviral vectors during lypholization at low osmolalities: Concentrating suspensions by rehydration to reduced volumes," Journal of pharmaceutical sciences, vol. 94, Iss. 6, Jun. 2005, pp. 1226-1236.
Brus C. et al., "Stabilization of oligonucleotide—polyethylenimine complexes by freeze-drying: physicochemical and biological characterization" Journal of Controlled Release, vol. 95, Iss. 1, Feb. 20, 2004, pp. 119-131.
Choi, W. et al., "Hepatocyte Growth Factor Regulates the miR-206-HDAC4 Cascade to Control Neurogenic Muscle Atrophy following Surgical Denervation in Mice," Molecular Therapy: Nucleic Acids, vol. 12, Sep. 2018, pp. 568-577.
Courtney, L., et al., "*Homo sapiens* PAC clone RP5-1098B1 from 7q11.223-q21, complete sequence," GenBank Database, Accession No. AC004960, Jun. 12, 1998, 41 pgs.
Deng, et al., "Secretory Expression of the Deleted Variant of Human Hepatocyte Growth Factor (hdHGF) in Pichia pastoris," Chinese Journal of Biochemistry and Molecular Biology, vol. 17, Oct. 2001, pp. 590-594 (with English abstract).
Dimitriadis, G., "Entrapment of Plasmid DNA in Liposomes" Nucleic Acids Research 6(8), Apr. 1979, pp. 2697-2705.
Jo, J. et al., "Liver Targeting of Plasmid DNA with a Cationized Pullulan for Tumor Suppression" Journal of Nanoscience and Nanotechnology, vol. 6, No. 9-10, Sep./Oct. 2006, pp. 2853-2859.
Kato, N., et al., "Nonviral HVJ (hemagglutinating virus of Japan) liposome mediated retrograde gene transfer of human hepatocyte

(56) References Cited

OTHER PUBLICATIONS growth factor into rat nervous system promotes functional and histological Yecovery of the crushed nerve," Neuroscience Research, vol. 52, May 5, 2005, pp. 299-310.
Ko, K. et al., "c-Fos is necessary for HGF-mediated gene regulation and cell migration in Schwann cells." Biochemical and Biophysical Research Communications, vol. 5053, Aug. 10, 2018, pp. 2855-2860.
Lee, N. et al., "Disproportionately high levels of HGF induce the degradation of the c-met receptor through the proteasomal degradation pathway," Biochemical and Biophysical Research Communications, vol. 505, Oct. 8, 2018, pp. 925-930.
Liu, Y., "The Human Hepatocyte Growth Factor Receptor Gene: Complete Structural Organization and Promoter Characterization," Gene, vol. 215, Iss. 1, Jul. 17, 1998, pp. 159-169.
Liu. Y., et al., "Secretory Expression of the Deleted Variant of Human Hepatocyte Growth Factor in Pichia pastoris," World Journal of Gastroenterology, vol. 11, No. 45, Dec. 7, 2005, pp. 7097-7103.
Miyazawa, K.., et al., "Molecular Cloning and Sequence Analysis of cDNA for Human Hepatocyte Growth Factor," Biochem.Biophys. Res. Commun., vol. 163, Iss. 2, Sep. 15, 1989, pp. 967-973.
Morishita, R. et al., "Therapeutic Angiogenesis using Hepatocyte Growth Factor (HGF)" Current Gene Therapy, vol. 4, No. 2, Jun. 1, 2004, pp. 199-206.
Nakagami, H. et al., "Hepatocyte growth factor as potential cardiovascular therapy" Expert Review of Cardiovascular Therapy, vol. 3, Iss. 3, Jan. 10, 2014, pp. 513-519.
Nakamura, T., et al., "Molecular cloning and expression of human hepatocyte growth factor," Nature, vol. 342, Nov. 23, 1989, pp. 440-443.
PCT International Search Report and Written Opinion, PCT Application No. PCT/US2019/042702, dated Oct. 29, 2019, 17 pages.
Poxon, S. W. et al., "The effect of lypholization on plasmid DNA activity," Pharmaceutical development and technology 5(1), Jan. 18, 2000, pp. 115-122.
Quaak, S. G. L. et al., "Naked Plasmid DNA Formulation: Effect of Different Disaccharides on Stability after Lyophilisation," AAPS PharmSciTech, vol. 11, Iss. 1, Mar. 2010, pp. 344-350.
Rubin, J., et al., "A broad-spectrum human lung fibroblast-derived mitogen is a variant of hepatocyte growth factor," Proc. Natl. Acad. Sci., vol. 88, Jan. 1991, pp. 415-419.
Seki, T., et al., "Isolation and Expression of cDNA for Different Forms of Hepatocyte Growth Factor from Human Leukocyte," Biochem. Biophys. Res. Commun., vol. 172, No. 1, Oct. 15, 1990, pp. 321-327.
Seki, T., et al., "Organization of the human hepatocyte growth factor-encoding gene," Gene, vol. 102, No. 2, Jan. 1991, pp. 213-219.
Sharma, V. et al., "Moisture-Induced Aggregation of Lyophilized DNA and its Prevention" Pharmaceutical Research 24(1), Oct. 16, 2006, pp. 168-175.
Shima, N., et al., "Hepatocyte growth factor and its variant with a deletion of five amino acids are distinguishable in their biological activity and tertiary structure," Biochem. Biophys. Res. Commun, vol. 200, No. 2, Apr. 29, 1994, pp. 808-815.
Taniyama et al., "Therapeutic angiogenesis induced by human hepatocyte growth factor gene in rat and rabbit hindlimb ischemia models: preclinical study for treatment of peripheral arterial disease" Gene Therapy, vol. 8, Apr. 6, 2001, pp. 181-189.
United States Office Action, U.S. Appl. No. 12/421,425, filed Aug. 19, 2010, 15 pages.
United States Office Action, U.S. Appl. No. 12/421,425, filed Dec. 17, 2010, 16 pages.
Yang, et al., "Sustained Expression of Naked Plasmid DNA Encoding Hepatocyte Growth Factor in Mice Promotes Liver and Overall Body Growth," Hepatology, vol. 33, Iss. 4, Apr. 2001, pp. 848-859.
Budylskaya, T. V. et al. "Pharmaceutical Development of Formulation Based on Biopharmaceutical Preparations for Gene Therapy." Drug Development & Registration, vol. 1, 2016, pp. 74-85, (with English abstract).
Federal Service for Intellectual Property, Office Action, Russian Patent Application No. 2021102590, dated Apr. 15, 2022, 23 pages.
Saeed, M. et al. "MR Assessment of Myocardial Perfusion, Viability, and Function after Intramyocardial Transfer of VM202, a New Plasmid Human Hepatocyte Growth Factor in Ischemic Swine Myocardium." Radiology, vol. 249, No. 1, Oct. 2008, pp. 107-118.
The Japan Patent Office, Notice of Reasons for Refusal, Japanese Patent Application No. 2021-502948, dated Jul. 12, 2022, seven pages.
European Patent Office, Extended European Search Report, European Patent Application No. 19838143.6, dated Apr. 29, 2022, 10 pages.
Kasper, J.C., "Lyophilization of Nucleic Acid Nanoparticles: Formulation Development, Stabilization Mechanisms, and Process Monitoring," Ludwig-Maximilians-Universitat Munchen, Dissertation, Mar. 13, 2012, pp. 1-336.
Kaufman, R.J., "Overview of Vector Design for Mammalian Gene Expression," Methods in Molecular Biology, vol. 62 Recombinant Gene Expression Protocols, Mar. 6, 1997, pp. 287-300.
Makrides, S.C., "Vectors for gene expression in mammalian cells," Chapter 2: Gene Transfer and Expression in Mammalian Cells, 2003, pp. 9-26.
Muller, S. et al., "Spliceosomal Peptide P140 for Immunotherapy of Systemic Lupus Erythematosus Results of an Early Phase II Clinical Trial," Arthritis & Rheumatism, vol. 58, No. 12, Dec. 2008, pp. 3873-3883.
Murase, N. et al., "Salt precipitation during the freeze-concentration of phosphate buffer solutions," Biophysical Chemistry, vol. 34, 1989, pp. 293-300.

\* cited by examiner

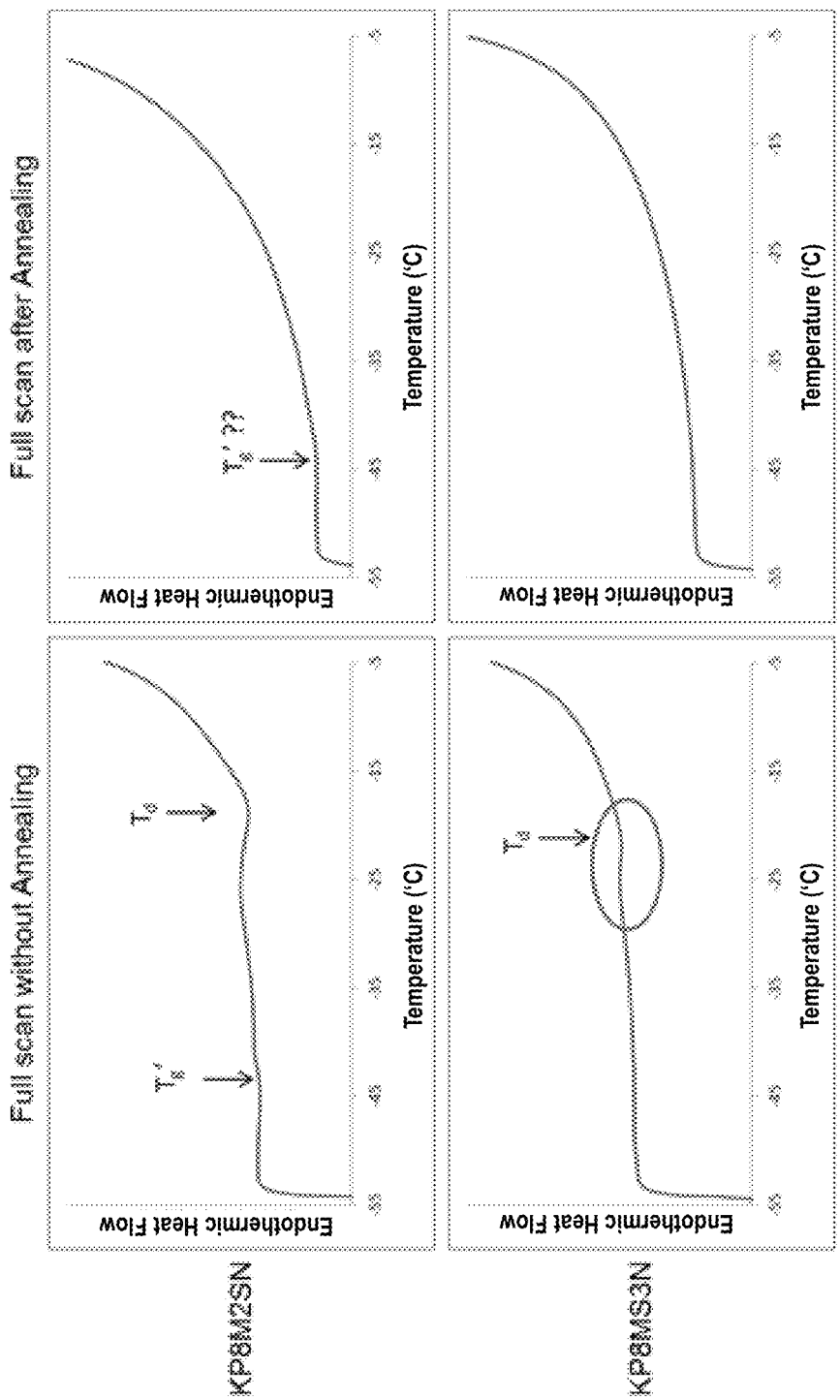

VM202 before Lyophilization

VM202 after Lyophilization

VM202 after Reconstitution

VM202 after Reconstitution

VM202 after Reconstitution

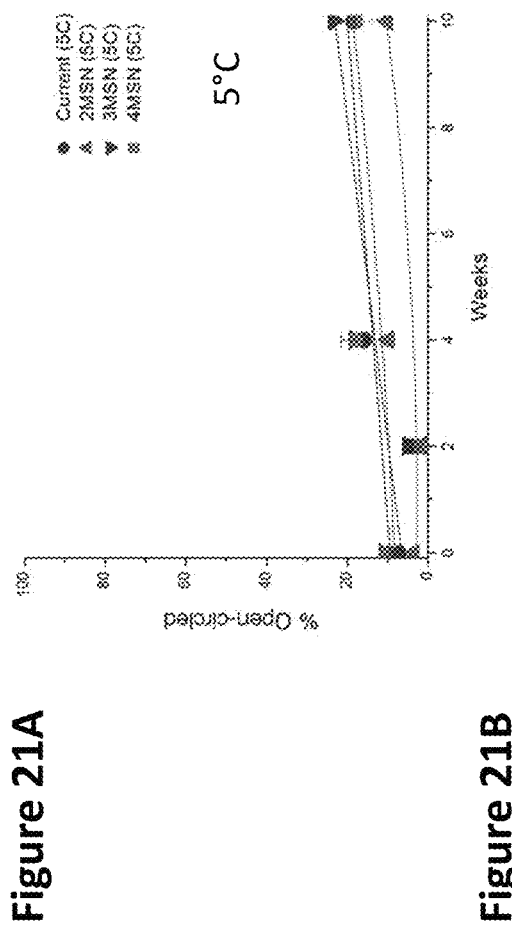
Figure 21A
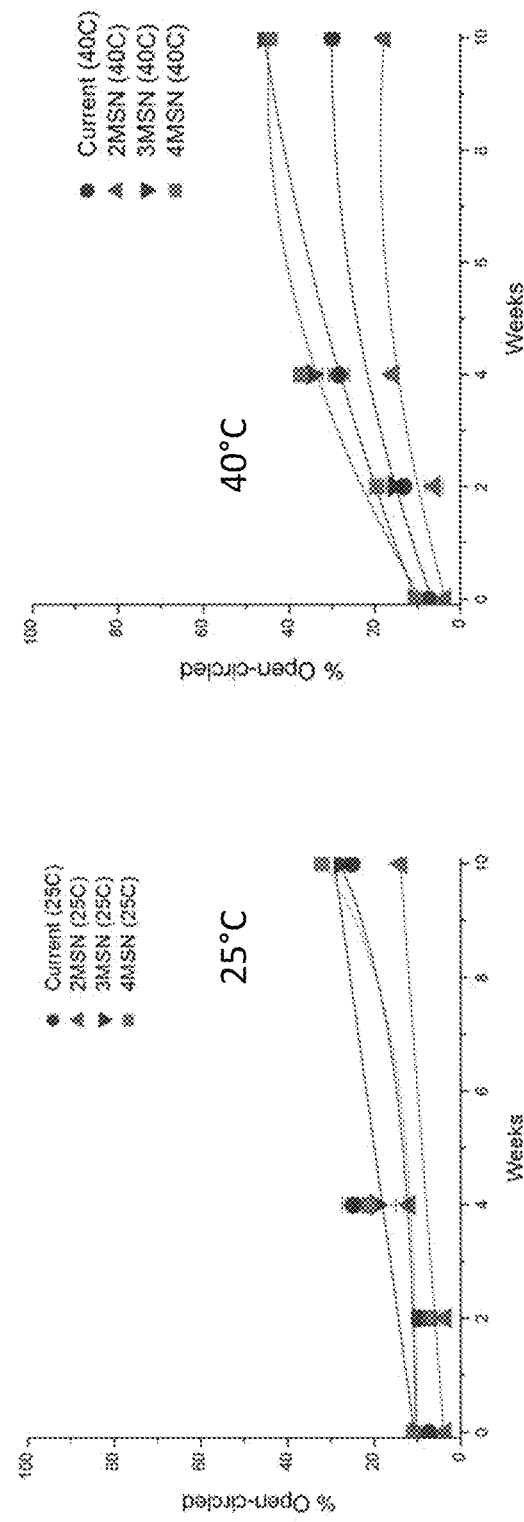
Figure 21B
Figure 21C

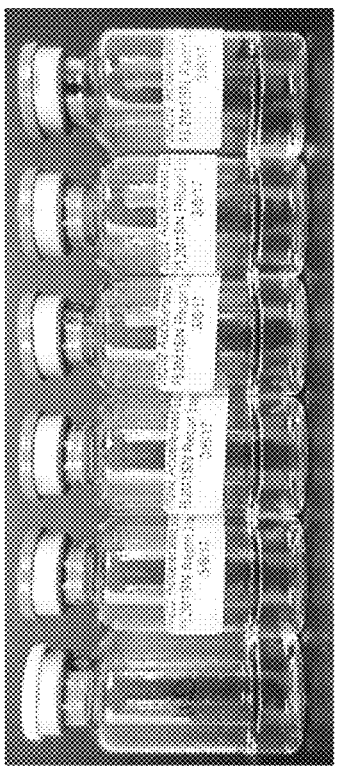
Figure 22A
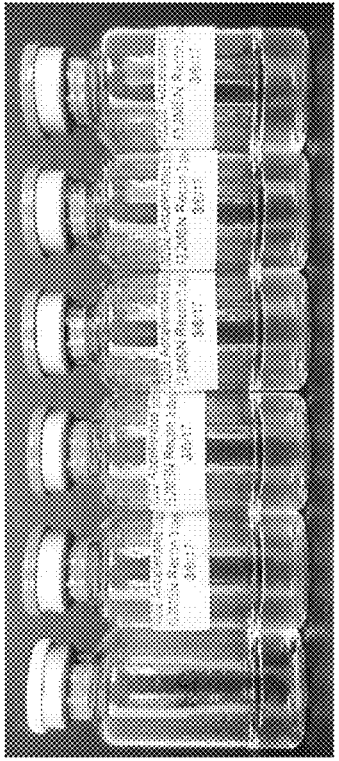
Figure 22C
(a) Storage at 25°C for 3 days after Reconstitution
(b) Storage at 25°C for 7 days after Reconstitution
Figure 22B
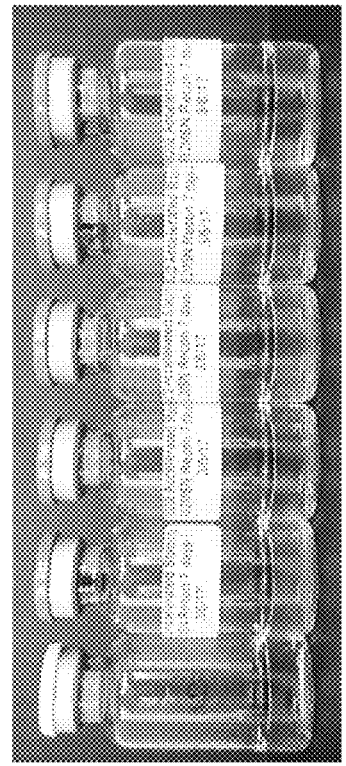
Figure 22D (a) 3 Days (b) 7 Days (a) 25°C (b) 40°C (c) 5°C

F1

| White background | Black background | Appearance |
|---|---|---|
|  <br>Lyo cake    Reconstituted |  <br>Lyo cake    Reconstituted | Clear, colorless solution<br><B9-Colour<br><1-Clarity |

F2

| White background | Black background | Appearance |
|---|---|---|
|  <br>Lyo cake    Reconstituted |  <br>Lyo cake    Reconstituted | Clear, colorless solution<br><B9-Colour<br><1-Clarity |

F3

F4

F5

F6

F7

F8

F1

F2

F3

| White background | Black background | Appearance |
|---|---|---|
|  <br>Lyo cake  Reconstituted |  <br>Lyo cake  Reconstituted | Clear, colourless solution<br><B9-Colour<br><I-Clarity |

F4

| White background | Black background | Appearance |
|---|---|---|
|  <br>Lyo cake  Reconstituted |  <br>Lyo cake  Reconstituted | Clear, colourless solution<br><B9-Colour<br><I-Clarity |

F5

F6

Figure 52

F7

| White background | Black background | Appearance |
|---|---|---|
| Lyo cake  Reconstituted | Lyo cake  Reconstituted | Clear, colorless solution <B9-Colour <I-Clarity |

Figure 53

F8

| White background | Black background | Appearance |
|---|---|---|
| Lyo cake  Reconstituted | Lyo cake  Reconstituted | Clear, colorless solution <B9-Colour <I-Clarity |

US 11,554,179 B2

LYOPHILIZED PHARMACEUTICAL COMPOSITIONS FOR NAKED DNA GENE THERAPY

1. CROSS-REFERENCE TO RELATED APPLICATIONS

This application claims priority to U.S. Provisional Application No. 62/700,655, filed Jul. 19, 2018, which is hereby incorporated by reference in its entirety.

2. SEQUENCE LISTING

The instant application contains a Sequence Listing which has been submitted via EFS-Web and is hereby incorporated by reference in its entirety. Said ASCII copy, created on Jul. 16, 2019, is named 40319US_CRF_sequencelisting and is 125,979 bytes in size.

3. BACKGROUND

There is now substantial clinical evidence that gene therapy involving direct in vivo delivery of nucleic acid constructs that have not been packaged in virus or virus-like particles—so-called "naked" DNA or RNA constructs—can be effective in treating various diseases. For example, direct intramuscular injection of a DNA plasmid construct that expresses two isoforms of human HGF protein (i.e., pCK-HGF-X7, also called "VM202") has been demonstrated to be effective in treating neuropathic pain. In a phase II clinical trial, injections of VM202 into the calf muscle of patients with diabetic peripheral neuropathy were shown to significantly reduce pain—two days of treatment, spaced two weeks apart, were sufficient to provide symptomatic relief with improvement in quality of life for 3 months. Kessler et al., *Annals Clin. Transl. Neurology* 2(5):465-478 (2015). The same DNA plasmid construct has also been shown to be effective in treating patients with amyotrophic lateral sclerosis (ALS). In a phase I clinical trial, close to half of the ALS patients remained stable or improved after administration of VM202, with 47%, 50%, and 24% of subjects at months 1, 2, and 3, respectively, experiencing either no decline or an improvement in the ALSFRS-R (Amyotrophic Lateral Sclerosis Functional Rating Scale-revised) score indicating physical functioning of ALS patients, which is better than observed in historical controls. Robert L. Sufit et al., *Amyotrophic Lateral Sclerosis and Frontoemporal Degeneration* 18:269-278 (2017).

However, despite the recent approval of two antisense oligonucleotide drugs for direct injection—nusinersen, for intrathecal injection, and eteplirsen, for intravenous injection—few naked DNA or RNA constructs have actually been approved for human gene therapy. Thus, despite decades of experience with formulating naked nucleic acids for laboratory use, and more recent experience formulating nucleic acids for ex vivo gene therapy approaches, little research has been conducted into formulating DNA as a pharmaceutical product for direct therapeutic delivery. In particular, there have been few investigations into stability of the nucleic acid active ingredient under various storage conditions, or into excipients required to permit uniform reconstitution of the formulation for administration, or into methods for reducing contaminant load, etc. These properties are important for better and more reproducible therapeutic efficacy and safety of the DNA-based drugs, as well as for the economic feasibility of scaling up the production and distribution of the drugs.

There is, therefore, a need for a formulation for a pharmaceutical product of a naked DNA-based drug that provides improved stability, safety and economic feasibility.

4. SUMMARY

In an aspect, the present invention provides a novel lyophilized pharmaceutical composition that maintains the stability of the DNA construct (e.g., a plasmid) during lyophilization. Specifically, the formulation reduces conformational change of DNA constructs during lyophilization from a more stable supercoiled form to a less stable open circular and linear form. The novel lyophilized formulation further allows uniform reconstitution of the DNA constructs in a pharmaceutically acceptable solution, enabling complete recovery of the active ingredients, minimizing partial loss of potency and allowing administration of the active ingredients in an accurate and consistent manner. Additionally, the novel lyophilized formulation produces a uniform and elegant cake appearance following lyophilization, thus making a visual inspection of the quality of the DNA-based drug feasible.

In some embodiments, the novel lyophilized formulation comprises plasmid DNA, wherein the pharmaceutical composition is obtained by lyophilizing a liquid composition that comprises, prior to lyophilization: a. DNA of a first plasmid; b. potassium phosphate buffer with pH in the range from 7.0 to 9.0; c. mannitol at a concentration in the range from 0% to 3% (w/v); d. sucrose at a concentration greater than 0.5% and less than 1.1% (w/v); and e. NaCl at a concentration in the range from 0.1% to 0.9% (w/v). The first plasmid can be selected from the group consisting of VM202, pTx-HGF-X7, pTx-IGF-1Ec, pTx-IGF-1Ea, pTx-IGF-1X6, pTx-IGF-10X10, and pCK-SDF-1α.

In some embodiments, the first plasmid is VM202. In some embodiments, the lyophilized pharmaceutical composition further comprises DNA of a second plasmid, wherein the second plasmid is selected from the group consisting of pTx-HGF-X7, pTx-IGF-1Ec, pTx-IGF-1Ea, pTx-IGF-1X6, pTx-IGF-1X10, and pCK-SDF-1α.

In some embodiments, the first plasmid is pTx-HGF-X7. In some embodiments, the lyophilized pharmaceutical composition further comprises DNA of a second plasmid, wherein the second plasmid is selected from the group consisting of VM202, pTx-IGF-1Ec, pTx-IGF-1Ea, pTx-IGF-1X6, pTx-IGF-1X10, and pCK-SDF-1α.

In some embodiments, the first plasmid is pTx-IGF-1Ec. In some embodiments, the lyophilized pharmaceutical composition further comprises DNA of a second plasmid, wherein the second plasmid is selected from the group consisting of VM202, pTx-HGF-X7, pTx-IGF-1Ea, pTx-IGF-1X6, pTx-IGF-1X10, and pCK-SDF-1α.

In some embodiments, the first plasmid is pTx-IGF-1Ea. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1X6, pTx-IGF-1X10, and pCK-SDF-1α.

In some embodiments, the first plasmid is pTx-IGF-1X6. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X10, and pCK-SDF-1α.

In some embodiments, the first plasmid is pTx-IGF-1X10. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X6, and pCK-SDF-1α.

In some embodiments, the first plasmid is pCK-SDF-1α. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X6, and pTx-IGF-1X10.

In some embodiments, at least 90% of the plasmid DNA in the liquid composition is supercoiled. In some embodiments, at least 92.5% of the plasmid DNA in the liquid composition is supercoiled. In some embodiments, at least 95% of the plasmid DNA in the liquid composition is supercoiled. In some embodiments, at least 97% of the plasmid DNA in the liquid composition is supercoiled. In some embodiments, at least 98% of the plasmid DNA in the liquid composition is supercoiled.

In some embodiments, at least 90% of the plasmid DNA remains supercoiled 30 minutes after reconstitution of the lyophilized pharmaceutical composition. In some embodiments, at least 92.5% of the plasmid DNA remains supercoiled 30 minutes after reconstitution of the lyophilized pharmaceutical composition. In some embodiments, at least 95% of the plasmid DNA remains supercoiled 30 minutes after reconstitution of the lyophilized pharmaceutical composition. In some embodiments, at least 97% of the plasmid DNA remains supercoiled 30 minutes after reconstitution of the lyophilized pharmaceutical composition. In some embodiments, at least 98% of the plasmid DNA remains supercoiled 30 minutes after reconstitution of the lyophilized pharmaceutical composition.

In some embodiments, at least 90% of the plasmid DNA remains supercoiled after storage at 25° C. for 3 to 7 days following reconstitution of the lyophilized pharmaceutical composition. In some embodiments, at least 92.5% of the plasmid DNA remains supercoiled after storage at 25° C. for 3 to 7 days following reconstitution of the lyophilized pharmaceutical composition. In some embodiments, at least 95% of the plasmid DNA remains supercoiled after storage at 25° C. for 3 to 7 days following reconstitution of the lyophilized pharmaceutical composition.

In some embodiments, at least 80% of the plasmid DNA remains supercoiled 30 minutes after reconstitution, wherein the lyophilized pharmaceutical composition had been stored at 40° C. for 10 weeks before reconstitution.

In some embodiments, the lyophilized pharmaceutical composition comprises supercoiled DNA in an amount of at least 90% of a total amount of supercoiled DNA in the liquid composition. In some embodiments, the lyophilized pharmaceutical composition comprises supercoiled DNA in an amount of at least 92.5% of a total amount of supercoiled DNA in the liquid composition. In some embodiments, the lyophilized pharmaceutical composition comprises supercoiled DNA in an amount of at least 95% of a total amount of supercoiled DNA in the liquid composition.

In some embodiments, the liquid composition comprises the first plasmid DNA at a concentration in the range from 0.1 to 1 mg/ml. In some embodiments, the liquid composition comprises the first plasmid DNA at a concentration in the range from 0.25 to 0.75 mg/ml. In some embodiments, the liquid composition comprises the first plasmid DNA at a concentration in the range from 0.4 to 0.6 mg/ml. In some embodiments, the liquid composition comprises the first plasmid DNA at a concentration of 0.5 mg/ml.

In some embodiments, the liquid composition comprises the second plasmid DNA at a concentration in the range from 0.1 to 1 mg/ml. In some embodiments, the liquid composition comprises the second plasmid DNA at a concentration in the range from 0.25 to 0.75 mg/ml. In some embodiments, the liquid composition comprises the second plasmid DNA at a concentration in the range from 0.4 to 0.6 mg/ml. In some embodiments, the liquid composition comprises the second plasmid DNA at a concentration of 0.5 mg/ml.

In some embodiments, the liquid composition comprises potassium phosphate at a concentration in the range from 5 mM to 15 mM. In some embodiments, the liquid composition comprises potassium phosphate at a concentration in the range from 7.5 mM to 12.5 mM. In some embodiments, the liquid composition comprises potassium phosphate at a concentration in the range from 9 mM to 11 mM. In some embodiments, the liquid composition comprises potassium phosphate at a concentration of 10 mM.

In some embodiments, the liquid composition comprises potassium phosphate buffer with pH in the range from 7.0 to 8.5. In some embodiments, the liquid composition comprises potassium phosphate buffer with pH in the range from 7.0 to 8.0. In some embodiments, the liquid composition comprises potassium phosphate buffer of pH 8.0.

In some embodiments, the liquid composition comprises mannitol at a concentration in the range from 1.5% to 3% (w/v). In some embodiments, the liquid composition comprises mannitol at a concentration in the range from 2% to 3% (w/v). In some embodiments, the liquid composition comprises mannitol at a concentration of 2% (w/v).

In some embodiments, the liquid composition comprises sucrose at a concentration in the range from 0.75% to 1.1% (w/v). In some embodiments, the liquid composition comprises sucrose at a concentration in the range from 0.9% to 1.0% (w/v). In some embodiments, the liquid composition comprises sucrose at a concentration of 1.0% (w/v).

In some embodiments, the liquid composition comprises NaCl at a concentration in the range from 0.1% to 0.75% (w/v). In some embodiments, the liquid composition comprises NaCl at a concentration in the range from 0.1% to 0.6% (w/v). In some embodiments, the liquid composition comprises NaCl at a concentration in the range from 0.4% to 0.5% (w/v). In some embodiments, the liquid composition comprises NaCl at a concentration of 0.45% (w/v).

Some embodiments of the present invention relate to a lyophilized pharmaceutical composition comprising plasmid DNA, wherein the pharmaceutical composition is obtained by lyophilizing a liquid composition that comprises, prior to lyophilization: a. DNA of a first plasmid at a concentration of 0.5 mg/ml; b. 10 mM potassium phosphate buffer of pH 8.0; c. mannitol at a concentration of 2% (w/v); d. sucrose at a concentration of 1.0% (w/v); and e. NaCl at a concentration of 0.45% (w/v), wherein at least 95% of the plasmid DNA is supercoiled, and at least 90% of the plasmid DNA remains supercoiled after storage at 25° C. for 3 to 7 days following reconstitution of the lyophilized pharmaceutical composition. The first plasmid can be selected from the group consisting of VM202, pTx-HGF-X7, pTx-IGF-1Ec, pTx-IGF-1Ea, pTx-IGF-1X6, pTx-IGF-1X10, and pCK-SDF-1α.

In some embodiments, the first plasmid is VM202. In some embodiments, the lyophilized pharmaceutical composition further comprises DNA of a second plasmid, wherein the second plasmid is selected from the group consisting of pTx-HGF-X7, pTx-IGF-1Ec, pTx-IGF-1Ea, pTx-IGF-1X6, pTx-IGF-1X10, and pCK-SDF-1α.

In some embodiments, the first plasmid is pTx-HGF-X7. In some embodiments, the lyophilized pharmaceutical composition further comprises DNA of a second plasmid, wherein the second plasmid is selected from the group consisting of VM202, pTx-IGF-1Ec, pTx-IGF-1Ea, pTx-IGF-1X6, pTx-IGF-1X10, and pCK-SDF-1α.

In some embodiments, the first plasmid is pTx-IGF-1Ec. In some embodiments, the lyophilized pharmaceutical composition further comprises DNA of a second plasmid, wherein the second plasmid is selected from the group consisting of VM202, pTx-HGF-X7, pTx-IGF-1Ea, pTx-IGF-1X6, pTx-IGF-1X10, and pCK-SDF-1α.

In some embodiments, the first plasmid is pTx-IGF-1Ea. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1X6, pTx-IGF-1X10, and pCK-SDF-1α.

In some embodiments, the first plasmid is pTx-IGF-1X6. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X10, and pCK-SDF-1α.

In some embodiments, the first plasmid is pTx-IGF-1X10. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X6, and pCK-SDF-1α.

In some embodiments, the first plasmid is pCK-SDF-1α. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X6, and pTx-IGF-1X10.

Some aspects of the present invention relate to a reconstituted composition produced by dissolving the lyophilized pharmaceutical composition in water.

In some embodiments, light absorbance of the reconstituted composition at 450 nm is less than 0.002. In some embodiments, the light absorbance of the reconstituted composition at 450 nm is 0.001 or less than 0.001. In some embodiments, the light absorbance is measured on the day of reconstitution. In some embodiments, the light absorbance of the reconstituted composition at 450 nm is measured after storage of the lyophilized pharmaceutical composition for 10 weeks.

Some aspects of the present invention relate to a lyophilized pharmaceutical composition comprising plasmid DNA in a unit dose, wherein the pharmaceutical composition is obtained by lyophilizing a liquid composition that comprises, prior to lyophilization: a. DNA of a first plasmid at a concentration of 0.5 mg/ml; b. 10 mM potassium phosphate buffer of pH 8.0; c. mannitol at a concentration of 2% (w/v); d. sucrose at a concentration of 1.0% (w/v); and e. NaCl at a concentration of 0.45% (w/v), wherein the lyophilized pharmaceutical composition is in a vial and the vial contains 2.5 mg of plasmid DNA in total. The first plasmid can be selected from the group consisting of VM202, pTx-HGF-X7, pTx-IGF-1Ec, pTx-IGF-1Ea, pTx-IGF-1X6, pTx-IGF-1X10, and pCK-SDF-1α.

In some embodiments, the first plasmid is VM202. In some embodiments, the lyophilized pharmaceutical composition further comprises DNA of a second plasmid, wherein the second plasmid is selected from the group consisting of pTx-HGF-X7, pTx-IGF-1Ec, pTx-IGF-1Ea, pTx-IGF-1X6, pTx-IGF-1X10, and pCK-SDF-1α.

In some embodiments, the first plasmid is pTx-HGF-X7. In some embodiments, the lyophilized pharmaceutical composition further comprises DNA of a second plasmid, wherein the second plasmid is selected from the group consisting of VM202, pTx-IGF-1Ec, pTx-IGF-1Ea, pTx-IGF-1X6, pTx-IGF-1X10, and pCK-SDF-1α.

In some embodiments, the first plasmid is pTx-IGF-1Ec. In some embodiments, the lyophilized pharmaceutical composition further comprises DNA of a second plasmid, wherein the second plasmid is selected from the group consisting of VM202, pTx-HGF-X7, pTx-IGF-1Ea, pTx-IGF-1X6, pTx-IGF-1X10, and pCK-SDF-1α.

In some embodiments, the first plasmid is pTx-IGF-1Ea. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1X6, pTx-IGF-1X10, and pCK-SDF-1α.

In some embodiments, the first plasmid is pTx-IGF-1X6. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X10, and pCK-SDF-1α.

In some embodiments, the first plasmid is pTx-IGF-1X10. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X6, and pCK-SDF-1α.

In some embodiments, the first plasmid is pCK-SDF-1α. In some embodiments, the lyophilized pharmaceutical composition further comprises DNA of a second plasmid, wherein the second plasmid is selected from the group consisting of VM202, pTx-HGF-X7, pTx-IGF-1Ec, pTx-IGF-1Ea, pTx-IGF-1X6, and pTx-IGF-1X10.

Some aspects of the present invention relate to a reconstituted composition produced by dissolving the lyophilized pharmaceutical composition.

Some aspects of the present invention relate to a method of making a lyophilized pharmaceutical composition comprising plasmid DNA, the method comprising: providing a liquid composition comprising: a. DNA of a first plasmid; b. potassium phosphate buffer with pH in the range from 7.0 to 9.0; c. mannitol at a concentration in the range from 0%/a to 3% (w/v); d. sucrose at a concentration greater than 0.5% and less than 1.1% (w/v); and e. NaCl at a concentration in the range from 0.1% to 0.9% (w/v); and lyophilizing the liquid composition, thereby generating the lyophilized pharmaceutical composition. The first plasmid can be selected from the group consisting of VM202, pTx-HGF-X7, pTx-IGF-1Ec, pTx-IGF-1Ea, pTx-IGF-1X6, pTx-IGF-1X10, and pCK-SDF-1α.

In some embodiments, the first plasmid is VM202. In some embodiments, the first plasmid is pTx-HGF-X7. In some embodiments, the first plasmid is pTx-IGF-1X6. In some embodiments, the first plasmid is pTx-IGF-1X10. In some embodiments, the first plasmid is pTx-IGF-1Ec. In some embodiments, the first plasmid is pTx-IGF-1Ea. In some embodiments, the first plasmid is pCK-SDF-1α.

In some embodiments, the step of lyophilizing comprises: (i) loading the liquid composition; (ii) freezing; (iii) primary drying; and (iv) secondary drying.

In some embodiments, the step of loading is performed at 5° C.

In some embodiments, the step of freezing is performed while raising temperatures in the range from −50° C. to −20° C.

In some embodiments, the step of primary drying is performed at −20° C.

In some embodiments, the step of secondary drying is performed while raising temperatures in the range from −20° C. to 20° C.

In some embodiments, at least 90% of the plasmid DNA in the liquid composition is supercoiled. In some embodiments, at least 92.5% of the plasmid DNA in the liquid composition is supercoiled. In some embodiments, at least 95% of the plasmid DNA in the liquid composition is supercoiled. In some embodiments, at least 97% of the plasmid DNA in the liquid composition is supercoiled.

In some embodiments, at least 90% of the plasmid DNA remains supercoiled 30 minutes after reconstitution of the lyophilized pharmaceutical composition. In some embodiments, at least 92.5% of the plasmid DNA remains supercoiled 30 minutes after reconstitution of the lyophilized pharmaceutical composition. In some embodiments, at least 95% of the plasmid DNA remains supercoiled 30 minutes after reconstitution of the lyophilized pharmaceutical composition. In some embodiments, at least 97% of the plasmid DNA remains supercoiled 30 minutes after reconstitution of the lyophilized pharmaceutical composition. In some embodiments, at least 98% of the plasmid DNA remains supercoiled 30 minutes after reconstitution of the lyophilized pharmaceutical composition.

In some embodiments, at least 90% of the plasmid DNA remains supercoiled after storage at 25° C. for 3 to 7 days following reconstitution of the lyophilized pharmaceutical composition. In some embodiments, at least 92.5% of the plasmid DNA remains supercoiled after storage at 25° C. for 3 to 7 days following reconstitution of the lyophilized pharmaceutical composition. In some embodiments, at least 95% of the plasmid DNA remains supercoiled after storage at 25° C. for 3 to 7 days following reconstitution of the lyophilized pharmaceutical composition.

In some embodiments, at least 80% of the plasmid DNA remains supercoiled 30 minutes after reconstitution of the lyophilized pharmaceutical composition, wherein the lyophilized pharmaceutical composition had been stored at 40° C. for 10 weeks before reconstitution.

In some embodiments, the lyophilized pharmaceutical composition comprises supercoiled DNA in an amount of at least 90% of a total amount of supercoiled DNA in the liquid composition. In some embodiments, the lyophilized pharmaceutical composition comprises supercoiled DNA in an amount of at least 92.5% of a total amount of supercoiled DNA in the liquid composition. In some embodiments, the lyophilized pharmaceutical composition comprises supercoiled DNA in an amount of at least 95% of a total amount of supercoiled DNA in the liquid composition.

In some embodiments, the liquid composition comprises the plasmid at a concentration in the range from 0.1 to 1 mg/ml. In some embodiments, the liquid composition comprises the first plasmid at a concentration in the range from 0.25 to 0.75 mg/ml. In some embodiments, the liquid composition comprises the first plasmid at a concentration in the range from 0.4 to 0.6 mg/ml. In some embodiments, the liquid composition comprises the first plasmid at a concentration of 0.5 mg/ml.

In some embodiments, the liquid composition comprises potassium phosphate at a concentration in the range from 5 mM to 15 mM. In some embodiments, the liquid composition comprises potassium phosphate at a concentration in the range from 7.5 mM to 12.5 mM. In some embodiments, the liquid composition comprises potassium phosphate at a concentration in the range from 9 mM to 11 mM. In some embodiments, the liquid composition comprises potassium phosphate at a concentration of 10 mM.

In some embodiments, the liquid composition comprises potassium phosphate buffer with pH in the range from 7.0 to 8.5. In some embodiments, the liquid composition comprises potassium phosphate buffer with pH in the range from 7.0 to 8.0. In some embodiments, the liquid composition comprises potassium phosphate buffer of pH 8.0.

In some embodiments, the liquid composition comprises mannitol at a concentration in the range from 1.5% to 3% (w/v). In some embodiments, the liquid composition comprises mannitol at a concentration in the range from 2% to 3% (w/v). In some embodiments, the liquid composition comprises mannitol at a concentration of 2% (w/v).

In some embodiments, the liquid composition comprises sucrose at a concentration greater than 0.75% and less than 1.1% (w/v). In some embodiments, the liquid composition comprises sucrose at a concentration greater than 0.9% and less than 1.1% (w/v). In some embodiments, the liquid composition comprises sucrose at a concentration of 1.0% (w/v).

In some embodiments, the liquid composition comprises NaCl at a concentration in the range from 0.1% to 0.75% (w/v). In some embodiments, the liquid composition comprises NaCl at a concentration in the range from 0.1% to 0.6%. In some embodiments, the liquid composition comprises NaCl at a concentration in the range from 0.4% to 0.5% (w/v). In some embodiments, the liquid composition comprises NaCl at a concentration of 0.45% (w/v).

Another aspect of the present invention relates to a method of treating a disease, comprising the step of: administering an effective amount of a reconstituted drug to a patient with the disease, wherein the reconstituted drug is generated by reconstituting the lyophilized pharmaceutical composition of the present invention.

In some embodiments, the method further comprises the step of dissolving the lyophilized pharmaceutical composition in water, thereby generating the reconstituted drug.

In some embodiments, light absorbance of the reconstituted drug at 450 nm (A450) is less than 0.003. In some embodiments, the light absorbance is less than 0.002. In some embodiments, the light absorbance is 0.001 or less than 0.001.

In some embodiments, the disease is selected from the group consisting of neuropathy, ischemic disease, muscle atrophy, vascular disease, and a heart disease. In some embodiments, the disease is selected from ischemic limb disease, diabetic peripheral neuropathy (DPN), amyotrophic lateral sclerosis (ALS), peripheral vascular disease, and coronary artery disease (CAD).

In some embodiments, the step of administering comprises an intramuscular injection of the reconstituted drug.

5. BRIEF DESCRIPTION OF THE DRAWINGS

FIG. 1 provides an exemplary result from capillary electrophoresis (CE) of VM202. The result shows two peaks—one for the supercoiled form and the other for the open circle form.

Figures 2C, 2D:
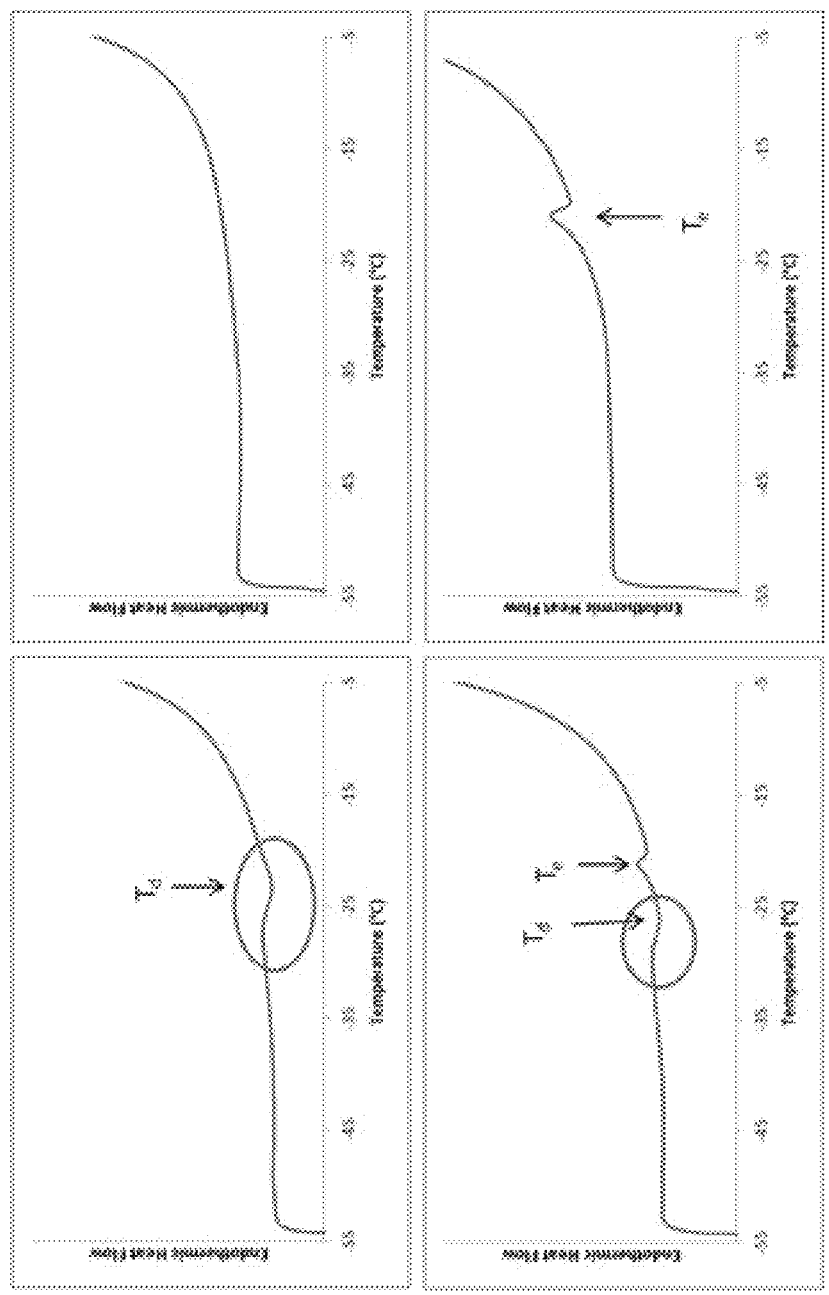

FIGS. 2A-2D provide subambient DSC analysis results for the liquid state of various formulations from $1^{st}$ round small scale lyophilization cycle with or without the annealing step. Specifically, FIG. 2A provides a result for KP8M2SN, FIG. 2B provides a result for KP8MS3N, FIG. 2C provides a result for KP8MT3N, and FIG. 2D provides a result for Control. The glass transition temperature (Tg'), the eutectic melting temperature (Te), and the devitrification temperature (Td) are marked on the graphs.

Figure 3:
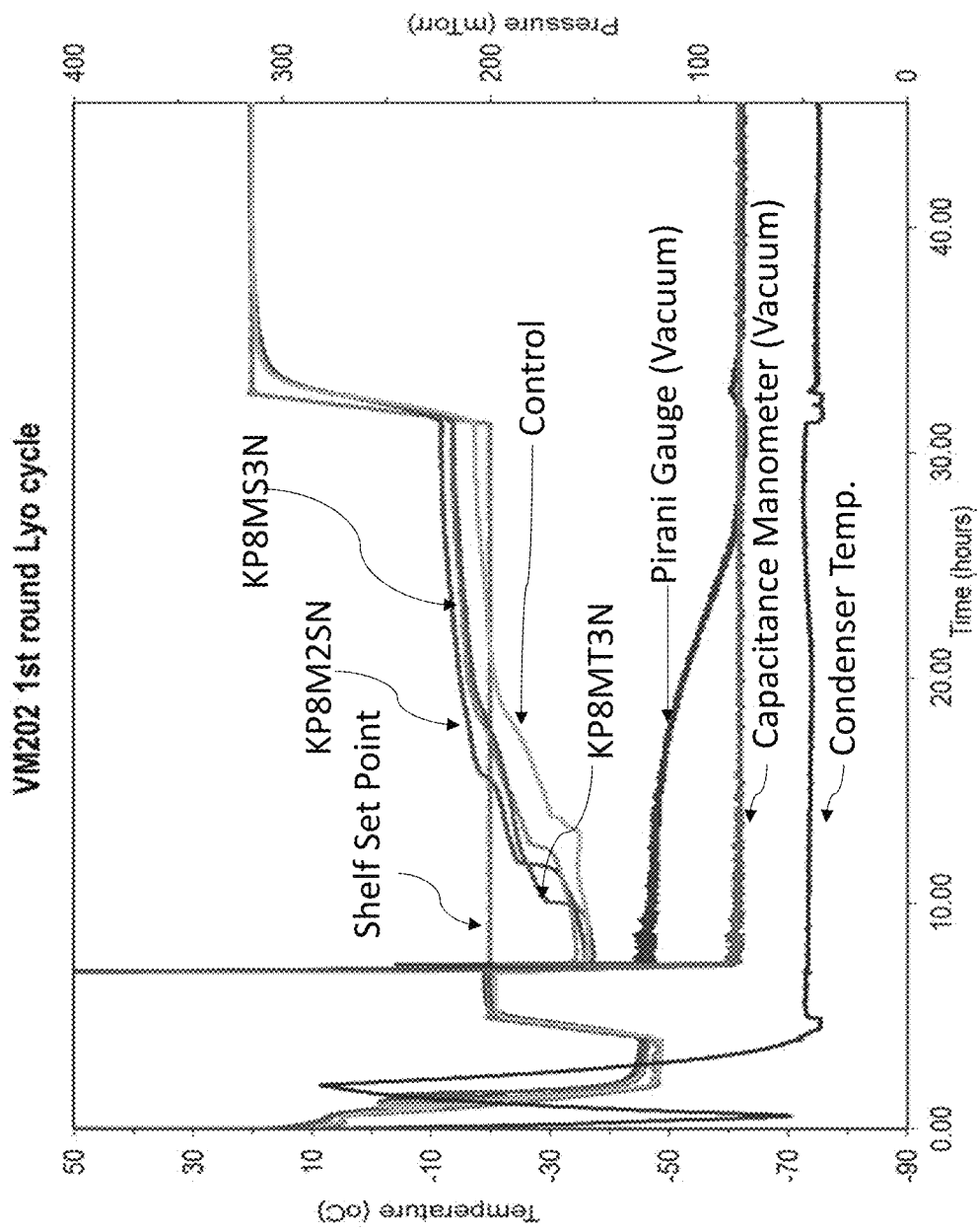

FIG. 3 provides a time-lapse change of temperatures (y-axis on the left) and pressures (y-axis on the right) during $1^{st}$ round lyophilization cycle of KP8M2SN, KP8MS3N, KP8MT3N, and Control.

Figure 4A:
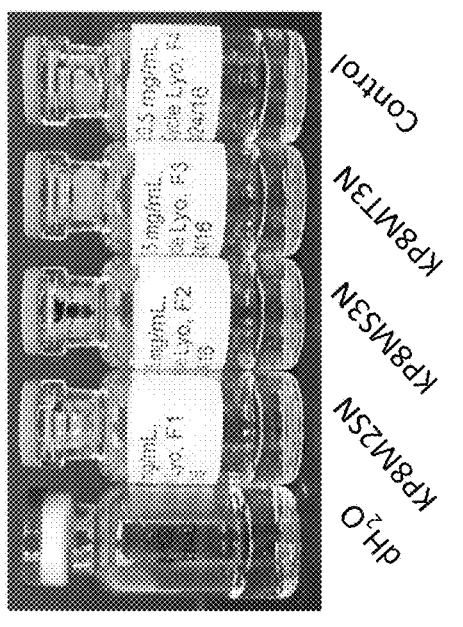
Figure 4B:
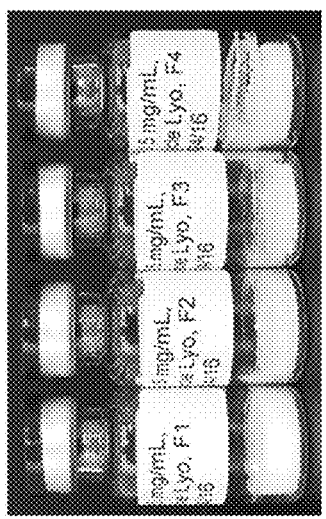
Figure 4C:
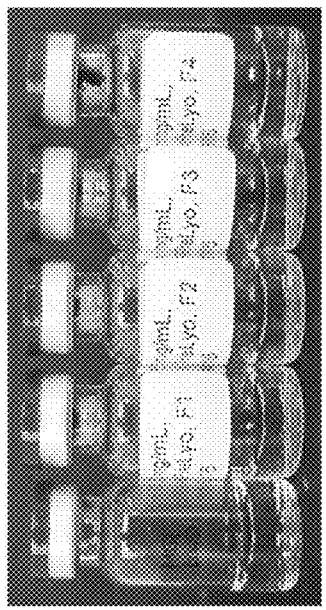

FIGS. 4A-4C provide pictures of vials containing various formulations from the $1^{st}$ round small scale lyophilization cycle before lyophilization (FIG. 4A), after lyophilization (FIG. 4B), and after reconstitution (FIG. 4C).

Figure 5:
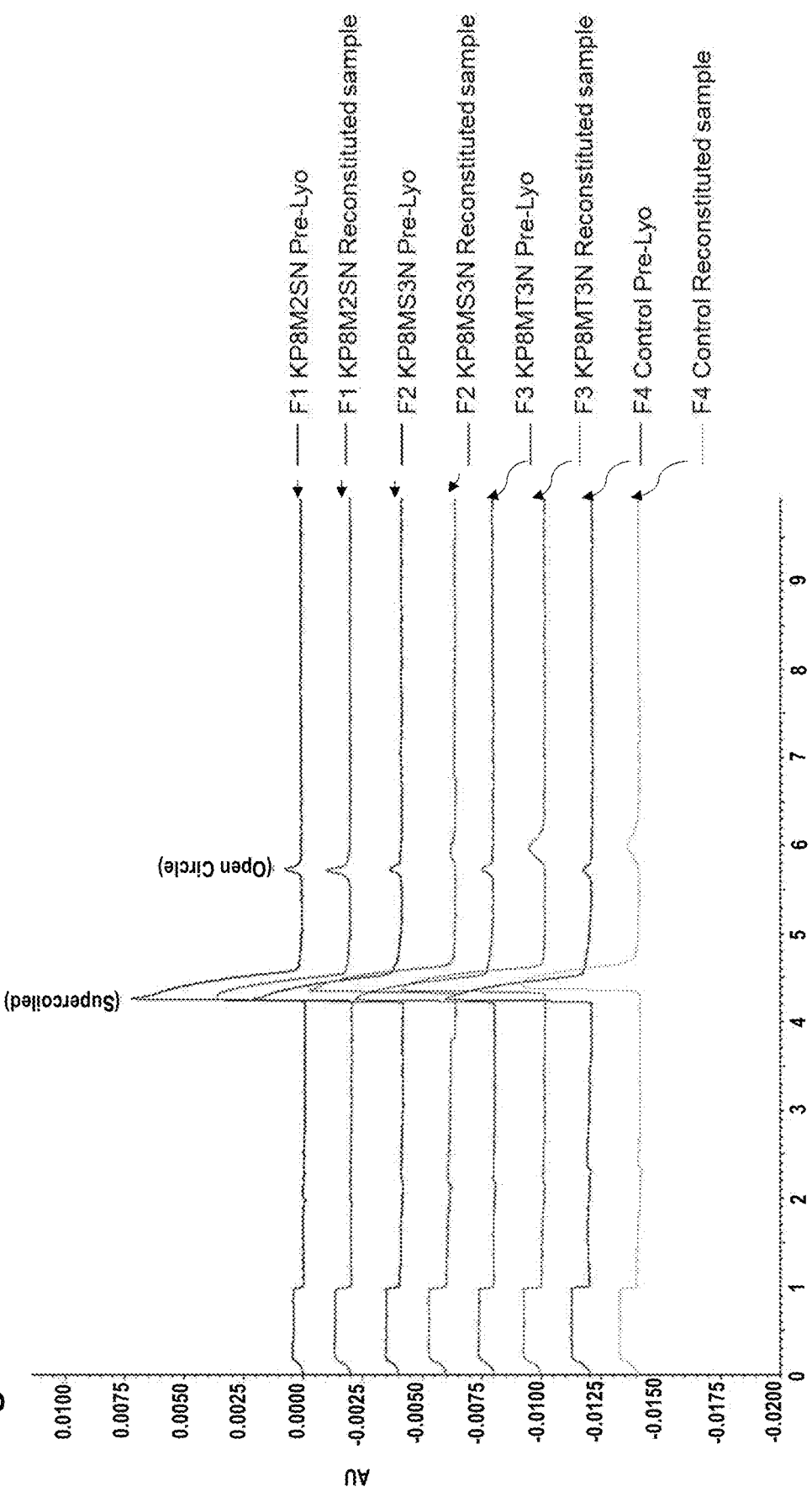

FIG. 5 provides a result from capillary electrophoresis (CE) of VM202 formulations from $1^{st}$ round small scale lyophilization cycle before lyophilization or after reconstitution.

Figures 6A, 6B:
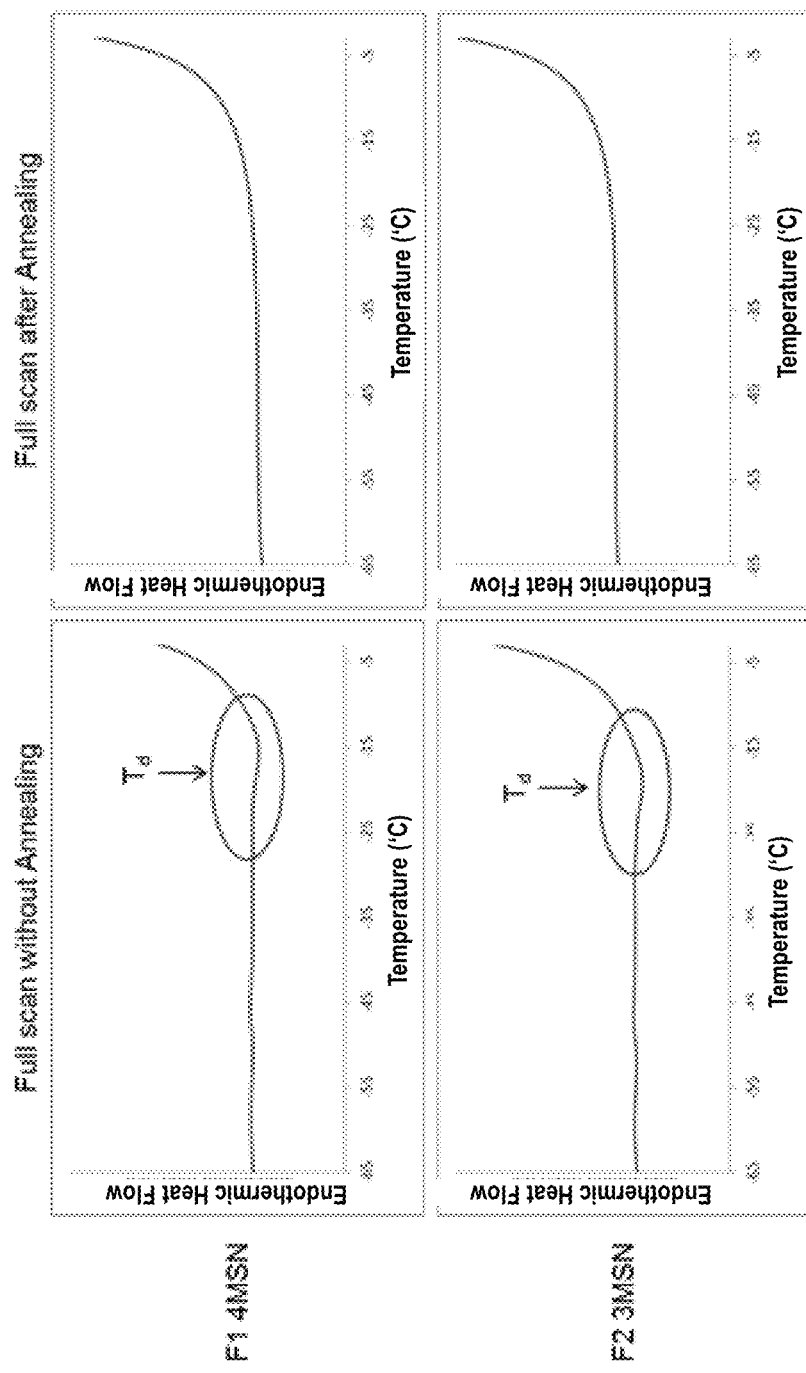
Figures 6C, 6D:
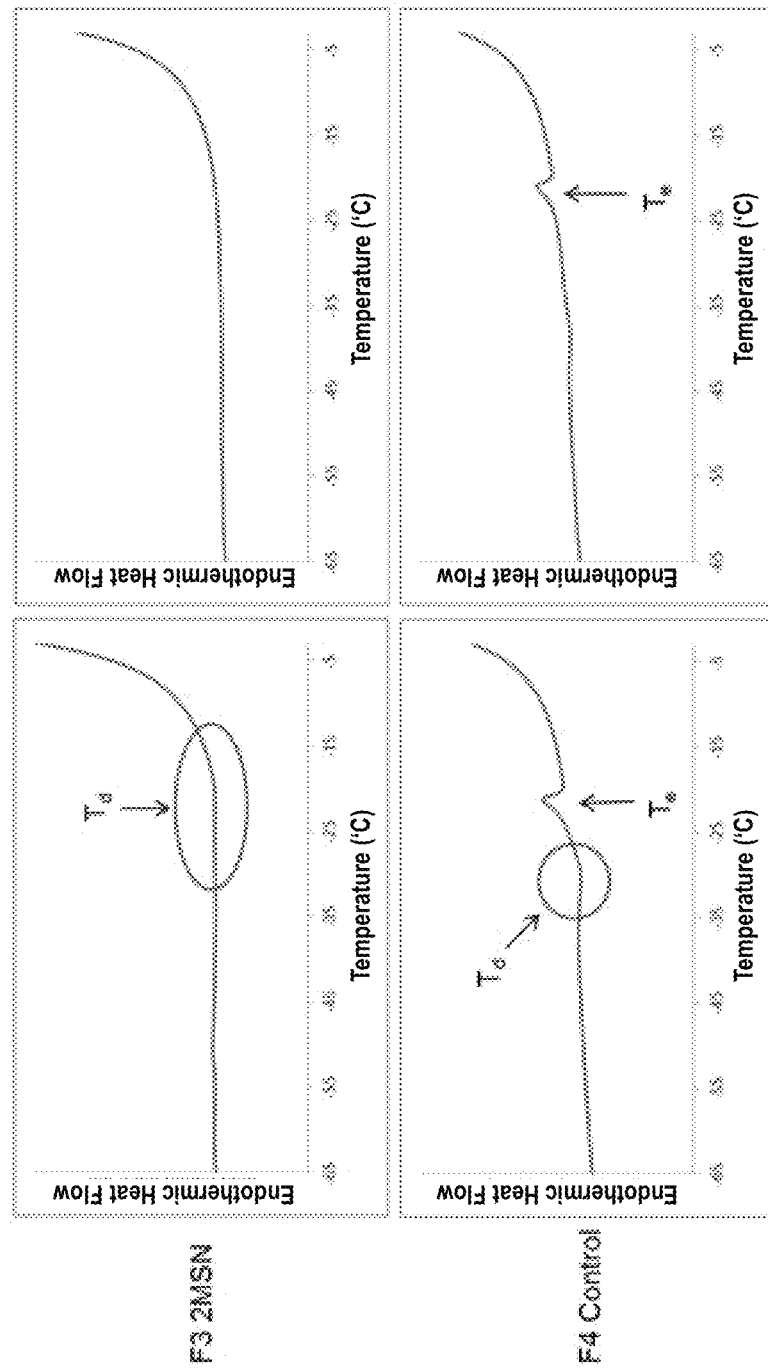

FIGS. 6A-6D provide subambient DSC analysis results for the liquid state of various formulations from $2^{nd}$ round small scale lyophilization cycle with or without the annealing step. Specifically, FIG. 6A provides a result for 4MSN, FIG. 6B provides a result for 3MSN, FIG. 6C provides a result for 2MSN, and FIG. 6D provides a result for Control.

Figure 7:
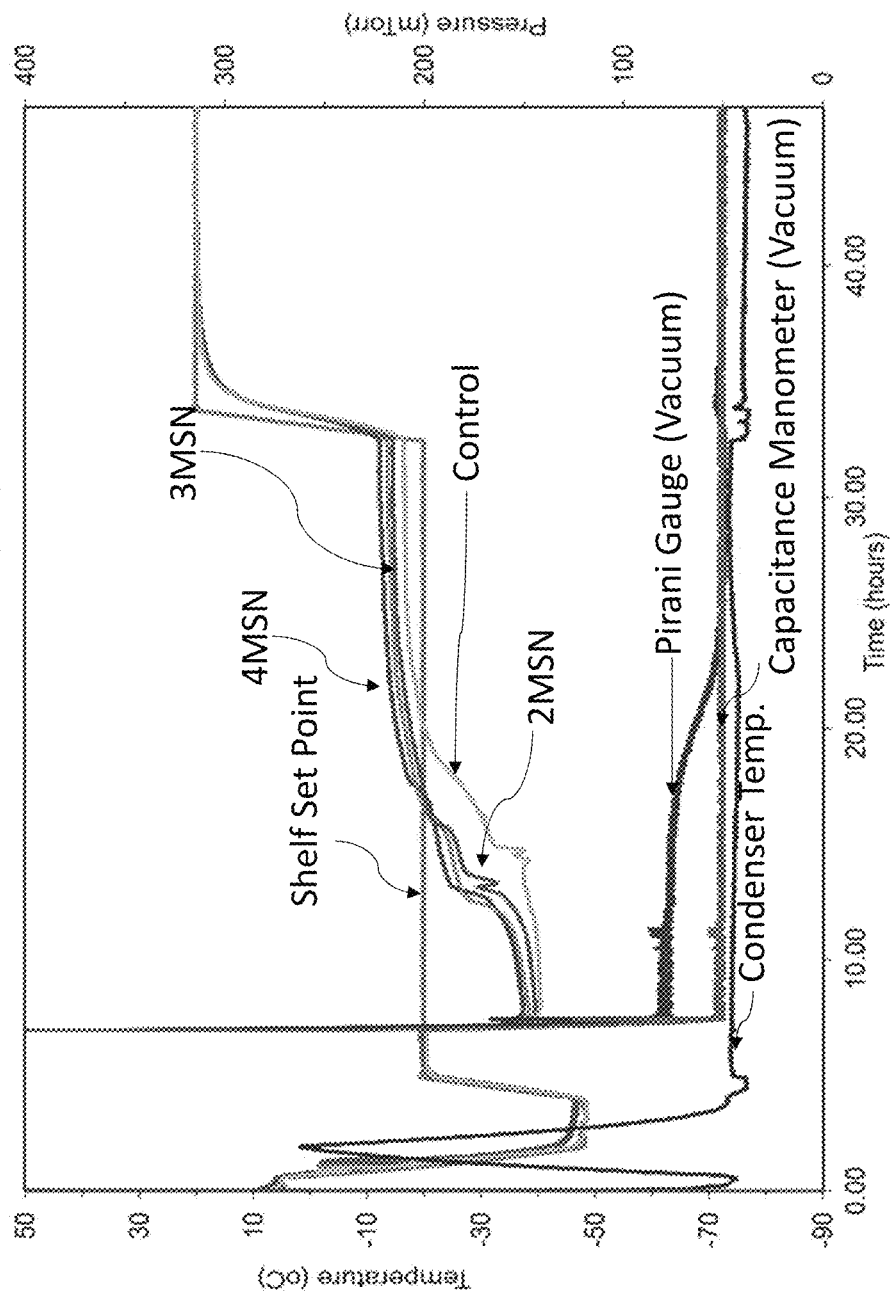

FIG. 7 provides a time-lapse change of temperatures (y-axis on the left) and pressures (y-axis on the right) during $2^{nd}$ round lyophilization cycle of the first set of 4MSN, 3MSN, 2MSN, and Control.

Figure 8C:
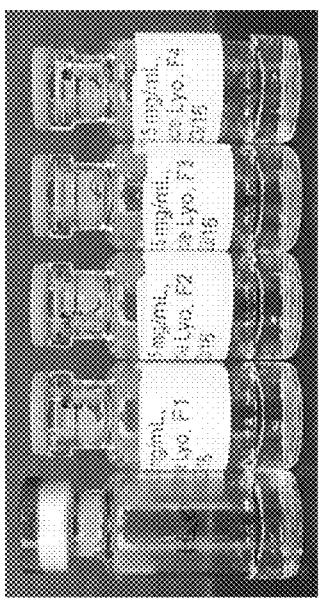
Figure 8B:
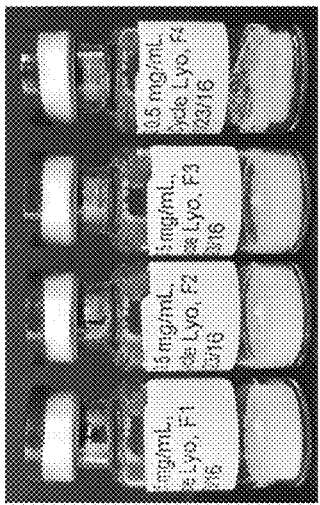
Figure 8A:
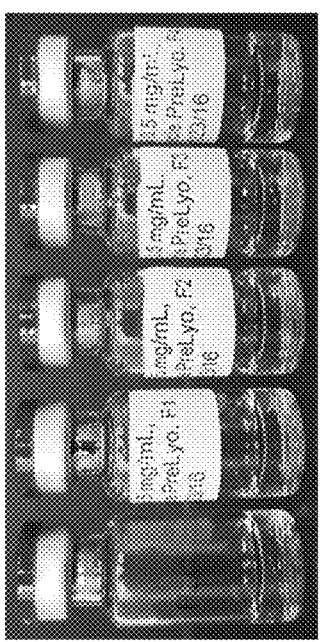

FIGS. 8A-8C provide pictures of vials containing the first set of 4MSN, 3MSN, 2MSN, and Control from the $2^{nd}$ round small scale lyophilization cycle before lyophilization (FIG. 8A), after lyophilization (FIG. 8B), and after reconstitution (FIG. 8C).

Figure 9:
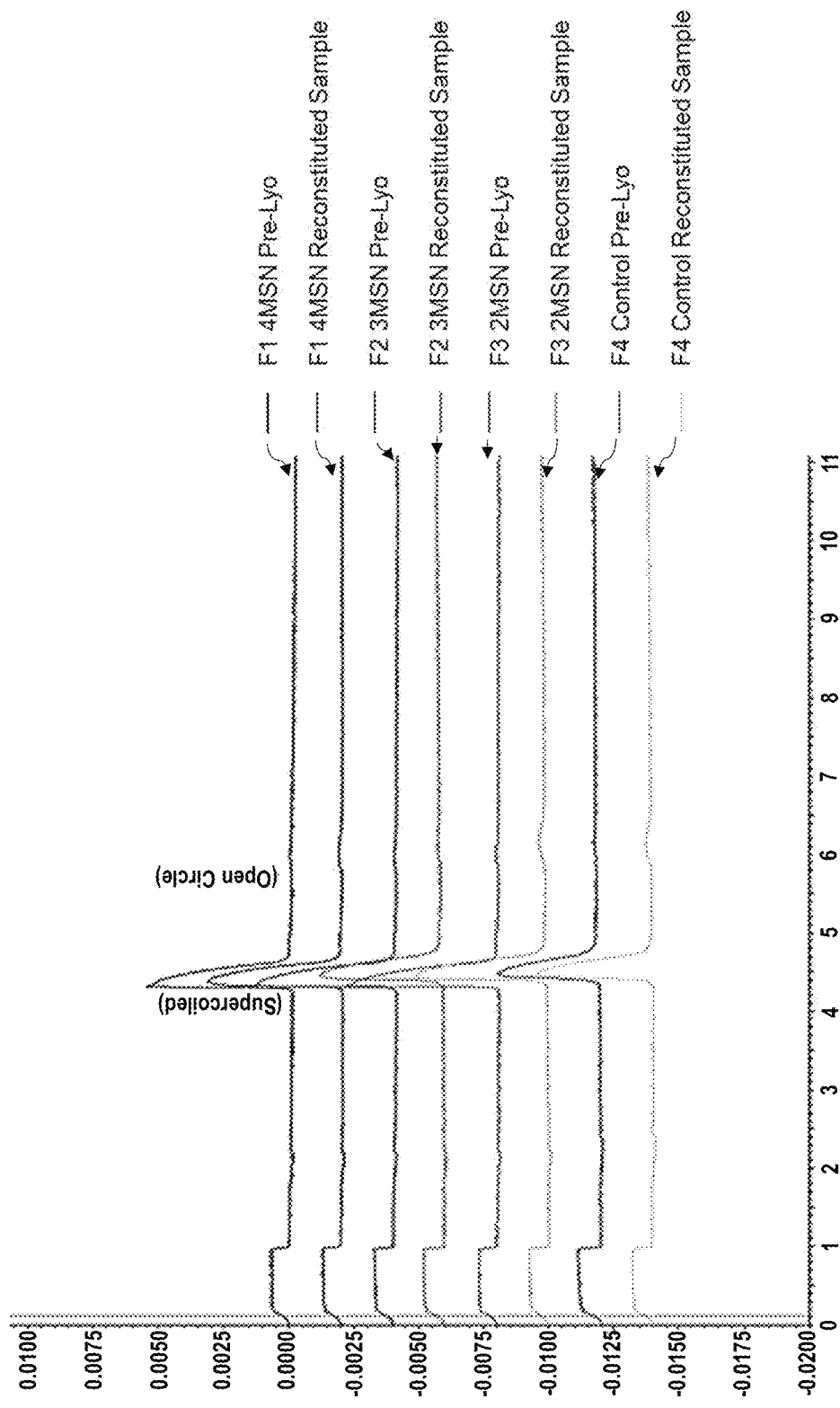

FIG. 9 provides a result from capillary electrophoresis (CE) of the first set of 4MSN, 3MSN, 2MSN, and Control from $2^{nd}$ round small scale lyophilization cycle before lyophilization or after reconstitution.

Figure 10:
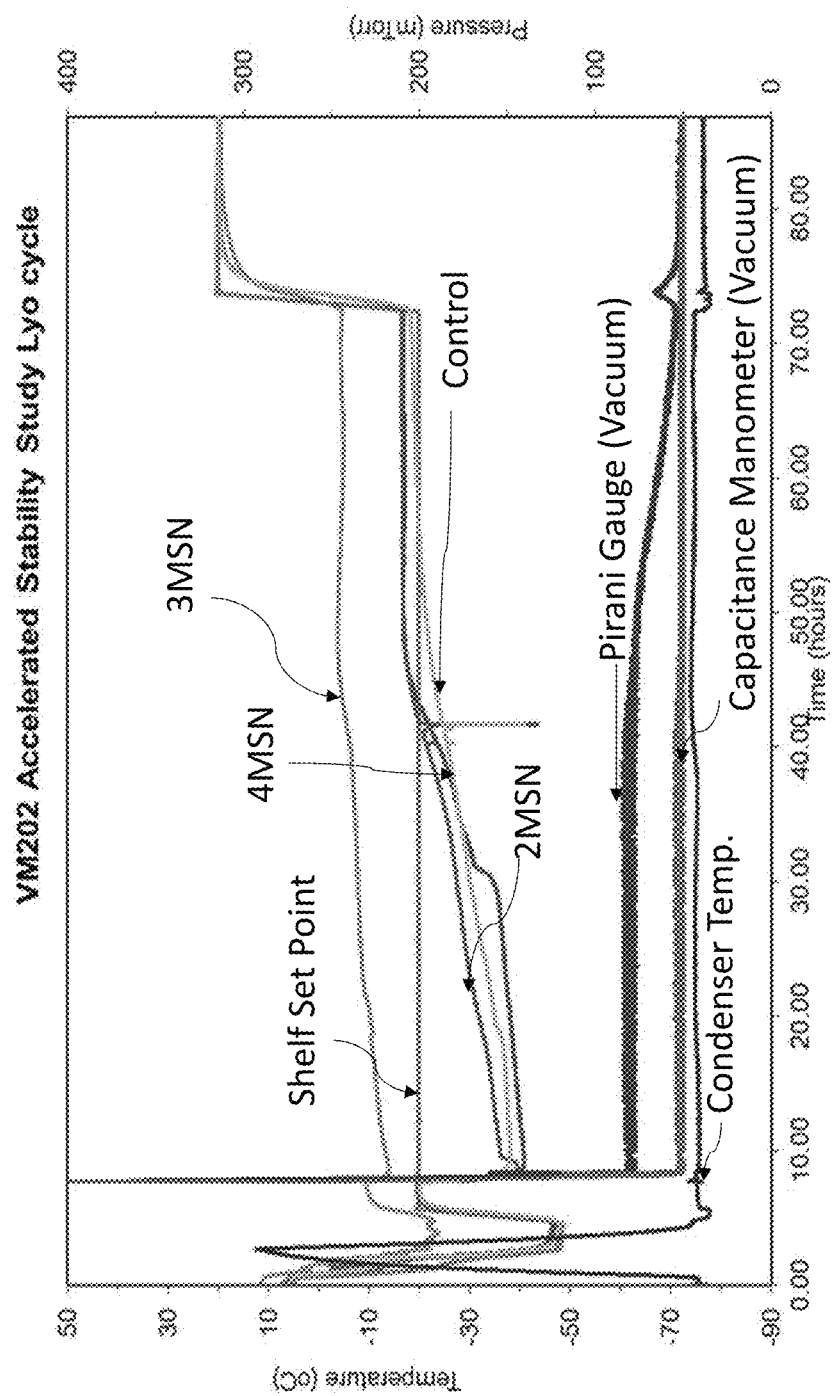

FIG. 10 provides a time-lapse change of temperatures (y-axis on the left) and pressures (y-axis on the right) during the second of $2^{nd}$ round lyophilization cycle of the second set of 4MSN, 3MSN, 2MSN, and Control.

Figures 11A, 11B:
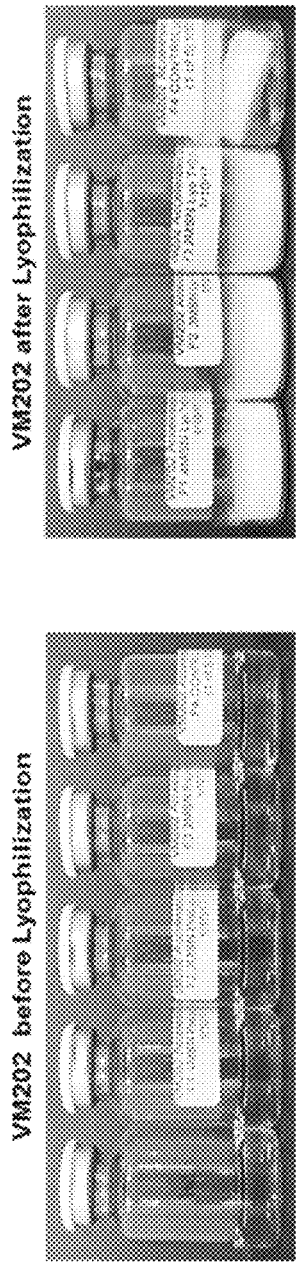
Figure 11C:
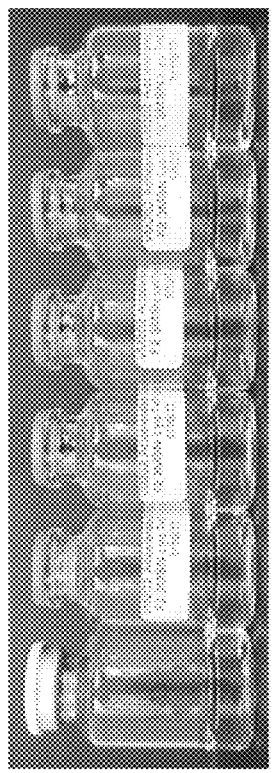
Figure 11D:
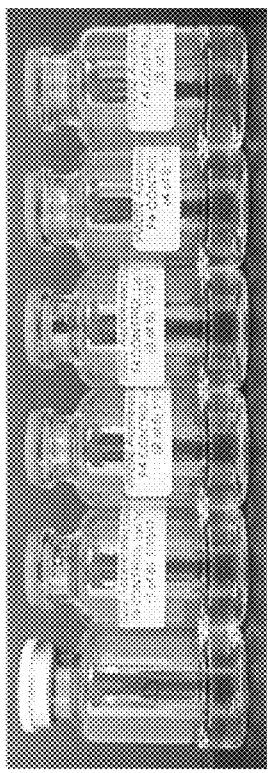
Figure 11E:
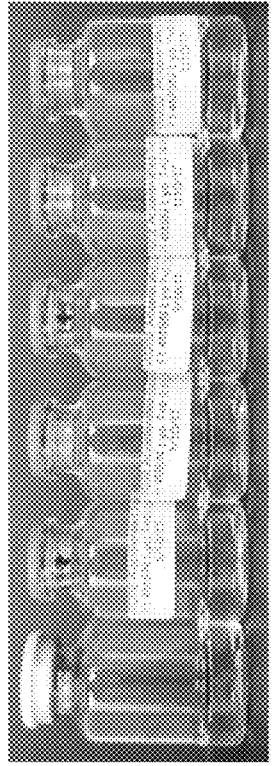
Figure 11F:
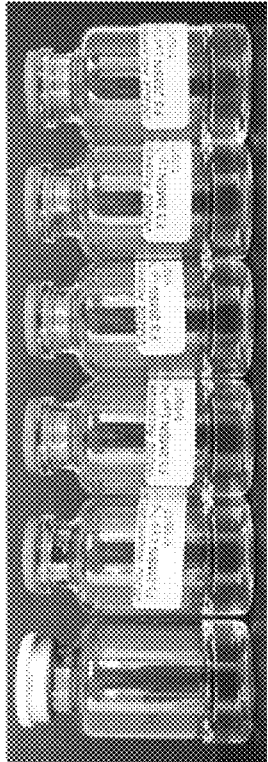

FIGS. 11A-11B provide pictures of vials containing the second set of 4MSN, 3MSN, 2MSN, and Control from the second of $2^{nd}$ round small scale lyophilization cycle before lyophilization (FIG. 11A) and after lyophilization (FIG. 11B). FIGS. 11C-11F show pictures of vials containing the second set of 4MSN (FIG. 11C), 3MSN (FIG. 11D), 2MSN (FIG. 11E), and Control (FIG. 11F) after reconstitution.

Figure 12:
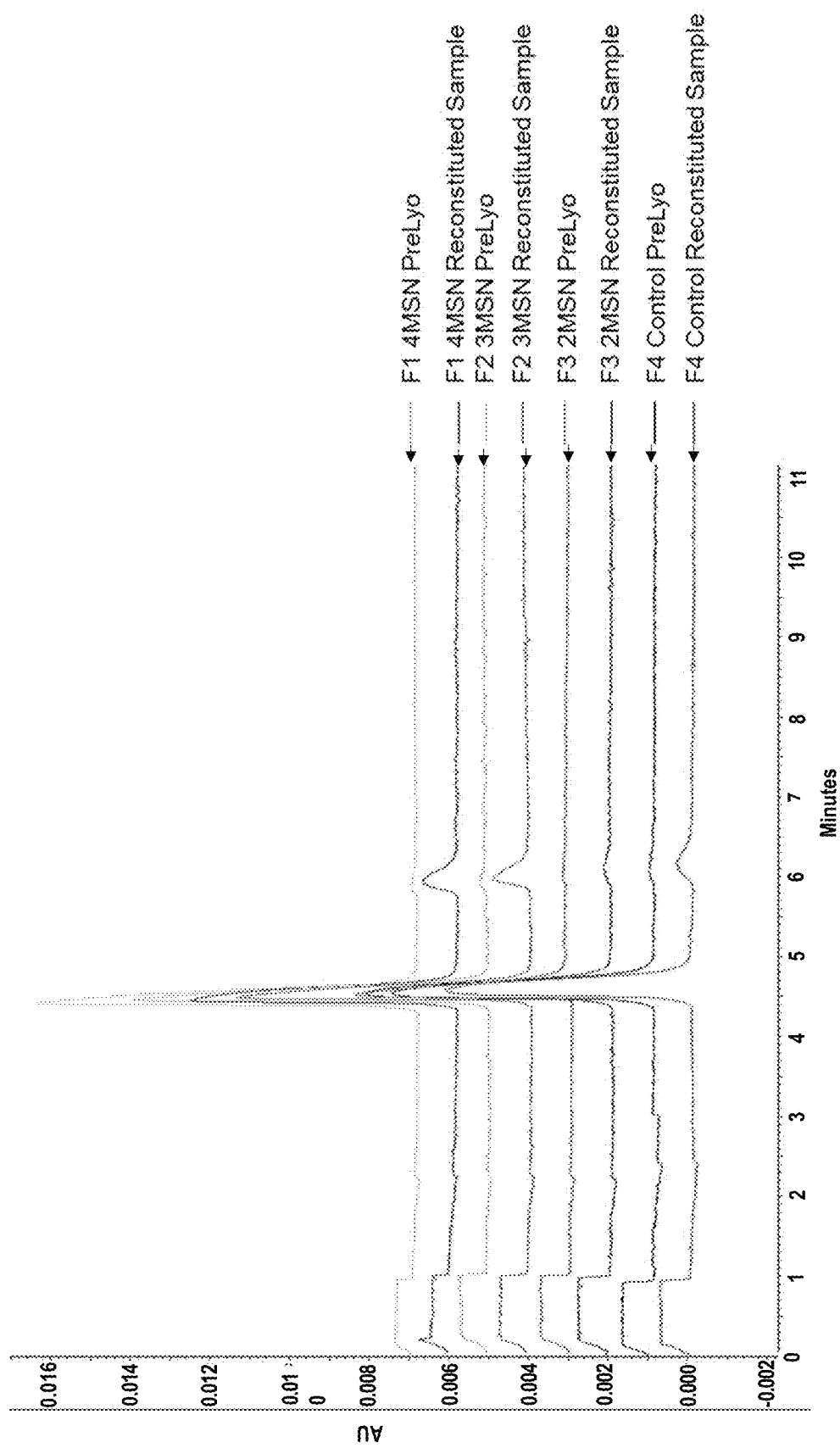

FIG. 12 provides a result from capillary electrophoresis (CE) of the second set of 4MSN, 3MSN, 2MSN, and Control from the second of $2^{nd}$ round small scale lyophilization cycle before lyophilization or after reconstitution.

Figure 13:
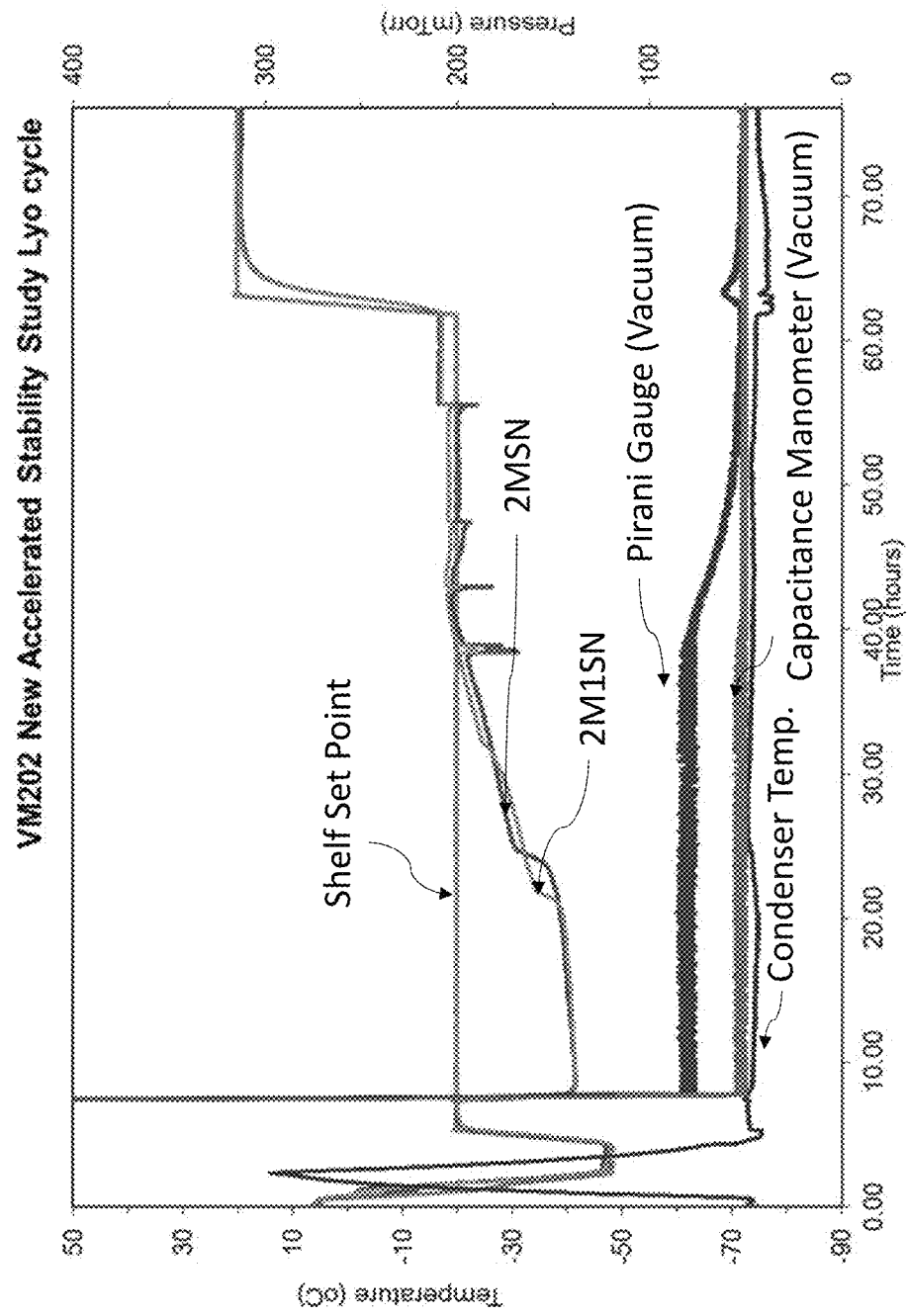

FIG. 13 provides a time-lapse change of temperatures (y-axis on the left) and pressures (y-axis on the right) during lyophilization cycle of 2MSN and 2M1SN.

Figure 14B:
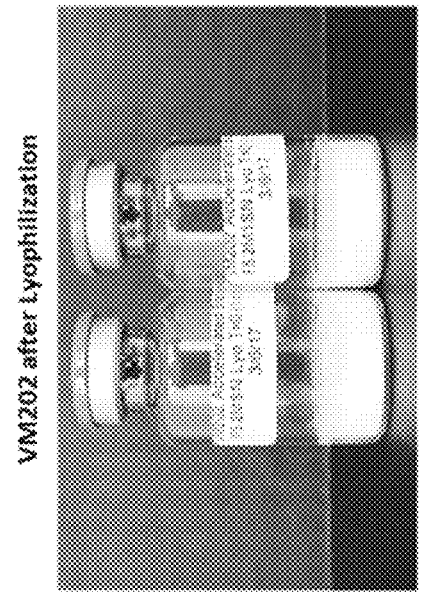
Figure 14A:
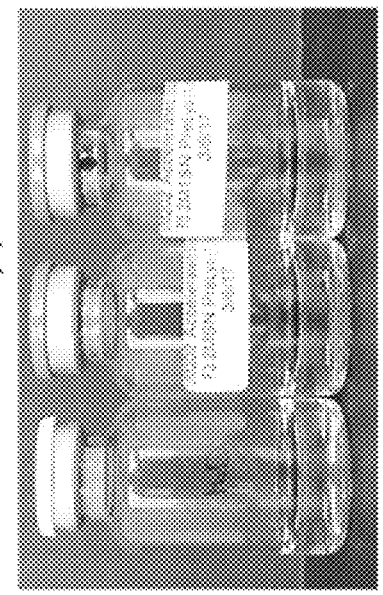
Figure 14D:
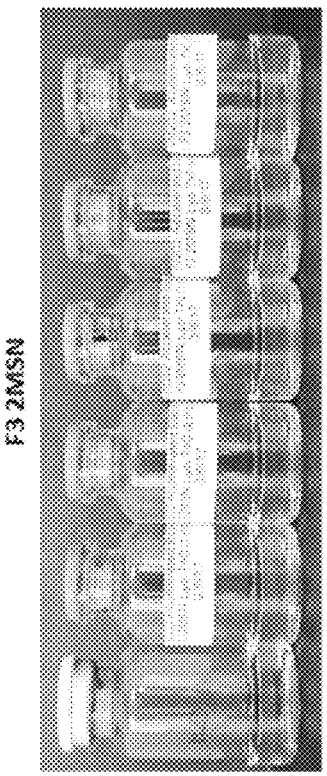
Figure 14C:
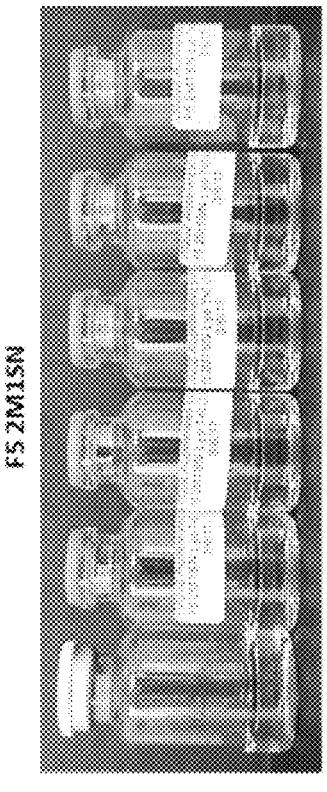

FIGS. 14A-14B provide pictures of vials containing 2MSN or 2M1SN before lyophilization (FIG. 14A) and after lyophilization (FIG. 14B). FIGS. 14C-14D show pictures of vials containing 2MSN (FIG. 14C) and 2M1SN (FIG. 14D) after reconstitution.

Figure 15:
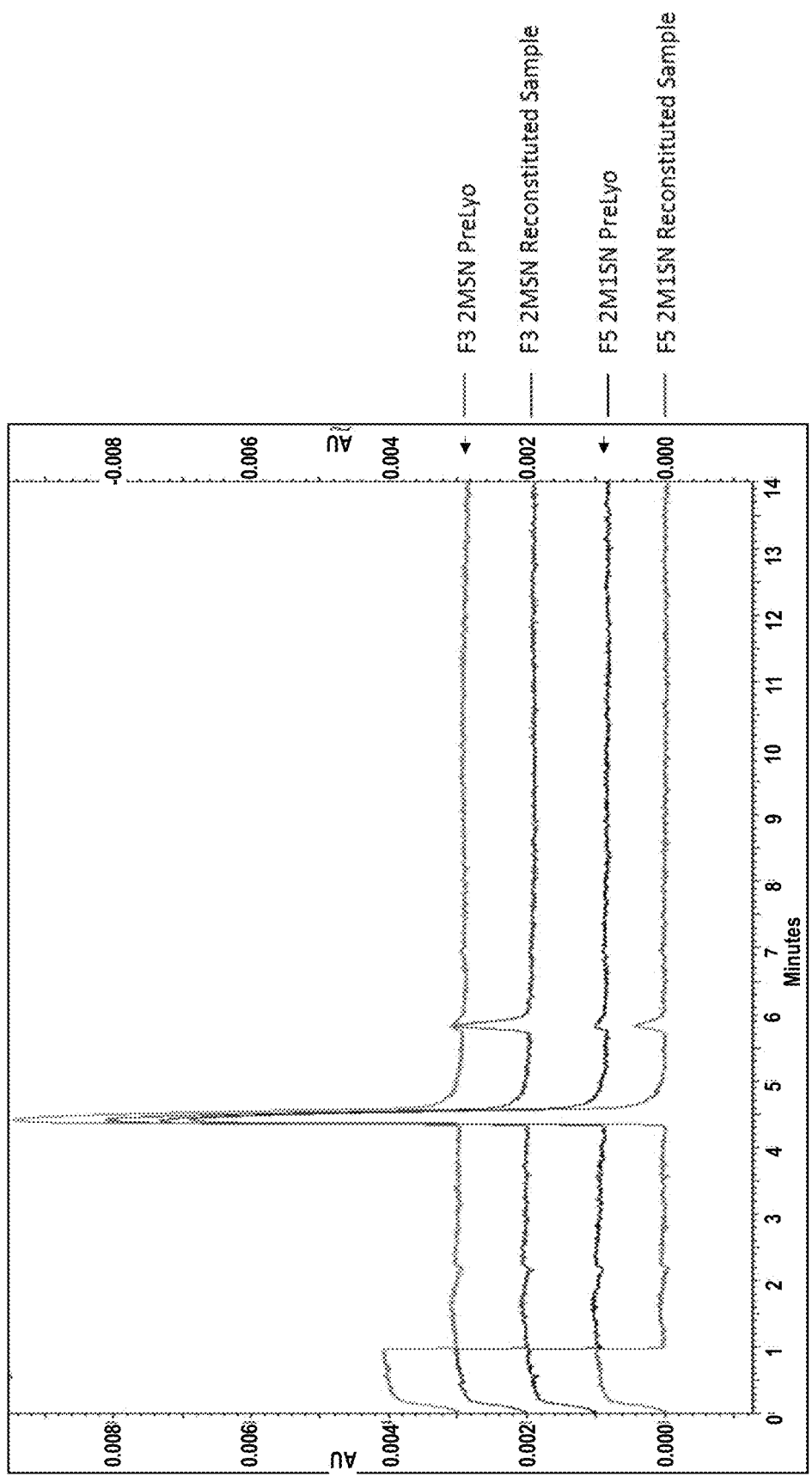

FIG. 15 provides a result from capillary electrophoresis (CE) of 2MSN and 2M1SN before lyophilization or after reconstitution.

Figure 16A:
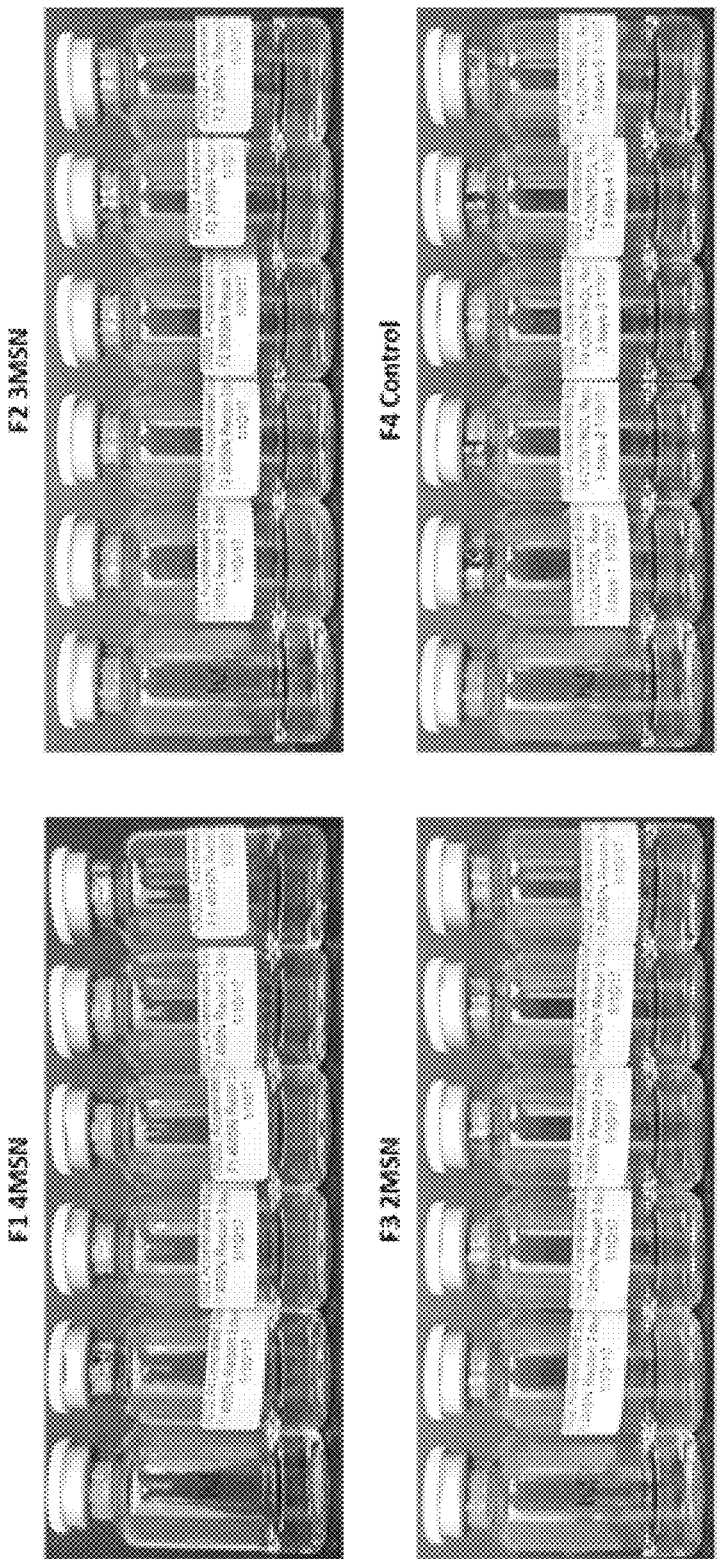
Figure 16B:
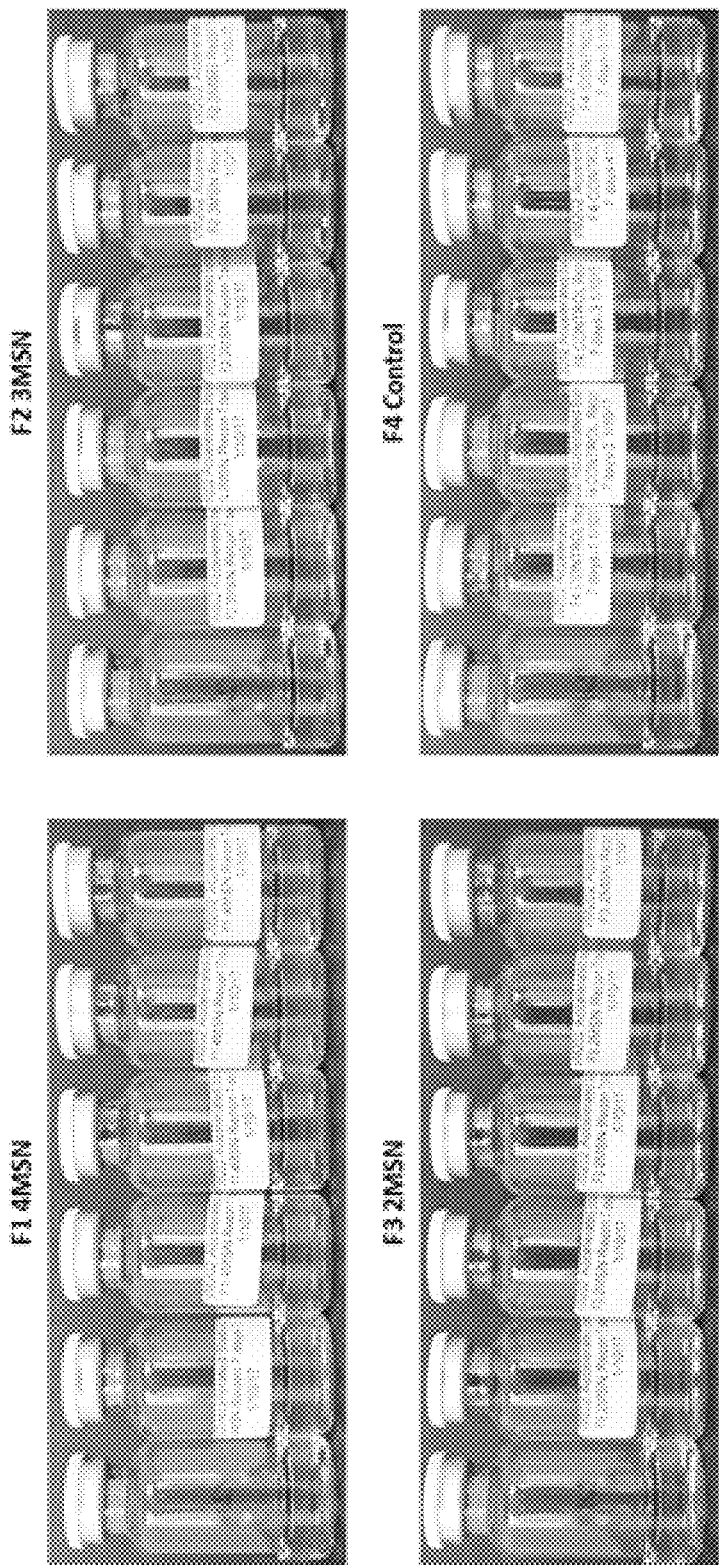

FIGS. 16A-16B provide pictures of vials containing 4MSN, 3MSN, 2MSN, and Control after storage at 25° C. for 3 days (FIG. 16A) or 7 days (FIG. 16B) following reconstitution at T=0.

Figure 17A:
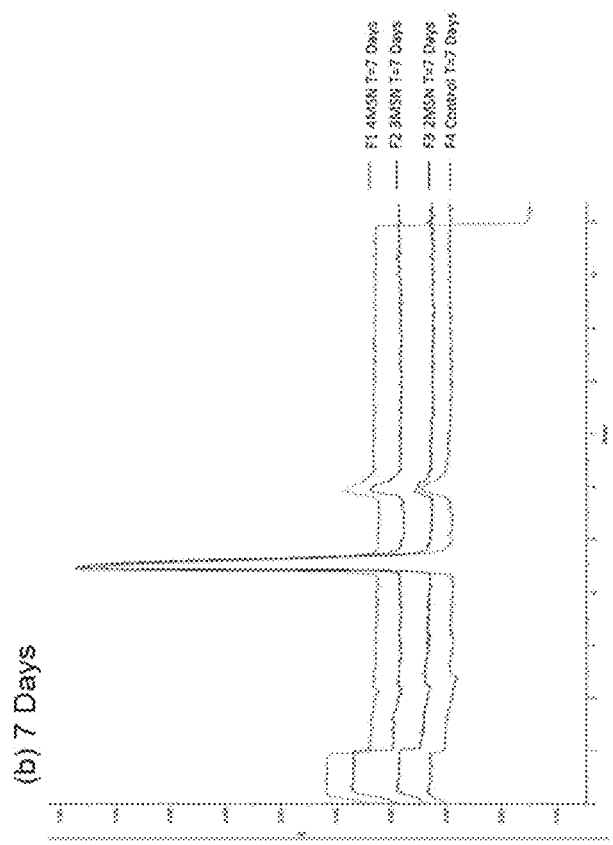
Figure 17B:
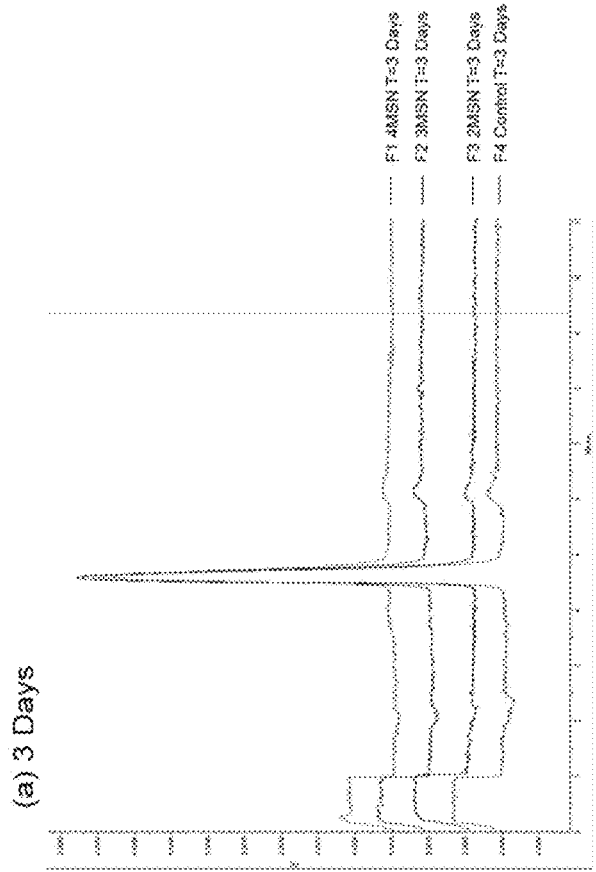

FIGS. 17A-17B provide results from capillary electrophoresis (CE) of 4MSN, 3MSN, 2MSN and Control following storage at 25° C. for 3 days (FIG. 17A) or 7 days (FIG. 17B).

Figure 18A:
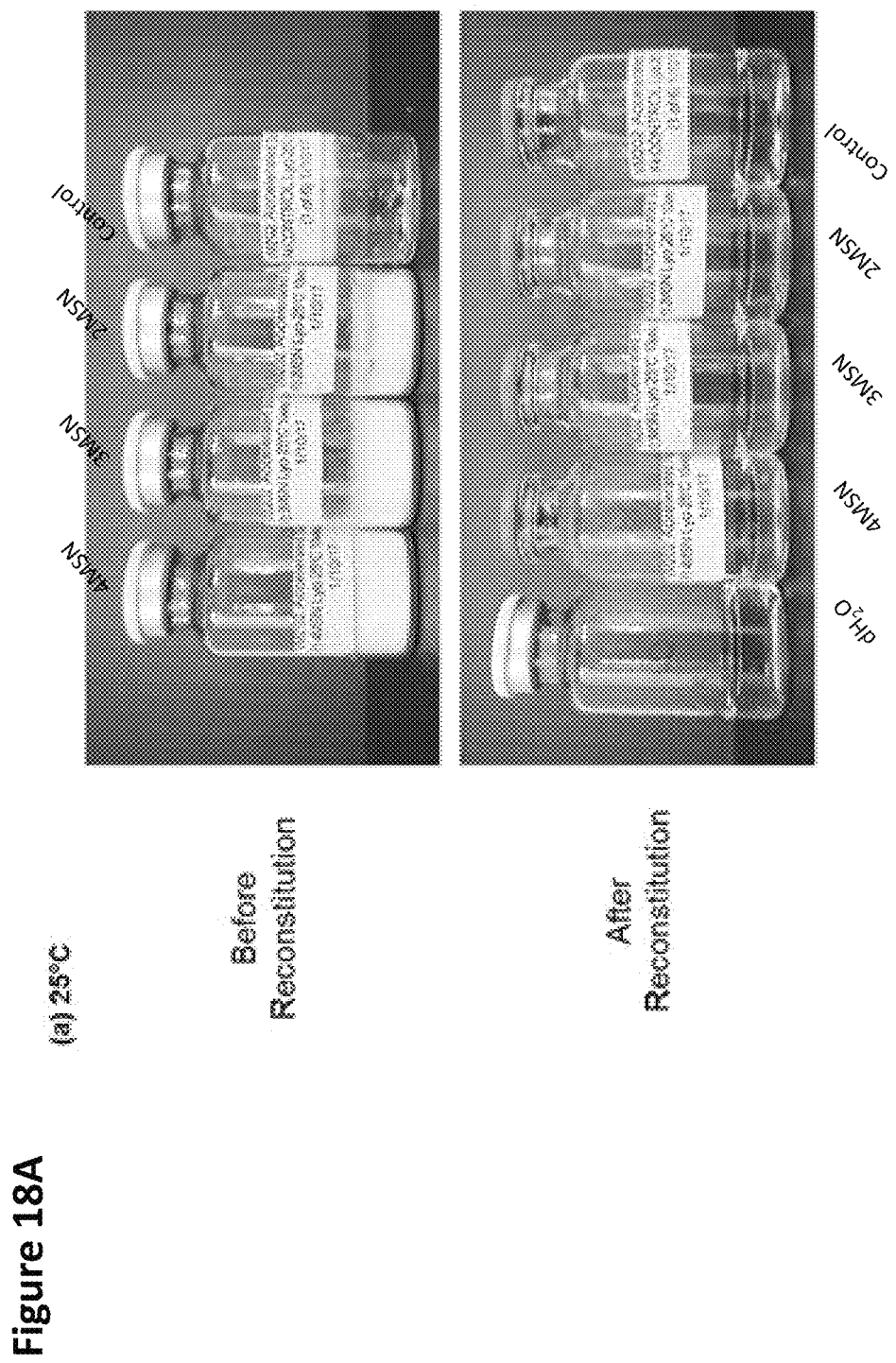
Figure 18B:
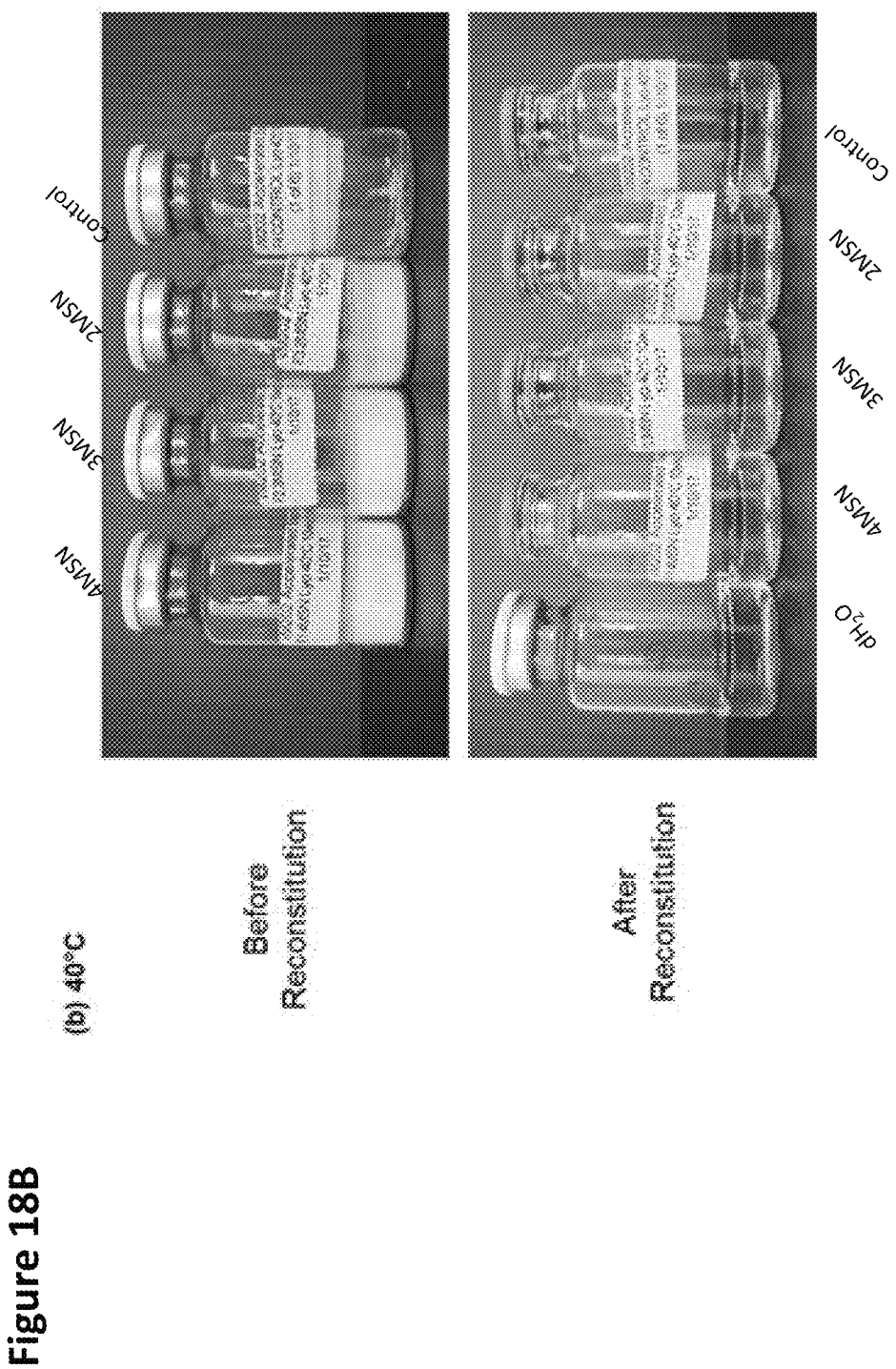
Figure 18C:
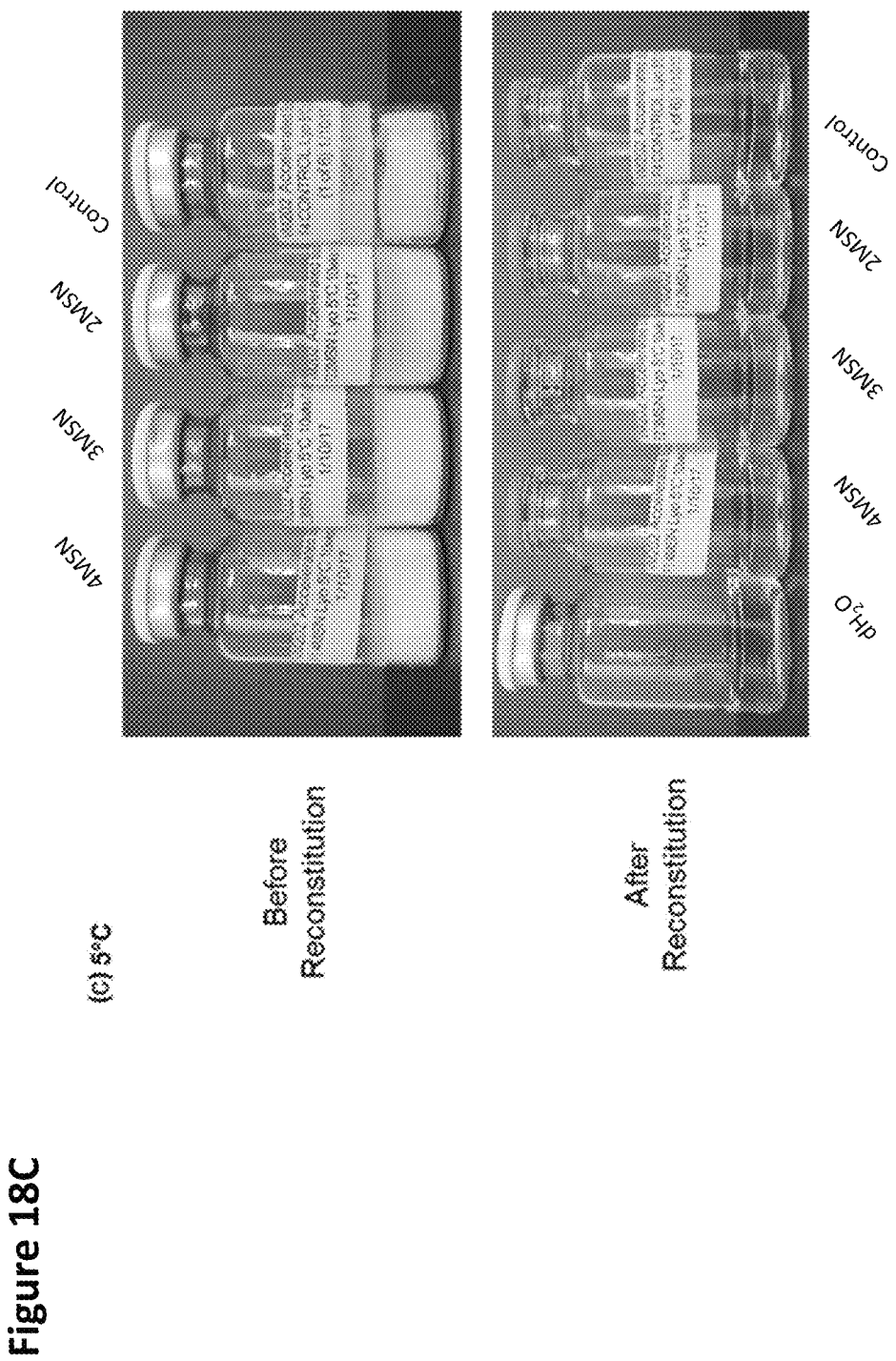

FIG. 18A-18C provide pictures of vials containing 4MSN, 3MSN, 2MSN, and Control before or after reconstitution of the lyophilized formulation stored for 10 weeks at 25° C. (FIG. 18A), at 40° C. (FIG. 18B) or at 5° C. (FIG. 18C).

Figure 19:
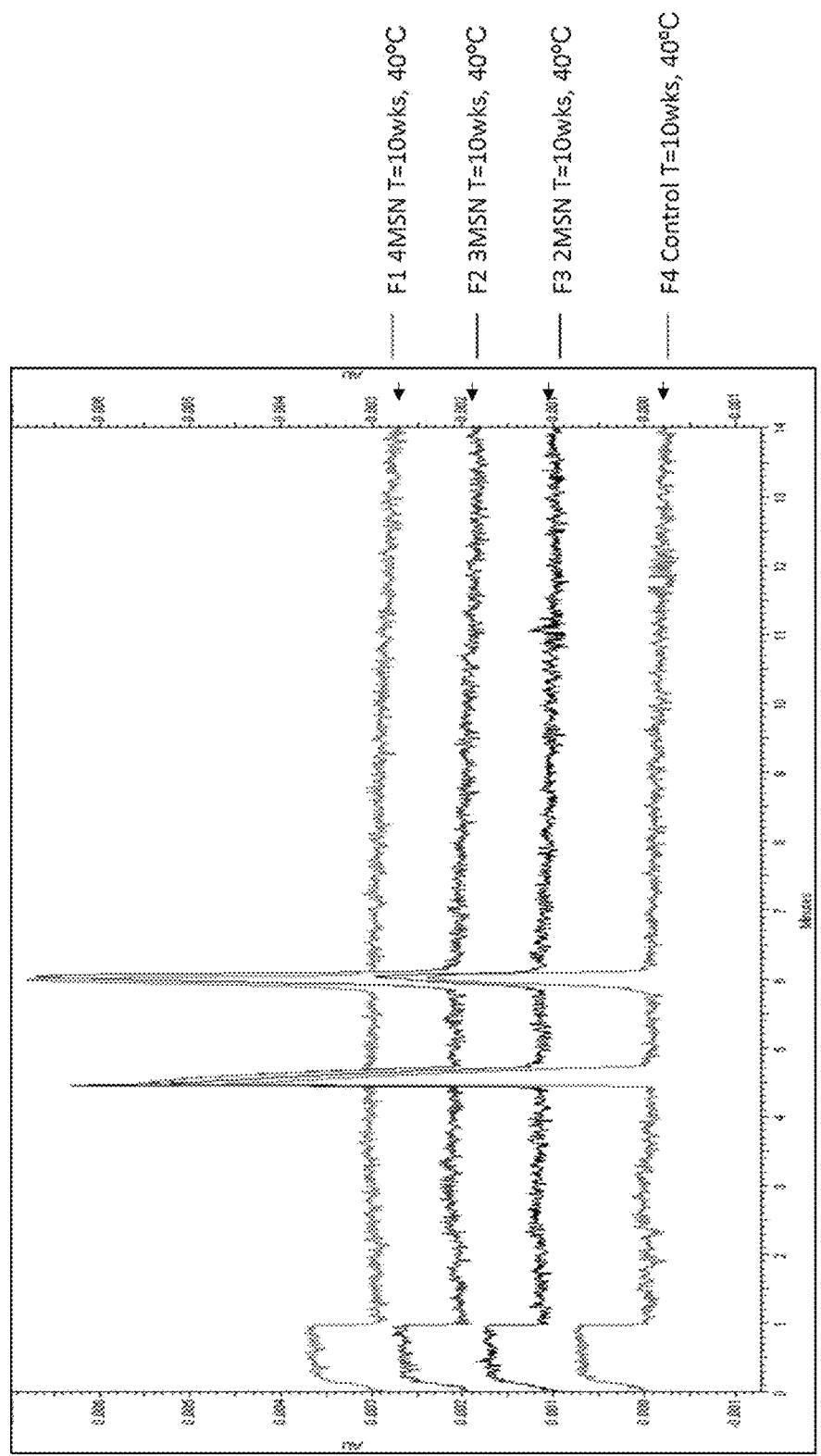

FIG. 19 provides a result from capillary electrophoresis (CE) of 4MSN, 3MSN, 2MSN, and Control after storage at 40° C. for 10 weeks.

Figure 20C:
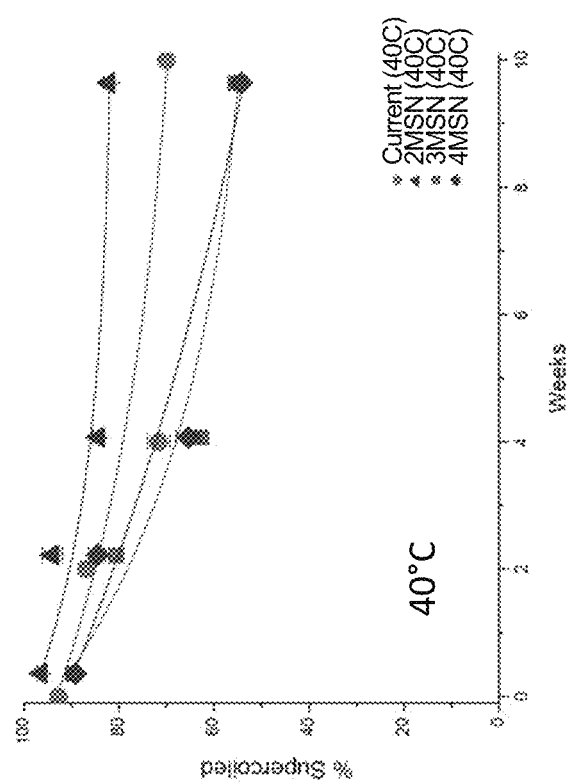
Figure 20A:
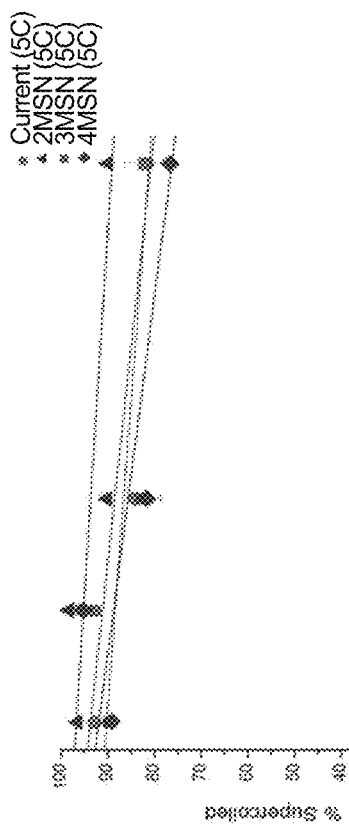
Figure 20B:
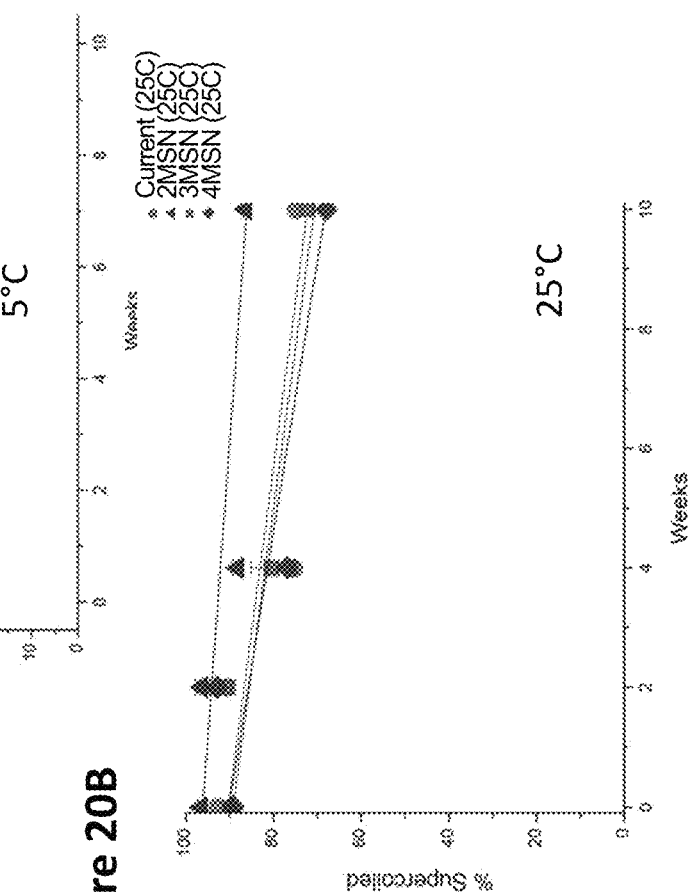

FIGS. 20A-20C provide time-lapse changes of super-coiled DNA percentages measured based on capillary electrophoresis (CE) results for 4MSN, 3MSN, 2MSN and Control, when the formulations were stored at 5° C. (FIG. 20A), 25° C. (FIG. 20B) or 40° C. (FIG. 20C).

FIGS. 21A-21C provide time-lapse changes of open-circled DNA percentages measured based on capillary electrophoresis (CE) results for 4MSN, 3MSN, 2MSN and Control, when the formulations were stored at 5° C. (FIG. 21A), 25° C. (FIG. 21B) or 40° C. (FIG. 21C).

FIGS. 22A-22B provide pictures of vials containing 2MSN (FIG. 22A) or 2M1SN (FIG. 22B) stored at 25° C. for 3 days after reconstitution. FIGS. 22C-22D provide pictures of vials containing 2MSN (FIG. 22C) or 2M1SN (FIG. 22D) stored at 25° C. for 7 days after reconstitution.

Figure 23A:
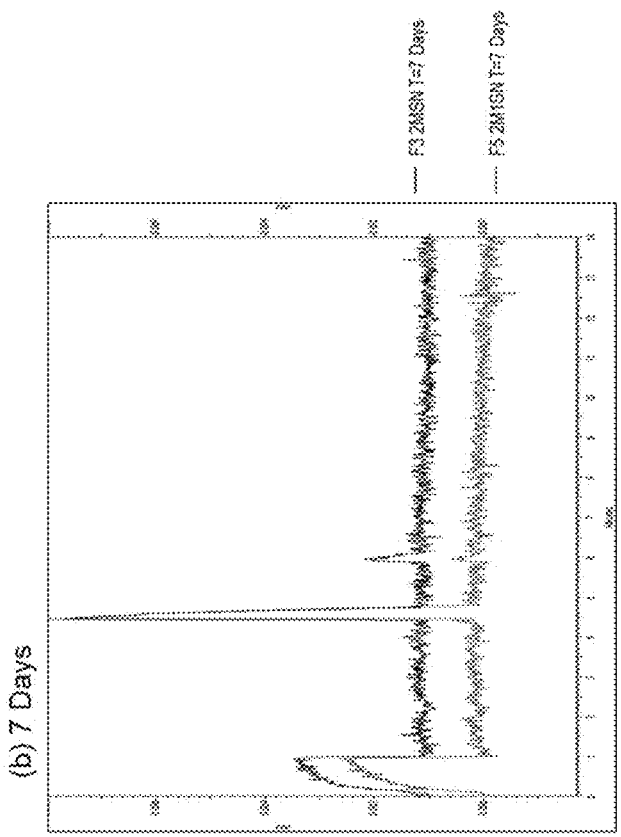
Figure 23B:
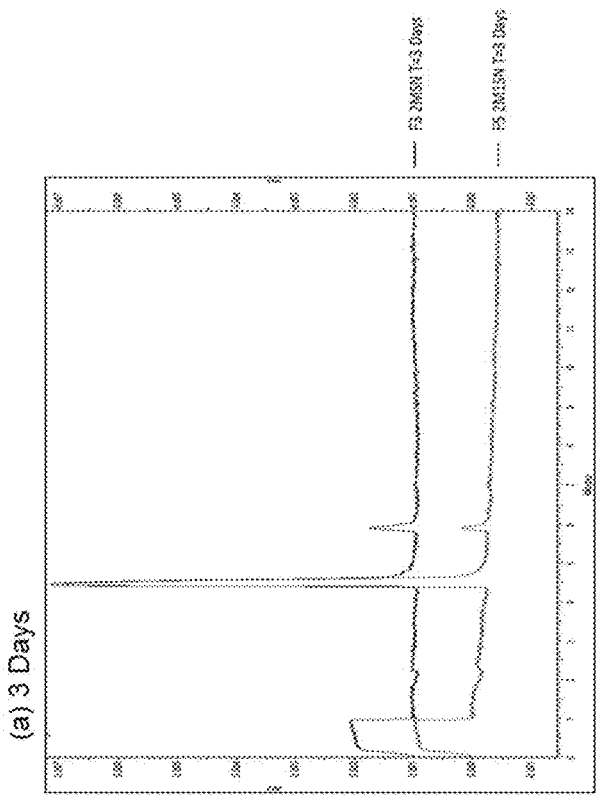

FIGS. 23A-23B provide results from capillary electrophoresis (CE) of 2MSN and 2M1SN after storage at 25° C. for 3 days (FIG. 23A) or 7 days (FIG. 23B).

Figure 24A:
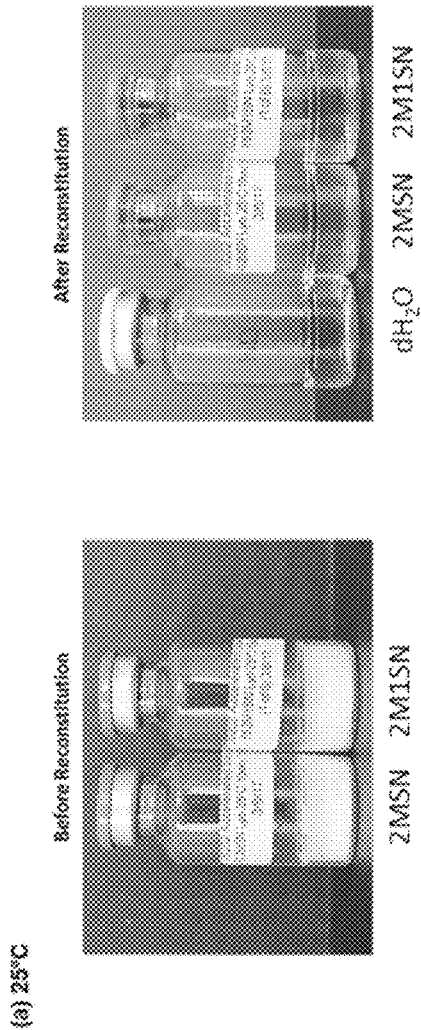
Figure 24B:
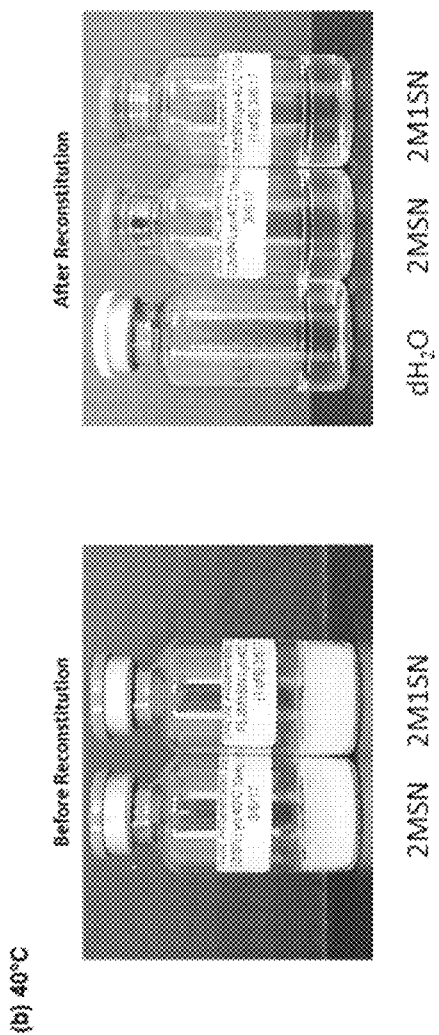
Figure 24C:
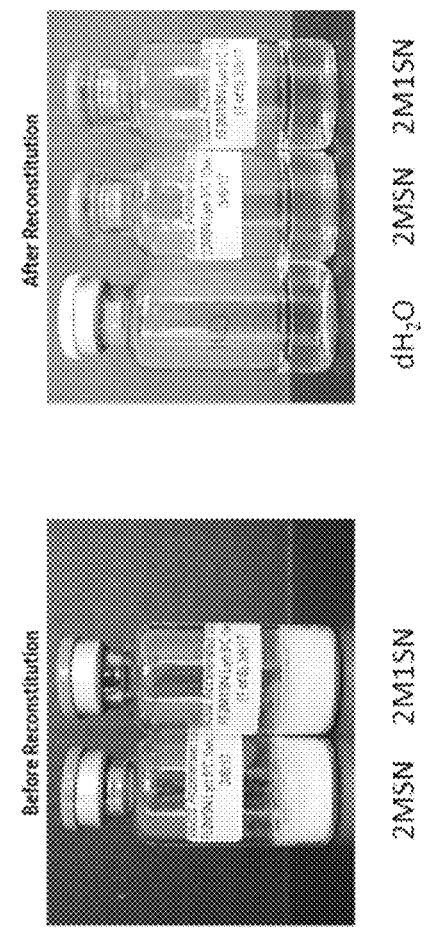

FIGS. 24A-24C provide pictures of vials containing 2MSN or 2M1SN before or after reconstitution of the lyophilized formulation stored for 10 weeks at 25° C. (FIG. 24A), at 40° C. (FIG. 24B), or at 5° C. (FIG. 24C).

Figure 25:
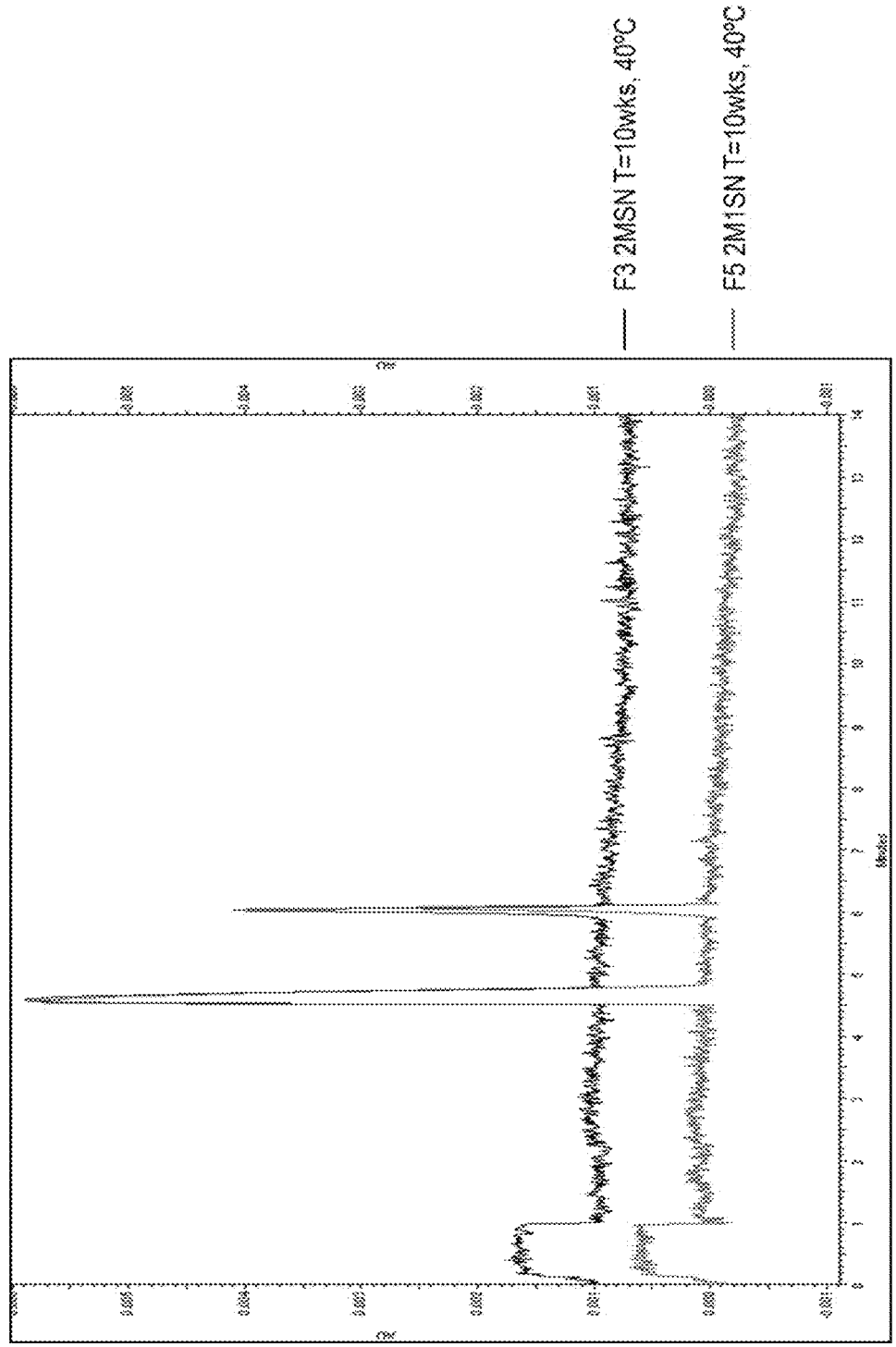
Figure 26A:
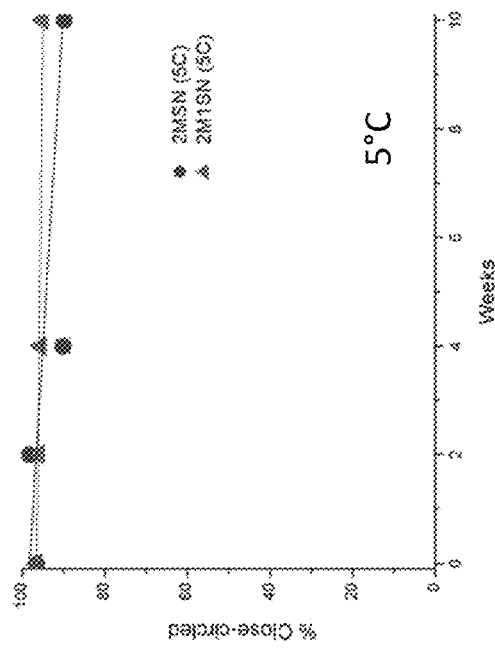
Figure 26C:
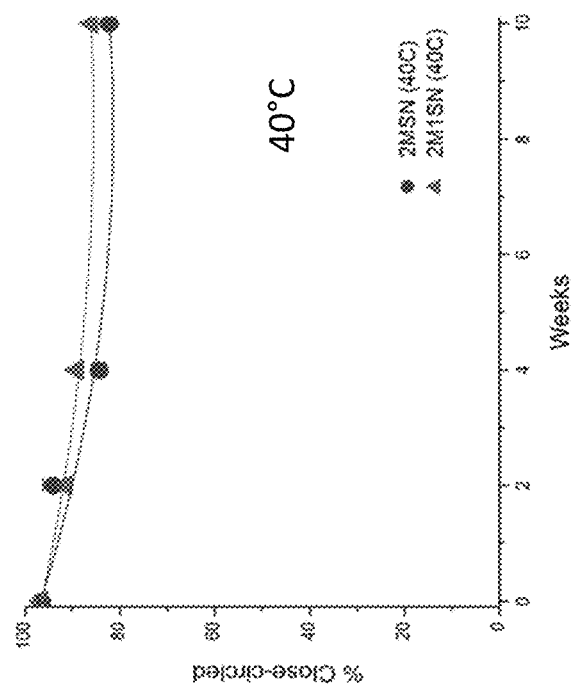
Figure 26B:
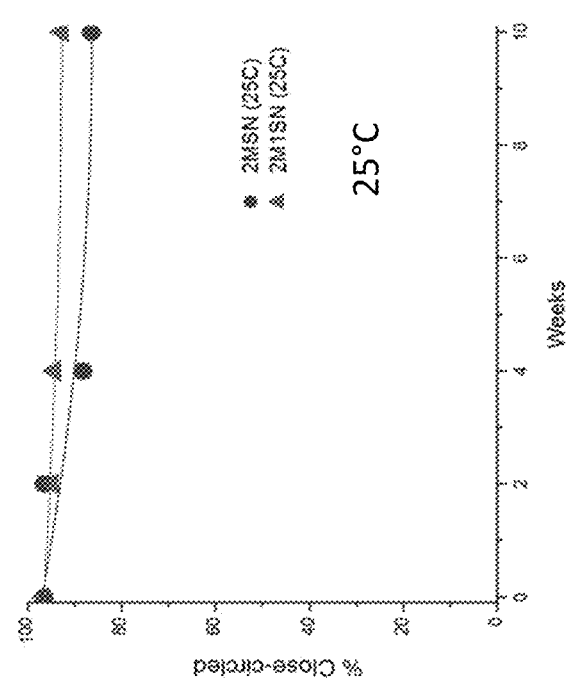

FIG. 25 provides a result from capillary electrophoresis (CE) of 2MSN and 2M1SN after storage at 40° C. for 10 weeks FIGS. 26A-26C provide time-lapse changes of super-coiled DNA percentages measured based on capillary electrophoresis (CE) results for 2MSN and 2M1SN, when the formulations were stored at 5° C. (FIG. 26A), 25° C. (FIG. 26B) or 40° C. (FIG. 26C).

Figure 27A:
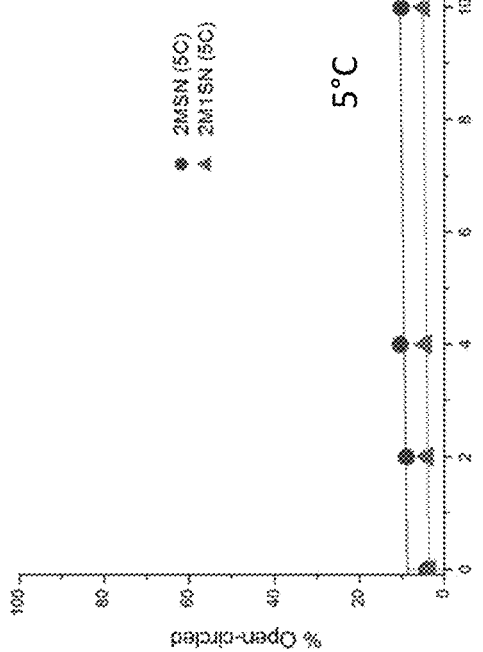
Figure 27C:
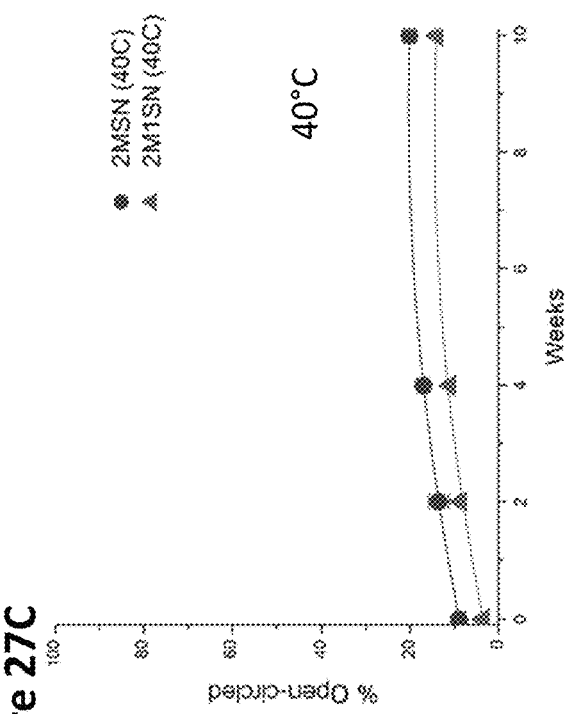
Figure 27B:
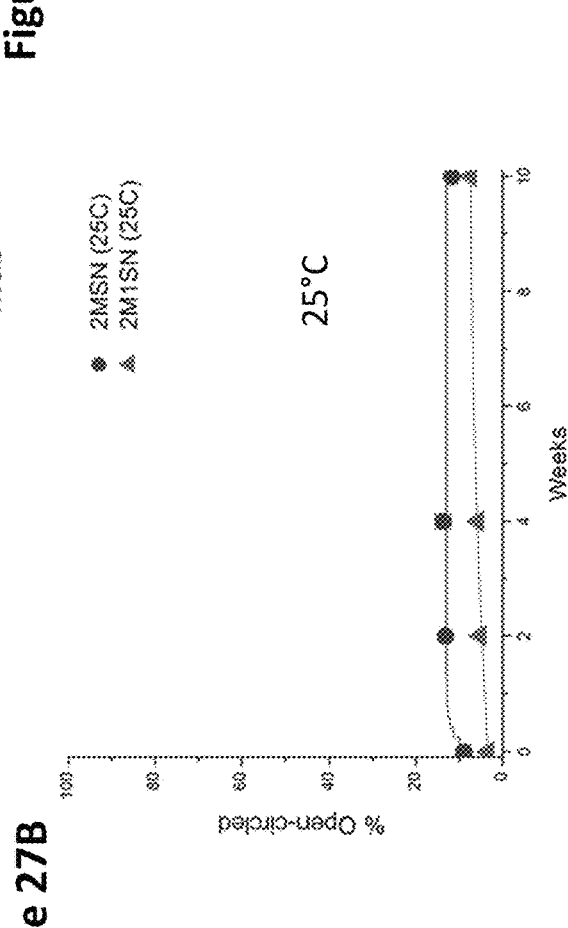

FIGS. 27A-27C provide time-lapse changes of open-circled DNA percentages measured based on capillary electrophoresis (CE) results for 2MSN and 2M1SN, when the formulations were stored at 5° C. (FIG. 27A), 25° C. (FIG. 27B) or 40° C. (FIG. 27C).

Figure 28:
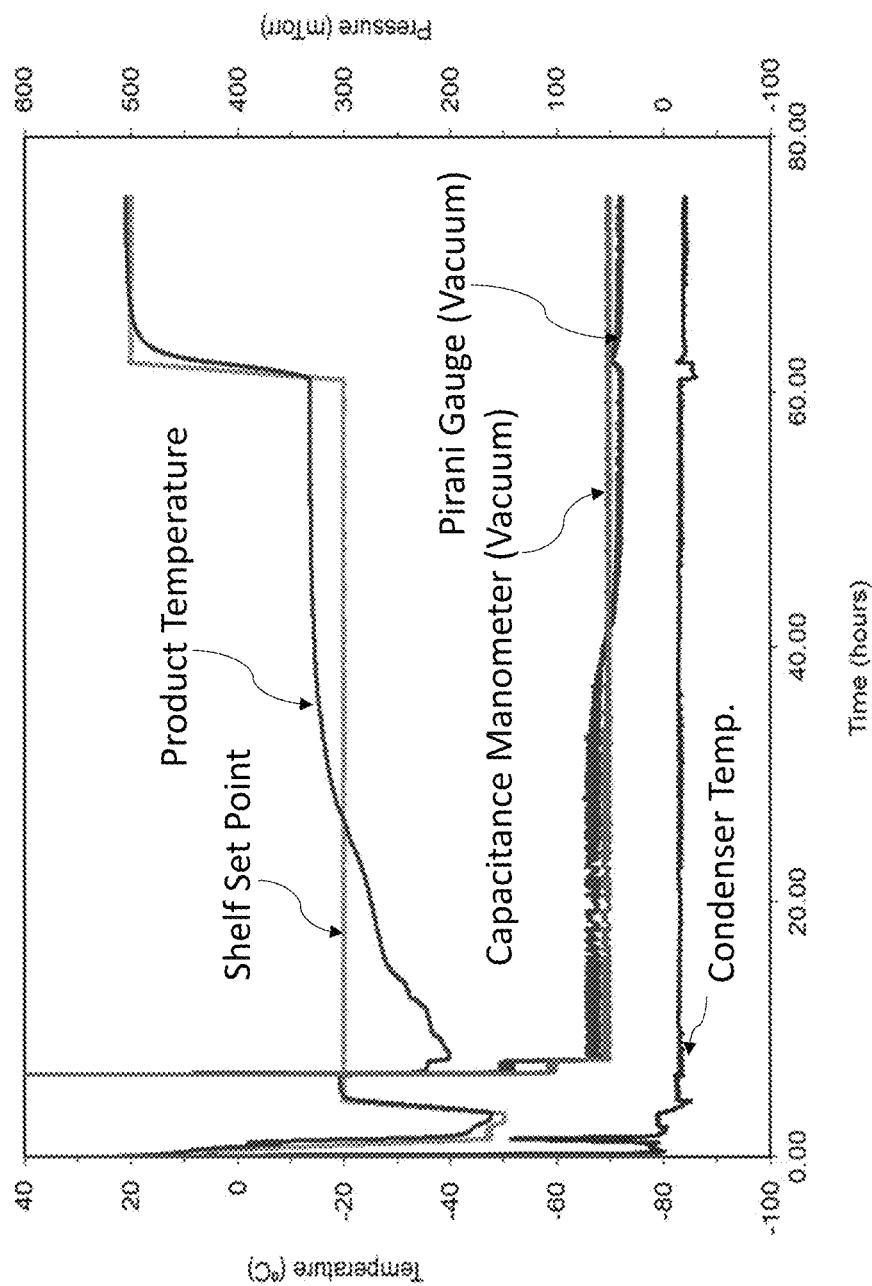

FIG. 28 provide a time-lapse change of temperatures (y-axis on the left) and pressures (y-axis on the right) during lyophilization cycle used in Example 2.

Figure 29:
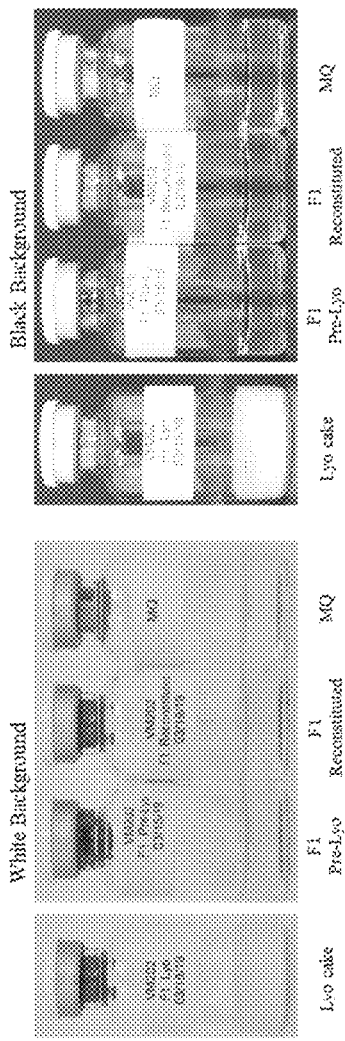

FIG. 29 provides pictures of vials containing F1 of Example 2 before or after reconstitution of the lyophilized formulation over white background (left) or black background (right).

Figure 30:
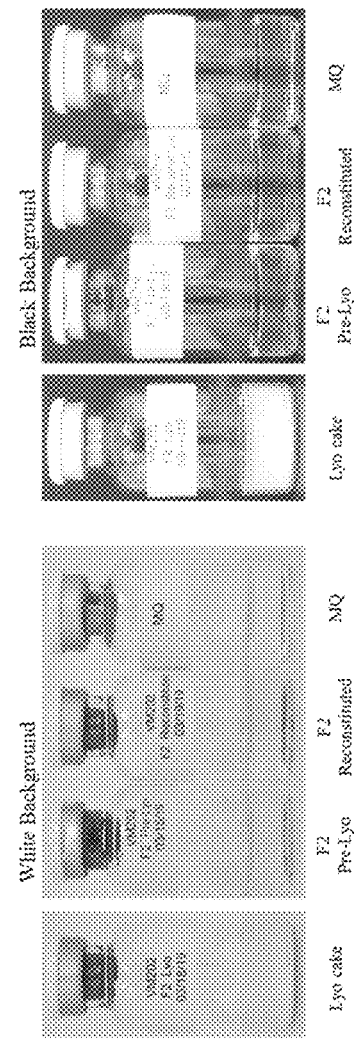

FIG. 30 provides pictures of vials containing F2 of Example 2 before or after reconstitution of the lyophilized formulation over white background (left) or black background (right).

Figure 31:
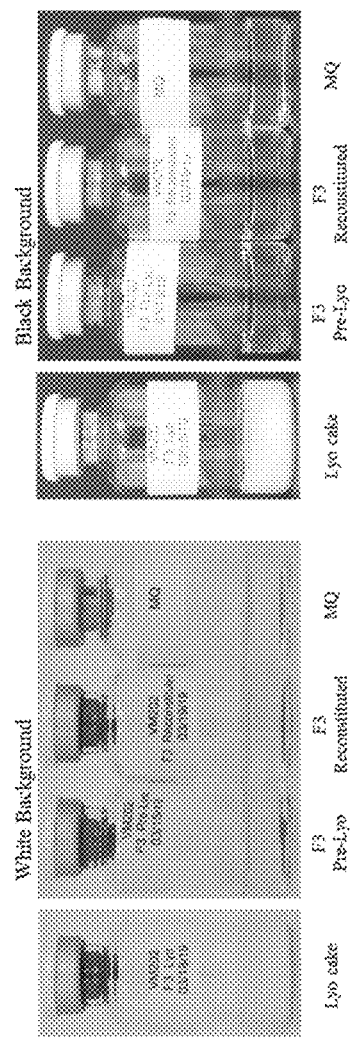

FIG. 31 provides pictures of vials containing F3 of Example 2 before or after reconstitution of the lyophilized formulation over white background (left) or black background (right).

Figure 32:
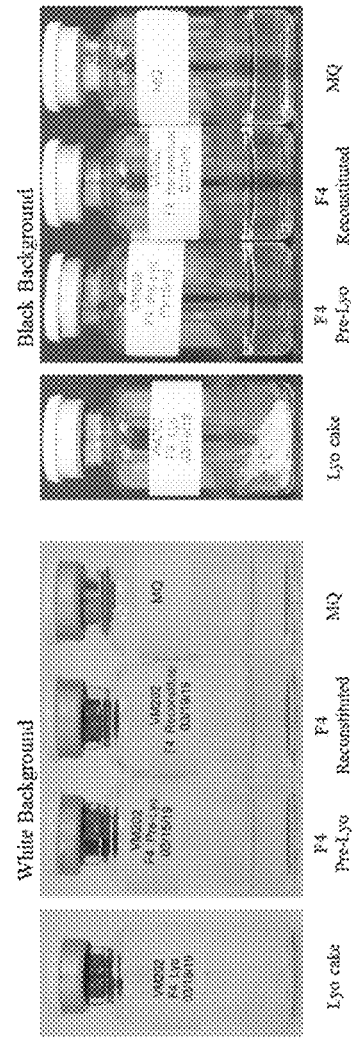

FIG. 32 provides pictures of vials containing F4 of Example 2 before or after reconstitution of the lyophilized formulation over white background (left) or black background (right).

Figure 33:
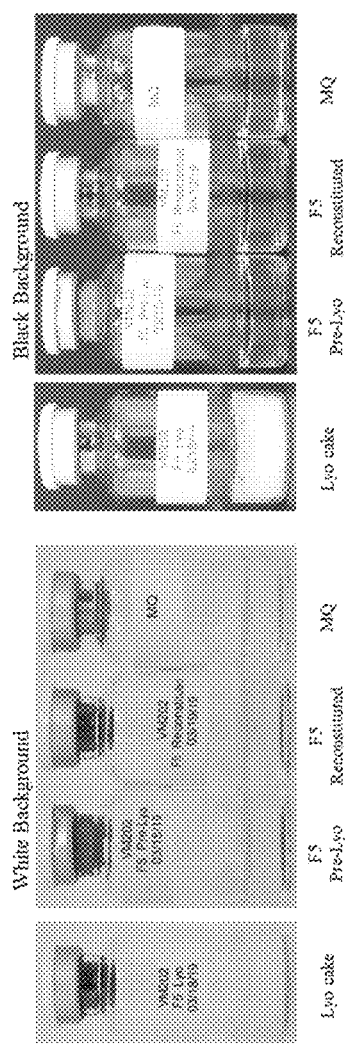

FIG. 33 provides pictures of vials containing F5 of Example 2 before or after reconstitution of the lyophilized formulation over white background (left) or black background (right).

Figure 34:
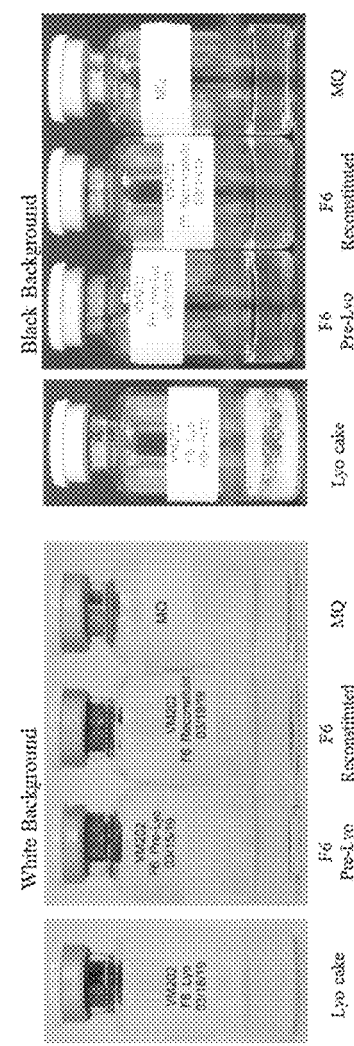

FIG. 34 provides pictures of vials containing F6 of Example 2 before or after reconstitution of the lyophilized formulation over white background (left) or black background (right).

Figure 35:
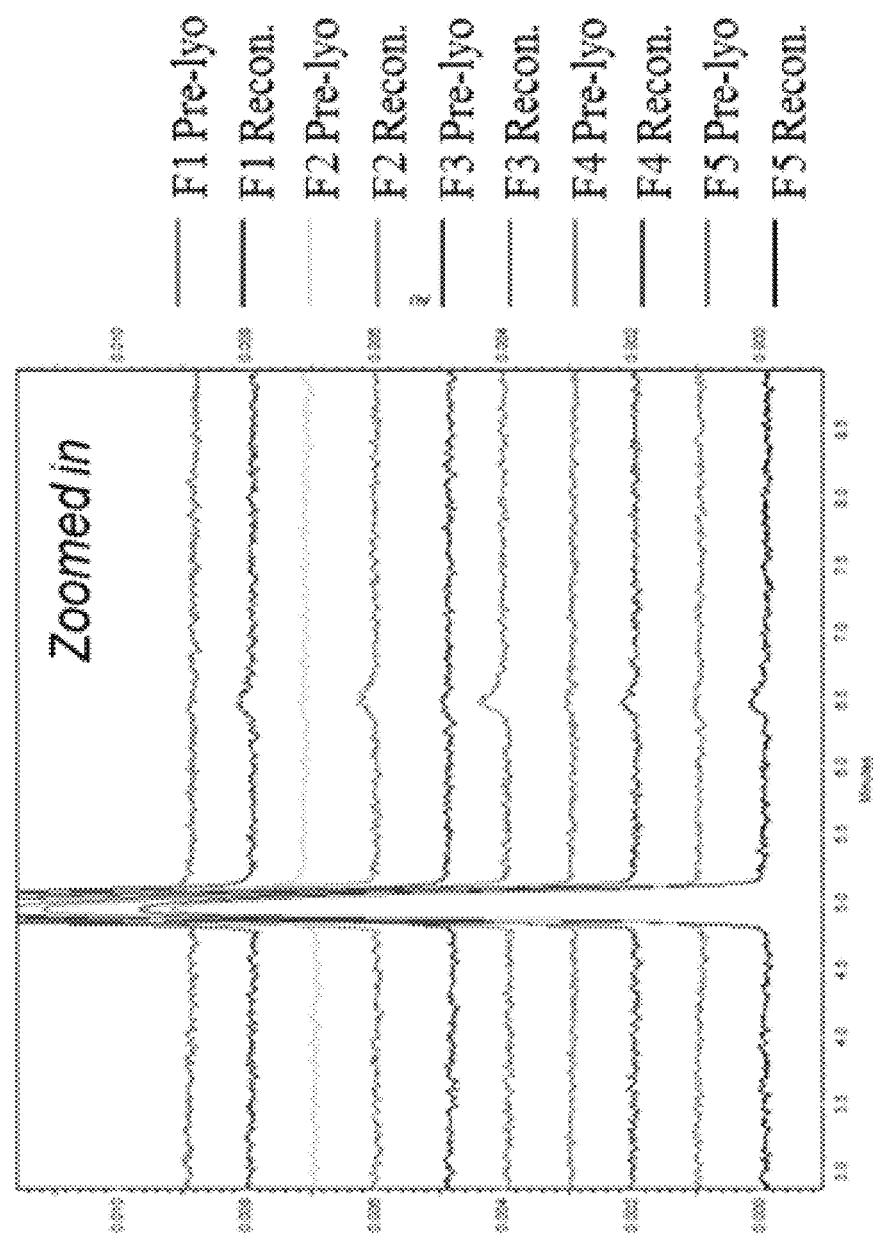

FIG. 35 provides a result from capillary electrophoresis (CE) of F1, F2, F3, F4, and F5 of Example 2.

Figure 36:
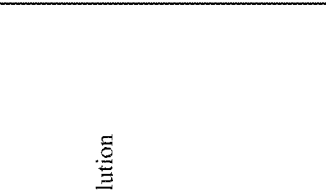
Figure 36:
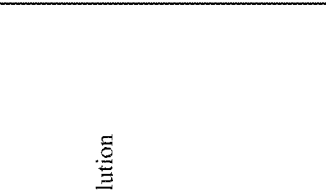
Figure 36:
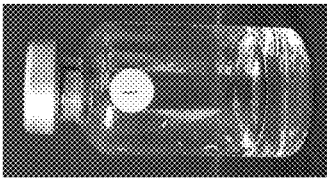
Figure 36:
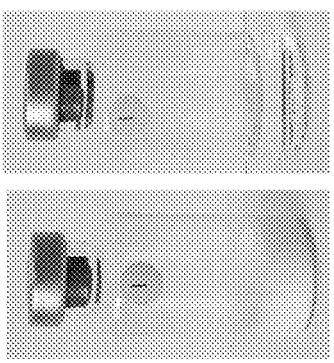

FIG. 36 provides pictures of vials containing F1 of Example 3 before or after reconstitution of the lyophilized formulation over white background (left) or black background (right).

Figure 37:
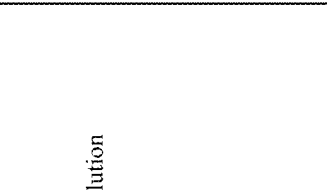
Figure 37:
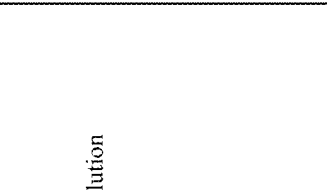
Figure 37:
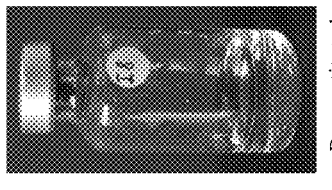
Figure 37:
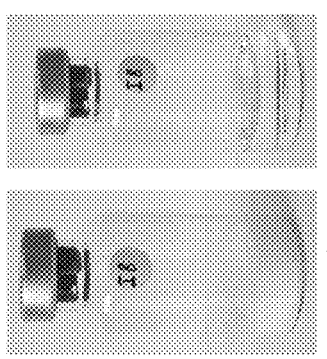

FIG. 37 provides pictures of vials containing F2 of Example 3 before or after reconstitution of the lyophilized formulation over white background (left) or black background (right).

Figures 38, 39:
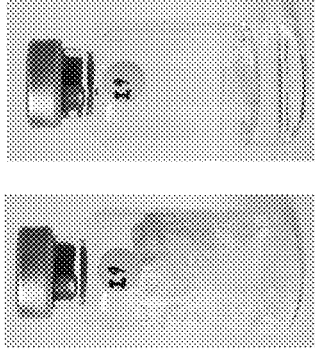

FIG. 38 provides pictures of vials containing F3 of Example 3 before or after reconstitution of the lyophilized formulation over white background (left) or black background (right).

FIG. 39 provides pictures of vials containing F4 of Example 3 before or after reconstitution of the lyophilized formulation over white background (left) or black background (right).

Figure 40:
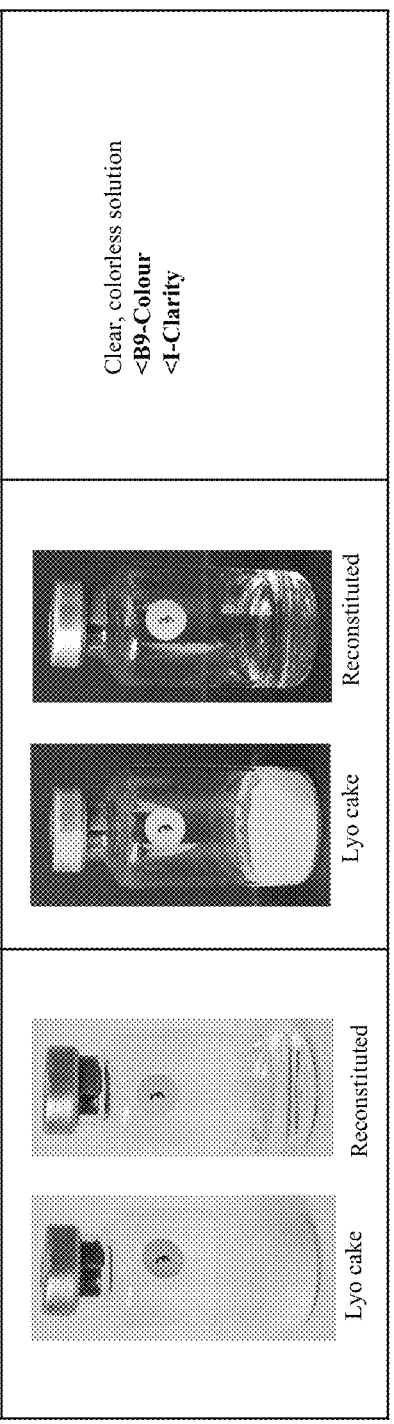

FIG. 40 provides pictures of vials containing F5 of Example 3 before or after reconstitution of the lyophilized formulation over white background (left) or black background (right).

Figure 41:

FIG. 41 provides pictures of vials containing F6 of Example 3 before or after reconstitution of the lyophilized formulation over white background (left) or black background (right).

Figure 42:
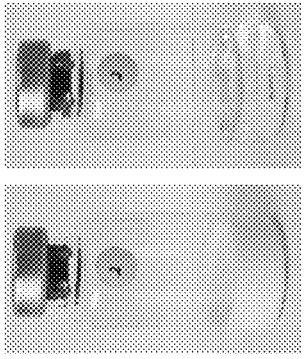

FIG. 42 provides pictures of vials containing F7 of Example 3 before or after reconstitution of the lyophilized formulation over white background (left) or black background (right).

Figure 43:
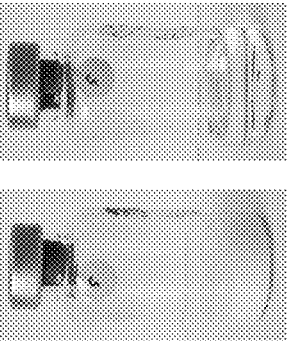

FIG. 43 provides pictures of vials containing F8 of Example 3 before or after reconstitution of the lyophilized formulation over white background (left) or black background (right).

Figure 44:
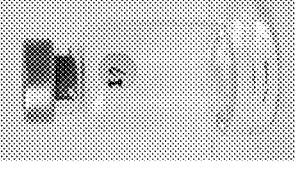

FIG. 44 provides pictures of vials containing F9 of Example 3 before or after reconstitution of the lyophilized formulation over white background (left) or black background (right).

Figure 45:
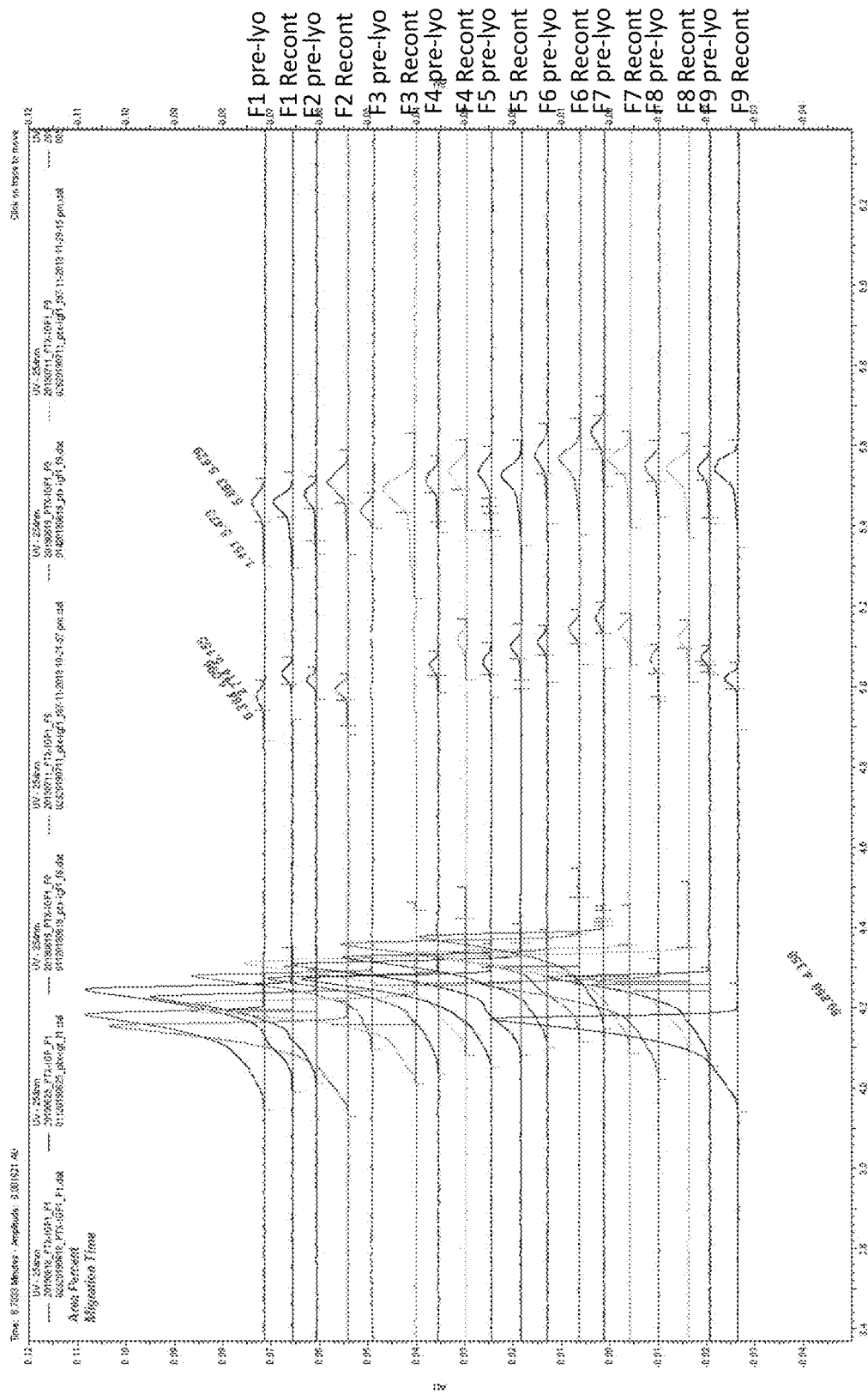

FIG. 45 provides a result from capillary electrophoresis (CE) of F1, F2, F3, F4, F5, F6, F7, F8, and F9 of Example 3 (TABLE 40).

Figure 46:
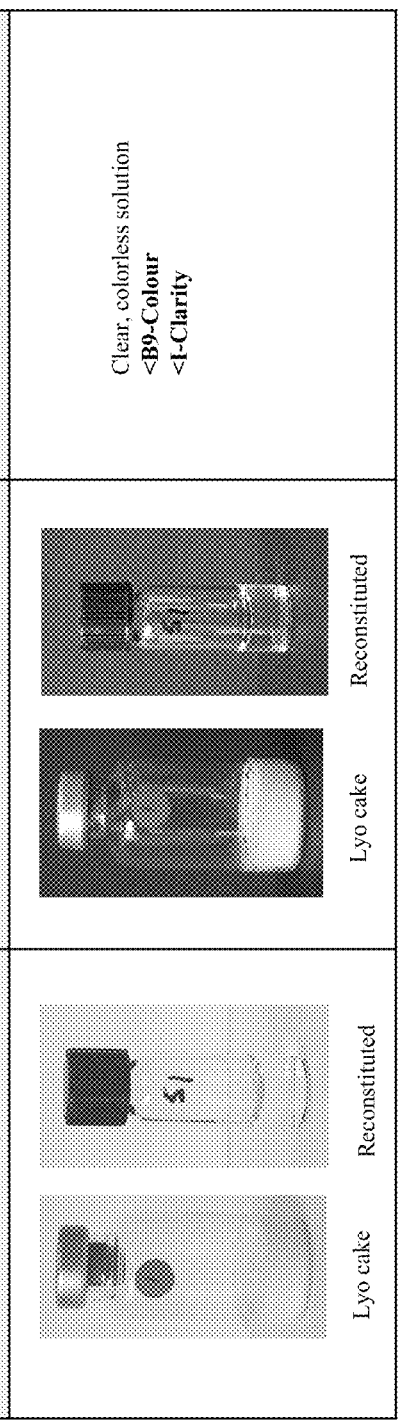

FIG. 46 provides pictures of vials containing F1 of Example 4 before or after reconstitution of the lyophilized formulation over white background (left) or black background (right).

Figure 47:

FIG. 47 provides pictures of vials containing F2 of Example 4 before or after reconstitution of the lyophilized formulation over white background (left) or black background (right).

Figure 48:
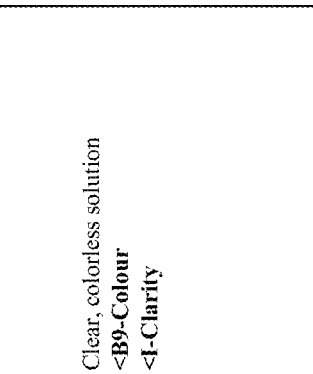
Figure 48:
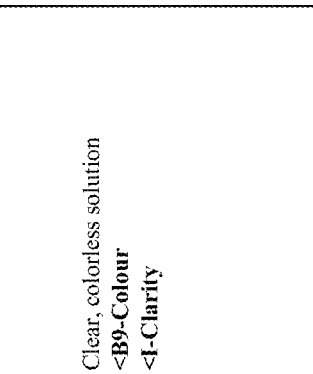
Figure 48:
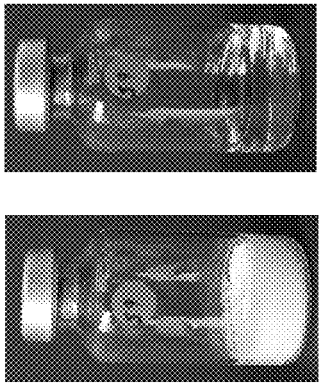
Figure 48:
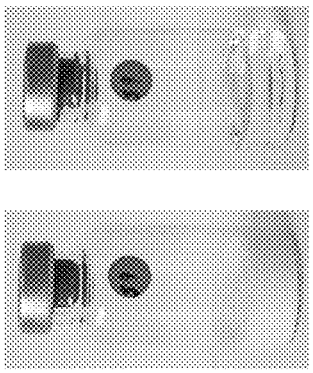

FIG. 48 provides pictures of vials containing F3 of Example 4 before or after reconstitution of the lyophilized formulation over white background (left) or black background (right).

Figure 49:
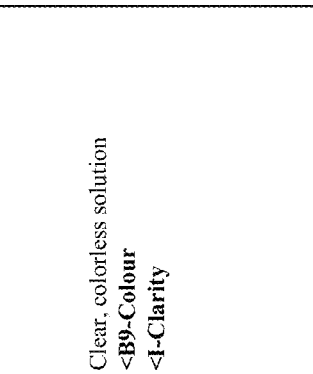
Figure 49:
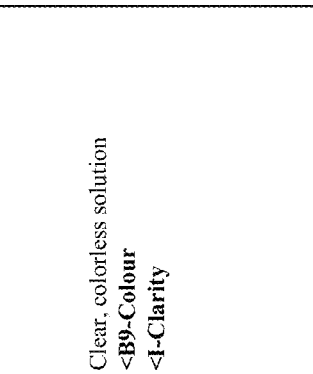
Figure 49:
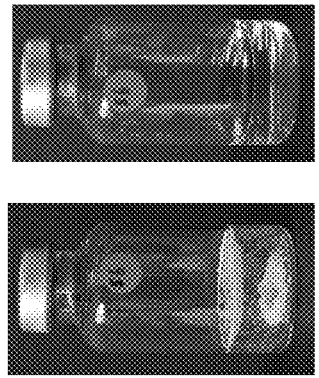
Figure 49:
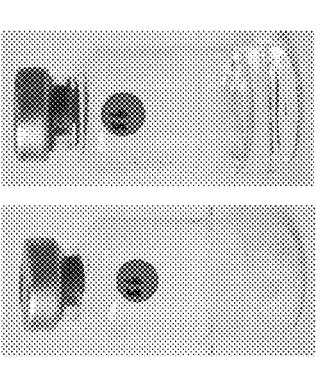

FIG. 49 provides pictures of vials containing F4 of Example 4 before or after reconstitution of the lyophilized formulation over white background (left) or black background (right).

Figure 50:
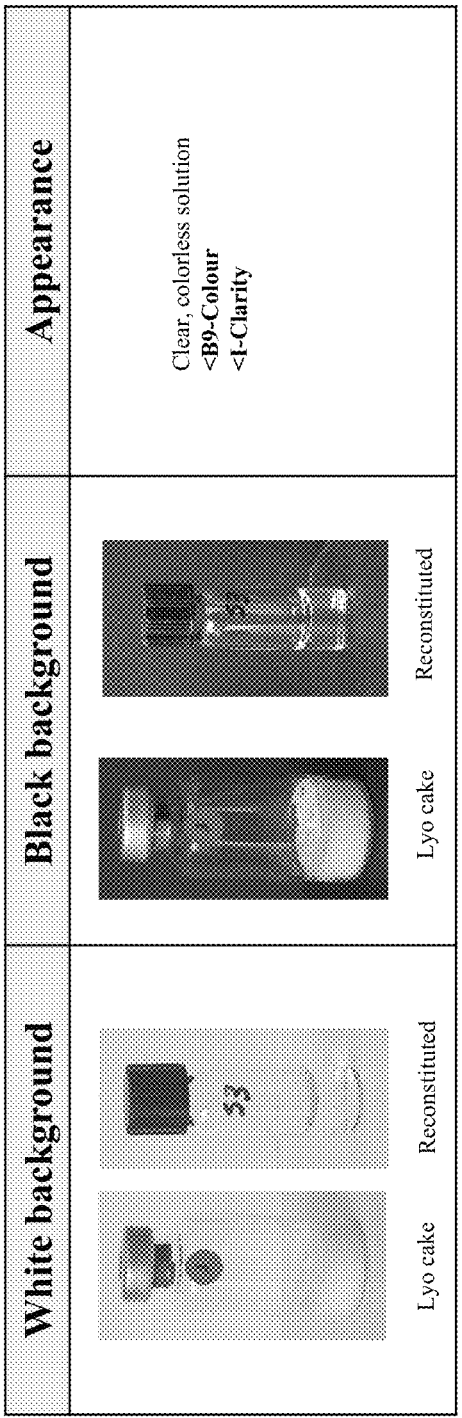

FIG. 50 provides pictures of vials containing F5 of Example 4 before or after reconstitution of the lyophilized formulation over white background (left) or black background (right).

Figure 51:
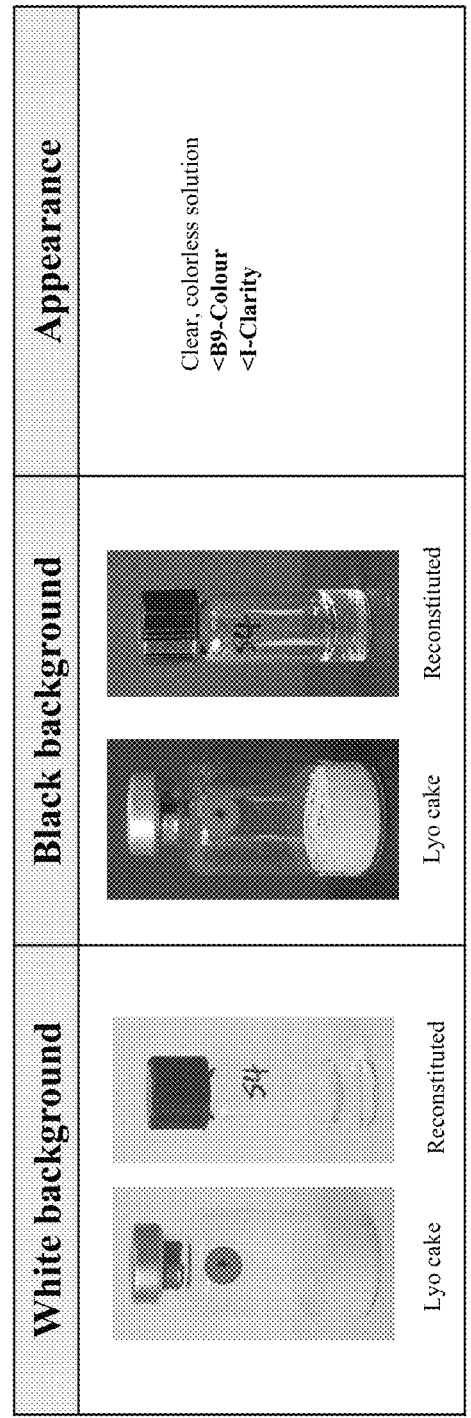

FIG. 51 provides pictures of vials containing F6 of Example 4 before or after reconstitution of the lyophilized formulation over white background (left) or black background (right).

FIG. 52 provides pictures of vials containing F7 of Example 4 before or after reconstitution of the lyophilized formulation over white background (left) or black background (right).

FIG. 53 provides pictures of vials containing F8 of Example 4 before or after reconstitution of the lyophilized formulation over white background (left) or black background (right).

Figure 54:
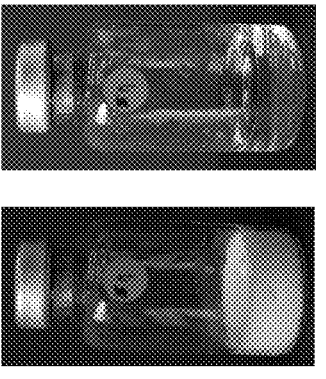

FIG. 54 provides pictures of vials containing F9 of Example 4 before or after reconstitution of the lyophilized formulation over white background (left) or black background (right).

Figure 55:
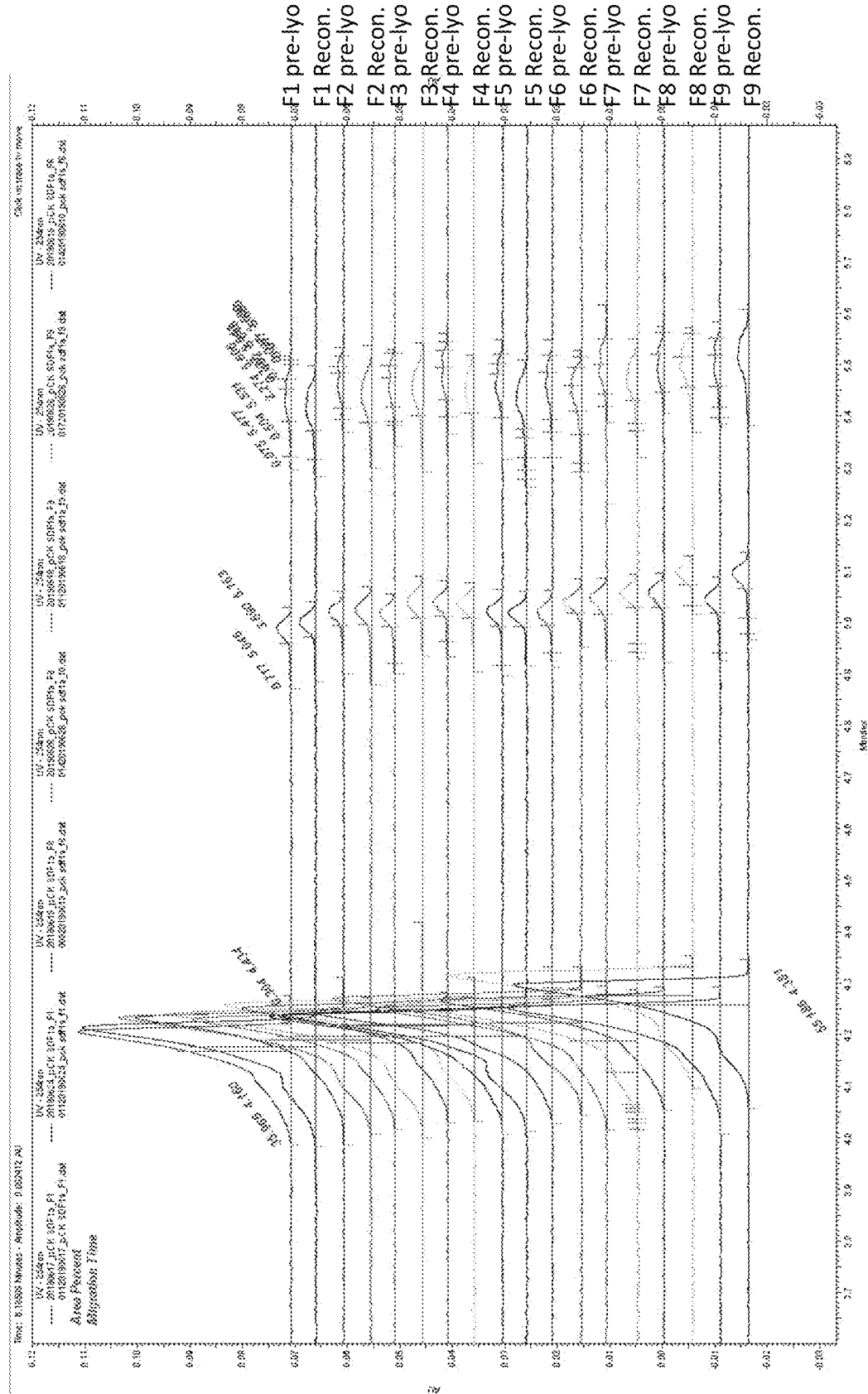

FIG. 55 provides a result from capillary electrophoresis (CE) of F1, F2, F3, F4, F5, F6, F7, F8, and F9 of Example 4 (TABLE 44).

The figures depict various embodiments of the present invention for purposes of illustration only. One skilled in the art will readily recognize from the following discussion that alternative embodiments of the structures and methods illustrated herein may be employed without departing from the principles of the invention described herein.

6. DETAILED DESCRIPTION

6.1. Definitions

Unless defined otherwise, all technical and scientific terms used herein have the meaning commonly understood by a person skilled in the art to which this invention belongs. As used herein, the following terms have the meanings ascribed to them below.

The term "liquid composition" as used herein refers to a composition in liquid form that comprises plasmid DNA and at least one pharmaceutically acceptable excipient, and that can be lyophilized to generate a lyophilized pharmaceutical composition as described herein.

The term "lyophilized composition" or "lyophilized pharmaceutical composition" as used herein refers to any composition or pharmaceutical composition in dry form that is prepared by lyophilization. "Lyophilizing" or "lyophilization" have the meanings understood by those skilled in the art, referring broadly to any process of freezing followed by dehydration in the frozen state under vacuum. Lyophilized compositions can be reconstituted for injection.

The term "reconstituted" or "reconstitution" as used herein refers to the restoration to the original form of a substance previously altered for preservation and storage, such as rehydration, i.e., the restoration to a liquid state of a DNA plasmid formulation that has been previously lyophilized and stored. The lyophilized composition of the present invention may be reconstituted in any aqueous solution which produces a stable solution suitable for pharmaceutical administration. Such aqueous solutions include, but are not limited to, sterile water, Tris-EDTA (TE), phosphate-buffered saline (PBS), Tris buffer and normal saline.

The term "isolated" or "biologically pure" as used herein refers to material that is substantially free from components which normally accompany the material as it is found in its native state. Thus, isolated plasmid DNA as used herein is substantially free from components normally associated with the plasmid DNA in its in situ environment, such as bacterial proteins, lipids, or cell wall components.

The term "VM202" as used herein refers to a plasmid DNA also called as pCK-HGF-X7, comprising pCK vector (SEQ ID NO: 5) and HGF-X7 (SEQ ID NO: 13) cloned into the pCK vector. VM202 was deposited under the terms of the Budapest Treaty at the Korean Culture Center of Microorganisms (KCCM) under accession number KCCM-10361 on Mar. 12, 2002.

The term "isoforms of HGF" as used herein refers to a polypeptide having an amino acid sequence that is at least 80% identical to the amino acid sequence of a naturally occurring HGF polypeptide in an animal. The term includes polypeptides having an amino acid sequence that is at least 80% identical to any full length wild type HGF polypeptide, and includes polypeptides having an amino acid sequence that is at least 80% identical to a naturally occurring HGF allelic variant, splice variant, or deletion variant. Isoforms of HGF preferred for use in the present invention include two or more isoforms selected from the group consisting of full-length HGF (flHGF) (synonymously, fHGF), deleted variant HGF (dHGF), NK1, NK2, and NK4. According to a more preferred embodiment of the present invention, the isoforms of HGF used in the methods described herein include flHGF (SEQ ID NO: 1) and dHGF (SEQ ID NO: 2).

The terms "human flHGF", "flHGF" and "fHGF" are used interchangeably herein to refer to a protein consisting of amino acids 1-728 of the human HGF protein. The sequence of flHGF is provided in SEQ ID NO: 1.

The terms "human dHGF" and "dHGF" are used interchangeably herein to refer to a deleted variant of the HGF protein produced by alternative splicing of the human HGF gene. Specifically, "human dHGF" or "dHGF" refers to a human HGF protein with deletion of five amino acids (F, L, P, S, and S) in the first kringle domain of the alpha chain from the full length HGF sequence. Human dHGF is 723 amino acids in length. The amino acid sequence of human dHGF is provided in SEQ ID NO: 2.

The term "isoform of IGF-1," "human IGF-1 isoform" or "IGF-1 isoform" as used herein refers to a polypeptide having an amino acid sequence that is at least 80% identical to the amino acid sequence of one of naturally occurring pre-pro-IGF-1 polypeptides of humans, or their allelic variant, splice variant, or deletion variant. The naturally occurring pre-pro-IGF-1 polypeptides include Class I, Ec (SEQ ID NO: 25); Class II, Ea (SEQ ID NO: 27); Class I, Eb (SEQ ID NO: 29); and Class I, Ea isoforms (SEQ ID NO: 23).

The terms "Isoform #1," "Class I, Ec isoform," "Class I, IGF-1 Ec isoform" or "Class I, IGF-1 Ec" are used interchangeably herein to refer to a polypeptide of SEQ ID NO: 25.

The terms "Isoform #2," "Class II, Ea isoform," "Class II, IGF-1 Ea isoform" or "Class H, IGF-1 Ea" are used interchangeably herein to refer to a polypeptide of SEQ ID NO: 27.

The terms "Isoform #3," "Class I, Eb isoform," "Class I, IGF-1 Eb isoform" or "Class I, IGF-1 Eb" are used interchangeably herein to refer to a polypeptide of SEQ ID NO: 29.

The terms "Isoform #4," "Class I, Ea isoform," "Class I, IGF-1 Ea isoform" or "Class I, IGF-1 Ea" are used interchangeably herein to refer to a polypeptide of SEQ ID NO: 23.

The term "treatment" as used herein refers to at least one of (a) suppressing a symptom of a disease; (b) alleviating a symptom of a disease; and (c) eliminating a symptom of a disease. In some embodiments, the composition of the present invention can treat a symptom associated with neuropathy, ischemic disease, muscle atrophy or a heart disease.

The term "therapeutically effective dose" or "effective amount" as used herein refers to a dose or an amount that produces the desired effect for which it is administered. In the context of the present methods, a therapeutically effective amount is an amount effective to treat a symptom of a disease. The exact dose or amount will depend on the purpose of the treatment, and will be ascertainable by one skilled in the art using known techniques (see, e.g., Lloyd (1999) The Art, Science and Technology of Pharmaceutical Compounding).

The term "sufficient amount" as used herein refers to an amount sufficient to produce a desired effect.

The term "degenerate sequence" as used herein refers to a nucleic acid sequence that can be translated to provide an amino acid sequence identical to that translated from the reference nucleic acid sequence.

6.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

6.3. Lyophilized Pharmaceutical Composition

In a first aspect, lyophilized pharmaceutical compositions are presented. The lyophilized pharmaceutical compositions comprise plasmid DNA, and are obtained by lyophilizing a liquid composition that comprises, prior to lyophilization:
  a. plasmid DNA of a first plasmid;
  b. potassium phosphate buffer with pH from 7.0 to 9.0;
  c. mannitol at a concentration from 0%/a to 3% (w/v);
  d. sucrose at a concentration greater than 0.5% and less than 1.1% (w/v); and
  e. NaCl at a concentration from 0.1% to 0.9% (w/v).

The first plasmid can be selected from the group consisting of VM202, pTx-HGF-X7, pTx-IGF-1Ec, pTx-IGF-1Ea, pTx-IGF-1X6, pTx-IGF-1X10, and pCK-SDF-1α.

6.3.1. Plasmid DNA

The liquid composition includes plasmid DNA, which is an active ingredient of the pharmaceutical composition. The plasmid DNA can include a genetic material for gene therapy. Specifically, the plasmid DNA can encode a gene product that can correct the function of a defective gene or transcript, or encode polypeptides, sense or antisense oligonucleotides, or RNAs (coding or non-coding; e.g., siRNAs, shRNAs, micro-RNAs, and their antisense counterparts (e.g., antagoMiR)). A formulation containing any plasmid DNA known in the art to be used for gene therapy falls within the scope of the present invention.

The liquid composition can comprise the plasmid DNA at a concentration that allows subsequent reconstitution of the lyophilized pharmaceutical composition to provide a concentration effective for the therapeutic application of the reconstituted drug. The concentration of the plasmid DNA can be adjusted depending on various factors, including the amount of a composition to be delivered, diseases to be treated, the age and weight of the subject, the delivery method, and route of administration, etc.

Specifically, the liquid composition can include the plasmid DNA at a concentration from 0.1 to 5 mg/ml, from 0.1 to 3 mg/ml, from 0.1 to 2 mg/ml, from 0.1 to 1 mg/ml, from 0.25 to 0.75 mg/ml, from 0.4 to 0.6 mg/ml, or at a concentration of 0.5 mg/ml.

The plasmid DNA can be a polynucleotide of a length from 3,000 to 15,000 base pairs, from 3,000 to 10,000 base pairs, from 3,000 to 9,000 base pairs, from 3,000 to 8,000 base pairs, from 3,000 to 7,000 base pairs, from 3,000 to 6,000 base pairs, from 3,000 to 5,000 base pairs, from 4,000 to 8,000 base pairs, from 4,000 to 7,500 base pairs, from 4,000 to 6,000 base pairs, from 6,000 to 9,000 base pairs, or from 7,000 to 8,000 base pairs. The plasmid DNA can be a polynucleotide of a length that falls within the scope provided herein.

6.3.1.1. Vector

The plasmid DNA used in the methods of the present invention typically comprises a vector with one or more regulatory sequences (e.g., a promoter or an enhancer) operatively linked to the expressed sequences. The regulatory sequence regulates expression of a protein (e.g., one or more isoforms of HGF or IGF-1).

It is preferred that the polynucleotide encoding a protein is operatively linked to a promoter in an expression construct. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

In typical embodiments, the promoter linked to the polynucleotide is operable in, preferably, animal, more preferably, mammalian cells, to control transcription of the polynucleotide, including the promoters derived from the genome of mammalian cells or from mammalian viruses, for example, CMV (cytomegalovirus) promoter, the adenovirus late promoter, the vaccinia virus 7.5K promoter, SV40 promoter, HSV tk promoter, RSV promoter, EFI alpha promoter, metallothionein promoter, beta-actin promoter, human IL-2 gene promoter, human IFN gene promoter, human IL-4 gene promoter, human lymphotoxin gene promoter and human GM-CSF gene promoter, but not limited thereto. More preferably, the promoter useful in this invention is a promoter derived from the IE (immediately early) gene of human CMV (hCMV) or EFI alpha promoter, most preferably hCMV IE gene-derived promoter/enhancer and 5'-UTR (untranslated region) comprising the overall sequence of exon 1 and exon 2 sequence spanning a sequence immediately before the ATG start codon.

The expression cassette used in this invention may comprise a polyadenylation sequence, for example, including bovine growth hormone terminator (Gimmi, E. R., et al., Nucleic Acids Res. 17:6983-6998 (1989)), SV40-derived polyadenylation sequence (Schek, N, et al., Mol. Cell Biol. 12:5386-5393 (1992)), HIV-1 polyA (Klasens, B. I. F., et al., Nucleic Acids Res. 26:1870-1876 (1998)), β-globin polyA (Gil, A., et al, Cell 49:399-406 (1987)), HSV TK polyA (Cole, C. N. and T. P. Stacy, Mol. Cell. 5 Biol. 5: 2104-2113 (1985)) or polyoma virus polyA (Batt, D. Band G. G. Carmichael, Mol. Cell. Biol. 15:4783-4790 (1995)), but not limited to.

In currently preferred embodiments, the vector is pCK, pCP, pVAX1, pTx or pCY. In particularly preferred embodiments, the vector is pCK, details of which can be found in WO 2000/040737 and Lee et al., Biochem. Biophys. Res. Comm. 272:230-235 (2000), both of which are incorporated herein by reference in their entireties. E. coli transformed with pCK (Top10-pCK) was deposited at the Korean Culture Center of Microorganisms (KCCM) under the terms of the Budapest Treaty on Mar. 21, 2003 (Accession NO: KCCM-10476). E. coli transformed with pCK-VEGF165 (i.e., pCK vector with VEGF coding sequence—Top10-pCK/VEGF 165') was deposited at the Korean Culture Center of Microorganisms (KCCM) under the terms of the Budapest Treaty on Dec. 27, 1999 (Accession NO: KCCM-10179).

The pCK vector is constructed such that the expression of a gene, e.g., an HGF gene or an IGF-1 gene, is regulated under enhancer/promoter of the human cytomegalovirus (HCMV), as disclosed in detail in Lee et al., Biochem. Biophys. Res. Commun. 272: 230 (2000); WO 2000/040737, both of which are incorporated by reference in their entirety. pCK vector has been used for clinical trials on human body, and its safety and efficacy were confirmed (Henry et al., Gene Ther. 18:788 (2011)).

In other preferred embodiments, the vector is pTx (SEQ ID NO: 15), a plasmid vector derived from pCK. pTx was generated by two sequential rounds of mutagenesis of pCK. The first deletion mutagenesis campaign was conducted to remove the unnecessary sequence between Kanamycin resistance gene and ColE1 of pCK. Specifically, deletion mutagenesis PCR was performed using a first primer pair (SEQ ID NOs: 17 and 18). The deletion of 228 base pairs between Kanamycin resistance and ColE1 was confirmed by sequencing the plasmid. The second deletion mutagenesis campaign was then performed using a second primer pair (SEQ ID NOs: 19 and 20), to optimize the size of HCMV intron sequence. HCMV intron sequence (421 base pairs) between IE1 exon 1 and exon 2 was deleted and the deletion was confirmed by sequencing.

6.3.1.2. Plasmid DNA Encoding a Human HGF

In some embodiments, the plasmid DNA encodes a human HGF or a variant thereof.

Hepatocyte growth factor (HGF) is a heparin binding glycoprotein also known as scatterfactor or hepatopoietin-A. An endogenous gene encoding human HGF is located at chromosome 7q21.1 and comprises 18 exons and 17 introns (Seki T., et al., Gene 102:213-219 (1991)). A transcript of about 6 kb is transcribed from the HGF gene, and then, a polypeptide HGF precursor (flHGF) consisting of 728 amino acids is synthesized therefrom. Simultaneously, a polypeptide of dHGF precursor consisting of 723 amino acids is also synthesized by an alternative splicing of the HGF gene. The biologically inactive precursors may be converted into active forms of disulfide-linked heterodimer by protease in serum. In the heterodimers, the alpha chain having a high molecular weight forms four kringle domains and an N-terminal hairpin loop like a preactivated peptide region of plasminogen. The kringle domains of a triple disulfide-bonded loop structure consisting of about 80 amino acids may play an important role in protein-protein interaction. The low molecular weight beta chain forms an inactive serine protease-like domain. dHGF consisting 723 amino acids is a polypeptide with deletion of five amino acids in the 1st kringle domain of the alpha chain, i.e., F. L. P. S and S.

HGF has various biological functions, e.g., 1) inducing epithelial cells into a tubular structure; 2) stimulating vascularization from endothelial cells in vitro and in vivo; 3) regeneration of liver and kidney, owing to its anti-apoptosis activity; 4) organogenesis of kidney, ovary and testis; 5) controlling osteogenesis; 6) stimulating the growth and differentiation of erythroid hematopoietic precursor cells; and 7) axon sprouting of neurons (Stella, M. C. and Comoglio, P. M., The International Journal of Biochemistry & Cell Biology 31:1357-1362 (1999)). Based on these various functions, HGF or a gene encoding HGF or a variant thereof, can be developed as a therapeutic agent.

In fact, plasmids encoding one or more isoforms of human HGF have been developed and used for treating various diseases as described in U.S. Pat. Nos. 7,812,146, 8,338,385 and 8,389,492, and US Publication Nos. 20140296142 and 20160250291, which are incorporated by reference in their entirety herein. The plasmids can be used in various embodiments of the present disclosure.

Specifically, the plasmid can express two or more isoforms of HGF by comprising an expression regulatory sequence for each isoform coding sequence (CDS). In some embodiments, the construct comprises an internal ribosomal entry site (IRES) between two coding sequences, for example, in the order of (1) expression regulatory sequence—(2) coding sequence of first isoform—(3) IRES—(4) coding sequence of second isoform—(5) transcription termination sequence. IRES allows translation to start at the IRES sequence, thereby allowing expression of two genes of interest from a single construct. In yet further embodiments, a plurality of constructs, each encoding a single isoform of HGF, are used together to induce expression of more than one isoforms of HGF in the subject to whom administered.

Preferred embodiments of the methods use a construct that simultaneously expresses two or more different types of isoforms of HGF—i.e., flHGF and dHGF—by comprising an alternative splicing site. It was previously demonstrated in U.S. Pat. No. 7,812,146, incorporated by reference herein, that a construct encoding two isoforms of HGF (flHGF and dHGF) through alternative splicing has much higher (almost 250-fold higher) expression efficiency than a construct encoding one isoform of HGF (either flHGF or dHGF). In typical embodiments, the construct comprises (i) a first sequence comprising exons 1-4 of a human HGF gene (SEQ ID NO: 3) or a degenerate sequence of the first sequence; (ii) a second sequence comprising intron 4 of the human HGF gene (SEQ ID NO: 6) or a fragment of the second sequence; and (iii) a third sequence comprising exons 5-18 of the human HGF gene (SEQ ID NO: 4) or a degenerate sequence of the third sequence. From the construct, two isoforms of HGF (flHGF and dHGF) can be generated by alternative splicing between exon 4 and exon 5.

In some embodiments, the construct comprises a full sequence of intron 4. In some embodiments, the construct comprises a fragment of intron 4. In preferred embodiments, the construct comprises a nucleotide sequence selected from the group consisting of SEQ ID NO: 7 to SEQ ID NO: 14. The nucleotide sequence of SEQ ID NO:7 corresponds to a 7113 bp polynucleotide encoding flHGF and dHGF, and including the full sequence of intron 4. The nucleotide sequences of SEQ ID NOS: 8-14 correspond to polynucleotides encoding flHGF and dHGF and including various fragments of intron 4.

Various nucleic acid constructs comprising cDNA corresponding exon 1-18 of human HGF and intron 4 of a human HGF gene or its fragment are named "HGF-X" followed by a unique number as described in U.S. Pat. No. 7,812,146. The HGF-X tested by Applicant includes, but not limited to, HGF-X1 (SEQ ID NO:7), HGF-X2 (SEQ ID NO:8), HGF-X3 (SEQ ID NO:9), HGF-X4 (SEQ ID NO:10), HGF-X5 (SEQ ID NO: 11), HGF-X6 (SEQ ID NO:12), HGF-X7 (SEQ ID NO:13), and HGF-X8 (SEQ ID NO:14).

It was previously demonstrated that two isoforms of HGF (i.e., flHGF and dHGF) can be generated by alternative splicing between exon 4 and exon 5 from each of the constructs. In addition, among the various HGF constructs, HGF-X7 showed the highest level of expression of two isoforms of HGF (i.e., flHGF and dHGF) as disclosed in U.S. Pat. No. 7,812,146, incorporated by reference in its entirety herein. Accordingly, a nucleic acid construct comprising HGF-X7 can be used in preferred embodiments of the methods of the present invention.

In particularly preferred embodiments, the pCK plasmid containing the HGF-X7 expression sequences is used as the nucleic acid construct in the methods of the present invention. Specifically, pCK-HGF-X7 (also called "VM202") can be used. pCK-HGF-X7 is a construct comprising pCK vector (SEQ ID NO: 5) and HGF-X7 (SEQ ID NO: 13) cloned into the pCK vector. pCK-HGF-X7 was deposited under the terms of the Budapest Treaty at the Korean Culture Center of Microorganisms (KCCM) under accession number KCCM-10361 on Mar. 12, 2002.

The amino acid sequences and nucleotide sequences of HGF isoforms used in the methods described herein may further include amino acid sequences and nucleotide sequences substantially identical to sequences of the wild type human HGF isoforms. The substantial identity includes sequences with at least 80% identity, more preferably at least 90% identity and most preferably at least 95% identity where the amino acid sequence or nucleotide sequence of the wild type human HGF isoform is aligned with a sequence in the maximal manner. Methods of alignment of sequences for comparison are well-known in the art. Specifically, alignment algorithm disclosed in the NCBI Basic Local Alignment Search Tool (BLAST) of the National Center for Biological Information (NBCl, Bethesda, Md.) website and used in connection with the sequence analysis programs blastp, blasm, blastx, tblastn and tblastx can be used to determine the percent identity.

6.3.1.3. Plasmid DNA Encoding IGF-1

In some embodiments, the plasmid DNA encodes a human IGF-1 or a variant thereof.

Insulin-like growth factor 1 (IGF-1) is a hormone similar in molecular structure to insulin which plays an important role in childhood growth, and has anabolic effects in adults. The human IGF-1 gene contains six exons (exons 1, 2, 3, 4, 5, and 6 (6-1 and 6-2)) spanning nearly 90 kb of genomic DNA. Exons 1 and 2 are mutually exclusive leader exons, each having multiple promoter sites that are variably used. Further, the IGF-1 gene can be differentially spliced to create multiple transcript variants. Each transcript variant encodes a different pre-pro-IGF-1 protein ("IGF-1 isoform") possessing variable signaling peptide leader sequences. Yet all the transcript isoforms give rise to the same mature 70-amino acid IGF-1 peptide that uses the same receptor after processing.

The pre-pro-IGF-1 peptides differ in their leader, or signal, sequences and in their carboxy (C)-terminus. Incorporation of exon 1 or exon 2 is mutually exclusive and one of them serves as a leader sequence of the pre-pro-IGF-1 peptide; the different leader exons create different 5'-UTRs. The pre-pro-IGF-1 polypeptides undergo posttranscriptional proteolytic cleavage to remove the leader and the E-peptide carboxy-terminus giving rise to the mature 70-amino acid IGF-1.

Transcripts containing exon 1 are referred to as Class 1 transcripts (e.g., Class I, Ec; Class I, Eb; and Class I, Ea) whereas those containing exon 2 are referred to as Class 2 transcripts (e.g., Class II, Ea). Nearly all pre-pro peptides include 27 amino acids in the signaling peptide derived from exon 3 with the remaining signal sequences derived from the inclusion of exon 1 or 2. A minority of transcripts utilize a different transcription initiation site within exon 3 generating a shorter signaling peptide of 22 amino acids. Exons 3 and 4 are invariant and encode the B, C, A, and D domains of the mature IGF-1 peptide; exon 4 encodes two thirds of the mature IGF-1 peptide. The human Eb peptide is composed of only exons 4 and 5 whereas Ec contains exons 4, 5, and 6.

Alternative splicing and mutually exclusive initiation of transcription result in generation of different pre-pro-IGF-1 polypeptides (i.e., IGF-1 isoforms). Specifically, Class I, Ec IGF-1 isoform (SEQ ID NO: 25), comprising at least a fragment of exons 1, 3/4, 5 and 6, is generated from a transcript comprising a sequence of SEQ ID NO: 26. Class II, Ea IGF-1 isoform (SEQ ID NO:27), comprising at least a fragment of exons 2, 3/4 and 6, is generated from a transcript comprising a sequence of SEQ ID NO:28. Class I, Eb IGF-1 isoform (SEQ ID NO:29), comprising at least a fragment of exons 1, 3/4 and 5, is generated from a transcript comprising a sequence of SEQ ID NO:30. Class I, Ea IGF-1 isoform (SEQ ID NO:23), comprising at least a fragment of exons 1, 3/4 and 6 are generated from a transcript comprising a sequence of SEQ ID NO: 24.

Although the mature IGF-1 protein derived from the various transcripts does not differ, the various transcript isoforms have been suggested to have different regulatory roles. The variant forms possess different stabilities, binding partners, and activity indicating a pivotal regulatory role for the isoforms. The biological significance of the isoforms remains unclear, although it has been hypothesized that Class I isoforms with exon 1 are autocrine/paracrine forms while Class II isoforms with exon 2 are secreted endocrine forms. This is based on the finding that Class II transcripts include a typical signal peptide motif associated with efficient secretion, whereas Class I transcripts have a longer signal peptide that can possibly interfere with secretion.

Plasmids encoding one or more isoforms of human IGF-1 have been developed and tested for treating neuropathy as described in U.S. application Ser. Nos. 16/513,560 and/or 16/513,564, which are incorporated by reference in their entirety herein. The plasmids can be used in various embodiments of the present disclosure.

Specifically, in some embodiments, the plasmid contains a coding sequence of one of the IGF-1 isoforms. For example, the DNA construct can comprise a sequence encoding Class I, Ea (SEQ ID NO: 24); Class I, Eb (SEQ ID NO:30); Class I, Ec (SEQ ID NO:26); or Class II, Ea (SEQ ID NO:28).

In some embodiments, the DNA construct is a dual expression construct, a DNA construct that can express more than one IGF-1 isoforms, by comprising an expression regulatory sequence for each isoform coding sequence (CDS). In some embodiments, the construct comprises an internal ribosomal entry site (IRES) between two coding sequences, for example, in the order of (1) expression regulatory sequence—(2) coding sequence of first isoform—(3) IRES—(4) coding sequence of second isoform—(5) transcription termination sequence. IRES allows translation to start at the IRES sequence, thereby allowing expression of two protein products from a single transcript. In yet further embodiments, a plurality of constructs, each encoding a single isoform of IGF-1, are used together to induce expression of more than one isoforms of IGF-1 in the subject to whom administered.

In preferred embodiments, a DNA construct is capable of expressing two or more IGF-1 isoforms simultaneously—e.g., (i) Class I, Ec isoform (Isoform #1) and Class II, Ea isoform (Isoform #2); (ii) Class I, Ec isoform (Isoform #1) and Class I, Eb isoform (Isoform #3); (iii) Class I, Ec isoform (Isoform #1) and Class I, Ea isoform (Isoform #4); (iv) Class II, Ea isoform (Isoform #2) and Class I, Eb isoform (Isoform #3); (v) Class II, Ea isoform (Isoform #2) and Class I, Ea isoform (Isoform #4); (vi) Class I, Eb isoform (Isoform #3) and Class I, Ea isoform (Isoform #4)—by comprising an alternative splicing site.

For example, the DNA construct can comprise (i) a first sequence comprising exons 1, 3 and 4 of a human IGF-1 gene (SEQ ID NO:31) or a degenerate sequence of the first sequence; (ii) a second sequence comprising intron 4 of the human IGF-1 gene (SEQ ID NO:32) or a fragment of the second sequence; (iii) a third sequence comprising exons 5 and 6-1 of the human IGF-1 gene (SEQ ID NO:33) or a degenerate sequence of the third sequence; (iv) a fourth sequence comprising intron 5 of the human IGF-1 gene (SEQ ID NO:34) or a fragment of the second sequence; and (v) a fifth sequence comprising exon 6-2 of the human IGF-1 gene (SEQ ID NO:35) or a degenerate sequence of the fifth sequence. Introns 4 and 5 can be alternatively spliced, resulting in production of two isoforms of IGF-1 (e.g., Class I, Ec and Class I, Ea).

In some embodiments, the DNA construct is tested in vitro and/or in vivo related to its capability to express one or more IGF-1 isoforms. In preferred embodiments, DNA constructs capable of expressing both Class I, Ec and Class I, Ea IGF-1 isoforms are selected.

Various DNA constructs comprising cDNA corresponding (i) exons 1-6 of the human IGF-1 gene and (ii) introns 4 and 5 of the human IGF-1 gene or various fragments of introns 4 and 5 are named "IGF-1X" followed by a unique number. The IGF-1X constructs tested by Applicant include, but are not limited to, IGF-1X1, IGF-1X2, IGF-1X3, IGF-1X4, IGF-1X5, IGF-1X6, IGF-1X7, IGF-1X8, IGF-1X9 and IGF-1X10. Among the tested constructs, IGF-1X6 and IGF-1X10 were identified to express both Class I, Ec and Class I, Ea IGF-1 isoforms.

In preferred embodiments, IGF-1X6 (SEQ ID NO:21) or IGF-1X10 (SEQ ID NO:22) is used. IGF-1X6 (SEQ ID NO:21) and IGF-1X10 (SEQ ID NO:22) cloned into a pCK vector are named pCK-IGF-1X6 and pCK-IGF-1X10, respectively. E.coli cells transformed with pCK-IGF-1X6 ("DH5α_pCK-IGF1 X6") were deposited under the terms of the Budapest Treaty at the Korea Collection for Type Cultures (KCTC, Korea Research Institute of Bioscience and Biotechnology (KRIBB) 181, Ipsin-gil, Jeongeup-si, Jeollabuk-do, 56212, Republic of Korea) with accession number KCTC 13539BP on May 30, 2018. E.coli cells transformed with pCK-IGF-1X10 ("DH5α_pCK-IGF1 X10") were deposited under the terms of the Budapest Treaty at the Korea Collection for Type Cultures (KCTC, Korea Research Institute of Bioscience and Biotechnology (KRIBB) 181, Ipsin-gil, Jeongeup-si, Jeollabuk-do, 56212, Republic of Korea) with accession number KCTC 13540BP on May 30, 2018.

In some embodiments, the pTx plasmid contains IGF-1X6 (i.e., pTx-IGF-1X6) or IGF-1 X10 (i.e., pTx-IGF-1X10). For example, pTx-IGF-1X10 (SEQ ID NOs: 16) generated by ligating IGF-1X10 in pTx digested with ClaI enzyme at 5' and SalI enzyme at 3' can be used.

In some embodiments, the pTx plasmid contains IGF-1Ec or IGF-1Ea. For example, pTx-IGF-1Ec is generated by ligating IGF-1Ec (SEQ ID NO: 26) in pTx, and pTx-IGF-1Ea is generated by ligating IGF-1Ea (SEQ ID NO: 24) in pTx. The plasmids express the IGF-1Ec isoform (SEQ ID NO:25) or IGF-1Ea isoform (SEQ ID NO:23), respectively.

IGF-1 isoforms or plasmids encoding IGF-1 isoforms described herein can include modifications from the wild type human IGF-1 isoforms. The modified sequences can include sequences with at least 80% identity, more preferably at least 90% identity and most preferably at least 95% identity when the modified sequences are aligned with the wild type human IGF-1 isoform sequences in the maximal manner. Methods of alignment of sequences for comparison are well-known in the art. Specifically, alignment algorithm disclosed in the NCBI Basic Local Alignment Search Tool (BLAST) of the National Center for Biological Information (NBCl, Bethesda, Md.) website and used in connection with the sequence analysis programs blastp, blasm, blastx, tblastn and tblastx can be used to determine the percent identity.

6.3.1.4. Plasmid DNA Encoding SDF-1α

The stromal cell-derived factor 1 (SDF-1), also known as C-X-C motif chemokine 12 (CXCL12) is a chemokine protein that in human is encoded by the CXCL12 gene on chromosome 10. It is ubiquitously expressed in many tissues and cell types. Stromal cell-derived factors 1α (SDF-1α) and 10 (SDF-1β) are small cytokines that belong to the chemokine family, members of which activate leukocytes and are often induced by proinflammatory stimuli such as lipopolysaccharide, TNF, or IL1. SDF-1 is produced in two forms, SDF-1α/CXCL12a and SDF-1β/CXCL12b, by alternate splicing of the same gene.

Plasmids encoding one or more isoforms of human SDF-1 have been developed and tested for treating peripheral vascular disease as described in U.S. application Ser. No. 15/514,244, incorporated herein by reference in its entirety. Specifically, a polynucleotide encoding the SDF-1α effectively promoted vascular endotherlial cell migration and angiogenesis when administered together with a polynucleotide encoding human HGF.

Plasmids encoding one or more isoforms of SDF-1 can be used in various embodiments of the present disclosure. In some embodiments, the plasmid encoding one or more SDF-1 disclosed in U.S. application Ser. No. 15/514,244 is used. In some embodiments, the plasmid comprising a coding sequence of SDF-1α is used. In some embodiments, the plasmid comprising a coding sequence of SDF-1β is used. In some embodiments, the plasmid encoding both SDF-1α and SDF-1β is used. In a particular embodiment, the plasmid comprising the sequence of SEQ ID NO: 36 is used.

6.3.2. Buffer

A liquid composition further comprises a buffer to maintain pH of the pharmaceutical composition. The buffer can include a buffer compound known in the art, such as TAPS, Bicine, Tris, Tricine, TAPSO, HEPES, TES, MPOS, PIPES, Cacodylate, or MES. The buffer can contain citric acid, monopotassium phosphate, boric acid, or diethyl barbituric acid. The buffer can be PBS, HEPES, TRIS or TRIS/EDTA buffer. The buffer can be other phosphate buffer. Phosphate buffers can comprise a mixture of monobasic dihydrogen phosphate and dibasic monohydrogen phosphate.

Specifically, the buffer can be potassium phosphate buffer. The potassium phosphate buffer can comprise potassium phosphate at a concentration from 5 mM to 15 mM, from 7.5 mM to 12.5 mM, from 9 mM to 11 mM, or at 10 mM.

The buffer contained in the liquid composition can have pH from 7 to 9. In some embodiments, the pH is from 7.0 to 8.5 or 8.0. In some embodiments, the pH is from 7.0 to 8.0.

In some embodiments, the liquid composition comprises a 7.5-12 mM potassium phosphate buffer of pH from 7 to 9. In some embodiments, the liquid composition comprises a 7.5-12 mM potassium phosphate buffer of pH from 7.0 to 8.0. In some embodiments, the liquid composition comprises 9-11 mM potassium phosphate buffer of pH from 7.0 to 8.5. In some embodiments, the liquid composition includes 10 mM potassium phosphate buffer at pH 8.0.

6.3.3. Carbohydrate

The stability of the plasmid DNA in the lyophilized pharmaceutical composition can be increased by formulating the plasmid DNA prior to lyophilization with an aqueous solution comprising a stabilizing amount of carbohydrate. The carbohydrate can be mannitol or sucrose.

The carbohydrate can be added to the liquid composition to have a final concentration of the carbohydrate about 0.05% to about 30%, about 0.1% to about 15%, about 0.2% to about 15%, about 0.2% to about 10%, about 0.5% to about 10%, about 1% to about 5%, about 1% to about 3%, about 0.75% and 1.1%, about 0.9% and 1.1%, about 1.0% or about 1.1%.

In some embodiments, the liquid composition has a final concentration of at least one carbohydrate, greater than 0.1% and less than 15%, greater than 0.2% and less than 10%, greater than 0.3% and less than 7.5%, greater than 0.5% and less than 5%, greater than 0.5% and less than 3%, greater than 0.5% and less than 2%, greater than 0.5% and less than 1.1%, greater than 0.75% and less than 1.1%, greater than 0.9% and less than 1.1%, or 1.0%.

Specifically, the liquid composition can have a final concentration of sucrose about 0.05% to about 30%, about 0.1% to about 15%, about 0.2% to about 15%, about 0.2% to about 10%, about 0.5% to about 10%, about 1% to about 5%, about 1% to about 3%, about 0.75% to about 1.1%, about 0.9% to about 1.1%, or about 1.0%.

In some embodiments, the liquid composition has a final concentration of sucrose, greater than 0.1% and less than 15%, greater than 0.2% and less than 10%, greater than 0.3% and less than 7.5%, greater than 0.5% and less than 5%, greater than 0.5% and less than 3%, greater than 0.5% and less than 2%, greater than 0.5% and less than 1.1%, greater than 0.75% and less than 1.1%, greater than 0.9% and less than 1.1%, or 1.0%.

In some embodiments, the liquid composition has a final concentration of mannitol less than 5%, less than 4%, less than 3%. In some embodiments, the liquid composition has a final concentration of mannitol from 0% to 10%, from 1% to 9%, from 2% to 7.5%, from 2% to 3%, from 2% to 5%, from 2% to 4%, from 0% to 3%, from 0% to 2%, from 1% to 2%, from 1.5% to 3%, or 2%.

In some embodiments, the liquid composition has a final concentration of mannitol greater than 0% and less than 10%, greater than 0% and less than 7.5%, greater than 0% and less than 5%, greater than 0% and less than 4%, greater than 0% and less than 3% or greater than 0% and less than 2.5%, or greater than 1% and less than 2.5%.

In some embodiments, the liquid composition has a final concentration of sucrose greater than 0.5% and less than 1.1%, and a final concentration of mannitol greater than 0% and less than 3%. In some embodiments, the liquid composition has a final concentration of sucrose from 0.7% to 1.1%, and a final concentration of mannitol from 1.5% to 3% or 2%. In some embodiments, the liquid composition has a final concentration of sucrose from 0.9% to 1.1%, and a final concentration of mannitol from 1.5% to 3% or 2%. In some embodiments, the liquid composition has a final concentration of sucrose at 1.0% and a final concentration of mannitol from 1.5% to 3%, from 2% to 3%, or 2%.

In some embodiments, other carbohydrate is used in the composition. The carbohydrate can be a mono-, oligo-, or polysaccharide, such as sucrose, glucose, lactose, trehalose, arabinose, pentose, ribose, xylose, galactose, hexose, idose, mannose, talose, heptose, fructose, glu conic acid, sorbitol, mannitol, methyl a-glucopyranoside, maltose, isoascorbic acid, ascorbic acid, lactone, Sorbose, glucaric acid, erythrose, threose, allose, altrose, gulose, erythrulose, ribulose, xylulose, psicose, tagatose, glucuronic acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dext ran, cyclodextrin, pustulan, chitin, agarose, keratin, chon droitin, dermatan, hyaluronic acid, alginic acid, xantham gum, or starch.

6.3.4. Salt

The liquid composition further contains a salt. The salt can be NaCl or KCl.

In some embodiments, the liquid composition comprises a salt at a concentration greater than 0.1% and less than 0.9%, greater than 0.25% and less than 0.75%, greater than 0.4% and less than 0.6%, greater than 0.4% and 0.5% or at a concentration of 0.45%. In some embodiments, the liquid composition comprises a salt at a concentration from 0.1% to 0.9%, from 0.1% to 0.6%, from 0.25% to 0.75%, from 0.4% to 0.6%, from 0.4% to 0.5% or at a concentration of 0.45%.

In some embodiments, the liquid composition comprises NaCl at a concentration greater than 0.1% and less than 0.9%, greater than 0.25% and less than 0.75%, greater than 0.4% and less than 0.6%, greater than 0.4% and 0.5% or at a concentration of 0.45%. In some embodiments, the liquid composition comprises NaCl at a concentration from 0.1% to 0.9%, from 0.1% to 0.6%, from 0.25% to 0.75%, from 0.4% to 0.6%, from 0.4% to 0.5% or at a concentration of 0.45%.

In some embodiments, the liquid composition comprises KCl at a concentration greater than 0.1% and less than 0.9%, greater than 0.25% and less than 0.75%, greater than 0.4% and less than 0.6%, greater than 0.4% and 0.5% or at a concentration of 0.45%. In some embodiments, the liquid composition comprises KCl at a concentration from 0.1% to 0.9%, from 0.25% to 0.75%, from 0.4% to 0.6%, from 0.4% to 0.5% or at a concentration of 0.45%.

In some embodiments, other salt is used in the composition. The salt can a monovalent cationic halide salt (e.g., sodium chloride, potassium chloride, sodium bromide, lithium chloride, sodium iodide, potassium bromide, lithium bromide, sodium fluoride, potassium fluoride, lithium fluoride, and/or lithium iodide), a divalent or trivalent salt (e.g., calcium chloride, magnesium chloride, calcium sulfate, sodium sulfate, magnesium sulfate, chromium trichloride, chromium sulfate, sodium citrate, Iron (III) chloride, Yttrium (III) chloride, potassium phosphate, potassium sulfate, potassium chloride, sodium acetate, sodium phosphate, potassium phosphate, ferrous chloride, ferric chloride), or a combination thereof.

6.4. Lyophilization Conditions

A lyophilized composition of the present invention is generated by lyophilizing a liquid composition described herein. The liquid composition can be lyophilized under standard lyophilization conditions known in the art or modifications thereof.

A method for lyophilizing the liquid composition of the invention can comprise (a) loading a container with the liquid composition at a starting temperature of about 5° C. to about −50° C.; (b) cooling the DNA formulation to subzero temperatures (e.g., −10° C. to −50° C.); and (c) substantially drying the DNA formulation. The conditions for lyophilization, e.g., temperature and duration, of the DNA formulation of the invention can be adjusted by a person of ordinary skill in the art taking into consideration factors that affect lyophilization parameters, e.g., the type of lyophilization machine used, the amount of DNA used, and the size of the container used.

In some embodiments, the steps of (b) cooling and (c) drying are performed while changing temperatures. For example, the step of freezing can be performed while raising temperatures from −50° C. to −40° C., from −50° C. to −30° C., from −50° C. to −20° C., from −50° C. to −10° C., or from −50° C. to 0° C. In some embodiments, the step of freezing can be performed while reducing temperatures from −40° C. to −50° C., from −30° C. to −50° C., from −20° C. to −50° C., from −10° C. to −50° C., from 0° C. to −50° C., or from 5° C. to −50° C. In some embodiments, the step of freezing is performed while reducing the temperature and then raising the temperature.

Some amorphous products (such as mannitol or glycine) form a metastable glass with incomplete crystallization when first frozen. These products can benefit from a thermal treatment process, which is also called annealing. During annealing, the product temperature is cycled (for example: from −40° C. to −20° C. for a few hours and then back to −40° C.; from −50° C. to −20° C., holding for two (2) hours, and then introducing the vacuum; or from −50° C. to −20° C. and then back to −50° C.) to obtain more complete crystallization. Annealing has the added advantage of larger crystal growth and corresponding shorter drying times. Water trapped in the amorphous phase can be further removed during the secondary drying.

In some embodiments, the step of drying is performed in two steps—(i) primary drying and (ii) secondary drying.

In some embodiments, primary drying is performed while maintaining the temperature, or while raising or reducing temperatures. In some embodiments, primary drying is performed while maintaining the temperature at −50° C., −40° C., −30° C., −20° C., −10° C., or 0° C. In some embodiments, secondary drying is performed while maintaining the temperature, or while raising or reducing temperatures. In some embodiments, the secondary drying can be performed while raising temperatures from −50° C. to 20° C., from −40° C. to 20° C., from −30° C. to 20° C., from −20° C. to 20° C., from −10° C. to 20° C., from −50° C. to 10° C., from −40° C. to 10° C., from −30° C. to 10° C., from −20° C. to 10° C., from −10° C. to 10° C.

During lyophilization process, a phase separation can occur. For example, a pure crystalline phase can be separate from saturated amorphus phase. The crystalline phase can include ice or any other crystallizing excipients. Thus, during primary drying, the pure ice phase can be removed, leaving behind other crystalline phases and any saturated amorphous phases. Conditions for primary drying can be adjusted to effectively remove this unbound water while maintaining the cake structure and DNA stability. Primary drying (sublimation) is a slow process conducted at cooler temperatures, safely below the product's critical collapse temperature. Sublimation requires heat energy to drive the phase change process from solid to gas. All three methods of heat transfer—conduction, convection and radiation, must be considered when freeze drying a product Each liquid composition has a unique critical temperature. It is necessary to keep the composition at a temperature safely below this critical temperature during primary drying to avoid collapse. The temperature is dependent on the vapor pressure at the ice interface and in turn, this vapor pressure is dependent on both the rate of heat transfer into the composition (which is controlled by adjusting the shelf temperature) and the system vacuum level set point. During primary drying, the system pressure and the shelf temperature are set and controlled in combination to yield the appropriate product temperature. With the temperature and pressure parameters set, primary drying is then continued for a length of time sufficient for all of the ice crystals to be sublimed.

In addition to the free ice that is sublimed during primary drying, there remains a substantial amount of water molecules that are bound to the product. This is the water that is removed (desorbed) during secondary drying. Since all of the free ice has been removed in primary drying, the product temperature can now be increased considerably without fear of melting or collapse. Secondary drying actually starts during the primary phase, but at elevated temperatures (typically in the 20 to 50° C. range), desorption proceeds much more quickly.

Secondary drying rates are dependent on the product temperature. System vacuum may be continued at the same level used during primary drying; lower vacuum levels will not improve secondary drying times.

Secondary drying is continued until the product has acceptable moisture content for long term storage. Depending on the application, moisture content in fully dried products is typically from 0.5% to 3%. In most cases, the more dry the product, the longer its shelf life will be. However, certain complex biological products may actually become too dry for optimum storage results and the secondary drying process should be controlled accordingly.

The step of secondary drying can be performed while raising temperatures from −50° C. to 20° C., from −40° C. to 20° C., from −30° C. to 20° C., from −20° C. to 20° C., from −10° C. to 20° C., from −50° C. to 10° C., from −40° C. to 10° C., from −30° C. to 10° C., from −20° C. to 10° C., from −10° C. to 10° C.

6.5. Lyophilized Composition in a Unit Dose

Another aspect of the present invention is a lyophilized pharmaceutical composition in a unit dose. In some embodiments, the unit dosage form is a vial, ampule, bottle, or pre-filled syringe. In some embodiments, a unit dose contains about 50 µg to 1 g of plasmid DNA, 100 µg to 1 g of plasmid DNA, 100 µg to 100 mg of plasmid DNA, 1 mg to 100 mg of plasmid DNA, 10 mg to 100 mg of plasmid DNA, or 10 mg to 50 mg of plasmid DNA. A unit dose can comprise about 10 µg, 50 µg, 100 µg, 1 mg, 10 mg, 100 mg or 1 g of plasmid DNA. The unit dosage form can contain 0.01 mg, 0.1 mg, 0.2 mg, 0.25 mg, 0.5 mg, 1 mg, 2.5 mg, 5 mg, 8 mg, 10 mg, 12.5 mg, 16 mg, 24 mg, 25 mg, 50 mg, 75 mg, 100 mg, 150 mg, or 200 mg of the plasmid DNA.

In typical embodiments, the unit dosage form is a vial containing 50 mg, 10 mg, 7.5 mg, 5 mg, 1 mg, 100 µg or 50 µg of the lyophilized pharmaceutical composition suitable for administration after reconstitution. The administration includes subcutaneous, intradermal, or intramuscular administration using preloaded syringes, auto-injectors, and auto-inject pens, each containing a predetermined amount of the pharmaceutical composition described hereinabove.

The unit dose in a container can be determined based on various factors, such as an active ingredient (e.g., plasmid DNA), a disease to be treated, a subject, a route and method of administration. The unit dose can be determined based on in vitro or in vivo studies, including clinical trials.

The unit dose in a container can be sealed and stored for an extended period of time at various temperatures (e.g., room temperature to about −180° C., preferably about 2-8° C. to about −80° C., more preferably about −20° C. to about −80° C., and most preferably about −20° C.).

The lyophilized DNA compositions stored in the container are preferably stable within a range of from about 2-20° C. to about −80° C., for a period of at least 1 month, 3 months, 6 months or 1 year without losing significant activity. Storage time may be as long as several months, 1 year, 5 years, 10 years, 15 years, or up to 20 years. Preferably the preparation is stable for a period of at least about 3 years.

6.6. Characterization of the Lyophilized Composition

The present invention provides a lyophilized pharmaceutical composition having one or more desired properties as a pharmaceutical product. The properties can include stability and potency of the active ingredient in various storage conditions, cake formation, a uniform reconstitution of the formulation for administration, less contaminations, etc. Various properties provided herein can be used to select a preferred lyophilized composition or to determine ideal storage conditions for the lyophilized composition.

Stability of plasmid DNA in the lyophilized composition can be determined based on methods known in the art. In particular, stability can be determined based on the conformation of plasmid DNA, for example, whether they exist as a more stable supercoiled form or a less stable open circle and linear form. Conformation of plasmid DNA can be determined by capillary electrophoresis of a sample containing plasmid DNA. The supercoiled DNA contents compared to the open circle and linear form can be measured in various conditions. For example, the supercoiled DNA contents can be determined before, during or after lyophilization, or before, during or after reconstitution of the lyophilized composition. The supercoiled DNA contents can be also determined before, during or after a storage at different temperatures to select a stable lyophilized composition as well as to determine an ideal storage condition.

Another way to determine stability of plasmid DNA is based on DNA concentrations. Various methods of measuring DNA concentrations known in the art can be adopted. For example, DNA concentrations can be measured based on light absorbance at 260 nm. The method can further involve measurement of contaminants to better quantify DNA concentrations in the sample.

Cake appearance can be another important attribute of a lyophilized product. Uniform and elegant cake appearance is generally preferred. The non-ideal cake appearance can affect product quality, for example, by making it difficult to determine product quality based on visual inspection or making it difficult to recover the full amount of the active ingredient in a container. In addition, partial or complete meltback of the cake can result in instability and degradation of the active ingredient. Meltback is a form of cake collapse and is caused by the change from the solid to liquid state. That is, there is incomplete sublimation (change from the solid to vapor state) in the vial. These changes can involve a change in the physical form of the drug substance and a pocket of moisture.

Cake appearance can be determined by visual inspection that may involve taking a photograph. Visual inspections can be performed largely based on historical precedent. A robust qualification program for visual inspection is important before judging product quality. The qualification program can be based on past experience or published information. Visual inspection guidelines for a particular drug product can be developed specific to the drug product, for example, based on the information provided in the inspection guide, "Lyophilization of Parenterals: Guide To Inspections of Lyophilization of Parenterals (July 1993)," published by the US Food and Drug Administration.

Another attribute of a lyophilized product that can affect the quality of a drug product is turbidity of a reconstituted drug obtained by dissolving the lyophilized product. Turbidity of a reconstituted drug can correlate with recovery of active ingredients in the lyophilized composition. In general, a complete dissolution, i.e., a low turbidity of the reconstituted drug, is preferred. Incomplete dissolution can result in waste of active ingredients of the pharmaceutical composition and blockage of a syringe for administering the reconstituted drug.

Turbidity of a reconstituted drug can be measured by visual inspections or by measuring light absorbance at certain wavelengths, e.g., at 450 nm and 650 nm. Light absorbance can be measured using a device available in the art, for example, a Molecular Devices ThermoMAX microplate.

Reconstitution time is another factor that can be related with the quality of a drug product. In general, a short reconstitution time is preferred. Increased time for reconstitution at the user stage may result in partial loss of potency if the drug is not completely dissolved, since it is common to use in-line filters during administration to the patient. Time required for reconstitution of the lyophilized product can be determined, for example, by measuring turbidity of the reconstituted drug at various time points after reconstitution. For example, turbidity can be measured after 1 min, 5 mins, 10 mins, 15 mins, 20 mins, 25 mins, 30 mins, 1 hour, 2 hour, or more.

Residual moisture after lyophilization can be also important. Various methods known in the art can be adopted to measure residual moisture in the lyophilized composition. For example, a Karl Fisher Coulometer C20 (Mettler Toledo) can be used for moisture content analysis. A pocket of moisture in a lyophilized composition can result in greater instability and increased product degradation. Thus, less moisture content can be preferred.

6.7. Methods of Treating a Disease Using the Lyophilized Composition

Methods of treating diseases using the lyophilized composition is within the scope of the present invention.

6.7.1. Reconstitution of the Lyophilized Composition

Various methods for reconstitution can be employed, such as the swirling methods, methods using a mechanical orbital shaker or methods of keeping the vial remained stationary.

The final concentration of reconstituted drug for administration can be adjusted depending on many factors, including the amount of a formulation to be delivered, the age and weight of the subject, the delivery method and route and the immunogenicity of the antigen being delivered.

The lyophilized composition of the present invention can be reconstituted with an acceptable solution, such as water, TE, PBS, Tris buffer, or normal saline, to the final concentration of about 10 mg/ml, 5 mg/ml, 1 mg/ml, 0.5 mg/ml, 0.3 mg/ml, 0.2 mg/ml, 0.1 mg/ml, or 0.05 mg/ml.

6.7.2. Administration of the Reconstituted Drug

The reconstituted drug of the present invention can be administered to a mammalian subject to treat various diseases. The reconstituted lyophilized composition of the invention may be administered by various delivery medthods—e.g., orally or via parenteral routes such as intravenous, intramuscular, intraendocardial, intramyocardial, intrapericardial, intraventricular, intraar ticular, intradermal, intracerebral, intrarenal, intrahepatic, intrasplenic, intralymphatic, subcutaneous, intraabdominal, intratesticular, intraovarian, intrauterine, sternal, intratra cheal, intraplueral, intrathoracic, intradural, intraspinal, intramedullary, intramural, intrascorionic and arterial injec tion or infusion, or topically through rectal, intranasal, inha lational or intraocular administration. In certain embodiments, the method of delivery is intramuscular, intramyocardial, intravenous, intracerebral, or intrarenal.

In typical embodiments, the nucleic acid construct is administered by injection of a liquid pharmaceutical composition. In currently preferred embodiments, the polynucleotide construct is administered by intramuscular injection. Typically, the polynucleotide construct is administered by intramuscular injection close to the affected site. In some embodiments, the polynucleotide constructs are administered to the muscles of limbs, heart, or other body parts of the subject.

In some embodiments, the construct is injected subcutaneously or intradermally. In some embodiments, the polynucleotide construct is administered by intravascular delivery. In certain embodiments, the construct is injected by retrograde intravenous injection.

It should be understood that the typical daily dose of the reconstituted lyophilized composition of the present invention ought to be determined in light of various relevant factors including the conditions to be treated, the chosen route of administration, the age, sex and body weight of the individual patient, and the severity of the patient's symptom, and can be administrated in a single dose or in divided doses. The polynucleotide construct is administered in a therapeutically effective dose.

In some embodiments of the methods described herein, the polynucleotide construct is administered at a total dose of 1 µg to 200 mg, 1 mg to 200 mg, 1 mg to 100 mg, 1 mg to 50 mg, 1 mg to 20 mg, 5 mg to 10 mg, 16 mg, 8 mg, or 4 mg.

In typical embodiments, the total dose is divided into a plurality of individual injection doses. In some embodiments, the total dose is divided into a plurality of equal injection doses. In some embodiments, the total dose is divided into unequal injection doses.

In various divided dose embodiments, the total dose is administered to 4, 8, 16, 24, or 32 different injection sites.

In some embodiments, the injection dose is 0.1-5 mg. In certain embodiments, the injection dose is 0.1 mg, 0.15 mg, 0.2 mg, 0.25 mg, 0.3 mg, 0.35 mg, 0.4 mg, 0.45 mg, or 0.5 mg.

The total dose can be administered during one visit or over two or more visits.

In typical divided dose embodiments, all of the plurality of injection doses are administered within 1 hour of one another. In some embodiments, all of the plurality of injection doses are administered within 1.5, 2, 2.5 or 3 hours of one another.

In various embodiments of the methods, a total dose of polynucleotide construct, whether administered as a single unitary dose or divided into plurality of injection doses, is administered only once to the subject.

In some embodiments, administration of a total dose of polynucleotide construct into a plurality of injection sites over one, two, three or four visits can comprise a single cycle. In particular, administration of 32 mg, 16 mg, 8 mg, or 4 mg of polynucleotide construct into a plurality of injection sites over two visits can comprise a single cycle. The two visits can be 3, 5, 7, 14, 21 or 28 days apart.

In some embodiments, the cycle can be repeated. The cycle can be repeated twice, three times, four times, five times, six times, or more.

In some embodiments, the cycle can be repeated 1, 2, 3, 4, 5, 6, 7, 8, 9, 10, 11, 12, or more months after the previous cycle.

In some embodiments, the total dose administered in the subsequent cycle is same as the total dose administered in the prior cycle. In some embodiments, the total dose administered in the subsequent cycle is different from the total dose administered in the prior cycle.

In currently preferred embodiments, the nucleic acid construct is administered at a dose of 8 mg per affected limb, equally divided into a plurality of intramuscular injections and plurality of visits, wherein each of the plurality of injections in any single visit is performed at a separate injection site. In certain embodiments, the nucleic acid construct is administered at a dose of 8 mg per affected limb, equally divided into a first dose of 4 mg per limb on day 0 and a second dose of 4 mg per limb on day 14, wherein each of the first and second dose is equally divided into a plurality of injection doses.

The actual amount administered, and rate and time-course of administration, will depend on the nature and severity of the disease being treated. In typical embodiments, the polynucleotide construct is administered in an amount effective to reduce symptoms of the disease, for example, pain. In some embodiments, the amount is effective to reduce the symptom within 1 week of administration. In some embodiments, the amount is effective to reduce the symptom within 2 weeks, 3 weeks, or 4 weeks of administration.

The plasmid DNA can be administered alone or in combination with other plasmid DNA, either simultaneously or sequentially dependent upon the condition to be treated.

In some embodiments, the reconstituted composition comprises a plasmid DNA encoding a human HGF. The reconstituted drug can be administered to treat various diseases, for example, a disease previously demonstrated to be treatable by administration of a plasmid DNA. The plasmid DNA can encode a therapeutic gene, such as human HGF. The disease includes but is not limited to ischemic or liver disease, coronary artery disease ("CAD"), amytrophic lateral sclerosis ("ALS"), peripheral artery disease ("diabetic ulcer"), and diabetic peripheral neuropathy ("DPN") or neuropathy caused by diseases, injuries, infections or vitamin deficiency states. For example, the neuropathy can be caused by diabetes, vitamin deficiencies, autoimmune diseases, genetic or inherited disorders, amyloidosis, uremia, toxins or poisons, trauma or injury, tumors, or can be idiopathic. Methods described in U.S. Pat. Nos. 7,812,146; 7,838,505; 7,745,174; 8,338,385; 8,389,492 and U.S. application Ser. Nos. 12/359,137; 14/355,792; 15/030,999 can be adopted to treat the diseases by administering the lyophilized composition. The references provided herein are incorporated by reference in their entirety herein.

In some embodiments, the reconstituted composition comprises a plasmid DNA encoding a human IGF-1. The reconstituted drug can be administered to treat various diseases, for example, a disease previously demonstrated to be treatable by administration of a plasmid DNA encoding a human IGF-1 or a human IGF-1 protein. The disease includes but is not limited to neuropathy caused by diseases, injuries, infections or vitamin deficiency states. For example, the neuropathy can be caused by diabetes, vitamin deficiencies, autoimmune diseases, genetic or inherited disorders, amyloidosis, uremia, toxins or poisons, trauma or injury, tumors, or can be idiopathic. In some embodiments, a plasmid encoding a human IGF-1 protein (pTx-IGF-1) is administered with another plasmid encoding human HGF (e.g., VM202) to treat a disease. Methods described in U.S. application Ser. Nos. 16/513,560 and/or 16/513,564 can be adopted to treat the diseases by administering the lyophilized composition.

In some embodiments, the reconstituted composition comprises a plasmid DNA encoding human SDF-1α. The plasmid can be administered alone or together with a different plasmid DNA to treat a disease. In some embodiments, a plasmid encoding human SDF-1α (e.g., pCK-SDF-1α) is administered with another plasmid DNA encoding human HGF (e.g., VM202) to treat a disease. The disease includes but is not limited to vascular disease, such as peripheral vascular disease. Methods described in U.S. application Ser. No. 15/514,244 can be adopted to treat a disease by administering a plasmid encoding human SDF-1α.

6.8. Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); nt, nucleotide(s); and the like.

The practice of the present invention will employ, unless otherwise indicated, conventional methods of protein chemistry, biochemistry, recombinant DNA techniques and pharmacology, within the skill of the art.

6.8.1. Example 1: Lyophilized Composition of VM202 (Study 001)

6.8.1.1. Tested Pharmaceutical Composition Comprising VM202

Various formulations containing VM202 as provided below in TABLE 1 were prepared. The active ingredient, the VM202 plasmid, was obtained from frozen stocks containing either 1.6 mg/mL of VM202 in 0.9% NaCl or 1.3 mg/mL of VM202 in 0.9% NaCl.

TABLE 1

| Code | Buffer | pH | Bulking Agent | Stabilizer(s) | VM202 Concentration (mg/mL) |
|---|---|---|---|---|---|
| KP8M2SN | 10 mM Potassium Phosphate | 8.0 | 2% Mannitol | 1.0% Sucrose, 0.1% NaCl | 0.5 |
| KP8MS3N** | 10 mM Potassium Phosphate | 8.0 | 2% Mannitol | 0.5% Sucrose, 0.45% NaCl | 0.5 |
| KP8MT3N | 10 mM Potassium Phosphate | 8.0 | 2% Mannitol | 0.5% Trehalose, 0.45% NaCl | 0.5 |
| 4MSN | 10 mM Potassium Phosphate | 8.0 | 4% Mannitol | 0.5% Sucrose, 0.45% NaCl | 0.5 |
| 3MSN | 10 mM Potassium Phosphate | 8.0 | 3% Mannitol | 0.5% Sucrose, 0.45% NaCl | 0.5 |
| 2MSN** | 10 mM Potassium Phosphate | 8.0 | 2% Mannitol | 0.5% Sucrose, 0.45% NaCl | 0.5 |
| 2M1SN | 10 mM Potassium Phosphate | 8.0 | 2% Mannitol | 1.0% Sucrose, 0.45% NaCl | 0.5 |
| Control* | None | — | None | 0.9% NaCl, 1.1% Sucrose | 0.5 |

*Control is a formulation previously described in U.S. Pat. No. 8,389,492, which is incorporated hereinby reference in its entirety.
**KP8MS3N and 2MSN are lyophilized formulations of the same compositions.

The formulations were prepared using commercially available materials and equipment, for example, Potassium Phosphate monobasic (Spectrum, catalog #PO200), Potassium Phosphate dibasic (EMD, catalog #PX1570-1), Mannitol (J.T.Baker, catalog #2553-05), Sucrose (J.T.Baker, catalog #4074-05), Sodium Chloride (Millipore, catalog #1.06404.5000) and Trehalose (Pfanstiehl, catalog #T-104-04), a dialysis cassette (Thermo Scientific, catalog #66380 (10,000 MWCO)), glass vials (3 cc or 20 cc glass vials (Schott Type I borosilicate, catalog #68000316 or 68000321)), and stoppers (13 mm or 20 mm single-vent lyo stopper, Flurotec®, (West Pharmaceutical, catalog #19700034 or 19700311)). Excipients such as Dextran (MP Biomedicals, catalog #101514), Lithium Hydroxide (Sigma Aldrich, catalog #L4533-100G), and Phosphiric acid (J.T.Baker, catalog #0262-01) were also used.

6.8.1.2. Small Scale Test of Various Formulations

6.8.1.2.1. Sample Preparation

To generate various formulations, vials with VM202 at 1.6 mg/mL in 0.9% NaCl were removed from −70° C. storage and thawed at ambient temperature.

Samples for the 1$^{st}$ round of small scale test: KP8M2SN (see Table 1) was then prepared by dialyzing out using a 10,000 MWCO Thermo dialysis cassette at ≥10,000-fold volume exchange against the target formulation buffer (10 mM potassium phosphate, 2% mannitol, 1.0% sucrose, 0.1% NaCl, pH 8.0) over 24 hours at 2-8° C. Following dialysis, the concentration of KP8M2SN was adjusted to 0.5 mg/mL of VM202 with formulation buffer.

KP8MS3N, KP8MT3N and Control were prepared by diluting the drug substance. Specifically, 1.7 mL of VM202 (i.e., VM202 in 0.9% NaCl) was diluted with 0.85 mL of the dilution buffers (Buffer No. 2 for KP8MS3N, Buffer No. 3 for KP8MT3N, and Buffer No. 8 for Control) provided below in TABLE 2. Following the dilutions, each formulation was adjusted to contain 0.5 mg/mL of VM202 for KP8MS3N and KP8MT3N respectively, with a formulation buffer containing 0.45% NaCl.

Samples for the 2$^{nd}$ round of small scale tests: 4MSN, 3MSN, and 2MSN were prepared by diluting 0.84 mL of the drug substance (i.e., VM202 in 0.9% NaCl) with 0.42 mL of dilution buffers (Buffer 4 for 4MSN, Buffer 5 for 3MSN, and Buffer 6 for 2MSN) also provided below in TABLE 2. Following dilution, each formulation except Control was adjusted to include 0.5 mg/mL of VM202 using each formulation buffer containing 0.45% NaCl.

TABLE 2

| Dilution Buffer No. | Buffer | pH | Bulking Agent | Stabilizer(s) |
|---|---|---|---|---|
| 2 (for KP8MS3N) | 30 mM Potassium Phosphate | 8.0 | 6% Mannitol | 1.5% Sucrose |
| 3 (for KP8MT3N) | 30 mM Potassium Phosphate | 8.0 | 6% Mannitol | 1.5% Trehalose |
| 4 (for 4MSN) | 30 mM Potassium Phosphate | 8.0 | 12% Mannitol | 1.5% Sucrose |
| 5 (for 3MSN) | 30 mM Potassium Phosphate | 8.0 | 9% Mannitol | 1.5% Sucrose |
| 6 (for 2MSN) | 30 mM Potassium Phosphate | 8.0 | 6% Mannitol | 1.5% Sucrose |
| 7 (for 2M1SN) | 30 mM Potassium Phosphate | 8.0 | 6% Mannitol | 3.0% Sucrose |
| 8 (for Control) | None | — | None | 0.9% NaCl, 3.3% Sucrose |

Sample preparation for accelerated stability test: A separate set of the formulations was further prepared for accelerated stability test. For the separate set, 4MSN, 3MSN, 2MSN, 2M1SN and Control were prepared by diluting the drug substance (i.e., VM202 in 0.9% NaCl) with dilution buffers provided above in TABLE 2, at a ratio of 2:1 (Buffer 4 for 4MSN, Buffer 5 for 3MSN, Buffer 6 for 2MSN, Buffer 7 for 2M1SN, and Buffer 8 for Control). Following dilutions, all formulations except Control were adjusted to contain VM202 at 0.5 mg/mL with each formulation buffer containing 0.45% NaCl.

A surrogate formulation was prepared using dextran at 0.5 mg/mL in 0.9% NaCl and 1.1% sucrose.

Lyophilization of the samples: After adjustment of the concentration to 0.5 mg/mL, formulated VM202 was sterile filtered through a 0.2 μm PES filter (small scale and accelerated stability studies) or cellulose acetate (CA) filter (additional accelerated stability study) under aseptic conditions. All samples were filled under aseptic conditions into sterilized 3 cc vials at a fill volume 0.75 mL per vial for small scale lyophilization, or sterilized 20 cc vials at a fill volume 5 mL per vial for accelerated stability studies in a biosafety cabinet. Specifically, the formulations were filled using a syringe filter (PALL Life Science, Acrodisc 13 mm with 0.2 μm PES membrane, catalog #4602) with a vacuum filtration system (Corning, 1 L Vacuum Filter/Storage Bottle System, 0.2 μm CA membrane, catalog #431-205; Thermo scientific, Rapid Flow Filter Unit, 0.2 μm PES membrane, catalog #567-0020) under a safety cabinet (NuAire biological safety cabinet, Class II Type A/B3 Model No. NU-425-600)).

After filling, the vials were partially stoppered with sterile stoppers and loaded into the lyophilizer (VirTis (Model No. 25L Genesis SQ Super XL-70) for freeze-drying using the cycle described in TABLE 3. The surrogate vials were used to completely surround VM202 vials so that the comparable irradiation thermal transfer from neighboring vials are provided during the drying process for small scale lyophilization.

TABLE 3

| Step | Temperature | Time (min) | Ramp Rate (° C./min) | Chamber Pressure (mT) |
|---|---|---|---|---|
| 1st round of small scale lyophilization cycle | | | | |
| Loading | 5° C. | N/A | N/A | N/A |
| Freezing | 5° C. to −50° C. | 55 | 1° C. | N/A |
| | −50° C. | 120 | N/A | N/A |
| | −50° C. to −20° C. | 60 | 0.5 | N/A |
| | −20° C. | 120 | N/A | N/A |
| Primary Drying | −20° C. | 1440 | N/A | 80 |
| Secondary Drying | −20° C. to 20° C. | 80 | 0.5 | 80 |
| | 20° C. | 780 | N/A | 80 |
| 2nd round of small scale lyophilization cycle | | | | |
| Loading | 5° C. | N/A | N/A | N/A |
| Freezing | 5° C. to −50° C. | 55 | 1° C. | N/A |
| | −50° C. | 120 | N/A | N/A |
| | −50° C. to −20° C. | 60 | 0.5 | N/A |
| | −20° C. | 120 | N/A | N/A |
| Primary Drying | −20° C. | 1500 or 3840 or 3240 | N/A | 50 |
| Secondary Drying | −20° C. to 20° C. | 80 | 0.5 | 50 |
| | 20° C. | 780 | N/A | 50 |

Following lyophilization, the vials were fully stoppered under partial vacuum at 600 mtorr, crimped with aluminum seals, and labeled. Labels included information regarding project, date, incubation temperature/stress condition, and time point. After labeling, samples were placed into their respective stability conditions.

6.8.1.2.2. Assays for Testing Various Formulations

The lyophilized formulations were exposed to varying stress conditions to assess their relative stability. To thermally stress the samples, all formulations were stored at 5° C., 25° C., or 40° C. for up to 10 weeks. For the assessment of stability after reconstitution, samples were reconstituted in a biosafety cabinet using a target volume of 5.0 mL with filtered water for injection (WFI), restoppered, and resealed. Following reconstitution, samples were stored at 25° C. for 3 or 7 days. Various conditions tested in this experiment are summarized below in TABLE 4.

TABLE 4

| Stress | Storage Conditions | Time Point(s) |
|---|---|---|
| Temperature | 5° C. (Lyophilized) | 2 weeks, 4 weeks, 10 weeks |
| | 25° C. (Reconstituted liquid) | 0, 3, 7 days |
| | 25° C. (Lyophilized) | 2 weeks, 4 weeks, 10 weeks |
| | 40° C. (Lyophilized) | 2 weeks, 4 weeks, 10 weeks |

The following assays were performed to analyze stability of various formulations in different conditions.
(1) Visual Inspection: Visual inspection was performed against a dark and white background. Digital photographs were acquired.
(2) UV Spectrophotometry: UV spectrophotometry analysis was performed with an Implen Nanophotometer with a lid factor of 10. The plasmid DNA concentration of the test samples was determined by measuring absorbance at 230, 260, 280 and 350 nm. Concentration analyses were performed using ViroMed's UV/Vis protocol. Calculations were performed using the following equations:

Concentration (μg/mL)=$[(D-E)/C] \times (B/A)$

Recovery=(low μg/mL)/(high μg/mL)×100%

$OD^{260nm}/OD^{280nm}=D/F$ $OD^{260nm}/OD^{230nm}=D/G$ where,
A=weight of sample taken to give the dilution.
B=total weight of sample and buffer to give the dilution.
C=extinction coefficient of a 0.005% solution in a 1 cm pathlength cuvette (0.02).
D=optical density for the maximum at 260 nm.
E=absorbance measured at 350 nm.
F=absorbance measured at 280 nm.
G=absorbance measured at 230 nm.
Acceptance Criteria:
D shall fall in the range 0.5 to 1.5 OD units.
Recovery shall be ≥98%
$OD_{260nm}/OD_{280nm}$=shall lie in the range 1.8 to 2.0
$OD_{260nm}/OD_{230nm}$=shall be ≥1.1
(3) Capillary Electrophoresis: A Beckman Coulter, ProteomeLab™ PA 800 CE instrument equipped with a P/ACE™ MDQ UV detector module was used for plasmid DNA structural analysis (purity of supercoiled DNA). 32 Karat software (version 7.0) was used to analyze the results. Prior to capillary electrophoresis analysis, a Beckman Coulter Neutral coated 40 cm capillary with a 50 μm internal diameter (Part No. 477441) and a 8 μm aperture window was conditioned by running HPLC ultrapure grade water at 20 psi for 1 minute, followed by a rinse of 100 mM phosphoric acid (pH 2.6) at 20 psi for 1 minute. The separation occurred by applying a constant voltage of 17 kV for 14 minutes. 40 μL of sample at a concentration of 0.5 mg/mL was added into a polyethylene insert for the analyses. The following parameters were used:
Pressure/injection time: 0.5 psi/11 sec.
Separation buffer/pressure: 100 mM phosphoric acid (pH 2.60), 85%/20 psi; 60 sec.
Wash buffer/pressure: HPLC ultrapure grade water/20 psi; 60 sec Detector wavelength: 254 nm.
Separation voltage: 17 KV; 0.17 min; 14 min.
An exemplary capillary electrophoresis result of VM202 is provided in FIG. 1.
(4) Turbidity: Turbidity was determined by measuring sample absorbance at 450 nm and 650 nm using a Molecular Devices ThermoMAX microplate reader.
(5) Subambient DSC Analysis: Using a Pyris Diamond DSC with an Intercooler II, approximately 10 µL of each formulation was frozen at −60° C. At a ramp rate of 5° C./min, the sample was warmed to 25° C. and the heat flow during the warming process was recorded. Also, the program incorporating an annealing step was performed. The annealing step was conducted by warming the sample to −15° C. at a ramp rate of 5° C./min.
(6) Karl Fisher Moisture Analysis: A Karl Fisher Coulometer C20 (Mettler Toledo) was used for moisture content analysis. AquaStar Water Standard Oven 1% was used to determine system accuracy. Sample vials were brought to room temperature before caps were removed for analysis. Weigh boats were weighed before and after adding samples to determine the amount of lyophilized powder used for analysis. Approximately 10-160 mg of material was used for analysis.

6.8.1.2.3. Analysis of KP8M2SN, KP8MS3N and KP8MT3N (1st Round of Small Scale Test)

Subambient DSC Analysis: Prior to the lyophilization process, 10 µL samples of formulated VM202—i.e., KP8M2SN, KP8MS3N, KP8MT3N, and Control (TABLE 1)—at 0.5 mg/mL were analyzed by subambient differential scanning calorimetry (DSC) to characterize candidate formulations. Analyzed signals include collapse temperature (Tg'), devitrification temperature (Td), and the benefit of annealing of various formulations with VM202 in the frozen states. FIGS. 2A-D illustrate the DSC results of the liquid state for 1st round of small scale lyophilization of KP8M2SN (FIG. 2A), KP8MS3N (FIG. 2B), KP8MT3N (FIG. 2C) and Control (FIG. 2D) without annealing (left) or with annealing (right) of VM202. The glass transition (Tg') temperature of KP8M2SN was observed at −44° C. Control displayed the eutectic melting temperature (Te) at ~−21° C. A devitrification temperature (Td) was observed in all formulations and disappeared after annealing. Since some of the additives showed devitrification signals which disappeared after annealing, lyophilization cycle 1 (TABLE 3) was designed to incorporate an annealing step during freezing for the 1st round of small scale.

Ramping of the freezing temperature from −50° C. to −20° C. and holding for two (2) hours, then subsequently introducing the vacuum allowed for annealing and the induction of the crystallization of mannitol. Primary drying was performed at −20° C. shelf temperature (24 hours) with 80 mTorr chamber pressure (TABLE 3). Secondary drying at a shelf temperature of 20° C. was designed to remove residual water that was not sublimated during the primary drying step.

FIG. 3 shows the time-lapse graph of temperatures (left y-axis) and pressures (right y-axis) during the lyophilization process for the 1st round of small scale testing. The product temperature dropped below −36° C. due to heat-loss of sublimation when vacuum was applied. The pirani gauge value merged with the capacitance manometer reading at approximately 30 hours during the primary drying stage which confirmed the completion of the primary drying process. Secondary drying was initiated and the samples were allowed to dry for an additional 13 hours. The entire cycle lasted 46 hours, with the potential of a reduction to 43 hours if secondary drying was initiated immediately upon the completion of primary drying.

Upon completing the 1st round small scale lyophilization cycle, all vials were stoppered with 600 torr vacuum pressure. The lyophilates were removed from the chamber and analyzed. The lyophilized cake of KP8M2SN was elegant in appearance. The other cakes showed signs of collapse, especially Control. Reconstituted samples were clear and comparable to pre-lyophilization samples (FIGS. 4A-C). Moisture contents of the cakes were 1.37% (KP8M2SN), 2.40% (KP8MS3N), 1.44% (KP8MT3N), and 1.25% (Control), respectively.

The concentration of VM202 in each sample was measured after reconstitution of the sample from 1st round small scale lyophilization cycle and the results are summarized in TABLE 5. The results showed that each sample contained VM202 at a similar concentration.

TABLE 5

| | Concentration of VM202 (mg/mL) | |
|---|---|---|
| Code | Pre-Lyophilization | Reconstituted Sample |
| KP8M2SN | 0.51 | 0.49 |
| KP8MS3N | 0.52 | 0.50 |
| KP8MT3N | 0.51 | 0.49 |
| Control | 0.52 | 0.49 |

Capillary Electrophoresis: Reconstituted samples were further examined by CE for product purity. Chromatograms and the peak area (%) data following CE are shown in FIG. 5 and TABLE 6. Results from CE assays showed a decrease in super coiled peak area in KP8M2SN, KP8MT3N and Control following lyophilization and reconstitution. KP8MS3N had the highest super coiled peak area following lyophilization and reconstitution.

TABLE 6

| Form. Code | Sample | Super Coiled Peak Area (%) | Open Circle Peak Area (%) | Total Area |
|---|---|---|---|---|
| KP8M2SN | Pre-Lyophilization | 97.3 | 2.7 | 18058 |
| | Reconstituted Sample | 95.0 | 5.0 | 15523 |
| KP8MS3N | Pre- Lyophilization | 97.1 | 2.9 | 16328 |
| | Reconstituted Sample | 97.7 | 2.3 | 14789 |
| KP8MT3N | Pre- Lyophilization | 97.5 | 2.5 | 15696 |
| | Reconstituted Sample | 91.8 | 8.2 | 15586 |
| Control | Pre- Lyophilization | 97.6 | 2.4 | 15104 |
| | Reconstituted Sample | 92.4 | 7.6 | 13937 |

In summary, the results show that KP8M2SN, containing 1.0% Sucrose and 0.1% NaCl produces a better lyophilization cake than KP8MS3N containing 0.5% Sucrose and 0.45% NaCl, or KP8MT3N containing 0.5% Trehalose and 0.45% NaCl. The results further showed that KP8MS3N containing 0.5% Sucrose and 0.45% NaCl had the least amount of degradation as measured by CE. These together suggest that formulations containing Sucrose (KP8M2SN and KP8MS3N) had better properties (e.g., elegant cake formation and stability) than the formulation containing Trehalose (KP8MT3N).

6.8.1.2.4. Analysis of 1st Set of 4MSN, 3MSN and 2MSN (2nd Round of Small Scale Lyophilization Cycle)

Based on the results from the $1^{st}$ round of small scale lyophilization cycle, the next lyophilization cycle ($2^{nd}$ Round of small scale test) focused on enhancing the cake appearance by altering the concentrations of mannitol in KP8MS3N while keeping its Sucrose (0.5%) and NaCl (0.45%) concentrations.

Prior to the lyophilization process, 10 µL samples of formulated VM202—i.e., 4MSN, 3MSN, 2MSN, and Control (TABLE 1)—at 0.5 mg/mL were analyzed by subambient DSC to characterize candidate formulations. FIGS. 6A-D illustrate the DSC results of the liquid state from the 2nd round of small scale lyophilization testing. Control (FIG. 6D) displayed a eutectic melting temperature (Te) of ~−21° C. A devitrification temperature (Td) was observed in all formulations (without annealing on the left) and disappeared after annealing (on the right). Due to the observance of devitrification signals, lyophilization cycle 2 (TABLE 3) was designed to incorporate an annealing step during freezing for the 2nd round of small scale testing.

Ramping of the freezing temperature from −50° C. to −20° C. and holding for two (2) hours, then subsequently introducing the vacuum allowed for annealing and the induction of the crystallization of mannitol. Primary drying was performed at −20° C. shelf temperature (25 hours) with 50 mTorr chamber pressure (TABLE 3). Secondary drying at a shelf temperature of 20° C. was designed to remove residual water that was not sublimated during the primary drying step.

FIG. 7 shows the time-lapse graph of temperatures (left y-axis) and pressures (right y-axis) during the lyophilization process for the 2nd round of small scale testing. The product temperature dropped below −37° C., due to heat-loss of sublimation when vacuum was applied. The pirani gauge value merged with the capacitance manometer reading at approximately 23 hours during the primary drying stage which confirmed the completion of the primary drying process. Secondary drying was initiated and the samples were allowed to dry for an additional 13 hours. The entire cycle lasted 47 hours, with the potential of a reduction to 42 hours if secondary drying was initiated immediately upon the completion of primary drying.

Once the cycle was complete, samples were removed from the lyophilizer and analyzed. By visual inspection, 4MSN displayed elegant cake. 3MSN and 2MSN also showed decent cake with shrinkage, whereas Control showed signs of cake collapse following lyophilization. The samples were clear and colorless after reconstitution, comparable to pre-lyophilization samples (FIGS. 8A-C). Moisture contents of the cake were 2.51% (4MSN), 2.15% (3MSN), 2.01% (2MSN), and 1.12% (Control).

The concentration of VM202 in each sample was measured after reconstitution of the sample from $2^{nd}$ round small scale lyophilization cycle and the results are summarized in TABLE 7. The results showed that each sample contained VM202 at a similar concentration.

TABLE 7

| Form. Code | Concentration (mg/mL) | |
| --- | --- | --- |
| | Pre-Lyophilization | Reconstituted Sample |
| 4MSN | 0.53 | 0.51 |
| 3MSN | 0.53 | 0.51 |
| 2MSN | 0.52 | 0.52 |
| Control | 0.53 | 0.51 |

Capillary Electrophoresis: The reconstituted samples were further examined by CE for product purity. The chromatograms and the tabular results from CE are detailed in FIG. 9 and TABLE 8. 4MSN and 3MSN displayed minimal degradation in the super coiled peak area, whereas 2MSN and Control showed decreases in the super coiled peak are following lyophilization and reconstitution.

TABLE 8

| Form. Code | Sample | Super Coiled Peak Area (%) | Open Circle Peak Area (%) | Total Area |
| --- | --- | --- | --- | --- |
| 4MSN | Pre-Lyo | 97.6 | 2.4 | 15030 |
| | Reconstituted Sample | 97.2 | 2.8 | 14482 |
| 3MSN | Pre-Lyo | 98.2 | 1.8 | 14788 |
| | Reconstituted Sample | 97.8 | 2.2 | 13352 |
| 2MSN | Pre-Lyo | 97.5 | 2.5 | 15143 |
| | Reconstituted Sample | 95.6 | 4.4 | 14258 |
| Control | Pre-Lyo | 98.4 | 1.6 | 14761 |
| | Reconstituted Sample | 94.1 | 5.9 | 12058 |

These results suggested that 4MSN (10 mM Potassium Phosphate, 4% Mannitol, 0.5% Sucrose, 0.45% NaCl at pH 8.0) produced the best lyophilized cake and the least amount of degradation by CE in the 2nd round small scale lyophilization cycle.

6.8.1.2.5. Analysis of 2nd Set of 4MSN, 3MSN and 2MSN (2nd Round of Small Scale Lyophilization Cycle)

Another set of 4MSN, 3MSN, 2MSN and Control was prepared by the $2^{nd}$ round of small scale lyophilization cycle designed with a primary drying shelf temperature of −20° C. at a chamber pressure of 50 mTorr, and a secondary drying shelf temperature of 20° C. at a chamber pressure of 50 mTorr (TABLE 3). FIG. 10 shows the time-lapse graph of temperatures and pressures obtained during this cycle. The product temperature dropped below −37° C., due to heat-loss of sublimation when vacuum was applied. The pirani gauge values merged with the capacitance manometer reading around 75 hours during primary drying. Secondary drying was initiated and the samples were allowed to dry for an additional 13 hours. The entire cycle lasted 87 hours.

Once the cycle was complete, samples were removed from the lyophilizer and analyzed. By visual inspection, 4MSN displayed elegant cake. 3MSN and 2MSN also showed decent cake with shrinkage, whereas Control showed signs of cake collapse following lyophilization. Upon reconstitution, some vials in all formulations, except Control, showed haziness, whereas all samples were clear before lyophilization (FIGS. 11A-F). Moisture contents of the cake were 0.97% (4MSN), 0.95% (3MSN), 1.69% (2MSN), and 1.06% (Control).

Turbidity: Concentration and turbidity results are summarized in TABLE 9. All samples showed similar concentration values following reconstitution. No turbidity was detected for all formulations before lyophilization and after reconstitution.

TABLE 9

| Form. Code | Concentration (mg/mL) | | Turbidity ($A_{650}$) | |
|---|---|---|---|---|
| | Pre-Lyophilization | Reconstituted Sample | Pre-Lyophilization | Reconstituted Sample |
| 4MSN | 0.51 | 0.49 | −0.001 | 0.003 |
| 3MSN | 0.50 | 0.49 | 0.000 | 0.001 |
| 2MSN | 0.50 | 0.49 | −0.001 | 0.001 |
| Control | 0.52 | 0.51 | 0.000 | 0.000 |

Capillary Electrophoresis: The reconstituted samples were further examined by CE for product purity. The chromatograms and peak percentages from CE are shown in FIG. 12 and TABLE 10. 4MSN, 3MSN, and Control showed a significant decrease in the super coiled peak area following lyophilization and reconstitution. 2MSN displayed minimal degradation in the super coiled peak area after lyophilization and reconstitution.

TABLE 10

| | | Average (n = 5) | | |
|---|---|---|---|---|
| Form. Code | Sample | Super Coiled Peak Area (%) | Open Circle Peak Area (%) | Total Area |
| 4MSN | Pre-Lyophilization | 98.6 | 1.4 | 21510.6 |
| | Reconstituted Sample | 89.2 | 10.8 | 17033.7 |
| 3MSN | Pre- Lyophilization | 98.4 | 1.6 | 17025.0 |
| | Reconstituted Sample | 89.5 | 10.5 | 16855.6 |
| 2MSN | Pre- Lyophilization | 98.5 | 1.5 | 14671.2 |
| | Reconstituted Sample | 96.4 | 3.6 | 15813.1 |
| Control | Pre- Lyophilization | 98.2 | 1.8 | 18755.1 |
| | Reconstituted Sample | 92.7 | 7.3 | 17806.0 |

The results suggested that 2MSN (10 mM Potassium Phosphate, 2% Mannitol, 0.5% Sucrose, 0.45% NaCl at pH 8.0) produced the least amount of degradation by CE in this separate set of experiments for the $2^{nd}$ round small scale test.

The samples produced in this lyophilization cycle were used over 10 weeks for the accelerated stability study.

6.8.1.2.6. Analysis of 2MSN and 2M1SN

Given that KP8MS3N and 2MSN containing 2% Mannitol, 0.5% Sucrose and 0.45% NaCl showed the least amount of degradation as measured by CE in the $1^{st}$ round and certain $2^{nd}$ round small scale tests, the KP8MS3N and 2MSN formulations were further optimized by changing the sucrose concentration while keeping the Mannitol (2%) and NaCl (0.45%) concentrations at the same concentrations. Specifically, 2M1SN formulation containing 2% Mannitol, 0.45% NaCl and 1.0% Sucrose was made and analyzed compared to 2MSN.

2M1SN and 2MSN were lyophilized using similar lyophilization cycle parameters to those used in the accelerated stability study. FIG. 13 displays the temperature and pressure measurements from this cycle. The product temperature dropped below −41° C., due to heat-loss of sublimation when vacuum was applied. The pirani gauge values merged with the capacitance manometer reading around 60 hours during primary drying. Secondary drying was initiated and the samples were allowed to dry for an additional 13 hours. The entire cycle lasted 76 hours with the potential of a reduction to 70 hours if secondary drying was initiated immediately upon the completion of primary drying.

Following lyophilization, 2M1SN displayed elegant cake and 2MSN displayed decent cake with minor shrinkage (FIG. 14). Upon reconstitution, 2M1SN produced a clear solution, whereas 2MSN displayed haziness. Both formulations were clear before lyophilization. The moisture contents of the cakes were 1.31% (2MSN), and 1.44% (2M1SN).

Turbidity: Formulations were assessed for concentration and turbidity and the results are summarized in TABLE 11. All samples showed similar concentration values following reconstitution. For the additional accelerated stability study, it was determined that turbidity measurements at 450 nm were better able to assess differences in the formulations. No turbidity was detected for 2M1SN before lyophilization and after reconstitution. After reconstitution of 2MSN, a significant increase in turbidity was observed at 450 nm.

TABLE 11

| | Concentration (mg/mL) | | Turbidity ($A_{450}$) | |
|---|---|---|---|---|
| Form. Code | Pre-Lyo | Reconstituted Sample | Pre-Lyo | Reconstituted Sample |
| 2MSN | 0.51 | 0.50 | 0.000 | 0.013 |
| 2M1SN | 0.51 | 0.50 | 0.000 | 0.000 |

Capillary Electrophoresis: The reconstituted samples were further examined by CE for product purity. The chromatograms and tabular results from CE are detailed in FIG. 15 and TABLE 12. 2MSN displayed a decrease in the super coiled peak area following lyophilization and reconstitution. 2M1SN displayed minimal degradation in the super coiled peak area after lyophilization and reconstitution

TABLE 12

| | | Average (n = 5) | | |
|---|---|---|---|---|
| Form. Code | Sample | Super Coiled Peak Area (%) | Open Circle Peak Area (%) | Total Area |
| 2MSN | Pre-Lyophilization | 98.6 | 1.4 | 13755.3 |
| | Reconstituted Sample | 91.1 | 8.9 | 14135.3 |
| 2M1SN | Pre- Lyophilization | 98.5 | 1.5 | 13928.0 |
| | Reconstituted Sample | 96.6 | 3.4 | 13998.6 |

The samples produced in this lyophilization cycle were used over 10 weeks for the additional accelerated stability study.

6.8.1.3. Accelerated Stability Study of 4MSN, 3MSN, 2MSN and Control

Stabilities of lyophilized VM202 formulations, 4MSN, 3MSN, 2MSN, and Control, were evaluated under different storage conditions at refrigerated (5±3° C.), ambient (25±3° C.), and accelerated (40±3° C.) temperature and reconstituted VM202 formulations at ambient temperature for 3 or 7 days.

The lyophilized samples from the accelerated stability study were reconstituted with 5 mL of filtered water in a biological safety cabinet, re-stoppered, sealed, and incubated at 25° C. for 3 and 7 days. Following 3 and 7 days, the incubated samples were removed from the incubator and analyzed by visual, concentration, and CE analysis.

Visual inspection: No changes in visual appearance were observed after storage of the formulations 4MSN, 3MSN, 2MSN and Control at 25° C. for 3 days (FIG. 16A) and 7 days (FIG. 16B) following reconstitution when compared to T=0.

At each time point, samples were analyzed for absorbance at 260 nm to determine the concentration of VM202. The concentration of each formulation following storage at 25° C. for 3 and 7 days is similar to the results obtained at T=0 (TABLE 13). All samples were within 5% of the targeted concentration value. Therefore, temperature stress induced no major changes in VM202 concentration.

TABLE 13

| Form. Code | Concentration (mg/mL) | | |
|---|---|---|---|
| | T = 0 | 3 days | 7 days |
| 4MSN | 0.49 | 0.50 | 0.50 |
| 3MSN | 0.49 | 0.49 | 0.49 |
| 2MSN | 0.49 | 0.50 | 0.50 |
| Control | 0.51 | 0.52 | 0.52 |

Capillary Electrophoresis: CE analysis was employed to monitor product purity during temperature storage. The CE chromatograms and the tabular results of the formulations after storage are detailed in FIGS. 17A-B and TABLE 14. All formulations (i.e., 4MSN, 3MSN, 2MSN and Control) displayed decreases in supercoiled peak area following storage at 25° C. from 3 to 7 days. 2MSN exhibited the best stability from 3 to 7 days with only a 1.1% decrease in super coiled peak area.

TABLE 14

| Form. Code | T = 3 Days (n = 5) | | | T = 7 Days (n = 5) | | |
|---|---|---|---|---|---|---|
| | Super Coiled Peak Area (%) | Open Circle Peak Area (%) | Total Area | Super Coiled Peak Area (%) | Open Circle Peak Area (%) | Total Area |
| 4MSN | 95.6 | 4.4 | 12236.2 | 91.1 | 8.9 | 13628.1 |
| 3MSN | 96.4 | 3.6 | 12019.0 | 91.5 | 8.5 | 13912.7 |
| 2MSN | 96.7 | 3.3 | 14029.2 | 95.6 | 4.4 | 15672.4 |
| Control | 96.2 | 3.8 | 14029.0 | 92.6 | 7.4 | 17867.4 |

The lyophilized VM202 formulations were stored over 10 weeks at 5° C., 25° C., and 40° C. (TABLE 4). At each time point, samples were removed from temperature storage and visually assessed. Photographs of the vials were taken and samples were evaluated for cake shape. All lyophilized cakes remained intact and did not show any signs of change upon storage regardless of temperature condition (Control cake remained lifted). The samples were then reconstituted with 5 mL of filtered water and evaluated for clarity and precipitation. Most samples for 4MSN, 3MSN, and 2MSN exhibited slight differences in clarity when compared to T=0. The visual appearance of each formulation following 5° C. (FIG. 18C), 25° C. (FIG. 18A), and 40° C. (FIG. 18B) storage for 10 weeks is shown in FIGS. 18A-C.

Concentration, turbidity, moisture content, and capillary electrophoresis analyses were also performed to evaluate the stability of lyophilized VM202 during temperature stresses.

At each time point, samples were reconstituted and analyzed for absorbance at 260 nm to determine the concentration of VM202 in vials. TABLE 15 shows that the concentration of VM202 in lyophilized samples following 10 weeks of temperature storage is similar to the results obtained at T=0. Therefore, temperature stress induced no major changes in VM202 concentration.

TABLE 15

| Form. Code | Concentration (mg/mL), T = 0 or T = 10 wks | | | |
|---|---|---|---|---|
| | T = 0 | T = 10 wks | | |
| | | 5° C. | 25° C. | 40° C. |
| 4MSN | 0.49 | 0.49 | 0.49 | 0.49 |
| 3MSN | 0.49 | 0.49 | 0.49 | 0.49 |
| 2MSN | 0.49 | 0.50 | 0.49 | 0.50 |
| Control | 0.51 | 0.52 | 0.52 | 0.52 |

Turbidity: Turbidity of each sample was also evaluated at each time point in the study. The results are detailed in TABLE 16. Turbidity of the reconstituted formulations, 4MSN, 3MSN and 2MSN, did not change significantly following 10 weeks storage, regardless of temperature condition.

TABLE 16

| Form. Code | Turbidity ($Abs_{650}$), T = 0 and T = 10 wks | | | |
|---|---|---|---|---|
| | T = 0 | 5° C. | 25° C. | 40° C. |
| 4MSN | 0.003 | 0.004 | 0.004 | 0.002 |
| 3MSN | 0.001 | 0.004 | 0.004 | 0.003 |
| 2MSN | 0.001 | 0.004 | 0.002 | 0.002 |
| Control | 0.000 | 0.001 | 0.001 | 0.001 |

Moisture content analysis was also performed at each time point. TABLE 17 outlines the results for moisture content following 10 weeks of temperature storage. After 10 weeks of storage at 5° C., 25° C., and 40° C., slight decreases in moisture content were observed in a temperature dependent manner. Higher storage temperatures resulted in lower moisture content. 2MSN had the highest moisture content during the accelerated stability study.

TABLE 17

| Form. Code | Moisture content, T = 0 and T = 10 wks | | | |
|---|---|---|---|---|
| | T = 0 | T = 10 wks | | |
| | | 5° C. | 25° C. | 40° C. |
| 1% Water STD | 0.94 | | 0.94 | |
| 4MSN | 0.97 | 0.79 | 0.31 | 0.30 |
| 3MSN | 0.95 | 0.75 | 0.53 | 0.35 |
| 2MSN | 1.69 | 1.39 | 0.95 | 0.67 |
| Control | 1.06 | 1.07 | 0.79 | 0.61 |

Capillary Electrophoresis: Capillary electrophoresis analysis was used to monitor for product purity. The CE chromatograms and peak area values after 10 weeks of incubation at 40° C. are shown in FIG. 19 and TABLE 18, respectively. All formulations displayed significant decreases in the supercoiled peak area with corresponding increases in the open circle peak area compared to T=0 after reconstitution, following storage for 10 weeks at 40° C. 2MSN displayed the highest supercoiled peak area, although this value was significantly lower at 10 weeks storage at 40° C. than at time zero. Higher levels of open circle peak area were observed in the formulations containing 3% and 4% mannitol as well as in the Control formulation.

TABLE 18

| | Average (n = 5) | | |
| --- | --- | --- | --- |
| Form. Code | Super Coiled Peak Area (%) | Open Circle Peak Area (%) | Total Area |
| 4MSN | 54.3 | 45.7 | 8142.4 |
| 3MSN | 55.4 | 44.6 | 11305.2 |
| 2MSN | 82.2 | 17.8 | 10622.8 |
| Control | 70.0 | 30.0 | 14767.2 |

The CE supercoiled peak purity trends, weighted by standard deviation and including deviation error bars, over 10 weeks at various temperatures are detailed in FIGS. 20A-C-5° C. (FIG. 20A), 25° C. (FIG. 20B) or 40° C. (FIG. 20C). Significant differences in purity were observed following incubation at elevated temperature. As illustrated in FIGS. 20A-C, 2MSN containing 2% mannitol and 0.45% NaCl displayed the highest level of purity following 40° C. storage.

The trends of open circle peak impurities detected by CE after storage at different temperatures are also presented in FIGS. 21A-C. Slight increases in open circle peak areas were observed at 5° C. However, at ≥25° C., all formulations showed considerable degradation. Following 40° C. incubation, higher levels of open circle peak impurities were observed for 4MSN, 3MSN and Control. In comparison, 2MSN showed substantially less degradation at all temperatures.

6.8.1.4. Accelerated Stability Study of 2MSN and 2M1SN

Stabilities of lyophilized VM202 formulations, 2MSN, and 2M1SN, were also evaluated after incubation at ambient temperature (25° C.) for 3 or 7 days. Samples were reconstituted with 5 mL of filtered water in a biological safety cabinet, re-stoppered, sealed, and incubated at 25° C. for 3 and 7 days. Following 3 and 7 days, the incubated samples were removed from the incubator and analyzed by visual, concentration, and CE analysis.

Visual inspection: At both time points, visual inspection was performed (FIGS. 22A-D). Haziness was observed in 2MSN following 3 and 7 days of storage at 25° C. after reconstitution. 2M1SN remained clear at both time points.

At each time point, samples were analyzed for absorbance at 260 nm to determine the concentration of VM202. VM202 concentrations in both formulations were on target at T=0 and after incubation at 25° C. for 3 and 7 days following reconstitution (TABLE 19). Therefore, temperature stress induced no major changes in VM202 concentration.

TABLE 19

| | Concentration (mg/mL) | | |
| --- | --- | --- | --- |
| Form. Code | T = 0 | 3 days | 7 days |
| 2MSN | 0.50 | 0.50 | 0.50 |
| 2M1SN | 0.50 | 0.50 | 0.50 |

Capillary Electrophoresis: The samples were also analyzed by CE for product purity following temperature storage. The CE chromatograms and the peak area results of the samples after storage are illustrated in FIGS. 23A-B and TABLE 20. Both formulations exhibited similar supercoiled peak areas following storage. 2M1SN displayed a higher supercoiled peak area compared to 2MSN.

TABLE 20

| | T = 3 Days (n = 5) | | | T = 7 Days (n = 5) | | |
| --- | --- | --- | --- | --- | --- | --- |
| Form. Code | Super Coiled Peak Area (%) | Open Circle Peak Area (%) | Total Area | Super Coiled Peak Area (%) | Open Circle Peak Area (%) | Total Area |
| 2MSN | 92.9 | 7.1 | 13364.1 | 91.4 | 8.6 | 18054.2 |
| 2M1SN | 96.7 | 3.3 | 14702.0 | 97.2 | 2.8 | 20771.3 |

Stability during storage: The lyophilized VM202 formulations for the additional accelerated stability study were stored over a 10 week period at 5° C., 25° C., and 40° C. (TABLE 4). At each time point, samples were taken from temperature storage and visually evaluated. Photographs of the vials were taken and samples were assessed for cake shape. Samples were reconstituted with 5 mL of filtered water and evaluated for clarity and precipitation. All lyophilized cakes remained intact and did not show any sign of change upon storage regardless of temperature condition. Haziness was observed in reconstituted 2MSN following storage over 10 weeks. 2M1SN was clear after reconstitution following storage. The visual appearance of each formulation following 5° C., 25° C., and 40° C. storage for 10 weeks is shown in FIGS. 24A-C.

Concentration, turbidity, moisture content, and capillary electrophoresis analyses were performed to evaluate the stability of lyophilized VM202 during temperature stresses.

At each time point, samples were reconstituted and analyzed for absorbance at 260 nm to determine the concentration of VM202 in vials. TABLE 21 shows that the concentration of VM202 in lyophilized samples following 10 weeks of temperature storage is similar to the results obtained at T=0. Therefore, temperature stress induced no major changes in VM202 concentration.

TABLE 21

Concentration (mg/mL), T = 0 and T = 10 wks

| Form. Code | T = 0 | T = 10 wks 5° C. | T = 10 wks 25° C. | T = 10 wks 40° C. |
|---|---|---|---|---|
| 2MSN | 0.50 | 0.50 | 0.50 | 0.50 |
| 2M1SN | 0.50 | 0.49 | 0.50 | 0.50 |

Turbidity of each sample was also evaluated at each time point for two (2) different wavelengths. While operators detected visual haziness in samples, meaningful difference in turbidity was not observed when measured at a wavelength of 650 nm. Therefore, it was determined that 450 nm was adequate to assess differences in turbidity between formulations. The results from this evaluation are detailed in TABLE 22. 2MSN exhibited moderate absorbance at 450 nm regardless of the temperature storage condition. 2M1SN exhibited low absorbance at 450 nm at all temperatures.

TABLE 22

Turbidity ($Abs_{450}$), T = 0 and T = 10 wks

| Form. Code | T = 0 | T = 10 wks 5° C. | T = 10 wks 25° C. | T = 10 wks 40° C. |
|---|---|---|---|---|
| 2MSN | 0.013 | 0.011 | 0.012 | 0.005 |
| 2M1SN | 0.000 | 0.001 | 0.001 | 0.001 |

Moisture content analysis was also performed at each time point. TABLE 23 outlines the results for moisture content following 10 weeks of temperature storage. After 10 weeks of storage at 5° C., 25° C., and 40° C., similar moisture content was observed in all samples except 2M1SN stored at 5° C., which exhibited slightly elevated moisture content (1.56%).

TABLE 23

Moisture content, T = 0 and T = 10 wks

| Form. Code | T = 0 | T = 10 wks 5° C. | T = 10 wks 25° C. | T = 10 wks 40° C. |
|---|---|---|---|---|
| 1% Water STD | 0.95 | | 0.94 | |
| 2MSN | 1.31 | 1.20 | 1.18 | 1.15 |
| 2M1SN | 1.44 | 1.56 | 1.17 | 1.23 |

Capillary electrophoresis analysis was used to monitor product purity. The CE chromatograms and peak area values after 10 weeks of incubation at 40° C. are shown in FIG. 25 and TABLE 24, respectively. Both formulations displayed significant decreases in the supercoiled peak area with corresponding increases in the open circle peak area compared to T=0 after reconstitution, following storage for 10 weeks at 40° C. 2M1SN displayed the highest supercoiled peak area, although this value was significantly lower at 10 weeks storage at 40° C. than at time zero. Higher levels of open circle peak area were observed in 2MSN.

TABLE 24

| | Average (n = 5) | | |
|---|---|---|---|
| Form. Code | Super Coiled Peak Area (%) | Open Circle Peak Area (%) | Total Area |
| 2MSN | 79.9 | 20.1 | 7410.8 |
| 2M1SN | 86.0 | 14.0 | 9099.4 |

The CE supercoiled peak purity trends over 10 weeks at various temperatures are detailed in FIGS. 26A-C—at 5° C. (FIG. 26A), at 25° C. (FIG. 26B) or at 40° C. (FIG. 26C). Significant differences in purity were observed following elevated temperature incubation. As illustrated in TABLE 24, 2M1SN containing 1% sucrose and 0.45% NaCl displayed the highest level of purity following 40° C. storage.

The trends of open circle peak impurities detected by CE during temperature storage are presented in FIGS. 27A-C—at 5° C. (FIG. 27A), at 25° C. (FIG. 27B) or at 40° C. (FIG. 27C). These graphs demonstrate increases in open circle peak corresponding to increased temperature storage. Following 40° C. incubation, a higher level of open circle peak impurity was observed for 2MSN. 2M1SN exhibited less open circle peak at all temperatures, but followed the same trend as 2MSN.

6.8.1.5. Summary of Test Results

Prior to lyophilization, all the tested formulations comprising a plasmid DNA (VM202) remained clear, without discoloration or visible particulates. Additionally, capillary electrophoresis (CE) results consistently showed high purity of all of the compositions.

The first and second rounds of small scale lyophilization test were executed for VM202 using six (6) different formulations (KP8M2SN, KP8MS3N(=2MSN), KP8MT3N, 4MSN, 3MSN and Control), where the product was filled at 0.75 mL into 3 cc glass vials. The accelerated stability study was executed for VM202 using the same four (4) formulations (4MSN, 3MSN, 2MSN and Control) of second round of small scale lyophilization filled at 5 mL into 20 cc glass vials, and lyophilization parameters determined from data acquired from the small scale lyophilization studies. Also, two (2) different formulations (2MSN and 2M1SN) were tested in an additional accelerated stability study based on the data from the initial accelerated stability study. The lyophilization cycles were designed from results obtained following subambient DSC analysis. An annealing step was included in the lyophilization cycle, as it was determined that the devitrification temperature was eliminated after annealing.

Following lyophilization, elegant or decent cakes were observed for all compositions except Control comprising 0.9% NaCl and 1.1% sucrose. The Control is a formulation previously described in U.S. Pat. No. 8,389,492, which is incorporated herein by reference in its entirety.

After reconstitution of the lyophilized compositions, however, all the tested compositions except 2M1SN (10 mM Potassium Phosphate at pH 8.0, 2% Mannitol, 1% Sucrose, 0.45% NaCl) appeared to be hazy. The haziness remained even after storage of the reconstituted compositions at 25° C. for 3 and 7 days following reconstitution. Only 2M1SN remained clear following reconstitution and following storage at 25° C. for 3 and 7 days after reconstitution, and there was no change in the concentrations of VM202 in 2M1SN throughout the study.

Capillary electrophoresis was effective in evaluating VM202 product purity. Following lyophilization and reconstitution, all formulations showed decreases in the supercoiled peak area. A decrease in the supercoiled peak area was also observed in all formulations after 10 weeks of storage at 25° C. and 40° C. However, 2M1SN showed the highest supercoiled peak percentage corresponding with the least increase in open circle peak percentage during the 10 week stability study.

The results suggest that lyophilized VM202 maintains elegant cake appearance and the highest level of purity (supercoiled DNA) after lyophilization and storage when formulated at 0.5 mg/mL concentration with 10 mM Potassium Phosphate at pH 8.0, 2% Mannitol, 1% Sucrose, 0.45% NaCl, at a fill volume of 5 mL in 20 cc vials (2M1SN in TABLE 25). Although the rate of instability increases for VM202 at higher temperatures, less degradation was observed in this 2M1SN formulation than in the other tested formulations.

TABLE 25

| Form. Code | Buffer | Bulking pH Agent | Stabilizer(s) | VM202 Concentration (mg/mL) |
|---|---|---|---|---|
| 2M1SN | 10 mM Potassium Phosphate | 8.0 2% Mannitol | 1.0% Sucrose, 0.45% NaCl | 0.5 |

6.8.2. Example 2: Lyophilized Composition of VM202 (Study 002)

Various lyophilized formulations containing VM202 were generated and analyzed to test the quality of VM202 in the drug product formulation following lyophilization as well as the quality of VM202 in formulations with slight variations in pH and/or concentrations of bulking agents and stabilizers.

6.8.2.1. Experimental Design

Materials: The active pharmaceutical ingredient (API) examined in this study was VM202. The material used for this study was comprised of the following: The chemicals and materials used to formulate and analyze VM202 were as follows:

TABLE 26

| Drug Substance (DS): | VM202 in 0.9% (w/v) NaCl, pH 5.9 at 1.6 mg/mL, Lot # 2018#009S |
|---|---|
| Potassium Phosphate Monobasic | J. T. Baker, Cat# 3248-01, Lot# 0000163254 |
| Potassium Phosphate Dibasic | Sigma Aldrich, Cat# P222-500G, Lot# SLBS0610V |
| Sucrose | J. T. Baker, Cat# 4074-05, Lot# 0000159304 |
| D-Mannitol | Pfanstiehl, Cat# M-109-6, Lot 35517A |
| Sodium Chloride | EMD Millipore, Cat## 1.06404.5000, Lot# K49421004743 |
| 150 mL Nalgene Rapid-Flow 0.2 μm SFCA Filter Unit | Thermo Scientific, Cat# 0974028E, Lot#1233541 |
| 150 mL Nalgene Receiver Bottle | Thermo Scientific, Cat# 455-0150 |
| 20-cc, 20 mm Borosilicate Vials | Schott, Cat# 68000321 |
| 20 mm Stoppers | West Pharmaceutical, Cat#19700033 |

Formulation parameter: In this study, the following parameters were fixed:
(1) Fill volume: 5 mL
(2) API Concentration: 0.5 mg/mL
(3) Buffer Concentration: 10 mM Potassium Phosphate
(4) Sucrose Concentration: 1%

The following formulation parameters were examined in these formulations:
(1) pH: 7.0, 8.0, and 9.0
(2) Mannitol Concentration: 1% and 2%
(3) Sodium Chloride Concentration: 0.45%, 0.6%, and 0.9%

Formulation listed in the below in TABLE 27 were prepared for analysis:

TABLE 27

Formulation Matrix for the Lyophilization and Analysis Study

| Form. No. | Form. Code | Buffer (10 mM) | pH | Mannitol (%) | Sucrose (%) | NaCl (%) | API (mg/mL) |
|---|---|---|---|---|---|---|---|
| 1 | F1 | Potassium Phosphate | 8.0 | 2 | 1 | 0.45 | 0.5 |
| 2 | F2 | Potassium Phosphate | 7.0 | 2 | 1 | 0.45 | 0.5 |
| 3 | F3 | Potassium Phosphate | 9.0 | 2 | 1 | 0.45 | 0.5 |
| 4 | F4 | Potassium Phosphate | 8.0 | 1 | 1 | 0.45 | 0.5 |
| 5 | F5 | Potassium Phosphate | 8.0 | 2 | 1 | 0.60 | 0.5 |
| 6 | F6 | Potassium Phosphate | 8.0 | 2 | 1 | 0.90 | 0.5 |

6.8.2.2. Formulation Preparations

6.8.2.2.1. Small Scale Study

A small-scale test was performed to determine the buffer pH values required in order to dilute the drug substance (DS) to achieve the target formulation pH values in TABLE 27. To conserve the drug substance, the small-scale study dilutions were performed with a 0.9% NaCl placebo (same formulation as the DS) in lieu of the DS. The 0.9% NaCl placebo was prepared without pH adjustment, to better represent the DS formulation composition. The dilution buffer composition (TABLE 28) was calculated based on dilution of DS from 1.6 mg/mL to 0.5 mg/mL. The small-scale test revealed that after dilution with the formulation buffers, all the final formulations showed pH values on or near the target values in TABLE 27. However, as the pH of formulation F3 (9.0) was beyond the buffering range of phosphate, a downward drift in pH was observed. To best compensate for this, a higher pH diluent buffer was selected (9.5). Small scale testing showed a pH of 9.2 immediately following dilution then a decrease in pH to 9.1 and 8.5 after 24 and 48 hours, respectively.

To best achieve the target pH values for this study, formulations were prepared within one day of lyophilization and changes in pH following reconstitution were monitored. The dilution buffers shown in TABLE 28 were used for formulation preparation.

TABLE 28

Starting Dilution Buffer Composition

| Form. Code | Buffer (14.55 mM) | pH | Mannitol (%) | Sucrose (%) | NaCl (%) |
|---|---|---|---|---|---|
| D1 | Potassium Phosphate | 8.0 | 2.91 | 1.46 | 0.25 |
| D2 | Potassium Phosphate | 7.0 | 2.91 | 1.46 | 0.25 |
| D3 | Potassium Phosphate | 9.5 | 2.91 | 1.46 | 0.25 |
| D4 | Potassium Phosphate | 8.0 | 1.46 | 1.46 | 0.25 |
| D5 | Potassium Phosphate | 8.0 | 2.91 | 1.46 | 0.46 |
| D6 | Potassium Phosphate | 8.0 | 2.91 | 1.46 | 0.90 |

6.8.2.2.2. Lyophilization

VM202 at 1.6 mg/mL in 0.9% NaCl provided from Cobra was removed from −70° C. storage and thawed at 5° C. overnight. 35 mL of DS was diluted in 21 mL of dilution buffers (TABLE 28) to a concentration of 1.0 mg/ml. Following dilution, the pH and API concentration were measured. Despite the results of the small scale testing using placebo, in the presence of VM202 the formulations did not produce the target pH values, so the pH of starting dilution buffers were further adjusted during dilution of 1.0 mg/ml DS in 48 mL of dilution buffer (TABLE 29) to a final concentration of 0.5 mg/ml.

TABLE 29 pH and Amount of Dilution Buffers used for Dilution from 1 mg/mL to 0.5 mg/mL

| Form. Code | pH | Amount (mL) |
|---|---|---|
| D1 | 8.3 | 29 |
|  | 9.3 | 14 |
|  | 9.5 | 5 |
| D2 | 7.0 | 10 |
|  | 7.1 | 38 |
| D3 | 9.1 | 36 |
|  | 11.0 | 12 |
| D4 | 8.3 | 15 |
|  | 8.5 | 20 |
|  | 8.7 | 13 |
| D5 | 8.2 | 10 |
|  | 8.7 | 38 |
| D6 | 8.8 | 48 |

Following dilution, formulations were sterile filtered using 0.2 μm cellulose acetate filter, filled into 20 cc glass, depyrogenated vials at a 5 mL fill volume (2.5 mg dose) in the BSC. After filling, vials were partially stoppered and loaded into the lyophilizer for freeze-drying. Empty vials were used to completely surround VM202 DS containing vials. Following lyophilization, the vials were fully stoppered inside the lyophilization chamber with 600 Torr partial vacuum, before being removed. Vials were crimped, labeled and placed in −70° C. One (1) vial of each formulation was placed in 5° C. One (1) vial per each formulation was reconstituted with 5 mL of filtered Milli-Q water and analyzed with pre-lyo samples.

6.8.2.2.3. Analysis Methods

Lyophilized formulations were analyzed at different time points as summarized in TABLE 30.

TABLE 30

| Analytical Methods | Temperature Stress Time Points | | |
|---|---|---|---|
|  | Pre-Lyo | Lyophilized Cake | Reconstituted Liquid |
| Visual | X | X | X |
| Concentration ($A_{260}$) | X | — | X |
| pH | X | — | X |
| Reconstitution Time | — | X | — |
| Turbidity ($A_{350}$, $A_{450}$, $A_{650}$) | X | — | X |
| CZE | X | — | X |
| Residual Moisture Content | — | X | — |

Visual inspection: Visual inspection was performed under a white light source (13W fluorescent tube) against black and white backgrounds. Digital photographs were acquired of all formulations.

Concentration Measurement (A260): Spectrophotometry analysis was performed with a quartz cuvette with a 1 cm path length by a Beckman Coulter DU800. The plasmid DNA concentration of the test samples was determined by measuring absorbance at 230, 260, 280 and 350 nm. Concentration analyses were performed using Helixmith's UV/Vis protocol. Calculations were performed using the following equations:

$$\text{Concentration (μg/mL)} = [(D-E)/C] \times (B/A)$$

$$\text{Recovery} = (\text{low μg/mL})/(\text{high μg/mL}) \times 100\%$$

$$OD_{260nm}/OD_{280nm} = D/F$$

$$OD_{260nm}/OD_{230nm} = D/G$$

Where:
A=weight of sample taken for the dilution
B=total weight of sample and buffer used for the dilution
C=extinction coefficient of a 0.005% solution in a 1 cm path length cuvette (0.02)
D=optical density for the maximum at 260 nm.
E=absorbance measured at 350 nm
F=absorbance measured at 280 nm
G=absorbance measured at 230 nm
Acceptance Criteria:
D must fall in the range 0.5 to 1.5 OD units
Recovery must be ≥98% $OD_{260nm}/OD_{280nm}$=must fall in the range 1.8 to 2.0
$OD_{260nm}/OD_{230nm}$=must be ≥1.1
pH: pH analysis was performed with a SympHony® pH Meter (VWR Scientific, catalog #SB70P), calibrated with three pH standard solutions (pH 4, 7, and 10) with a calibration slope of 95% or higher. Samples were not temperature adjusted, and were allowed to equilibrate to ambient temperature and measured.

Turbidity Measurement (A350, A450, A650): Turbidity was determined by measuring sample absorbance at 350, 450, and 650 nm using a Beckman Coulter DU800. Formulations with an A650>0.01 are generally considered to exhibit increased turbidity.

Capillary Zone Electrophoresis: Prior to analysis, a capillary was conditioned by running Milli-Q water, 0.1N NaOH, 0.1N HCl, and Milli-Q water again at 20 psi for 10 minute each (the conditioning lasted a total of 40 minutes). 40 μL of sample at a concentration of 0.5 mg/mL was loaded into a polyethylene insert for analysis.

Instrument: Beckman Coulter PA 800+CE (S/N 3063309)
Capillary: Neutral coated capillary, 50 μm I.D, 40 cm total length, 30 cm effective length, 8 μm aperture (Beckman Coulter P/N 477441, lot #M812134)
Data Analysis: 32 Karat (version 9.0)
Pressure/injection time: 0.5 psi/11 sec.
Separation buffer/pressure: 100 mM phosphoric acid (pH 2.60), 85%/20 psi; 60 sec.
Wash buffer/pressure: Milli-Q water/20 psi; 60 sec
Detection: UV at 254 nm
Separation voltage: 17 KV; ramp 0.17 min; 14 min.
Residual Moisture Content: A Karl Fisher Coulometer C20 (Mettler Toledo) was used for moisture content analysis. An Apura Water Standard Oven 1% was used to determine system accuracy. Sample vials were brought to room temperature before caps were removed for analysis. Approximately 100 mg of material was used for each analysis.

6.8.2.3. Summary of Test Results

This section summarizes the quality of the lyophilized VM202 in various formulations.

6.8.2.3.1. Lyophilization Cycle Profile

The previously designed Lyo Cycle was utilized to lyophilize 2.5 mg doses of VM202 in various formulations. The ramping of the freezing temperature from −50° C. to −20° C. and holding for two (2) hours prior to pulling the vacuum allowed for annealing to occur. The annealing process aids the crystallization of amorphous excipients. Due to unique feature of the lyophilizer used in these experiments, which may abort the program if the vacuum does not reach the set point within a given time frame, a step at the beginning of primary drying where the vacuum is pulled to 100 mTorr initially and adjusted to final vacuum as primary drying starts was utilized. Primary drying was performed at shelf temperature of −20° C. (~53.4 hours) with 50 mTorr chamber pressure (TABLE 31). Secondary drying at a shelf temperature of 20° C. was designed to remove the residual water that was not sublimated during the primary drying step.

TABLE 31

Lyophilization Cycle Parameters

| Step | Temperature (° C.) | Time (Min) | Ramp Rate (° C./Min) | Chamber Pressure (mTorr) |
|---|---|---|---|---|
| Loading | 5 | N/A | N/A | N/A |
| Freezing | 5 to −50 | 55 | 1 | N/A |
|  | −50 | 120 | N/A | N/A |
|  | −50 to −20 | 60 | 0.5 | N/A |
|  | −20 | 120 | N/A | N/A |
|  | −20 | 60 | N/A | 100 |
| Primary Drying | −20 | 3200* | N/A | 50 |
| Secondary Drying | −20 to 20 | 80 | 0.5 | 50 |
|  | 20 | 780 | N/A | 50 |

*Primary drying time was changed from 3240 min to 3200 min due to software limitations. Pirani gauge and the capacitance manometer merged, before advancing to secondary drying.

FIG. 28 shows a chart of the entire lyophilization cycle. The product temperature dropped to around −40° C., due to heat-loss from sublimation when the vacuum was applied. The pirani gauge value merged with the capacitance manometer reading at approximately 41 hours, which confirmed the completion of the primary drying process. Following 62 hours of the entire cycle, secondary drying at 20° C. was initiated and the samples were allowed to dry for an additional 13 hours. The entire cycle lasted approximately 75 hours.

The measured moisture contents of the cakes are shown in TABLE 32.

TABLE 32

Moisture content results

| Form. Code | Moisture Content (%) |
|---|---|
| F1 | 2.30 |
| F2 | 1.51 |
| F3 | 1.78 |
| F4 | 1.90 |
| F5 | 2.39 |
| F6 | 3.02 |

6.8.2.3.2. Lyophilization Study

Visual inspection: Following lyophilization, F1, F2, and F3 displayed decent cakes, with only slight shrinkage. F5 displayed significant cake shrinkage. Total collapse of cakes was observed for F4 (FIG. 32) and F6 (FIG. 34). F1 (FIG. 29), F2 (FIG. 30), F3 (FIG. 31), F4 (FIG. 32), and F5 (FIG. 33) reconstituted liquid samples were clear, colorless, and free of visible particulates, comparable to the pre-lyo control. Following reconstitution, F6 was hazy.

Concentration ($A_{260}$): All samples were at their target concentrations before lyophilization and after reconstitution as provided in TABLE 33.

TABLE 33

Concentration results

| | Concentration (mg/mL) | |
|---|---|---|
| Form. Code | Pre-Lyo | Reconstituted Liquid |
| F1 | 0.5 | 0.5 |
| F2 | 0.5 | 0.5 |
| F3 | 0.5 | 0.5 |
| F4 | 0.5 | 0.5 |
| F5 | 0.5 | 0.5 |
| F6 | 0.5 | 0.5 | pH and Reconstitution Time: Due to the buffering limitation of formulation F3, the pH of F3 was not stable and decreased quickly during the fill. By the time the pre-lyo samples were analyzed they had already decreased from pH 9.0 to 8.7. Further decrease of pH value was observed after reconstitution ($\Delta=-0.4$), compared to the pre-lyo control. After reconstitution, F1, F2, F4, F5, F6 formulations showed the same pH values ($\Delta \leq 0.1$), compared to their pre-lyo controls. Reconstituted time analysis indicated that lyophilized cake dissolved between 1 and 1.5 minutes. The pH and reconstitution time results are detailed in TABLE 34.

TABLE 34 pH and Reconstitution Time Results

| Form. Code | pH Pre-Lyo | pH Reconstituted Liquid | Reconstitution Time (min) Lyo Cake |
|---|---|---|---|
| F1 | 7.9 | 8.0 | ~1.0 |
| F2 | 7.0 | 7.1 | ~1.0 |
| F3 | 8.7 | 8.3 | ~1.5 |
| F4 | 7.9 | 8.0 | ~1.5 |
| F5 | 7.9 | 7.9 | ~1.0 |
| F6 | 7.9 | 7.9 | ~1.5 |

Turbidity ($A_{350}$, $A_{450}$, $A_{650}$): Slight increases in turbidity were observed for F6 at 350 nm, 450 nm, and 650 nm after reconstitution. All other formulations showed no significant turbidity before lyophilization or after reconstitution as provided below in TABLE 35.

TABLE 35

Turbidity Results

| | Turbidity | | | | | |
|---|---|---|---|---|---|---|
| | $Abs_{350}$ | | $Abs_{450}$ | | $Abs_{650}$ | |
| Form. Code | Pre-Lyo | Reconstituted Liquid | Pre-Lyo | Reconstituted Liquid | Pre-Lyo | Reconstituted Liquid |
| F1 | 0.005 | 0.005 | 0.002 | −0.001 | 0.000 | −0.003 |
| F2 | −0.002 | 0.010 | −0.005 | 0.002 | −0.004 | −0.001 |
| F3 | 0.006 | 0.003 | 0.001 | −0.003 | 0.000 | −0.004 |
| F4 | 0.000 | −0.002 | −0.004 | −0.005 | −0.004 | −0.005 |
| F5 | −0.002 | 0.003 | −0.005 | −0.003 | −0.005 | −0.004 |
| F6 | 0.010 | 0.099 | −0.004 | 0.060 | −0.005 | 0.028 |

Note:
The absorbance of water was subtracted to obtain turbidity values for samples, with $A_{650} \geq 0.01$ considered to be turbid.

Capillary Zone Electrophoresis (CZE): The reconstituted samples were further examined by CZE for product purity. F6 was not analyzed due to turbidity. The electropherograms and tabular results from CZE are detailed in FIG. 35 and TABLE 36, respectively. After reconstitution, all formulations showed slight increases of open circle peak, with corresponding decreases in supercoil peak (97.5%-99.0%), compared to pre-lyo (99.1%-100.0%). F4 and F5 showed the smallest increase of open circle peak percentage, less than or equal to 0.4%, compared to other formulations. Excluding formulations with poor cake appearance, current formulation (F1), showed the highest purity, before (100%) and after lyophilization (98.6%).

TABLE 36

CZE Results

| Sample | | Supercoil Peak % | Open Circle Peak % | Total Area |
|---|---|---|---|---|
| F1 | Pre-Lyo | 100.0 | 0.0 | 8082 |
| | Reconstituted Liquid | 98.6 | 1.4 | 12253 |
| F2 | Pre-Lyo | 99.8 | 0.2 | 9082 |
| | Reconstituted Liquid | 98.3 | 1.7 | 12848 |
| F3 | Pre-Lyo | 99.4 | 0.6 | 9904 |
| | Reconstituted Liquid | 97.5 | 2.5 | 12202 |
| F4 | Pre-Lyo | 99.2 | 0.8 | 9535 |
| | Reconstituted Liquid | 99.0 | 1.0 | 13023 |
| F5 | Pre-Lyo | 99.1 | 0.9 | 9215 |
| | Reconstituted Liquid | 98.7 | 1.3 | 12542 |

Conclusions: The objective of the study was to assess the quality of VM202 in the drug product formulation, 0.5 mg/mL VM202 in 10 mM potassium phosphate with 2% mannitol, 1% sucrose, 0.45% NaCl at pH 8.0, following lyophilization, as well as the quality of VM202 in formulations with slight variations in pH and/or concentrations of bulking agents and stabilizers from the drug product formulation. The analytical methods implemented in this study included capillary zone electrophoresis (CZE), visual inspection for clarity and cake appearance, turbidity, concentration (A260), pH, and moisture content analyses (Karl Fischer), which have all been shown to be effective stability-indicating assays for the product.

In this lyophilized formulation study, VM202 was evaluated at 2.5 mg per vial at a fill volume of 5 mL. A small-scale pH testing was performed with 0.9% NaCl placebo to establish proper formulation preparation procedures by dilution method for VM202 on a larger scale.

Prior to lyophilization, all formulations of VM202 were clear, without discoloration, and free of visible particulates, and concentration was on target. pH of the 10 mM potassium phosphate formulation at pH 9.0 was not stable and decreased quickly during the fill, with further decreases observed after lyophilization and reconstitution. Capillary zone electrophoresis results for all formulations prior to lyophilization showed high purity, with the drug product formulation showing the highest percentage of supercoil peak.

Following lyophilization, decent cakes were observed for the drug product formulation and the drug product formulations at higher and lower pH. After reconstitution, the formulation with the highest concentration of NaCl exhibited haziness, while the rest of formulations were clear, colorless, and free of visible particulates, comparable to the pre-lyo control. After reconstitution, all formulations showed slight increases of open circle peak, with corresponding decreases in supercoil peak. Excluding formulations with poor cake appearance, the drug product formulation, showed the highest purity by capillary zone electrophoresis after lyophilization.

Results obtained from this study suggest that lyophilized VM202 maintains decent cake appearance and the highest level of purity (supercoiled DNA) after lyophilization at 0.5 mg/mL with 10 mM potassium phosphate at pH 8.0, 2% mannitol, 1% sucrose, 0.45% NaCl, at a fill volume of 5 mL in 20 cc vials.

6.8.3. Example 3: Lyophilized Composition of pTx-IGF-1X10

Various lyophilized formulations containing pTx-IGF-1X10 were generated and analyzed for the quality of pTx-IGF-1X10 in the formulation following lyophilization. Formulations listed below in TABLE 37 were prepared for analysis.

TABLE 37

| Form. Code | buffer | pH | Bulking agent | Stabilizers | PTX-IGF-1X10 concentration |
|---|---|---|---|---|---|
| F1 | 10 mM potassium phosphate | 8 | 2% mannitol | 1.0% sucrose, 0.45% NaCl | 0.5 mg/ml |
| F2 | 10 mM potassium phosphate | 7 | 2% mannitol | 1.0% sucrose, 0.45% NaCl | 0.5 mg/ml |
| F3 | 10 mM potassium phosphate | 9 | 2% mannitol | 1.0% sucrose, 0.45% NaCl | 0.5 mg/ml |
| F4 | 10 mM potassium phosphate | 8 | 1% mannitol | 1.0% sucrose, 0.45% NaCl | 0.5 mg/ml |
| F5 | 10 mM potassium phosphate | 8 | 2% mannitol | 1.0% sucrose, 0.60% NaCl | 0.5 mg/ml |
| F6 | 10 mM potassium phosphate | 8 | 2% mannitol | 1.0% sucrose, 0.90% NaCl | 0.5 mg/ml |
| F7 | 10 mM potassium phosphate | 8 | 2% mannitol | 1.0% Sucrose, 0.2% NaCl | 0.5 mg/ml |
| F8 | 10 mM potassium phosphate | 8 | 2% mannitol | 0.5% Sucrose, 0.45% NaCl | 0.5 mg/ml |
| F9 | 10 mM potassium phosphate | 8 | 3% mannitol | 1.0% sucrose, 0.45% NaCl | 0.5 mg/ml |

6.8.3.1. Summary of Test Results

Visual inspection: Following lyophilization, F1, F2, F7, F8 and F9 displayed decent cakes, with only slight shrinkage. F5 displayed significant cake shrinkage. F3 displayed splashing form. Total collapse of cakes was observed for F4 and F6. F1 (FIG. 36), F2 (FIG. 37), F3 (FIG. 38), F4 (FIG. 39), F5 (FIG. 40), F6 (FIG. 41), F7 (FIG. 42), F8 (FIG. 43) and F9 (FIG. 44) reconstituted liquid samples were clear, colorless, and free of visible particulates, comparable to the pre-lyo control. To determine the turbidity (Clarity) of samples, samples were compared to Turbidity 4000NTU calibration standard I, II, III, IV. Formulation with "<I Clarity" can be evaluated as not turbid.

Concentration (A260): All samples were at their target concentrations before lyophilization and after reconstitution as provided below in TABLE 38.

TABLE 38

| | Concentration results | |
|---|---|---|
| | Concentration (mg/mL) | |
| Form. Code | Pre-Lyo | Reconstituted Liquid |
| F1 | 0.5 | 0.5 |
| F2 | 0.5 | 0.5 |
| F3 | 0.5 | 0.5 |
| F4 | 0.5 | 0.5 |
| F5 | 0.5 | 0.5 |

TABLE 38-continued

| | Concentration results | |
|---|---|---|
| | Concentration (mg/mL) | |
| Form. Code | Pre-Lyo | Reconstituted Liquid |
| F6 | 0.5 | 0.5 |
| F7 | 0.5 | 0.5 |
| F8 | 0.5 | 0.5 |
| F9 | 0.5 | 0.5 |

DH and Reconstitution Time: The pH value of F3 decreased from pH 9.0 to 7.6 after reconstitution. After reconstitution, F1, F2, F4, F5, F6, F7, F8, F9 formulations showed the same pH values (Δ≤0.5), compared to their pre-lyo controls. Reconstituted time analysis indicated that lyophilized cake dissolved between 1min 20 sec and 4 min 05 sec. The pH and reconstitution time results are detailed in TABLE 39.

TABLE 39

| | pH and Reconstitution Time Results | | |
|---|---|---|---|
| | pH | | Reconstitution Time (min:sec) |
| Form. Code | Pre-Lyo | Reconstituted Liquid | Lyo Cake |
| F1 | 8.0 | 7.7 | 1:50 |
| F2 | 7.0 | 6.9 | 3:40 |
| F3 | 9.0 | 7.6 | 4:05 |
| F4 | 8.0 | 7.6 | 2:00 |
| F5 | 8.0 | 7.6 | 2:20 |
| F6 | 8.0 | 7.6 | 1:20 |
| F7 | 8.0 | 7.7 | 1:40 |
| F8 | 8.0 | 7.6 | 1:50 |
| F9 | 8.0 | 7.6 | 3:20 |

Capillary Electrophoresis (CE): The reconstituted samples were further examined by CE for product purity. The electropherograms and tabular results from CE are detailed in FIG. 45 and TABLE 40, respectively. After reconstitution, all formulations except F3 showed slight increases (0.5-3%) of open circle peak, with corresponding decreases in supercoil peak, compared to pre-lyo. Excluding formulations with poor cake appearance, current formulation (F1), showed the lowest decrease of supercoil peak after lyophilization.

TABLE 40

| | CE results | | |
|---|---|---|---|
| Sample | | Supercoil Peak % | Open Circle Peak % | Total Area |
| F1 | Pre-Lyo | 91.71 | 8.29 | 17702.24 |
| | Reconstituted Liquid | 91.21 | 8.79 | 20779.98 |
| F2 | Pre-Lyo | 92.67 | 7.33 | 15510.04 |
| | Reconstituted Liquid | 90.33 | 9.67 | 22004.75 |
| F3 | Pre-Lyo | 95.31 | 4.69 | 12198.69 |
| | Reconstituted Liquid | 84.62 | 15.38 | 22561.09 |
| F4 | Pre-Lyo | 92.55 | 7.45 | 15180.98 |
| | Reconstituted Liquid | 91.97 | 8.03 | 22858.45 |
| F5 | Pre-Lyo | 91.85 | 8.15 | 18847 |
| | Reconstituted Liquid | 90.69 | 9.31 | 23597.22 |
| F6 | Pre-Lyo | 92.19 | 7.81 | 19221.12 |
| | Reconstituted Liquid | 90.73 | 9.27 | 23951.71 |
| F7 | Pre-Lyo | 91.71 | 8.29 | 17919.92 |
| | Reconstituted Liquid | 90.51 | 9.49 | 22180.31 |
| F8 | Pre-Lyo | 92.08 | 7.92 | 18266.49 |
| | Reconstituted Liquid | 90.54 | 9.46 | 24314.31 |

TABLE 40-continued

| | | CE results | | |
|---|---|---|---|---|
| | Sample | Supercoil Peak % | Open Circle Peak % | Total Area |
| F9 | Pre-Lyo | 92.54 | 7.46 | 15054.62 |
| | Reconstituted Liquid | 89.10 | 10.90 | 23387.16 |

6.8.4. Example 4: Lyophilized Composition of pCK-SDF-1α

6.8.4.1. Experimental Design

Various lyophilized formulations containing pCK-SDF-1α were generated and analyzed for the quality of pCK-SDF-1α in the formulation following lyophilization. Formulations listed below in TABLE 41 were prepared for analysis.

TABLE 41

| Form. Code | buffer | pH | Bulking agent | Stabilizers | pCK-SDF-1α concentration |
|---|---|---|---|---|---|
| F1 | 10 mM potassium phosphate | 8 | 2% mannitol | 1.0% sucrose, 0.45% NaCl | 0.5 mg/ml |
| F2 | 10 mM potassium phosphate | 7 | 2% mannitol | 1.0% sucrose, 0.45% NaCl | 0.5 mg/ml |
| F3 | 10 mM potassium phosphate | 9 | 2% mannitol | 1.0% sucrose, 0.45% NaCl | 0.5 mg/ml |
| F4 | 10 mM potassium phosphate | 8 | 1% mannitol | 1.0% sucrose, 0.45% NaCl | 0.5 mg/ml |
| F5 | 10 mM potassium phosphate | 8 | 2% mannitol | 1.0% sucrose, 0.60% NaCl | 0.5 mg/ml |
| F6 | 10 mM potassium phosphate | 8 | 2% mannitol | 1.0% sucrose, 0.90% NaCl | 0.5 mg/ml |
| F7 | 10 mM potassium phosphate | 8 | 2% mannitol | 1.0% Sucrose, 0.2% NaCl | 0.5 mg/ml |
| F8 | 10 mM potassium phosphate | 8 | 2% mannitol | 0.5% Sucrose, 0.45% NaCl | 0.5 mg/ml |
| F9 | 10 mM potassium phosphate | 8 | 3% mannitol | 1.0% sucrose, 0.45% NaCl | 0.5 mg/ml |

6.8.4.2. Summary of Test Results

Visual inspection: Following lyophilization, F1, F2, F3, F7, F8 and F9 displayed decent cakes, with only slight shrinkage. F5 displayed significant cake shrinkage. Total collapse of cakes was observed for F4 and F6. F1 (FIG. 46), F2 (FIG. 47), F3 (FIG. 48), F4 (FIG. 49), F5 (FIG. 50), F6 (FIG. 51), F7 (FIG. 52), F8 (FIG. 53) and F9 (FIG. 54) reconstituted liquid samples were clear, colorless, and free of visible particulates, comparable to the pre-lyo control. To determine the turbidity (Clarity) of samples, samples were compared to Turbidity 4000NTU calibration standard I, II, III, IV. Formulation with "<I Clarity" can be evaluated as not turbid.

Concentration (A260): All samples were at their target concentrations before lyophilization and after reconstitution as provided below in TABLE 42.

TABLE 42

| | Concentration results | |
|---|---|---|
| | Concentration (mg/mL) | |
| Form. Code | Pre-Lyo | Reconstituted Liquid |
| F1 | 0.5 | 0.5 |
| F2 | 0.5 | 0.5 |
| F3 | 0.5 | 0.5 |
| F4 | 0.5 | 0.5 |
| F5 | 0.5 | 0.5 |
| F6 | 0.5 | 0.5 |
| F7 | 0.5 | 0.5 |
| F8 | 0.5 | 0.5 |
| F9 | 0.5 | 0.5 |

DH and Reconstitution Time: The pH value of F3 decreased from pH 9.0 to 7.9 after reconstitution. After reconstitution, F1, F2, F4, F5, F6, F7, F8, F9 formulations showed the same pH values (Δ≤0.5), compared to their pre-lyo controls. Reconstituted time analysis indicated that lyophilized cake dissolved between 1.5 min and 4 minutes. The pH and reconstitution time results are detailed below in TABLE 43.

TABLE 43

| | pH and reconstitution time results | | |
|---|---|---|---|
| | pH | | Reconstitution Time (min:sec) |
| Form. Code | Pre-Lyo | Reconstituted Liquid | Lyo Cake |
| F1 | 8.0 | 7.7 | 1:40 |
| F2 | 7.0 | 6.9 | 2:10 |
| F3 | 9.0 | 7.9 | 2:30 |
| F4 | 8.0 | 7.8 | 1:50 |
| F5 | 8.0 | 7.7 | 1:30 |
| F6 | 8.0 | 7.6 | 1:30 |
| F7 | 8.0 | 7.7 | 1:30 |
| F8 | 8.0 | 7.7 | 2:20 |
| F9 | 8.0 | 7.7 | 4:00 |

Capillary Electrophoresis: The reconstituted samples were further examined by CE for product purity. The electropherograms and tabular results from CE are detailed in FIG. 55 and TABLE 44, respectively. After reconstitution, all formulations showed slight increases (0.5-2%) of open circle peak, with corresponding decreases in supercoil peak, compared to pre-lyo. Excluding formulations with poor cake appearance, current formulation (F1), showed the lowest decrease of supercoil peak after lyophilization.

TABLE 44

| | | CE results | | |
|---|---|---|---|---|
| | Sample | Supercoil Peak % | Open Circle Peak % | Total Area |
| F1 | Pre-Lyo | 92.97 | 7.03 | 18689.15 |
| | Reconstituted Liquid | 92.35 | 7.65 | 21223.38 |
| F2 | Pre-Lyo | 92.89 | 7.11 | 18494.15 |
| | Reconstituted Liquid | 92.00 | 8.00 | 22748.49 |
| F3 | Pre-Lyo | 92.88 | 7.12 | 17540.79 |
| | Reconstituted Liquid | 91.52 | 8.48 | 22360.01 |
| F4 | Pre-Lyo | 93.14 | 6.86 | 18019.91 |
| | Reconstituted Liquid | 92.80 | 7.20 | 21975.46 |
| F5 | Pre-Lyo | 92.94 | 7.06 | 20043.63 |
| | Reconstituted Liquid | 92.57 | 7.43 | 22977.2 |
| F6 | Pre-Lyo | 93.15 | 6.85 | 19398.54 |
| | Reconstituted Liquid | 92.51 | 7.49 | 22958.31 |

TABLE 44-continued

| | | CE results | | |
|---|---|---|---|---|
| | Sample | Supercoil Peak % | Open Circle Peak % | Total Area |
| F7 | Pre-Lyo | 92.64 | 7.36 | 20243.28 |
| | Reconstituted Liquid | 91.86 | 8.14 | 21279.46 |
| F8 | Pre-Lyo | 93.20 | 6.80 | 19094.26 |
| | Reconstituted Liquid | 91.65 | 8.35 | 22253.88 |
| F9 | Pre-Lyo | 92.82 | 7.18 | 18334.58 |
| | Reconstituted Liquid | 91.36 | 8.64 | 21085.33 |

7. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

8. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

| SEQUENCE LISTING: | | |
|---|---|---|
| SEQ ID NO: 1 | Amino acid sequence of flHGF protein | MWVTKLLPALLLQHVLLHLLLLPIAIPYAEGQRKRRNTIH EFKKSAKTTLIKIDPALKIKTKKVNTADQCANRCTRNKGL PFTCKAFVFDKARKQCLWFPFNSMSSGVKKEFGHEFDLYE NKDYIRNCIIGKGRSYKGTVSITKSGIKCQPWSSMIPHEHSF LPSSYRGKDLQENYCRNPRGEEGGPWCFTSNPEVRYEVC DIPQCSEVECMTCNGESYRGLMDHTESGKICQRWDHQTP HRHKFLPERYPDKGFDDNYCRNPDGQPRPWCYTLDPHTR WEYCAIKTCADNTMNDTDVPLETTECIQGQGEGYRGTVN TIWNGIPCQRWDSQYPHEHDMTPENFKCKDLRENYCRNP DGSESPWCFTTDPNIRVGYCSQIPNCDMSHGQDCYRGNG KNYMGNLSQTRSGLTCSMWDKNMEDLHRHIFWEPDASK LNENYCRNPDDDAHGPWCYTGNPLIPWDYCPISRCEGDTT PTIVNL DHPVISCAKTKQLRVVNGIPTRTNIGWMVSLRYRNKHICG GSLIKESWVLTARQCFPSRDLKDYEAWLGIHDVHGRGDE KCKQVLNVSQLVYGPEGSDLVLMKLARPAVLDDFVSTID LPNYGCTIPEKTSCSVYGWGYTGLINYDGLLRVAHLYIMG NEKCSQHHRGKVTLNESEICAGAEKIGSGPCEGDYGGPLV CEQHKMRMVLGVIVPGRGCAIPNRPGIFVRVAYYAKWIH KIILTYKVPQS |
| SEQ ID NO: 2 | Amino acid sequence of dHGF protein | MWVTKLLPALLLQHVLLHLLLLPIAIPYAEGQRKRRNTIH EFKKSAKTTLIKIDPALKIKTKKVNTADQCANRCTRNKGL PFTCKAFVFDKARKQCLWFPFNSMSSGVKKEFGHEFDLYE NKDYIRNCIIGKGRSYKGTVSITKSGIKCQPWSSMIPHEHS YRGKDLQENYCRNPRGEEGGPWCFTSNPEVRYEVCDIPQ CSEVECMTCNGESYRGLMDHTESGKICQRWDHQTPHRHK FLPERYPDKGFDDNYCRNPDGQPRPWCYTLDPHTRWEYC AIKTCADNTMNDTDVPLETTECIQGQGEGYRGTVNTIWN GIPCQRWDSQYPHEHDMTPENFKCKDLRENYCRNPDGSE SPWCFTTDPNIRVGYCSQIPNCDMSHGQDCYRGNGKNYM GNLSQTRSGLTCSMWDKNMEDLHRHIFWEPDASKLNENY CRNPDDDAHGPWCYTGNPLIPWDYCPISRCEGDTTPTIVN LDHPVI SCAKTKQLRVVNGIPTRTNIGWMVSLRYRNKHICGGSLIK ESWVLTARQCFPSRDLKDYEAWLGIHDVHGRGDEKCKQ VLNVSQLVYGPEGSDLVLMKLARPAVLDDFVSTIDLPNYG CTIPEKTSCSVYGWGYTGLINYDGLLRVAHLYIMGNEKCS QHHRGKVTLNESEICAGAEKIGSGPCEGDYGGPLVCEQHK MRMVLGVIVPGRGCAIPNRPGIFVRVAYYAKWIHKIILTY KVPQS |
| SEQ ID NO: 3 | Nucleotide sequence of exons 1-4 of human hgf | ATGTGGGTGACCAAACTCCTGCCAGCCCTGCTGCTGCA GCATGTCCTCCTGCATCTCCTCCTGCTCCCCATCGCCAT CCCCTATGCAGAGGGACAAAGGAAAAGAAGAAATACA ATTCATGAATTCAAAAAATCAGCAAAGACTACCCTAAT CAAAATAGATCCAGCACTGAAGATAAAAACCAAAAA GTGAATACTGCAGACCAATGTGCTAATAGATGTACTAG GAATAAAGGACTTCCATTCACTTGCAAGGCTTTTGTTTT TGATAAAGCAAGAAAACAATGCCTCTGGTTCCCCTTCA ATAGCATGTCAAGTGGAGTGAAAAAAGAATTTGGCCAT GAATTTGACCTCTATGAAAACAAAGACTACATTAGAAA CTGCATCATTGGTAAAGGACGCAGCTACAAGGGAACAG TATCTATCACTAAGAGTGGCATCAAATGTCAGCCCTGG AGTTCCATGATACCACACGAACACAG |
| SEQ ID NO: 4 | Nucleotide sequence of | CCTACAGGAAAACTACTGTCGAAATCCTCGAGGGGAAG AAGGGGGACCCTGGTGTTTCACAAGCAATCCAGAGGTA |

| | | |
|---|---|---|
| | exons 5-18 of human hgf | CGCTACGAAGTCTGTGACATTCCTCAGTGTTCAGAAGTT<br>GAATGCATGACCTGCAATGGGAGAGTTATCGAGGTCT<br>CATGGATCATACAGAATCAGGCAAGATTTGTCAGCGCT<br>GGGATCATCAGACACCACACCGGCACAAATTCTTGCCT<br>GAAAGATATCCCGACAAGGGCTTTGATGATAATTATTG<br>CCGCAATCCCGATGGCCAGCCGAGGCCATGGTGCTATA<br>CTCTTGACCCTCACACCCGCTGGGAGTACTGTGCAATTA<br>AAACATGCGCTGACAATACTATGAATGACACTGATGTT<br>CCTTTGGAAACAACTGAATGCATCCAAGGTCAAGGAGA<br>AGGCTACAGGGGCACTGTCAATACCATTTGGAATGGAA<br>TTCCATGTCAGCGTTGGGATTCTCAGTATCCTCACGAGC<br>ATGACATGACTCCTGAAAATTTCAAGTGCAAGGACCTA<br>CGAGAAAATTACTGCCGAAATCCAGATGGGTCTGAATC<br>ACCCTGGTGTTTTACCACTGATCCAAACATCCGAGTTGG<br>CTACTGCTCCCAAATTCCAAACTGTGATATGTCACATGG<br>ACAAGATTGTTATCGTGGGAATGGCAAAAATTATATGG<br>GCAACTTATCCCAAACAAGATCTGGACTAACATGTTCA<br>ATGTGGGACAAGAACATGGAAGACTTACATCGTCATAT<br>CTTCTGGGAACCAGATGCAAGTAAGCTGAATGAGAATT<br>ACTGCCGAAATCCAGATGATGATGCTCATGGACCCTGG<br>TGCTACACGGGAAATCCACTCATTCCTTGGGATTATTGC<br>CCTATTTCTCGTTGTGAAGGTGATACCACACCTACAATA<br>GTCAATTTAGACCATCCCGTAATATCTTGTGCCAAAACG<br>AAACAATTGCGAGTTGTAAATGGGATTCCAACACGAAC<br>AAACATAGGATGGATGGTTAGTTTGAGATACAGAAATA<br>AACATATCTGCGGAGGATCATTGATAAAGGAGAGTTGG<br>GTTCTTACTGCACGACAGTGTTTCCCTTCTCGAGACTTG<br>AAAGATTATGAAGCTTGGCTTGGAATTCATGATGTCCA<br>CGGAAGAGGAGATGAGAAATGCAAACAGGTTCTCAAT<br>GTTTCCCAGCTGGTATATGGCCCTGAAGGATCAGATCTG<br>GTTTTAATGAAGCTTGCCAGGCCTGCTGTCCTGGATGAT<br>TTTGTTAGTACGATTGATTTACCTAATTATGGATGCACA<br>ATTCCTGAAAAGACCAGTTGCAGTGTTTATGGCTGGGG<br>CTACACTGGATTGATCAACTATGATGGCCTATTACGAGT<br>GGCACATCTCTATATAATGGGAAATGAGAAATGCAGCC<br>AGCATCATCGAGGGAAGGTGACTCTGAATGAGTCTGAA<br>ATATGTGCTGGGGCTGAAAAGATTGGATCAGGACCATG<br>TGAGGGGGATTATGGTGGCCCACTTGTTTGTGAGCAAC<br>ATAAAATGAGAATGGTTCTTGGTGTCATTGTTCCTGGTC<br>GTGGATGTGCCATTCCAAATCGTCCTGGTATTTTTGTCC<br>GAGTAGCATATTATGCAAAATGGATACACAAAATTATT<br>TTAACATATAAGGTACCACAGTCATAG |
| SEQ ID NO: 5 | Nucleotide sequence of pCK vector | CGCGTTGACATTGATTATTGACTAGTTATTAATAGTAAT<br>CAATTACGGGGTCATTAGTTCATAGCCCATATATGGAGT<br>TCCGCGTTACATAACTTACGGTAAATGGCCCGCCTGGCT<br>GACCGCCCAACGACCCCCGCCCATTGACGTCAATAATG<br>ACGTATGTTCCCATAGTAACGCCAATAGGGACTTTCCAT<br>TGACGTCAATGGGTGGAGTATTTACGGTAAACTGCCCA<br>CTTGGCAGTACATCAAGTGTATCATATGCCAAGTCCGCC<br>CCCTATTGACGTCAATGACGGTAAATGGCCCGCCTGGC<br>ATTATGCCCAGTACATGACCTTACGGGACTTTCCTACTT<br>GGCAGTACATCTACGTATTAGTCATCGCTATTACCATGG<br>TGATGCGGTTTTGGCAGTACACCAATGGGCGTGGATAG<br>CGGTTTGACTCACGGGGATTTCCAAGTCTCCACCCCATT<br>GACGTCAATGGGAGTTTGTTTTGGCACCAAAATCAACG<br>GGACTTTCCAAAATGTCGTAATAACCCCGCCCGTTGAC<br>GCAAATGGGCGGTAGGCGTGTACGGTGGGAGGTCTATA<br>TAAGCAGAGCTCGTTTAGTGAACCGTCAGATCGCCTGG<br>AGACGCCATCCACGCTGTTTTGACCTCCATAGAAGACA<br>CCGGGACCGATCCAGCCTCCGCGGCCGGGAACGGTGCA<br>TTGGAACGCGGATTCCCCGTGCCAAGAGTGACGTAAGT<br>ACCGCCTATAGACTCTATAGGCACACCCCTTTGGCTCTT<br>ATGCATGCTATACTGTTTTTGGCTTGGGGCCTATACACC<br>CCCGCTTCCTTATGCTATAGGTGATGGTATAGCTTAGCC<br>TATAGGTGTGGGTTATTGACCATTATTGACCACTCCCCT<br>ATTGGTGACGATACTTTCCATTACTAATCCATAACATGG<br>CTCTTTGCCACAACTATCTCTATTGGCTATATGCCAATA<br>CTCTGTCCTTCAGAGACTGACACGGACTCTGTATTTTTA<br>CAGGATGGGGTCCCATTTATTATTTACAAATTCACATAT<br>ACAACAACGCCGTCCCCCGTGCCCGCAGTTTTTATTAAA<br>CATAGCGTGGGATCTCCACGCGAATCTCGGGTACGTGT<br>TCCGGACATGGGCTCTTCTCCGGTAGCGGCGGAGCTTCC<br>ACATCCGAGCCCTGGTCCCATGCCTCCAGCGGCTCATG<br>GTCGCTCGGCAGCTCCTTGCTCCTAACAGTGGAGGCCA<br>GACTTAGGCACAGCACAATGCCCACCACCACCAGTGTG<br>CCGCACAAGGCCGTGGCGGTAGGGTATGTGTCTGAAAA |

| | | |
|---|---|---|
| | | TGAGCTCGGAGATTGGGCTCGCACCGCTGACGCAGATG |
| | | GAAGACTTAAGGCAGCGGCAGAAGAAGATGCAGGCAG |
| | | CTGAGTTGTTGTATTCTGATAAGAGTCAGAGGTAACTCC |
| | | CGTTGCGGTGCTGTTAACGGTGGAGGGCAGTGTAGTCT |
| | | GAGCAGTACTCGTTGCTGCCGCGCGCGCCACCAGACAT |
| | | AATAGCTGACAGACTAACAGACTGTTCCTTTCCATGGGT |
| | | CTTTTCTGCAGTCACCGTCCTTGACACGAAGCTTGGTAC |
| | | CGAGCTCGGATCCACTAGTCCAGTGTGGTGGAATTCTG |
| | | CAGATATCCAGCACAGTGGCGGCCGCTCGAGTCTAGAG |
| | | GGCCCGTTTAAACCCGCTGATCAGCCTCGACTGTGCCTT |
| | | CTAGTTGCCAGCCATCTGTTGTTTGCCCCTCCCCCGTGC |
| | | CTTCCTTGACCCTGGAAGGTGCCACTCCCACTGTCCTTT |
| | | CCTAATAAAATGAGGAAATTGCATCGCATTGTCTGAGT |
| | | AGGTGTCATTCTATTCTGGGGGGTGGGGTGGGGCAGGA |
| | | CAGCAAGGGGGAGGATTGGGAAGACAATAGCAGGCAT |
| | | GCTGGGGAGTCGAAATTCAGAAGAACTCGTCAAGAAGG |
| | | CGATAGAAGGCGATGCGCTGCGAATCGGGAGCGGCGAT |
| | | ACCGTAAAGCACGAGGAAGCGGTCAGCCCATTCGCCGC |
| | | CAAGCTCTTCAGCAATATCACGGGTAGCCAACGCTATG |
| | | TCCTGATAGCGGTCCGCCACACCCAGCCGGCCACAGTC |
| | | GATGAATCCAGAAAAGCGGCCATTTTCCACCATGATAT |
| | | TCGGCAAGCAGGCATCGCCATGGGTCACGACGAGATCC |
| | | TCGCCGTCGGGCATGCTCGCCTTGAGCCTGGCGAACAG |
| | | TTCGGCTGGCGCGAGCCCCTGATGCTCTTCGTCCAGATC |
| | | ATCCTGATCGACAAGACCGGCTTCCATCCGAGTACGTG |
| | | CTCGCTCGATGCGATGTTTCGCTTGGTGGTCGAATGGGC |
| | | AGGTAGCCGGATCAAGCGTATGCAGCCGCCGCATTGCA |
| | | TCAGCCATGATGGATACTTTCTCGGCAGGAGCAAGGTG |
| | | AGATGACAGGAGATCCTGCCCCGGCACTTCGCCCAATA |
| | | GCAGCCAGTCCCTTCCCGCTTCAGTGACAACGTCGAGC |
| | | ACAGCTGCGCAAGGAACGCCCGTCGTGGCCAGCCACGA |
| | | TAGCCGCGCTGCCTCGTCTTGCAGTTCATTCAGGGCACC |
| | | GGACAGGTCGGTCTTGACAAAAAGAACCGGGCGCCCCT |
| | | GCGCTGACAGCCGGAACACGGCGGCATCAGAGCAGCC |
| | | GATTGTCTGTTGTGCCCAGTCATAGCCGAATAGCCTCTC |
| | | CACCCAAGCGGCCGGAGAACCTGCGTGCAATCCATCTT |
| | | GTTCAATCATGCGAAACGATCCTCATCCTGTCTCTTGAT |
| | | CAGATCTTGATCCCCTGCGCCATCAGATCCTTGGCGGCA |
| | | AGAAAGCCATCCAGTTTACTTTGCAGGGCTTCCCAACCT |
| | | TACCAGAGGGCGCCCCAGCTGGCAATTCCGGTTCGCTT |
| | | GCTGTCCATAAAACCGCCCAGTCTAGCTATCGCCATGTA |
| | | AGCCCACTGCAAGCTACCTGCTTTCTCTTTGCGCTTGCG |
| | | TTTTCCCTTGTCCAGATAGCCCAGTAGCTGACATTCATC |
| | | CGGGGTCAGCACCGTTTCTGCGGACTGGCTTTCTACGTG |
| | | AAAAGGATCTAGGTGAAGATCCTTTTTGATAATCTCATG |
| | | ACCAAAATCCCTTAACGTGAGTTTTCGTTCCACTGAGCG |
| | | TCAGACCCCGTAGAAAAGATCAAAGGATCTTCTTGAGA |
| | | TCCTTTTTTTCTGCGCGTAATCTGCTGCTTGCAAACAAA |
| | | AAAACCACCGCTACCAGCGGTGGTTTGTTTGCCGGATC |
| | | AAGAGCTACCAACTCTTTTTCCGAAGGTAACTGGCTTCA |
| | | GCAGAGCGCAGATACCAAATACTGTTCTTCTAGTGTAG |
| | | CCGTAGTTAGGCCACCACTTCAAGAACTCTGTAGCACC |
| | | GCCTACATACCTCGCTCTGCTAATCCTGTTACCAGTGGC |
| | | TGCTGCCAGTGGCGATAAGTCGTGTCTTACCGGGTTGG |
| | | ACTCAAGACGATAGTTACCGGATAAGGCGCAGCGGTCG |
| | | GGCTGAACGGGGGGTTCGTGCACACAGCCCAGCTTGGA |
| | | GCGAACGACCTACACCGAACTGAGATACCTACAGCGTG |
| | | AGCTATGAGAAAGCGCCACGCTTCCCGAAGGGAGAAA |
| | | GGCGGACAGGTATCCGGTAAGCGGCAGGGTCGGAACA |
| | | GGAGAGCGCACGAGGGAGCTTCCAGGGGAAACGCCT |
| | | GGTATCTTTATAGTCCTGTCGGGTTTCGCCACCTCTGAC |
| | | TTGAGCGTCGATTTTTGTGATGCTCGTCAGGGGGGCGG |
| | | AGCCTATGGAAAAACGCCAGCAACGCGGCCTTTTTACG |
| | | GTTCCTGGCCTTTTGCTGGCCTTTTGCTCACATG |
| SEQ ID NO: 6 | Nucleotide sequence of intron 4 of human hgf | GTAAGAACAGTATGAAGAAAAGAGATGAAGCCTCTGTC |
| | | TTTTTTACATGTTAACAGTCTCATATTAGTCCTTCAGAA |
| | | TAATTCTACAATCCTAAAATAACTTAGCCAACTTGCTGA |
| | | ATTGTATTACGGCAAGGTTTATATGAATTCATGACTGAT |
| | | ATTTAGCAAATGATTAATTAATATGTTAATAAAATGTAG |
| | | CCAAAACAATATCTTACCTTAATGCCTCAATTTGTAGAT |
| | | CTCGGTATTTGTGAAATAATAACGTAAACTTCGTTTAAA |
| | | AGGATTCTTCTTCCTGTCTTTGAGAAAGTACGGCACTGT |
| | | GCAGGGGGAGAGGTTGATTGTGAAAAATCAGAGGTAG |
| | | ATGAGAATCTTACTGAGGGCTGAGGGTTCTTTAACCTTG |
| | | GTGGATCTCAACATTGGTTGCACATTAAAATCACCTGCT |
| | | GCAAGCCCTTGACGAATCTTACTTAGAAGATGACAACA |

SEQUENCE LISTING:

```
CAGAACAATTAAATCAGAATCTCTGGGGAGAATAGGGC
ACCAGTATTTTTGAGCTCCCACCATGATTCCAAAGTGC
AGCCAAATTTGAGAACCACTGCTAAAAGCTCAAGCTTC
AGATTGACCAGCTTTTCCATCTCACCTATCGCCTAAAGA
CCAAATTGGATAAATGTGTTCATTACGACAGATGGGTA
CTATTTAAAGATGAGTAAACACAATATACTTAGGCTCG
TCAGACTGAGAGTTTTAATCATCACTGAGGAAAAACAT
AGATATCTAATACTGACTGGAGTATTAGTCAAGGCTTAT
TTCACACACAATTTTATCAGAAACCAAAGTAGTTTAAA
ACAGCTCTCCCCTTATTAGTAATGCATTGGAGGGTTTAC
TTTACCATGTACCTTGCTGAGCACTGTACCTTGTTAATC
TCATTTACTTGTAATGAGAACCACACAGCGGGTAGTTTT
ATTGGTTCTATTTTACCTACATGACAAAACTGAAGCATA
AAAACACTTAGTAAGTTTTCAGTGTCATGCACAACTAG
GAAGTGACATGGCCAGAATATAAGCCCAGTCACCATCA
CTCTATAACCTGCGCTTTTAACAACTTCAGGGCATGACA
CATTTGGCCGGTCAGTAGAACCCATGCTGTGATTTGTTT
TTGCAGTGGTGGTGATGACTGCCTTGTTGAATCCACTTT
TTATTCTATTCCATTTTGGGGACACAATTCTGCAAGATG
ATTCTTCATTAGGAAACAGAGATGAGTTATTGACCAAC
ACAGAAAGAAAAAGAGTTTGTTGCTCCACACTGGGATT
AAACCTATGATCTTGGCCTAATTAACACTAGCTAGTAA
GTGTCCAAGCTGATCATCTCTACAACATTTCAATAACAG
AAAACAACAATTTTCAAAATTAGTTACTTACAATTATGT
AGAAATGCCTCTAAAACACAGTATTTTCCTTATATTACA
AAAACAAAATTATAATTGGTTTTGTCCTCTTTTGAGAG
TTTGCATGGTGTTACTCCCTGCATAGTGAAGAAAACATT
TTATTTAAGTAGATGGATCTAAGTTTTTCATGAACAAAG
GAATGACATTTGAAATCAATCCTACCCTAGTCCAGGAG
AATGCATTAGATTAACCTAGTAGAGGTCTTATTTCACCC
TGAGTTTTCTATGATCGTGATTCTCTGCTGGAGGAGTAA
TTGTGAAATAGATCTCTGGGAACTGGCTTCCTAGTCC
AATCAGCTCTTTTACCAATGAACACTTCCTTGTGATATA
GATGTTTATGGCCGAGAGGATCCAGTATATTAATAAAA
TCCCTTTTTGTATTCAATGAGGGAAACACATAATTTTCA
TCAATTAGCAGCTTATTGGAATATCTGCATGATGGTTTA
ACACTTTTAAGTGTTGACTAAAGATTAATTTTACAGAAA
ATAGAAAAGAAATATGTTTCTGTCTGGAGGAATGATT
TATTGTTGACCCCTAAATTGAAATATTTTACTAGTGGCT
TAATGGAAAGATGATGAAAGATGATGAAATTAATGTAG
AAGCTTAACTAGAAAATCAGGTGACCTGATATCTACAT
CTGTATCCTTCATTGGCCACCCAGCATTCATTAATGAAT
CAGATGATGGAATAGATCAAGTTTCCTAGGAACACAGT
GAATATTAAAAGAAAACAAAGGGAGCCTAGCACCTAG
AAGACCTAGTTTATATTTCAAAGTATATTTGGATGTAAC
CCAATTTTAAACATTTCCTCACTTGTCTCTCTTAAAGCCT
TGCCAACAGCAAGGACAGAGAACCAAAAATAGTGTAT
ATATGAATAAATGCTTATTACAGAATCTGCTGACTGGC
ACATGCTTTGTGTGTAATGGGTTCTCATAAACACTTGTT
GAATGAACACACATAAGTGAAAGAGCATGGCTAGGCTT
CATCCCTTGGTCAAATATGGGGTGCTAAAGAAAAGCAG
GGGAAATACATTGGGACACTAACAAAAAAAAACAGTT
AATTTAGGTAAAAGATAAAATACACCACAGAATGAAGA
AAAGAGATGACCCAGACTGCTCTTTAACCTTCATGTCCT
AGAGAGGTTTTTGATATGAATTGCATTCAGAATTGTGG
AAAGGAGCCCATCTTTTCTCTTCATTTTGATTTTATTAAC
TCCAATGGGGAATTTTATTCGTGTTTTGGCCATATCTA
CTTTTGATTTCTACATTATTCTCTCTTCCTTTCTACCTGT
ATTTGTCCTAATAAATTGTTGACTTATTAATTCACTACTT
CCTCACAGCTTTTTTTGGCTTTACAAATCCACTGGAAA
GGTATATGGGTGTATCACTTTGTGTATTTCGGTGTGCAT
GTGTAGAGGGGACAAAAATCCTCTCTCAAACTATAAAT
ATTGAGTATTTGTGTATTGAACATTTGCTATAACTACTA
GGTTTCTTAAATAATCTTAATATATAAAATGATATAGAA
AAAGGGAAATTATAGTTCGTATTATTCATCTAAGTGAA
GAGATTAAAACCCAGGGAGTAAATAAATTGTCTAAGGA
CTAAGGTTGTATACTATTTAGGTGATAGATATGGGGCA
ACCGTATGGGTTTTATGATTAACAAATAAACTTCTCACC
ACTCTACCATATCAACTTTTCCATAAAAGAGAGCTATAG
TATTCTTTGCTTAAATAAATTTGATTAGTGCATGACTTC
TTGAAAACATATAAAGCAAAAGTCACATTTGATTCTAT
CAGAAAAGTGAGTAAGCCATGGCCCAAACAAAAGATG
CATTAAAATATTCTGGAATGATGGAGCTAAAAGTAAGA
AAAATGACTTTTTAAAAAAGTTTACTGTTAGGAATTGTG
AAATTATGCTGAATTTTAGTTGCATTATAATTTTTGTCA
GTCATACGGTCTGACAACCTGTCTTATTTCTATTTCCCC
ATATGAGGAATGCTAGTTAAGTATGGATATTAACTATT
```

| | | |
|---|---|---|
| | SEQUENCE LISTING: | |
| | | ACTACTTAGATGCATTGAAGTTGCATAATATGGATAAT |
| | | ACTTCACTGGTTCCCTGAAAATGTTTAGTTAGTAATAAG |
| | | TCTCTTACACTATTTGTTTTGTCCAATAATTTATATTTTC |
| | | TGAAGACTTAACTCTAGAATACACTCATGTCAAAATGA |
| | | AAGAATTTCATTGCAAAATATTGCTTGGTACATGACGC |
| | | ATACCTGTATTTGTTTTGTGTCACAACATGAAAAATGAT |
| | | GGTTTATTAGAAGTTTCATTGGGTAGGAAACACATTTGA |
| | | ATGGTATTTACTAAGATACTAAAATCCTTGGACTTCACT |
| | | CTAATTTTAGTGCCATTTAGAACTCAAGGTCTCAGTAAA |
| | | AGTAGAAATAAAGCCTGTTAACAAAACACAAACTGAAT |
| | | ATTAAAAATGTAACTGGATTTTCAAAGAAATGTTTACTG |
| | | GTATTACCTGTAGATGTATATTCTTTATTATGATCTTTTG |
| | | TGTAAAGTCTGGCAGACAAATGCAATATCTAATTGTTG |
| | | AGTCCAATATCACAAGCAGTACAAAAGTATAAAAAAGA |
| | | CTTGGCCTTTTCTAATGTGTTAAAATACTTTATGCTGGT |
| | | AATAACACTAAGAGTAGGGCACTAGAAATTTTAAGTGA |
| | | AGATAATGTGTTGCAGTTACTGCACTCAATGGCTTACTA |
| | | TTATAAACCAAAACTGGGATCACTAAGCTCCAGTCAGT |
| | | CAAAATGATCAAAATTATTGAAGAGAATAAGCAATTCT |
| | | GTTCTTTATTAGGACACAGTAGATACAGACTACAAAGT |
| | | GGAGTGTGCTTAATAAGAGGTAGCATTTGTTAAGTGTC |
| | | AATTACTCTATTATCCCTTGGAGCTTCTCAAAATAACCA |
| | | TATAAGGTGTAAGATGTTAAAGGTTATGGTTACACTCA |
| | | GTGCACAGGTAAGCTAATAGGCTGAGAGAAGCTAAATT |
| | | ACTTACTGGGGTCTCACAGTAAGAAAGTGAGCTGAAGT |
| | | TTCAGCCCAGATTTAACTGGATTCTGGGCTCTTTATTCA |
| | | TGTTACTTCATGAATCTGTTTCTCAATTGTGCAGAAAAA |
| | | AGGGGGCTATTTATAAGAAAAGCAATAAACAAACAAGT |
| | | AATGATCTCAAATAAGTAATGCAAGAAATAGTGAGATT |
| | | TCAAAATCAGTGGCAGCGATTTCTCAGTTCTGTCCTAAG |
| | | TGGCCTTGCTCAATCACCTGCTATCTTTTAGTGGAGCTT |
| | | TGAAATTATGTTTCAGACAACTTCGATTCAGTTCTAGAA |
| | | TGTTTGACTCAGCAAATTCACAGGCTCATCTTTCTAACT |
| | | TGATGGTGAATATGGAAATTCAGCTAAATGGATGTTAA |
| | | TAAAATTCAAACGTTTTAAGGACAGATGGAAATGACAG |
| | | AATTTTAAGGTAAAATATATGAAGGAATATAAGATAAA |
| | | GGATTTTTCTACCTTCAGCAAAAACATACCCACTAATTA |
| | | GTAAAATTAATAGGCGAAAAAAAGTTGCATGCTCTTAT |
| | | ACTGTAATGATTATCATTTTAAAACTAGCTTTTTGCCTT |
| | | CGAGCTATCGGGGTAAAGA |
| SEQ ID NO: 7 | Nucleotide sequence of HGF-X1 | ATGTGGGTGACCAAACTCCTGCCAGCCCTGCTGCTGCA |
| | | GCATGTCCTCCTGCATCTCCTCCTGCTCCCCATCGCCAT |
| | | CCCCTATGCAGAGGGACAAAGGAAAAGAAGAAATACA |
| | | ATTCATGAATTCAAAAAATCAGCAAAGACTACCCTAAT |
| | | CAAAATAGATCCAGCACTGAAGATAAAAACCAAAAAA |
| | | GTGAATACTGCAGACCAATGTGCTAATAGATGTACTAG |
| | | GAATAAAGGACTTCCATTCACTTGCAAGGCTTTTGTTTT |
| | | TGATAAAGCAAGAAAACAATGCCTCTGGTTCCCCTTCA |
| | | ATAGCATGTCAAGTGGAGTGAAAAAAGAATTTGGCCAT |
| | | GAATTTGACCTCTATGAAAACAAAGACTACATTAGAAA |
| | | CTGCATCATTGGTAAAGGACGCAGCTACAAGGGAACAG |
| | | TATCTATCACTAAGAGTGGCATCAAATGTCAGCCCTGG |
| | | AGTTCCATGATACCACACGAACACAGGTAAGAACAGTA |
| | | TGAAGAAAAGAGATGAAGCCTCTGTCTTTTTTACATGTT |
| | | AACAGTCTCATATTAGTCCTTCAGAATAATTCTACAATC |
| | | CTAAAATAACTTAGCCAACTTGCTGAATTGTATTACGGC |
| | | AAGGTTTATATGAATTCATGACTGATATTTAGCAAATGA |
| | | TTAATTAATATGTTAATAAAATGTAGCCAAAACAATAT |
| | | CTTACCTTAATGCCTCAATTTGTAGATCTCGGTATTTGT |
| | | GAAATAATAACGTAAACTTCGTTTAAAAGGATTCTTCTT |
| | | CCTGTCTTTGAGAAAGTACGGCACTGTGCAGGGGGAGA |
| | | GGTTGATTGTGAAAATCAGAGGTAGATGAGAATCTTA |
| | | CTGAGGGCTGAGGGTTCTTTAACCTTGGTGGATCTCAAC |
| | | ATTGGTTGCACATTAAAATCACCTGCTGCAAGCCCTTGA |
| | | CGAATCTTACTTAGAAGATGACAACACAGAACAATTAA |
| | | ATCAGAATCTCTGGGGAGAATAGGGCACCAGTATTTTT |
| | | TGAGCTCCCACCATGATTCCAAAGTGCAGCCAAATTTG |
| | | AGAACCACTGCTAAAAGCTCAAGCTTCAGATTGACCAG |
| | | CTTTTCCATCTCACCTATCGCCTAAAGACCAAATTGGAT |
| | | AAATGTGTTCATTACGACAGATGGGTACTATTTAAAGA |
| | | TGAGTAAACACAATATACTTAGGCTCGTCAGACTGAGA |
| | | GTTTTAATCATCACTGAGGAAAAACATAGATATCTAAT |
| | | ACTGACTGGAGTATTAGTCAAGGCTTATTTCACACACA |
| | | ATTTTATCAGAAACCAAAGTAGTTTAAAACAGCTCTCCC |
| | | CTTATTAGTAATGCATTGGAGGGTTTACTTTACCATGTA |
| | | CCTTGCTGAGCACTGTACCTTGTTAATCTCATTTACTTGT |

SEQUENCE LISTING:

```
AATGAGAACCACACAGCGGGTAGTTTTATTGGTTCTATT
TTACCTACATGACAAAACTGAAGCATAAAAACACTTAG
TAAGTTTTCAGTGTCATGCACAACTAGGAAGTGACATG
GCCAGAATATAAGCCCAGTCACCATCACTCTATAACCT
GCGCTTTTAACAACTTCAGGGCATGACACATTTGGCCG
GTCAGTAGAACCCATGCTGTGATTTGTTTTTGCAGTGGT
GGTGATGACTGCCTTGTTGAATCCACTTTTTATTCTATTC
CATTTTGGGGACACAATTCTGCAAGATGATTCTTCATTA
GGAAACAGAGATGAGTTATTGACCAACACAGAAAGAA
AAAGAGTTTGTTGCTCCACACTGGGATTAAACCTATGAT
CTTGGCCTAATTAACACTAGCTAGTAAGTGTCCAAGCTG
ATCATCTCTACAACATTTCAATAACAGAAAACAACAAT
TTTCAAAATTAGTTACTTACAATTATGTAGAAATGCCTC
TAAAACACAGTATTTTCCTTATATTACAAAAACAAAAA
TTATAATTGGTTTTGTCCTCTTTTGAGAGTTTGCATGGTG
TTACTCCCTGCATAGTGAAGAAAACATTTTATTTAAGTA
GATGGATCTAAGTTTTTCATGAACAAAGGAATGACATT
TGAAATCAATCCTACCCTAGTCCAGGAGAATGCATTAG
ATTAACCTAGTAGAGGTCTTATTTCACCCTGAGTTTTCT
ATGATCGTGATTCTCTGCTGGAGGAGTAATTGTGAAAT
AGATCTCTCTGGGAACTGGCTTCCTAGTCCAATCAGCTC
TTTTACCAATGAACACTTCCTTGTGATATAGATGTTTAT
GGCCGAGAGGATCCAGTATATTAATAAAATCCCTTTTTG
TATTCAATGAGGGAAACACATAATTTTCATCAATTAGC
AGCTTATTGGAATATCTGCATGATGGTTTAACACTTTTA
AGTGTTGACTAAAGATTAATTTTACAGAAAATAGAAAA
AGAAATATGTTTCTGTCTGGAGGAATGATTTATTGTTGA
CCCCTAAATTGAAATATTTTACTAGTGGCTTAATGGAAA
GATGATGAAAGATGATGAAATTAATGTAGAAGCTTAAC
TAGAAAATCAGGTGACCTGATATCTACATCTGTATCCTT
CATTGGCCACCCAGCATTCATTAATGAATCAGATGATG
GAATAGATCAAGTTTCCTAGGAACACAGTGAATATTAA
AAGAAAACAAAGGGAGCCTAGCACCTAGAAGACCTAG
TTTATATTTCAAAGTATATTTGGATGTAACCCAATTTTA
AACATTTCCTCACTTGTCTCTCTTAAAGCCTTGCCAACA
GCAAGGACAGAGAACCAAAAATAGTGTATATATGAATA
AATGCTTATTACAGAATCTGCTGACTGGCACATGCTTTG
TGTGTAATGGGTTCTCATAAACACTTGTTGAATGAACAC
ACATAAGTGAAAGAGCATGGCTAGGCTTCATCCCTTGG
TCAAATATGGGTGCTAAAGAAAAGCAGGGGAAATAC
ATTGGGACACTAACAAAAAAAAACAGTTAATTTAGGTA
AAAGATAAAATACACCACAGAATGAAGAAAAGAGATG
ACCCAGACTGCTCTTTAACCTTCATGTCCTAGAGAGGTT
TTTGATATGAATTGCATTCAGAATTGTGGAAAGGAGCC
CATCTTTTCTCTTCATTTTGATTTTATTAACTCCAATGGG
GGAATTTTATTCGTGTTTTGGCCATATCTACTTTTGATTT
CTACATTATTCTCTCTTCCTTTCTACCTGTATTTGTCCTA
ATAAATTGTTGACTTATTAATTCACTACTTCCTCACAGC
TTTTTTTTGGCTTTACAAATCCACTGGAAAGGTATATGG
GTGTATCACTTTGTGTATTTCGGTGTGCATGTGTAGAGG
GGACAAAATCCTCTCTCAAACTATAAATATTGAGTATT
TGTGTATTGAACATTTGCTATAACTACTAGGTTTCTTAA
ATAATCTTAATATATAAAATGATATAGAAAAAGGGAAA
TTATAGTTCGTATTATTCATCTAAGTGAAGAGATTAAAA
CCCAGGGAGTAAATAAATTGTCTAAGGACTAAGGTTGT
ATACTATTTAGGTGATAGATATGGGGCAACCGTATGGG
TTTTATGATTAACAAATAAACTTCTCACCACTCTACCAT
ATCAACTTTTCCATAAAAGAGAGCTATAGTATTCTTTGC
TTAAATAAATTTGATTAGTGCATGACTTCTTGAAAACAT
ATAAAGCAAAAGTCACATTTGATTCTATCAGAAAAGTG
AGTAAGCCATGGCCCAAACAAAAGATGCATTAAAATAT
TCTGGAATGATGGAGCTAAAAGTAAGAAAAATGACTTT
TTAAAAAAGTTTACTGTTAGGAATTGTGAAATTATGCTG
AATTTTAGTTGCATTATAATTTTTGTCAGTCATACGGTC
TGACAACCTGTCTTATTTCTATTTCCCCATATGAGGAAT
GCTAGTTAAGTATGGATATTAACTATTACTACTTAGATG
CATTGAAGTTGCATAATATGGATAATACTTCACTGGTTC
CCTGAAAATGTTTAGTTAGTAATAAGTCTCTTACACTAT
TTGTTTTGTCCAATAATTTATATTTTCTGAAGACTTAACT
CTAGAATACACTCATGTCAAAATGAAAGAATTTCATTG
CAAAATATTGCTTGGTACATGACGCATACCTGTATTTGT
TTTGTGTCACAACATGAAAAATGATGGTTTATTAGAAGT
TTCATTGGGTAGGAAACACATTTGAATGGTATTTACTAA
GATACTAAAATCCTTGGACTTCACTCTAATTTTAGTGCC
ATTTAGAACTCAAGGTCTCAGTAAAAGTAGAAATAAAG
CCTGTTAACAAAACACAAACTGAATATTAAAAATGTAA
CTGGATTTTCAAAGAAATGTTTACTGGTATTACCTGTAG
```

| SEQUENCE LISTING: | |
|---|---|
| | ATGTATATTCTTTATTATGATCTTTTGTGTAAAGTCTGGC<br>AGACAAATGCAATATCTAATTGTTGAGTCCAATATCAC<br>AAGCAGTACAAAAGTATAAAAAAGACTTGGCCTTTTCT<br>AATGTGTTAAAATACTTTATGCTGGTAATAACACTAAG<br>AGTAGGGCACTAGAAATTTTAAGTGAAGATAATGTGTT<br>GCAGTTACTGCACTCAATGGCTTACTATTATAAACCAAA<br>ACTGGGATCACTAAGCTCCAGTCAGTCAAAATGATCAA<br>AATTATTGAAGAGAATAAGCAATTCTGTTCTTTATTAGG<br>ACACAGTAGATACAGACTACAAAGTGGAGTGTGCTTAA<br>TAAGAGGTAGCATTTGTTAAGTGTCAATTACTCTATTAT<br>CCCTTGGAGCTTCTCAAAATAACCATATAAGGTGTAAG<br>ATGTTAAAGGTTATGGTTACACTCAGTGCACAGGTAAG<br>CTAATAGGCTGAGAGAAGCTAAATTACTTACTGGGGTC<br>TCACAGTAAGAAAGTGAGCTGAAGTTTCAGCCCAGATT<br>TAACTGGATTCTGGGCTCTTTATTCATGTTACTTCATGA<br>ATCTGTTTCTCAATTGTGCAGAAAAAAGGGGGCTATTTA<br>TAAGAAAAGCAATAAACAAACAAGTAATGATCTCAAAT<br>AAGTAATGCAAGAAATAGTGAGATTTCAAAATCAGTGG<br>CAGCGATTTCTCAGTTCTGTCCTAAGTGGCCTTGCTCAA<br>TCACCTGCTATCTTTTAGTGGAGCTTTGAAATTATGTTT<br>CAGACAACTTCGATTCAGTTCTAGAATGTTTGACTCAGC<br>AAATTCACAGGCTCATCTTTCTAACTTGATGGTGAATAT<br>GGAAATTCAGCTAAATGGATGTTAATAAAATTCAAACG<br>TTTTAAGGACAGATGGAAATGACAGAATTTTAAGGTAA<br>AATATATGAAGGAATATAAGATAAAGGATTTTTCTACC<br>TTCAGCAAAAACATACCCACTAATTAGTAAAATTAATA<br>GGCGAAAAAAAGTTGCATGCTCTTATACTGTAATGATT<br>ATCATTTTAAAACTAGCTTTTTGCCTTCGAGCTATCGGG<br>GTAAAGACCTACAGGAAAACTACTGTCGAAATCCTCGA<br>GGGGAAGAAGGGGGACCCTGGTGTTTCACAAGCAATCC<br>AGAGGTACGCTACGAAGTCTGTGACATTCCTCAGTGTTC<br>AGAAGTTGAATGCATGACCTGCAATGGGAGAGTTATC<br>GAGGTCTCATGGATCATACAGAATCAGGCAAGATTTGT<br>CAGCGCTGGGATCATCAGACACCACACCGGCACAAATT<br>CTTGCCTGAAAGATATCCCGACAAGGGCTTTGATGATA<br>ATTATTGCCGCAATCCCGATGGCCAGCCGAGGCCATGG<br>TGCTATACTCTTGACCCTCACACCCGCTGGGAGTACTGT<br>GCAATTAAAACATGCGCTGACAATACTATGAATGACAC<br>TGATGTTCCTTTGGAAACAACTGAATGCATCCAAGGTC<br>AAGGAGAAGGCTACAGGGGCACTGTCAATACCATTTGG<br>AATGGAATTCCATGTCAGCGTTGGGATTCTCAGTATCCT<br>CACGAGCATGACATGACTCCTGAAAATTTCAAGTGCAA<br>GGACCTACGAGAAAATTACTGCCGAAATCCAGATGGGT<br>CTGAATCACCCTGGTGTTTTACCACTGATCCAAACATCC<br>GAGTTGGCTACTGCTCCCAAATTCCAAACTGTGATATGT<br>CACATGGACAAGATTGTTATCGTGGGAATGGCAAAAAT<br>TATATGGGCAACTTATCCCAAACAAGATCTGGACTAAC<br>ATGTTCAATGTGGGACAAGAACATGGAAGACTTACATC<br>GTCATATCTTCTGGGAACCAGATGCAAGTAAGCTGAAT<br>GAGAATTACTGCCGAAATCCAGATGATGATGCTCATGG<br>ACCCTGGTGCTACACGGGAAATCCACTCATTCCTTGGG<br>ATTATTGCCCTATTTCTCGTTGTGAAGGTGATACCACAC<br>CTACAATAGTCAATTTAGACCATCCCGTAATATCTTGTG<br>CCAAAACGAAACAATTGCGAGTTGTAAATGGGATTCCA<br>ACACGAACAAACATAGGATGGATGGTTAGTTTGAGATA<br>CAGAAATAAACATATCTGCGGAGGATCATTGATAAAGG<br>AGAGTTGGGTTCTTACTGCACGACAGTGTTTCCCTTCTC<br>GAGACTTGAAAGATTATGAAGCTTGGCTTGGAATTCAT<br>GATGTCCACGGAAGAGGAGATGAGAAATGCAAACAGG<br>TTCTCAATGTTTCCCAGCTGGTATATGGCCCTGAAGGAT<br>CAGATCTGGTTTTAATGAAGCTTGCCAGGCCTGCTGTCC<br>TGGATGATTTTGTTAGTACGATTGATTTACCTAATTATG<br>GATGCACAATTCCTGAAAAGACCAGTTGCAGTGTTTAT<br>GGCTGGGGCTACACTGGATTGATCAACTATGATGGCCT<br>ATTACGAGTGGCACATCTCTATATAATGGGAAATGAGA<br>AATGCAGCCAGCATCATCGAGGGAAGGTGACTCTGAAT<br>GAGTCTGAAATATGTGCTGGGGCTGAAAAGATTGGATC<br>AGGACCATGTGAGGGGATTATGGTGGCCCACTTGTTT<br>GTGAGCAACATAAAATGAGAATGGTTCTTGGTGTCATT<br>GTTCCTGGTCGTGGATGTGCCATTCCAAATCGTCCTGGT<br>ATTTTTGTCCGAGTAGCATATTATGCAAAATGGATACAC<br>AAAATTATTTTAACATATAAGGTACCACAGTCATAG |
| SEQ ID<br>NO: 8 | Nucleotide<br>sequence of<br>HGF-X2 | ATGTGGGTGACCAAACTCCTGCCAGCCCTGCTGCTGCA<br>GCATGTCCTCCTGCATCTCCTCCTGCTCCCCATCGCCAT<br>CCCCTATGCAGAGGGACAAAGGAAAGAAGAAATACA<br>ATTCATGAATTCAAAAAATCAGCAAAGACTACCCTAAT |

SEQUENCE LISTING:

```
CAAAATAGATCCAGCACTGAAGATAAAAACCAAAAAA
GTGAATACTGCAGACCAATGTGCTAATAGATGTACTAG
GAATAAAGGACTTCCATTCACTTGCAAGGCTTTTGTTTT
TGATAAAGCAAGAAAACAATGCCTCTGGTTCCCCTTCA
ATAGCATGTCAAGTGGAGTGAAAAAAGAATTTGGCCAT
GAATTTGACCTCTATGAAAACAAAGACTACATTAGAAA
CTGCATCATTGGTAAAGGACGCAGCTACAAGGGAACAG
TATCTATCACTAAGAGTGGCATCAAATGTCAGCCCTGG
AGTTCCATGATACCACACGAACACAGGTAAGAACAGTA
TGAAGAAAAGAGATGAAGCCTCTGTCTTTTTTACATGTT
AACAGTCTCATATTAGTCCTTCAGAATAATTCTACAATC
CTAAAATAACTTAGCCAACTTGCTGAATTGTATTACGGC
AAGGTTTATATGAATTCATGACTGATATTTAGCAAATGA
TTAATTAATATGTTAATAAAATGTAGCCAAAACAATAT
CTTACCTTAATGCCTCAATTTGTAGATCTCGGTATTTGT
GAAATAATAACGTAAACTTCGTTTAAAAGGATTCTTCTT
CCTGTCTTTGAGAAAGTACGGCACTGTGCAGGGGGAGA
GGTTGATTGTGAAAAATCAGAGGTAGATGAGAATCTTA
CTGAGGGCTGAGGGTTCTTTAACCTTGGTGGATCTCAAC
ATTGGTTGCACATTAAAATCACCTGCTGCAAGCCCTTGA
CGAATCTTACTTAGAAGATGACAACACAGAACAATTAA
ATCAGAATCTCTGGGGAGAATAGGGCACCAGTATTTTT
TGAGCTCCCACCATGATTCCAAAGTGCAGCCAAATTTG
AGAACCACTGCTAAAAGCTCAAGCTTCAGATTGACCAG
CTTTTCCATCTCACCTATCGCCTAAAGACCAAATTGGAT
AAATGTGTTCATTACGACAGATGGGTACTATTTAAAGA
TGAGTAAACACAATATACTTAGGCTCGTCAGACTGAGA
GTTTTAATCATCACTGAGGAAAAACATAGATATCTAAT
ACTGACTGGAGTATTAGTCAAGGCTTATTTCACACACA
ATTTTATCAGAAACCAAAGTAGTTTAAAACAGCTCTCCC
CTTATTAGTAATGCATTGGAGGGTTTACTTTACCATGTA
CCTTGCTGAGCACTGTACCTTGTTAATCTCATTTACTTGT
AATGAGAACCACACAGCGGGTAGTTTTATTGGTTCTATT
TTACCTACATGACAAAACTGAAGCATAAAAACACTTAG
TAAGTTTTCAGTGTCATGCACAACTAGGAAGTGACATG
GCCAGAATATAAGCCCAGTCACCATCACTCTATAACCT
GCGCTTTTAACAACTTCAGGGCATGACACATTTGGCCG
GTCAGTAGAACCCATGCTGTGATTTGTTTTTGCAGTGGT
GGTGATGACTGCCTTGTTGAATCCACTTTTTATTCTATTC
CATTTTGGGGACACAATTCTGCAAGATGATTCTTCATTA
GGAAACAGAGATGAGTTATTGACCAACACAGAAAGAA
AAAGAGTTTGTTGCTCCACACTGGGATTAAACCTATGAT
CTTGGCCTAATTAACACTAGCTAGTAAGTGTCCAAGCTG
ATCATCTCTACAACATTTCAATAACAGAAAACAACAAT
TTTCAAAATTAGTTACTTACAATTATGTAGAAATGCCTC
TAAAACACAGTATTTTCCTTATATTACAAAAACAAAAA
TTATAATTGGTTTTGTCCTCTTTTGAGAGTTTGCATGGTG
TTACTCCCTGCATAGTGAAGAAAACATTTTATTTAAGTA
GATGGATCTAAGTTTTTCATGAACAAAGGAATGACATT
TGAAATCAATCCTACCCTAGTCCAGGAGAATGCATTAG
ATTAACCTAGTAGAGGTCTTATTTCACCCTGAGTTTTCT
ATGATCGTGATTCTCTGCTGGAGGAGTAATTGTGAAAT
AGATCTCTCTGGGAACTGGCTTCCTAGTCCAATCAGCTC
TTTTACCAATGAACACTTCCTTGTGATATAGATGTTTAT
GGCCGAGAGGATCTCTTCCTTTCTACCTGTATTTGTCCT
AATAAATTGTTGACTTATTAATTCACTACTTCCTCACAG
CTTTTTTTTGGCTTTACAAATCCACTGGAAAGGTATATG
GGTGTATCACTTTGTGTATTTCGGTGTGCATGTGTAGAG
GGGACAAAAATCCTCTCTCAAACTATAAATATTGAGTA
TTTGTGTATTGAACATTTGCTATAACTACTAGGTTTCTT
AAATAATCTTAATATATAAAATGATATAGAAAAAGGGA
AATTATAGTTCGTATTATTCATCTAAGTGAAGAGATTAA
AACCCAGGGAGTAAATAAATTGTCTAAGGACTAAGGTT
GTATACTATTTAGGTGATAGATATGGGGCAACCGTATG
GGTTTTATGATTAACAAATAAACTTCTCACCACTCTACC
ATATCAACTTTTCCATAAAAGAGAGCTATAGTATTCTTT
GCTTAAATAAATTTGATTAGTGCATGACTTCTTGAAAAC
ATATAAAGCAAAAGTCACATTTGATTCTATCAGAAAAG
TGAGTAAGCCATGGCCCAAACAAAAGATGCATTAAAAT
ATTCTGGAATGATGGAGCTAAAAGTAAGAAAAATGACT
TTTTAAAAAAGTTTACTGTTAGGAATTGTGAAATTATGC
TGAATTTTAGTTGCATTATAATTTTTGTCAGTCATACGG
TCTGACAACCTGTCTTATTTCTATTTCCCATATGAGGA
ATGCTAGTTAAGTATGGATATTAACTATTACTACTTAGA
TGCATTGAAGTTGCATAATATGGATAATACTTCACTGGT
TCCCTGAAAATGTTTAGTTAGTAATAAGTCTCTTACACT
ATTTGTTTTGTCCAATAATTTATATTTTCTGAAGACTTAA
```

SEQUENCE LISTING:

```
CTCTAGAATACACTCATGTCAAAATGAAAGAATTTCATT
GCAAAATATTGCTTGGTACATGACGCATACCTGTATTTG
TTTTGTGTCACAACATGAAAAATGATGGTTTATTAGAAG
TTTCATTGGGTAGGAAACACATTTGAATGGTATTTACTA
AGATACTAAAATCCTTGGACTTCACTCTAATTTTAGTGC
CATTTAGAACTCAAGGTCTCAGTAAAAGTAGAAATAAA
GCCTGTTAACAAAACACAAACTGAATATTAAAAATGTA
ACTGGATTTTCAAAGAAATGTTTACTGGTATTACCTGTA
GATGTATATTCTTTATTATGATCTTTTGTGTAAAGTCTG
GCAGACAAATGCAATATCTAATTGTTGAGTCCAATATC
ACAAGCAGTACAAAAGTATAAAAAAGACTTGGCCTTTT
CTAATGTGTTAAAATACTTTATGCTGGTAATAACACTAA
GAGTAGGGCACTAGAAATTTTAAGTGAAGATAATGTGT
TGCAGTTACTGCACTCAATGGCTTACTATTATAAACCAA
AACTGGGATCACTAAGCTCCAGTCAGTCAAAATGATCA
AAATTATTGAAGAGAATAAGCAATTCTGTTCTTTATTAG
GACACAGTAGATACAGACTACAAAGTGGAGTGTGCTTA
ATAAGAGGTAGCATTTGTTAAGTGTCAATTACTCTATTA
TCCCTTGGAGCTTCTCAAAATAACCATATAAGGTGTAA
GATGTTAAAGGTTATGGTTACACTCAGTGCACAGGTAA
GCTAATAGGCTGAGAGAAGCTAAATTACTTACTGGGGT
CTCACAGTAAGAAAGTGAGCTGAAGTTTCAGCCCAGAT
TTAACTGGATTCTGGGCTCTTTATTCATGTTACTTCATG
AATCTGTTTCTCAATTGTGCAGAAAAAAGGGGGCTATTT
ATAAGAAAAGCAATAAACAAACAAGTAATGATCTCAA
ATAAGTAATGCAAGAAATAGTGAGATTTCAAAATCAGT
GGCAGCGATTTCTCAGTTCTGTCCTAAGTGGCCTTGCTC
AATCACCTGCTATCTTTTAGTGGAGCTTTGAAATTATGT
TTCAGACAACTTCGATTCAGTTCTAGAATGTTTGACTCA
GCAAATTCACAGGCTCATCTTTCTAACTTGATGGTGAAT
ATGGAAATTCAGCTAAATGGATGTTAATAAAATTCAAA
CGTTTTAAGGACAGATGGAAATGACAGAATTTTAAGGT
AAAATATATGAAGGAATATAAGATAAAGGATTTTTCTA
CCTTCAGCAAAAACATACCCACTAATTAGTAAAATTAA
TAGGCGAAAAAAAGTTGCATGCTCTTATACTGTAATGA
TTATCATTTTAAAACTAGCTTTTTGCCTTCGAGCTATCG
GGGTAAAGACCTACAGGAAAACTACTGTCGAAATCCTC
GAGGGGAAGAAGGGGGACCCTGGTGTTTCACAAGCAAT
CCAGAGGTACGCTACGAAGTCTGTGACATTCCTCAGTG
TTCAGAAGTTGAATGCATGACCTGCAATGGGGAGAGTT
ATCGAGGTCTCATGGATCATACAGAATCAGGCAAGATT
TGTCAGCGCTGGGATCATCAGACACCACACCGGCACAA
ATTCTTGCCTGAAAGATATCCCGACAAGGGCTTTGATG
ATAATTATTGCCGCAATCCCGATGGCCAGCCGAGGCCA
TGGTGCTATACTCTTGACCCTCACACCCGCTGGGAGTAC
TGTGCAATTAAAACATGCGCTGACAATACTATGAATGA
CACTGATGTTCCTTTGGAAACAACTGAATGCATCCAAG
GTCAAGGAGAAGGCTACAGGGGCACTGTCAATACCATT
TGGAATGGAATTCCATGTCAGCGTTGGGATTCTCAGTAT
CCTCACGAGCATGACATGACTCCTGAAAATTTCAAGTG
CAAGGACCTACGAGAAAATTACTGCCGAAATCCAGATG
GGTCTGAATCACCCTGGTGTTTTACCACTGATCCAAACA
TCCGAGTTGGCTACTGCTCCCAAATTCCAAACTGTGATA
TGTCACATGGACAAGATTGTTATCGTGGGAATGGCAAA
AATTATATGGGCAACTTATCCCAAACAAGATCTGGACT
AACATGTTCAATGTGGGACAAGAACATGGAAGACTTAC
ATCGTCATATCTTCTGGGAACCAGATGCAAGTAAGCTG
AATGAGAATTACTGCCGAAATCCAGATGATGATGCTCA
TGGACCCTGGTGCTACACGGGAAATCCACTCATTCCTTG
GGATTATTGCCCTATTTCTCGTTGTGAAGGTGATACCAC
ACCTACAATAGTCAATTTAGACCATCCCGTAATATCTTG
TGCCAAAACGAAACAATTGCGAGTTGTAAATGGGATTC
CAACACGAACAAACATAGGATGGATGGTTAGTTTGAGA
TACAGAAATAAACATATCTGCGGAGGATCATTGATAAA
GGAGAGTTGGGTTCTTACTGCACGACAGTGTTTCCCTTC
TCGAGACTTGAAAGATTATGAAGCTTGGCTTGGAATTC
ATGATGTCCACGGAAGAGGAGATGAGAAATGCAAACA
GGTTCTCAATGTTTCCCAGCTGGTATATGGCCCTGAAGG
ATCAGATCTGGTTTTAATGAAGCTTGCCAGGCCTGCTGT
CCTGGATGATTTTGTTAGTACGATTGATTTACCTAATTA
TGGATGCACAATTCCTGAAAAGACCAGTTGCAGTGTTT
ATGGCTGGGGCTACACTGGATTGATCAACTATGATGGC
CTATTACGAGTGGCACATCTCTATATAATGGGAAATGA
GAAATGCAGCCAGCATCATCGAGGGAAGGTGACTCTGA
ATGAGTCTGAAATATGTGCTGGGGCTGAAAAGATTGGA
TCAGGACCATGTGAGGGGGATTATGGTGGCCCACTTGT
TTGTGAGCAACATAAAATGAGAATGGTTCTTGGTGTCA
```

| | | |
|---|---|---|
| | | TTGTTCCTGGTCGTGGATGTGCCATTCCAAATCGTCCTG |
| | | GTATTTTGTCCGAGTAGCATATTATGCAAAATGGATAC |
| | | ACAAAATTATTTTAACATATAAGGTACCACAGTCATAG |
| SEQ ID NO: 9 | Nucleotide sequence of HGF-X3 | ATGTGGGTGACCAAACTCCTGCCAGCCCTGCTGCTGCA |
| | | GCATGTCCTCCTGCATCTCCTCCTGCTCCCCATCGCCAT |
| | | CCCCTATGCAGAGGGACAAAGGAAAAGAAGAAATACA |
| | | ATTCATGAATTCAAAAAATCAGCAAAGACTACCCTAAT |
| | | CAAAATAGATCCAGCACTGAAGATAAAAACCAAAAAA |
| | | GTGAATACTGCAGACCAATGTGCTAATAGATGTACTAG |
| | | GAATAAAGGACTTCCATTCACTTGCAAGGCTTTTGTTTT |
| | | TGATAAAGCAAGAAAACAATGCCTCTGGTTCCCCTTCA |
| | | ATAGCATGTCAAGTGGAGTGAAAAAAGAATTTGGCCAT |
| | | GAATTTGACCTCTATGAAAACAAAGACTACATTAGAAA |
| | | CTGCATCATTGGTAAAGGACGCAGCTACAAGGGAACAG |
| | | TATCTATCACTAAGAGTGGCATCAAATGTCAGCCCTGG |
| | | AGTTCCATGATACCACACGAACACAGGTAAGAACAGTA |
| | | TGAAGAAAGAGATGAAGCCTCTGTCTTTTTTACATGTT |
| | | AACAGTCTCATATTAGTCCTTCAGAATAATTCTACAATC |
| | | CTAAAATAACTTAGCCAACTTGCTGAATTGTATTACGGC |
| | | AAGGTTTATATGAATTCATGACTGATATTTAGCAAATGA |
| | | TTAATTAATATGTTAATAAAATGTAGCCAAAACAATAT |
| | | CTTACCTTAATGCCTCAATTTGTAGATCTCGGTATTTGT |
| | | GAAATAATAACGTAAACTTCGTTTAAAAGGATTCTTCTT |
| | | CCTGTCTTTGAGAAAGTACGGCACTGTGCAGGGGGAGA |
| | | GGTTGATTGTGAAAAATCAGAGGTAGATGAGAATCTTA |
| | | CTGAGGGCTGAGGGTTCTTTAACCTTGGTGGATCTCAAC |
| | | ATTGGTTGCACATTAAAATCACCTGCTGCAAGCCCTTGA |
| | | CGAATCTTACTTAGAAGATGACAACACAGAACAATTAA |
| | | ATCAGAATCTCTGGGGAGAATAGGGCACCAGTATTTTT |
| | | TGAGCTCCCACCATGATTCCAAAGTGCAGCCAAATTTG |
| | | AGAACCACTGCTAAAAGCTCAAGCTTCAGATTGACCAG |
| | | CTTTTCCATCTCACCTATCGCCTAAAGACCAAATTGGAT |
| | | AAATGTGTTCATTACGACAGATGGGTACTATTTAAAGA |
| | | TGAGTAAACACAATATACTTAGGCTCGTCAGACTGAGA |
| | | GTTTTAATCATCACTGAGGAAAAACATAGATATCTAAT |
| | | ACTGACTGGAGTATTAGTCAAGGCTTATTTCACACACA |
| | | ATTTTATCAGAAACCAAAGTAGTTTAAAACAGCTCTCCC |
| | | CTTATTAGTAATGCATTGGAGGGTTTACTTTACCATGTA |
| | | CCTTGCTGAGCACTGTACCTTGTTAATCTCATTTACTTGT |
| | | AATGAGAACCACACAGCGGGTAGTTTTATTGGTTCTATT |
| | | TTACCTACATGACAAAACTGAAGCATAAAAACACTTAG |
| | | TAAGTTTTCAGTGTCATGCACAACTAGGAAGTGACATG |
| | | GCCAGAATATAAGCCCAGTCACCATCACTCTATAACCT |
| | | GCGCTTTTAACAACTTCAGGGCATGACACATTTGGCCG |
| | | GTCAGTAGAACCCATGCTGTGATTTGTTTTTGCAGTGGT |
| | | GGTGATGACTGCCTTGTTGAATCCACTTTTTATTCTATTC |
| | | CATTTTGGGACACAATTCTGCAAGATGATTCTTCATTA |
| | | GGAAACAGAGATGAGTTATTGACCAACACAGAAAGAA |
| | | AAAGAGTTTGTTGCTCCACACTGGGATTAAACCTATGAT |
| | | CTTGGCCTAATTAACACTAGCTAGTAAGTGTCCAAGCTG |
| | | ATCATCTCTACAACATTTCAATAACAGAAAACAACAAT |
| | | TTTCAAAATTAGTTACTTACAATTATGTAGAAATGCCTC |
| | | TAAAACACAGTATTTTCCTTATATTACAAAAACAAAAA |
| | | TTATAATTGGTTTTGTCCTCTTTTGAGAGTTTGCATGGTG |
| | | TTACTCCCTGCATAGTGAAGAAAACATTTTATTTAAGTA |
| | | GATGGATCTAAGTTTTTCATGAACAAAGGAATGACATT |
| | | TGAAATCAATCCTACCCTAGTCCAGGAGAATGCATTAG |
| | | ATTAACCTAGTAGAGGTCTTATTTCACCCTGAGTTTTCT |
| | | ATGATCGTGATTCTCTGCTGGAGGAGTAATTGTGAAAT |
| | | AGATCTCTCTGGGAACTGGCTTCCTAGTCCAATCAGCTC |
| | | TTTTACCAATGAACACTTCCTTGTGATATAGATGTTTAT |
| | | GGCCGAGAGGATCCTGGGTAGGAAACACATTTGAATGG |
| | | TATTTACTAAGATACTAAAATCCTTGGACTTCACTCTAA |
| | | TTTTAGTGCCATTTAGAACTCAAGGTCTCAGTAAAAGTA |
| | | GAAATAAAGCCTGTTAACAAAACACAAACTGAATATTA |
| | | AAAATGTAACTGGATTTTCAAAGAAATGTTTACTGGTAT |
| | | TACCTGTAGATGTATATTCTTTATTATGATCTTTTGTGTA |
| | | AAGTCTGGCAGACAAATGCAATATCTAATTGTTGAGTC |
| | | CAATATCACAAGCAGTACAAAAGTATAAAAAAGACTTG |
| | | GCCTTTTCTAATGTGTTAAAATACTTTATGCTGGTAATA |
| | | ACACTAAGAGTAGGGCACTAGAAATTTTAAGTGAAGAT |
| | | AATGTGTTGCAGTTACTGCACTCAATGGCTTACTATTAT |
| | | AAACCAAAACTGGGATCACTAAGCTCCAGTCAGTCAAA |
| | | ATGATCAAAATTATTGAAGAGAATAAGCAATTCTGTTC |
| | | TTTATTAGGACACAGTAGATACAGACTACAAAGTGGAG |
| | | TGTGCTTAATAAGAGGGTAGCATTTGTTAAGTGTCAATTA |

| SEQUENCE LISTING: | |
|---|---|
| | CTCTATTATCCCTTGGAGCTTCTCAAAATAACCATATAA<br>GGTGTAAGATGTTAAAGGTTATGGTTACACTCAGTGCA<br>CAGGTAAGCTAATAGGCTGAGAGAAGCTAAATTACTTA<br>CTGGGGTCTCACAGTAAGAAAGTGAGCTGAAGTTTCAG<br>CCCAGATTTAACTGGATTCTGGGCTCTTTATTCATGTTA<br>CTTCATGAATCTGTTTCTCAATTGTGCAGAAAAAGGG<br>GGCTATTTATAAGAAAAGCAATAAACAAACAAGTAATG<br>ATCTCAAATAAGTAATGCAAGAAATAGTGAGATTTCAA<br>AATCAGTGGCAGCGATTTCTCAGTTCTGTCCTAAGTGGC<br>CTTGCTCAATCACCTGCTATCTTTTAGTGGAGCTTTGAA<br>ATTATGTTTCAGACAACTTCGATTCAGTTCTAGAATGTT<br>TGACTCAGCAAATTCACAGGCTCATCTTTCTAACTTGAT<br>GGTGAATATGGAAATTCAGCTAAATGGATGTTAATAAA<br>ATTCAAACGTTTTAAGGACAGATGGAAATGACAGAATT<br>TTAAGGTAAAATATATGAAGGAATATAAGATAAAGGAT<br>TTTTCTACCTTCAGCAAAAACATACCCACTAATTAGTAA<br>AATTAATAGGCGAAAAAAAGTTGCATGCTCTTATACTG<br>TAATGATTATCATTTTAAAACTAGCTTTTTGCCTTCGAG<br>CTATCGGGGTAAAGACCTACAGGAAAACTACTGTCGAA<br>ATCCTCGAGGGGAAGAAGGGGGACCCTGGTGTTTCACA<br>AGCAATCCAGAGGTACGCTACGAAGTCTGTGACATTCC<br>TCAGTGTTCAGAAGTTGAATGCATGACCTGCAATGGGG<br>AGAGTTATCGAGGTCTCATGGATCATACAGAATCAGGC<br>AAGATTTGTCAGCGCTGGGATCATCAGACACCCACACCG<br>GCACAAATTCTTGCCTGAAAGATATCCCGACAAGGGCT<br>TTGATGATAATTATTGCCGCAATCCCGATGGCCAGCCG<br>AGGCCATGGTGCTATACTCTTGACCCTCACACCCGCTGG<br>GAGTACTGTGCAATTAAAACATGCGCTGACAATACTAT<br>GAATGACACTGATGTTCCTTTGGAAACAACTGAATGCA<br>TCCAAGGTCAAGGAGAAGGCTACAGGGGCACTGTCAAT<br>ACCATTTGGAATGGAATTCCATGTCAGCGTTGGGATTCT<br>CAGTATCCTCACGAGCATGACATGACTCCTGAAAATTTC<br>AAGTGCAAGGACCTACGAGAAAATTACTGCCGAAATCC<br>AGATGGGTCTGAATCACCCTGGTGTTTTACCACTGATCC<br>AAACATCCGAGTTGGCTACTGCTCCCAAATTCCAAACT<br>GTGATATGTCACATGGACAAGATTGTTATCGTGGGAAT<br>GGCAAAAATTATATGGGCAACTTATCCCAAACAAGATC<br>TGGACTAACATGTTCAATGTGGGACAAGAACATGGAAG<br>ACTTACATCGTCATATCTTCTGGGAACCAGATGCAAGTA<br>AGCTGAATGAGAATTACTGCCGAAATCCAGATGATGAT<br>GCTCATGGACCCTGGTGCTACACGGGAAATCCACTCAT<br>TCCTTGGGATTATTGCCCTATTTCTCGTTGTGAAGGTGA<br>TACCACACCTACAATAGTCAATTTAGACCATCCCGTAAT<br>ATCTTGTGCCAAAACGAAACAATTGCGAGTTGTAAATG<br>GGATTCCAACACGAACAAACATAGGATGGATGGTTAGT<br>TTGAGATACAGAAATAAACATATCTGCGGAGGATCATT<br>GATAAAGGAGAGTTGGGTTCTTACTGCACGACAGTGTT<br>TCCCTTCTCGAGACTTGAAAGATTATGAAGCTTGGCTTG<br>GAATTCATGATGTCCACGGAAGAGGAGATGAGAAATGC<br>AAACAGGTTCTCAATGTTTCCCAGCTGGTATATGGCCCT<br>GAAGGATCAGATCTGGTTTTAATGAAGCTTGCCAGGCC<br>TGCTGTCCTGGATGATTTTGTTAGTACGATTGATTTACC<br>TAATTATGGATGCACAATTCCTGAAAAGACCAGTTGCA<br>GTGTTTATGGCTGGGGCTACACTGGATTGATCAACTATG<br>ATGGCCTATTACGAGTGGCACATCTCTATATAATGGGA<br>AATGAGAAATGCAGCCAGCATCATCGAGGGAAGGTGA<br>CTCTGAATGAGTCTGAAATATGTGCTGGGGCTGAAAAG<br>ATTGGATCAGGACCATGTGAGGGGGATTATGGTGGCCC<br>ACTTGTTTGTGAGCAACATAAAATGAGAATGGTTCTTG<br>GTGTCATTGTTCCTGGTCGTGGATGTGCCATTCCAAATC<br>GTCCTGGTATTTTTGTCCGAGTAGCATATTATGCAAAAT<br>GGATACACAAAATTATTTTAACATATAAGGTACCACAG<br>TCATAG |
| SEQ ID<br>NO: 10 | Nucleotide<br>sequence of<br>HGF-X4 | ATGTGGGTGACCAAACTCCTGCCAGCCCTGCTGCTGCA<br>GCATGTCCTCCTGCATCTCCTCCTGCTCCCCATCGCCAT<br>CCCCTATGCAGAGGGACAAAGGAAAAGAAGAAATACA<br>ATTCATGAATTCAAAAAATCAGCAAAGACTACCCTAAT<br>CAAAATAGATCCAGCACTGAAGATAAAAACCAAAAAA<br>GTGAATACTGCAGACCAATGTGCTAATAGATGTACTAG<br>GAATAAAGGACTTCCATTCACTTGCAAGGCTTTTGTTTT<br>TGATAAAGCAAGAAAACAATGCCTCTGGTTCCCCTTCA<br>ATAGCATGTCAAGTGGAGTGAAAAAAGAATTTGGCCAT<br>GAATTTGACCTCTATGAAAACAAAGACTACATTAGAAA<br>CTGCATCATTGGTAAAGGACGCAGCTACAAGGGAACAG<br>TATCTATCACTAAGAGTGGCATCAAATGTCAGCCCTGG<br>AGTTCCATGATACCACACGAACACAGGTAAGAACAGTA |

SEQUENCE LISTING:

```
TGAAGAAAAGAGATGAAGCCTCTGTCTTTTTTACATGTT
AACAGTCTCATATTAGTCCTTCAGAATAATTCTACAATC
CTAAAATAACTTAGCCAACTTGCTGAATTGTATTACGGC
AAGGTTTATATGAATTCATGACTGATATTTAGCAAATGA
TTAATTAATATGTTAATAAAATGTAGCCAAAACAATAT
CTTACCTTAATGCCTCAATTTGTAGATCTCGGTATTTGT
GAAATAATAACGTAAACTTCGTTTAAAAGGATTCTTCTT
CCTGTCTTTGAGAAAGTACGGCACTGTGCAGGGGGAGA
GGTTGATTGTGAAAAATCAGAGGTAGATGAGAATCTTA
CTGAGGGCTGAGGGTTCTTTAACCTTGGTGGATCTCAAC
ATTGGTTGCACATTAAAATCACCTGCTGCAAGCCCTTGA
CGAATCTTACTTAGAAGATGACAACACAGAACAATTAA
ATCAGAATCTCTGGGGAGAATAGGGCACCAGTATTTTT
TGAGCTCCCACCATGATTCCAAAGTGCAGCCAAATTTG
AGAACCACTGCTAAAAGCTCAAGCTTCAGATTGACCAG
CTTTTCCATCTCACCTATCGCCTAAAGACCAAATTGGAT
AAATGTGTTCATTACGACAGATGGGTACTATTTAAAGA
TGAGTAAACACAATATACTTAGGCTCGTCAGACTGAGA
GTTTTAATCATCACTGAGGAAAAACATAGATATCTAAT
ACTGACTGGAGTATTAGTCAAGGCTTATTTCACACACA
ATTTTATCAGAAACCAAAGTAGTTTAAAACAGCTCTCCC
CTTATTAGTAATGCATTGGAGGGTTTACTTTACCATGTA
CCTTGCTGAGCACTGTACCTTGTTAATCTCATTTACTTGT
AATGAGAACCACACAGCGGGTAGTTTTATTGGTTCTATT
TTACCTACATGACAAAACTGAAGCATAAAAACACTTAG
TAAGTTTTCAGTGTCATGCACAACTAGGAAGTGACATG
GCCAGAATATAAGCCCAGTCACCATCACTCTATAACCT
GCGCTTTTAACAACTTCAGGGCATGACACATTTGGCCG
GTCAGTAGAACCCATGCTGTGATTTGTTTTTGCAGTGGT
GGTGATGACTGCCTTGTTAATCCACTTTTTATTCTATTC
CATTTTGGGGACACAATTCTGCAAGATGATTCTTCATTA
GGAAACAGAGATGAGTTATTGACCAACACAGAAAGAA
AAAGAGTTTGTTGCTCCACACTGGGATTAAACCTATGAT
CTTGGCCTAATTAACACTAGCTAGTAAGTGTCCAAGCTG
ATCATCTCTACAACATTTCAATAACAGAAAACAACAAT
TTTCAAAATTAGTTACTTACAATTATGTAGAAATGCCTC
TAAAACACAGTATTTTCCTTATATTACAAAAACAAAAA
TTATAATTGGTTTTGTCCTCTTTTGAGAGTTTGCATGGTG
TTACTCCCTGCATAGTGAAGAAAACATTTTATTTAAGTA
GATGGATCTAAGTTTTTCATGAACAAAGGAATGACATT
TGAAATCAATCCTACCCTAGTCCAGGAGAATGCATTAG
ATTAACCTAGTAGAGGTCTTATTTCACCCTGAGTTTTCT
ATGATCGTGATTCTCTGCTGGAGGAGTAATTGTGAAAT
AGATCTCTCTGGGAACTGGCTTCCTAGTCCAATCAGCTC
TTTTACCAATGAACACTTCCTTGTGATATAGATGTTTAT
GGCCGAGAGGATCCTTATGTTTCAGACAACTTCGATTCA
GTTCTAGAATGTTTGACTCAGCAAATTCACAGGCTCATC
TTTCTAACTTGATGGTGAATATGGAAATTCAGCTAAATG
GATGTTAATAAAATTCAAACGTTTTAAGGACAGATGGA
AATGACAGAATTTTAAGGTAAAATATATGAAGGAATAT
AAGATAAAGGATTTTTCTACCTTCAGCAAAAACATACC
CACTAATTAGTAAAATTAATAGGCGAAAAAAAGTTGCA
TGCTCTTATACTGTAATGATTATCATTTTAAAACTAGCT
TTTTGCCTTCGAGCTATCGGGGTAAAGACCTACAGGAA
AACTACTGTCGAAATCCTCGAGGGGAAGAAGGGGGACC
CTGGTGTTTCACAAGCAATCCAGAGGTACGCTACGAAG
TCTGTGACATTCCTCAGTGTTCAGAAGTTGAATGCATGA
CCTGCAATGGGGAGAGTTATCGAGGTCTCATGGATCAT
ACAGAATCAGGCAAGATTTGTCAGCGCTGGGATCATCA
GACACCACACCGGCACAAATTCTTGCCTGAAAGATATC
CCGACAAGGGCTTTGATGATAATTATTGCCGCAATCCC
GATGGCCAGCCGAGGCCATGGTGCTATACTCTTGACCC
TCACACCCGCTGGGAGTACTGTGCAATTAAAACATGCG
CTGACAATACTATGAATGACACTGATGTTCCTTTGGAAA
CAACTGAATGCATCCAAGGTCAAGGAGAAGGCTACAGG
GGCACTGTCAATACCATTTGGAATGGAATTCCATGTCA
GCGTTGGGATTCTCAGTATCCTCACGAGCATGACATGA
CTCCTGAAAATTTCAAGTGCAAGGACCTACGAGAAAAT
TACTGCCGAAATCCAGATGGGTCTGAATCACCCTGGTG
TTTTACCACTGATCCAAACATCCGAGTTGGCTACTGCTC
CCAAATTCCAAACTGTGATATGTCACATGGACAAGATT
GTTATCGTGGGAATGGCAAAAATTATATGGGCAACTTA
TCCCAAACAAGATCTGGACTAACATGTTCAATGTGGGA
CAAGAACATGGAAGACTTACATCGTCATATCTTCTGGG
AACCAGATGCAAGTAAGCTGAATGAGAATTACTGCCGA
AATCCAGATGATGATGCTCATGGACCCTGGTGCTACAC
GGGAAATCCACTCATTCCTTGGGATTATTGCCCTATTTC
```

| | | |
|---|---|---|
| | | TCGTTGTGAAGGTGATACCACACCTACAATAGTCAATTT |
| | | AGACCATCCCGTAATATCTTGTGCCAAAACGAAACAAT |
| | | TGCGAGTTGTAAATGGGATTCCAACACGAACAAACATA |
| | | GGATGGATGGTTAGTTTGAGATACAGAAATAAACATAT |
| | | CTGCGGAGGATCATTGATAAAGGAGAGTTGGGTTCTTA |
| | | CTGCACGACAGTGTTTCCCTTCTCGAGACTTGAAAGATT |
| | | ATGAAGCTTGGCTTGGAATTCATGATGTCCACGGAAGA |
| | | GGAGATGAGAAATGCAAACAGGTTCTCAATGTTTCCCA |
| | | GCTGGTATATGGCCCTGAAGGATCAGATCTGGTTTTAAT |
| | | GAAGCTTGCCAGGCCTGCTGTCCTGGATGATTTTGTTAG |
| | | TACGATTGATTTACCTAATTATGGATGCACAATTCCTGA |
| | | AAAGACCAGTTGCAGTGTTTATGGCTGGGGCTACACTG |
| | | GATTGATCAACTATGATGGCCTATTACGAGTGGCACAT |
| | | CTCTATATAATGGGAAATGAGAAATGCAGCCAGCATCA |
| | | TCGAGGGAAGGTGACTCTGAATGAGTCTGAAATATGTG |
| | | CTGGGGCTGAAAAGATTGGATCAGGACCATGTGAGGGG |
| | | GATTATGGTGGCCCACTTGTTTGTGAGCAACATAAAAT |
| | | GAGAATGGTTCTTGGTGTCATTGTTCCTGGTCGTGGATG |
| | | TGCCATTCCAAATCGTCCTGGTATTTTTGTCCGAGTAGC |
| | | ATATTATGCAAATGGATACACAAAATTATTTTAACAT |
| | | ATAAGGTACCACAGTCATAG |
| SEQ ID NO: 11 | Nucleotide sequence of HGF-X5 | ATGTGGGTGACCAAACTCCTGCCAGCCCTGCTGCTGCA |
| | | GCATGTCCTCCTGCATCTCCTCCTGCTCCCCATCGCCAT |
| | | CCCCTATGCAGAGGGACAAAGGAAAAGAAGAAATACA |
| | | ATTCATGAATTCAAAAAATCAGCAAAGACTACCCTAAT |
| | | CAAAATAGATCCAGCACTGAAGATAAAAACCAAAAAA |
| | | GTGAATACTGCAGACCAATGTGCTAATAGATGTACTAG |
| | | GAATAAAGGACTTCCATTCACTTGCAAGGCTTTTGTTTT |
| | | TGATAAAGCAAGAAAACAATGCCTCTGGTTCCCCTTCA |
| | | ATAGCATGTCAAGTGGAGTGAAAAAAGAATTTGGCCAT |
| | | GAATTTGACCTCTATGAAAACAAAGACTACATTAGAAA |
| | | CTGCATCATTGGTAAAGGACGCAGCTACAAGGGAACAG |
| | | TATCTATCACTAAGAGTGGCATCAAATGTCAGCCCTGG |
| | | AGTTCCATGATACCACACGAACACAGGTAAGAACAGTA |
| | | TGAAGAAAAGAGATGAAGCCTCTGTCTTTTTTACATGTT |
| | | AACAGTCTCATATTAGTCCTTCAGAATAATTCTACAATC |
| | | CTAAAATAACTTAGCCAACTTGCTGAATTGTATTACGGC |
| | | AAGGTTTATATGAATTCATGACTGATATTTAGCAAATGA |
| | | TTAATTAATATGTTAATAAAATGTAGCCAAAACAATAT |
| | | CTTACCTTAATGCCTCAATTTGTAGATCTCGGTATTTGT |
| | | GGATCCAGTATATTAATAAAATCCCTTTTTGTATTCAAT |
| | | GAGGGAAACACATAATTTTCATCAATTAGCAGCTTATT |
| | | GGAATATCTGCATGATGGTTTAACACTTTTAAGTGTTGA |
| | | CTAAAGATTAATTTTACAGAAAATAGAAAAAGAAATAT |
| | | GTTTCTGTCTGGAGGAATGATTTATTGTTGACCCCTAAA |
| | | TTGAAATATTTTACTAGTGGCTTAATGGAAAGATGATG |
| | | AAAGATGATGAAATTAATGTAGAAGCTTAACTAGAAAA |
| | | TCAGGTGACCTGATATCTACATCTGTATCCTTCATTGGC |
| | | CACCCAGCATTCATTAATGAATCAGATGATGGAATAGA |
| | | TCAAGTTTCCTAGGAACACAGTGAATATTAAAAGAAAA |
| | | CAAAGGGAGCCTAGCACCTAGAAGACCTAGTTTTATATT |
| | | TCAAAGTATATTTGGATGTAACCCAATTTTAAACATTTC |
| | | CTCACTTGTCTCTCTTAAAGCCTTGCCAACAGCAAGGAC |
| | | AGAGAACCAAAAATAGTGTATATATGAATAAATGCTTA |
| | | TTACAGAATCTGCTGACTGGCACATGCTTTGTGTGTAAT |
| | | GGGTTCTCATAAACACTTGTTGAATGAACACACATAAG |
| | | TGAAAGAGCATGGCTAGGCTTCATCCCTTGGTCAAATA |
| | | TGGGGTGCTAAAGAAAAGCAGGGGAAATACATTGGGA |
| | | CACTAACAAAAAAAAACAGTTAATTTAGGTAAAAGATA |
| | | AAATACACCACAGAATGAAGAAAAGAGATGACCCAGA |
| | | CTGCTCTTTAACCTTCATGTCCTAGAGAGGTTTTTGATA |
| | | TGAATTGCATTCAGAATTGTGGAAAGGAGCCCATCTTTT |
| | | CTCTTCATTTTGATTTTATTAACTCCAATGGGGGAATTTT |
| | | ATTCGTGTTTTGGCCATATCTACTTTTGATTTCTACATTA |
| | | TTCTCTCTTCCTTTCTACCTGTATTTGTCCTAATAAATTG |
| | | TTGACTTATTAATTCACTACTTCCTCACAGCTTTTTTTTG |
| | | GCTTTACAAATCCACTGGAAAGGTATATGGGTGTATCA |
| | | CTTTGTGTATTTCGGTGTGCATGTGTAGAGGGGACAAA |
| | | AATCCTCTCTCAAACTATAAATATTGAGTATTTGTGTAT |
| | | TGAACATTTGCTATAACTACTAGGTTTCTTAAATAATCT |
| | | TAATATATAAAATGATATAGAAAAAGGGAAATTATAGT |
| | | TCGTATTATTCATCTAAGTGAAGAGATTAAAACCCAGG |
| | | GAGTAAATAAATTGTCTAAGGACTAAGGTTGTATACTA |
| | | TTTAGGTGATAGATATGGGCAACCGTATGGGTTTTATG |
| | | ATTAACAAATAAACTTCTCACCCACTCTACCATATCAACT |
| | | TTTCCATAAAAGAGAGCTATAGTATTCTTTGCTTAAATA |

SEQUENCE LISTING:

```
AATTTGATTAGTGCATGACTTCTTGAAAACATATAAAGC
AAAAGTCACATTTGATTCTATCAGAAAAGTGAGTAAGC
CATGGCCCAAACAAAAGATGCATTAAAATATTCTGGAA
TGATGGAGCTAAAAGTAAGAAAAATGACTTTTTAAAAA
AGTTTACTGTTAGGAATTGTGAAATTATGCTGAATTTTA
GTTGCATTATAATTTTTGTCAGTCATACGGTCTGACAAC
CTGTCTTATTTCTATTTCCCCATATGAGGAATGCTAGTT
AAGTATGGATATTAACTATTACTACTTAGATGCATTGAA
GTTGCATAATATGGATAATACTTCACTGGTTCCCTGAAA
ATGTTTAGTTAGTAATAAGTCTCTTACACTATTTGTTTTG
TCCAATAATTTATATTTTCTGAAGACTTAACTCTAGAAT
ACACTCATGTCAAAATGAAAGAATTTCATTGCAAAATA
TTGCTTGGTACATGACGCATACCTGTATTTGTTTTGTGT
CACAACATGAAAAATGATGGTTTATTAGAAGTTTCATT
GGGTAGGAAACACATTTGAATGGTATTTACTAAGATAC
TAAAATCCTTGGACTTCACTCTAATTTTAGTGCCATTTA
GAACTCAAGGTCTCAGTAAAAGTAGAAATAAAGCCTGT
TAACAAAACACAAACTGAATATTAAAAATGTAACTGGA
TTTTCAAAGAAATGTTTACTGGTATTACCTGTAGATGTA
TATTCTTTATTATGATCTTTTGTGTAAAGTCTGGCAGAC
AAATGCAATATCTAATTGTTGAGTCCAATATCACAAGC
AGTACAAAAGTATAAAAAAGACTTGGCCTTTTCTAATG
TGTTAAAATACTTTATGCTGGTAATAACACTAAGAGTA
GGGCACTAGAAATTTTAAGTGAAGATAATGTGTTGCAG
TTACTGCACTCAATGGCTTACTATTATAAACCAAAACTG
GGATCACTAAGCTCCAGTCAGTCAAAATGATCAAAATT
ATTGAAGAGAATAAGCAATTCTGTTCTTTATTAGGACAC
AGTAGATACAGACTACAAAGTGGAGTGTGCTTAATAAG
AGGTAGCATTTGTTAAGTGTCAATTACTCTATTATCCCT
TGGAGCTTCTCAAAATAACCATATAAGGTGTAAGATGT
TAAAGGTTATGGTTACACTCAGTGCACAGGTAAGCTAA
TAGGCTGAGAGAAGCTAAATTACTTACTGGGGTCTCAC
AGTAAGAAAGTGAGCTGAAGTTTCAGCCCAGATTTAAC
TGGATTCTGGGCTCTTTATTCATGTTACTTCATGAATCT
GTTTCTCAATTGTGCAGAAAAAAGGGGGCTATTTATAA
GAAAAGCAATAAACAAACAAGTAATGATCTCAAATAA
GTAATGCAAGAAATAGTGAGATTTCAAAATCAGTGGCA
GCGATTTCTCAGTTCTGTCCTAAGTGGCCTTGCTCAATC
ACCTGCTATCTTTTAGTGGAGCTTTGAAATTATGTTTCA
GACAACTTCGATTCAGTTCTAGAATGTTTGACTCAGCAA
ATTCACAGGCTCATCTTTCTAACTTGATGGTGAATATGG
AAATTCAGCTAAATGGATGTTAATAAAATTCAAACGTT
TTAAGGACAGATGGAAATGACAGAATTTTAAGGTAAAA
TATATGAAGGAATATAAGATAAAGGATTTTTCTACCTTC
AGCAAAAACATACCCACTAATTAGTAAAATTAATAGGC
GAAAAAAAGTTGCATGCTCTTATACTGTAATGATTATCA
TTTTAAAACTAGCTTTTTGCCTTCGAGCTATCGGGGTAA
AGACCTACAGGAAAACTACTGTCGAAATCCTCGAGGGG
AAGAAGGGGGACCCTGGTGTTTCACAAGCAATCCAGAG
GTACGCTACGAAGTCTGTGACATTCCTCAGTGTTCAGAA
GTTGAATGCATGACCTGCAATGGGGAGAGTTATCGAGG
TCTCATGGATCATACAGAATCAGGCAAGATTTGTCAGC
GCTGGGATCATCAGACACCACACCGGCACAAATTCTTG
CCTGAAAGATATCCCGACAAGGGCTTTGATGATAATTA
TTGCCGCAATCCCGATGGCCAGCCGAGGCCATGGTGCT
ATACTCTTGACCCTCACACCCGCTGGGAGTACTGTGCAA
TTAAAACATGCGCTGACAATACTATGAATGACACTGAT
GTTCCTTTGGAAACAACTGAATGCATCCAAGGTCAAGG
AGAAGGCTACAGGGGCACTGTCAATACCATTTGGAATG
GAATTCCATGTCAGCGTTGGGATTCTCAGTATCCTCACG
AGCATGACATGACTCCTGAAAATTTCAAGTGCAAGGAC
CTACGAGAAAATTACTGCCGAAATCCAGATGGGTCTGA
ATCACCCTGGTGTTTTACCACTGATCCAAACATCCGAGT
TGGCTACTGCTCCCAAATTCCAAACTGTGATATGTCACA
TGGACAAGATTGTTATCGTGGGAATGGCAAAAATTATA
TGGGCAACTTATCCCAAACAAGATCTGGACTAACATGT
TCAATGTGGGACAAGAACATGGAAGACTTACATCGTCA
TATCTTCTGGGAACCAGATGCAAGTAAGCTGAATGAGA
ATTACTGCCGAAATCCAGATGATGATGCTCATGGACCC
TGGTGCTACACGGGAAATCCACTCATTCCTTGGGATTAT
TGCCCTATTTCTCGTTGTGAAGGTGATACCACACCTACA
ATAGTCAATTTAGACCATCCCGTAATATCTTGTGCCAAA
ACGAAACAATTGCGAGTTGTAAATGGGATTCCAACACG
AACAAACATAGGATGGATGGTTAGTTTGAGATACAGAA
ATAAACATATCTGCGGAGGATCATTGATAAAGGAGAGT
TGGGTTCTTACTGCACGACAGTGTTTCCCTTCTCGAGAC
TTGAAAGATTATGAAGCTTGGCTTGGAATTCATGATGTC
```

| | | |
|---|---|---|
| | | CACGGAAGAGGAGATGAGAAATGCAAACAGGTTCTCA |
| | | ATGTTTCCCAGCTGGTATATGGCCCTGAAGGATCAGATC |
| | | TGGTTTTAATGAAGCTTGCCAGGCCTGCTGTCCTGGATG |
| | | ATTTTGTTAGTACGATTGATTTACCTAATTATGGATGCA |
| | | CAATTCCTGAAAAGACCAGTTGCAGTGTTTATGGCTGG |
| | | GGCTACACTGGATTGATCAACTATGATGGCCTATTACG |
| | | AGTGGCACATCTCTATATAATGGGAAATGAGAAATGCA |
| | | GCCAGCATCATCGAGGGAAGGTGACTCTGAATGAGTCT |
| | | GAAATATGTGCTGGGGCTGAAAAGATTGGATCAGGACC |
| | | ATGTGAGGGGGATTATGGTGGCCCACTTGTTTGTGAGC |
| | | AACATAAAATGAGAATGGTTCTTGGTGTCATTGTTCCTG |
| | | GTCGTGGATGTGCCATTCCAAATCGTCCTGGTATTTTTG |
| | | TCCGAGTAGCATATTATGCAAAATGGATACACAAAATT |
| | | ATTTTAACATATAAGGTACCACAGTCATAG |
| SEQ ID NO: 12 | Nucleotide sequence of HGF-X6 | ATGTGGGTGACCAAACTCCTGCCAGCCCTGCTGCTGCA |
| | | GCATGTCCTCCTGCATCTCCTCCTGCTCCCCATCGCCAT |
| | | CCCCTATGCAGAGGGACAAAGGAAAAGAAGAAATACA |
| | | ATTCATGAATTCAAAAAATCAGCAAAGACTACCCTAAT |
| | | CAAAATAGATCCAGCACTGAAGATAAAAACCAAAAAA |
| | | GTGAATACTGCAGACCAATGTGCTAATAGATGTACTAG |
| | | GAATAAAGGACTTCCATTCACTTGCAAGGCTTTTGTTTT |
| | | TGATAAAGCAAGAAAACAATGCCTCTGGTTCCCCTTCA |
| | | ATAGCATGTCAAGTGGAGTGAAAAAAGAATTTGGCCAT |
| | | GAATTTGACCTCTATGAAAACAAAGACTACATTAGAAA |
| | | CTGCATCATTGGTAAAGGACGCAGCTACAAGGGAACAG |
| | | TATCTATCACTAAGAGTGGCATCAAATGTCAGCCCTGG |
| | | AGTTCCATGATACCACACGAACACAGGTAAGAACAGTA |
| | | TGAAGAAAAGAGATGAAGCCTCTGTCTTTTTTACATGTT |
| | | AACAGTCTCATATTAGTCCTTCAGAATAATTCTACAATC |
| | | CTAAAATAACTTAGCCAACTTGCTGAATTGTATTACGGC |
| | | AAGGTTTATATGAATTCATGACTGATATTTAGCAAATGA |
| | | TTAATTAATATGTTAATAAAATGTAGCCAAAACAATAT |
| | | CTTACCTTAATGCCTCAATTTGTAGATCTCGGTATTTGT |
| | | GGATCTCTTCCTTTCTACCTGTATTTGTCCTAATAAATTG |
| | | TTGACTTATTAATTCACTACTTCCTCACAGCTTTTTTTTG |
| | | GCTTTACAAATCCACTGGAAAGGTATATGGGTGTATCA |
| | | CTTTGTGTATTTCGGTGTGCATGTGTAGAGGGGACAAA |
| | | AATCCTCTCTCAAACTATAAATATTGAGTATTTGTGTAT |
| | | TGAACATTTGCTATAACTACTAGGTTTCTTAAATAATCT |
| | | TAATATATAAAATGATATAGAAAAAGGGAAATTATAGT |
| | | TCGTATTATTCATCTAAGTGAAGAGATTAAAACCCAGG |
| | | GAGTAAATAAATTGTCTAAGGACTAAGGTTGTATACTA |
| | | TTTAGGTGATAGATATGGGGCAACCGTATGGGTTTTATG |
| | | ATTAACAAATAAACTTCTCACCCACTCTACCATATCAACT |
| | | TTTCCATAAAAGAGAGCTATAGTATTCTTTGCTTAAATA |
| | | AATTTGATTAGTGCATGACTTCTTGAAAACATATAAAGC |
| | | AAAAGTCACATTTGATTCTATCAGAAAAGTGAGTAAGC |
| | | CATGGCCCAAACAAAAGATGCATTAAAATATTCTGGAA |
| | | TGATGGAGCTAAAAGTAAGAAAAATGACTTTTTAAAAA |
| | | AGTTTACTGTTAGGAATTGTGAAATTATGCTGAATTTTA |
| | | GTTGCATTATAATTTTTGTCAGTCATACGGTCTGACAAC |
| | | CTGTCTTATTTCTATTTCCCCATATGAGGAATGCTAGTT |
| | | AAGTATGGATATTAACTATTACTACTTAGATGCATTGAA |
| | | GTTGCATAATATGGATAATACTTCACTGGTTCCCTGAAA |
| | | ATGTTTAGTTAGTAATAAGTCTCTTACACTATTTGTTTTG |
| | | TCCAATAATTTATATTTTCTGAAGACTTAACTCTAGAAT |
| | | ACACTCATGTCAAAATGAAAGAATTTCATTGCAAAATA |
| | | TTGCTTGGTACATGACGCATACCTGTATTTGTTTTGTGT |
| | | CACAACATGAAAAATGATGGTTTATTAGAAGTTTCATT |
| | | GGGTAGGAAACACATTTGAATGGTATTTACTAAGATAC |
| | | TAAAATCCTTGGACTTCACTCTAATTTTAGTGCCATTTA |
| | | GAACTCAAGGTCTCAGTAAAAGTAGAAATAAAGCCTGT |
| | | TAACAAAACACAAACTGAATATTAAAAATGTAACTGGA |
| | | TTTTCAAAGAAATGTTTACTGGTATTACCTGTAGATGTA |
| | | TATTCTTTATTATGATCTTTTGTGTAAAGTCTGGCAGAC |
| | | AAATGCAATATCTAATTGTTGAGTCCAATATCACAAGC |
| | | AGTACAAAAGTATAAAAAAGACTTGGCCTTTTCTAATG |
| | | TGTTAAAATACTTTATGCTGGTAATAACACTAAGAGTA |
| | | GGGCACTAGAAATTTTAAGTGAAGATAATGTGTTGCAG |
| | | TTACTGCACTCAATGGCTTACTATTATAAACCAAAACTG |
| | | GGATCACTAAGCTCCAGTCAGTCAAAATGATCAAAATT |
| | | ATTGAAGAGAATAAGCAATTCTGTTCTTTATTAGGACAC |
| | | AGTAGATACAGACTACAAAGTGGAGTGTGCTTAATAAG |
| | | AGGTAGCATTTGTTAAGTGTCAATTACTCTATTATCCCT |
| | | TGGAGCTTCTCAAAATAACCATATAAGGTGTAAGATGT |
| | | TAAAGGTTATGGTTACACTCAGTGCACAGGTAAGCTAA |

| | | |
|---|---|---|
| | SEQUENCE LISTING: | |
| | | TAGGCTGAGAGAAGCTAAATTACTTACTGGGGTCTCAC |
| | | AGTAAGAAAGTGAGCTGAAGTTTCAGCCCAGATTTAAC |
| | | TGGATTCTGGGCTCTTTATTCATGTTACTTCATGAATCT |
| | | GTTTCTCAATTGTGCAGAAAAAAGGGGGCTATTTATAA |
| | | GAAAAGCAATAAACAAACAAGTAATGATCTCAAATAA |
| | | GTAATGCAAGAAATAGTGAGATTTCAAAATCAGTGGCA |
| | | GCGATTTCTCAGTTCTGTCCTAAGTGGCCTTGCTCAATC |
| | | ACCTGCTATCTTTTAGTGGAGCTTTGAAATTATGTTTCA |
| | | GACAACTTCGATTCAGTTCTAGAATGTTTGACTCAGCAA |
| | | ATTCACAGGCTCATCTTTCTAACTTGATGGTGAATATGG |
| | | AAATTCAGCTAAATGGATGTTAATAAAATTCAAACGTT |
| | | TTAAGGACAGATGGAAATGACAGAATTTTAAGGTAAAA |
| | | TATATGAAGGAATATAAGATAAAGGATTTTTCTACCTTC |
| | | AGCAAAAACATACCCACTAATTAGTAAAATTAATAGGC |
| | | GAAAAAAAGTTGCATGCTCTTATACTGTAATGATTATCA |
| | | TTTTAAAACTAGCTTTTTGCCTTCGAGCTATCGGGGTAA |
| | | AGACCTACAGGAAAACTACTGTCGAAATCCTCGAGGGG |
| | | AAGAAGGGGGACCCTGGTGTTTCACAAGCAATCCAGAG |
| | | GTACGCTACGAAGTCTGTGACATTCCTCAGTGTTCAGAA |
| | | GTTGAATGCATGACCTGCAATGGGAGAGTTATCGAGG |
| | | TCTCATGGATCATACAGAATCAGGCAAGATTTGTCAGC |
| | | GCTGGGATCATCAGACACCACACCGGCACAAATTCTTG |
| | | CCTGAAAGATATCCCGACAAGGGCTTTGATGATAATTA |
| | | TTGCCGCAATCCCGATGGCCAGCCGAGGCCATGGTGCT |
| | | ATACTCTTGACCCTCACACCCGCTGGGAGTACTGTGCAA |
| | | TTAAAACATGCGCTGACAATACTATGAATGACACTGAT |
| | | GTTCCTTTGGAAACAACTGAATGCATCCAAGGTCAAGG |
| | | AGAAGGCTACAGGGGCACTGTCAATACCATTTGGAATG |
| | | GAATTCCATGTCAGCGTTGGGATTCTCAGTATCCTCACG |
| | | AGCATGACATGACTCCTGAAAATTTCAAGTGCAAGGAC |
| | | CTACGAGAAAATTACTGCCGAAATCCAGATGGGTCTGA |
| | | ATCACCCTGGTGTTTTACCACTGATCCAAACATCCGAGT |
| | | TGGCTACTGCTCCCAAATTCCAAACTGTGATATGTCACA |
| | | TGGACAAGATTGTTATCGTGGGAATGGCAAAAATTATA |
| | | TGGGCAACTTATCCCAAACAAGATCTGGACTAACATGT |
| | | TCAATGTGGGACAAGAACATGGAAGACTTACATCGTCA |
| | | TATCTTCTGGGAACCAGATGCAAGTAAGCTGAATGAGA |
| | | ATTACTGCCGAAATCCAGATGATGATGCTCATGGACCC |
| | | TGGTGCTACACGGGAAATCCACTCATTCCTTGGGATTAT |
| | | TGCCCTATTTCTCGTTGTGAAGGTGATACCACACCTACA |
| | | ATAGTCAATTTAGACCATCCCGTAATATCTTGTGCCAAA |
| | | ACGAAACAATTGCGAGTTGTAAATGGGATTCCAACACG |
| | | AACAAACATAGGATGGATGGTTAGTTTGAGATACAGAA |
| | | ATAAACATATCTGCGGAGGATCATTGATAAAGGAGAGT |
| | | TGGGTTCTTACTGCACGACAGTGTTTCCCTTCTCGAGAC |
| | | TTGAAAGATTATGAAGCTTGGCTTGGAATTCATGATGTC |
| | | CACGGAAGAGGAGATGAGAAATGCAAACAGGTTCTCA |
| | | ATGTTTCCCAGCTGGTATATGGCCCTGAAGGATCAGATC |
| | | TGGTTTTAATGAAGCTTGCCAGGCCTGCTGTCCTGGATG |
| | | ATTTTGTTAGTACGATTGATTTACCTAATTATGGATGCA |
| | | CAATTCCTGAAAAGACCAGTTGCAGTGTTTATGGCTGG |
| | | GGCTACACTGGATTGATCAACTATGATGGCCTATTACG |
| | | AGTGGCACATCTCTATATAATGGGAAATGAGAAATGCA |
| | | GCCAGCATCATCGAGGGAAGGTGACTCTGAATGAGTCT |
| | | GAAATATGTGCTGGGGCTGAAAAGATTGGATCAGGACC |
| | | ATGTGAGGGGGATTATGGTGGCCCACTTGTTTGTGAGC |
| | | AACATAAAATGAGAATGGTTCTTGGTGTCATTGTTCCTG |
| | | GTCGTGGATGTGCCATTCCAAATCGTCCTGGTATTTTTG |
| | | TCCGAGTAGCATATTATGCAAAATGGATACACAAAATT |
| | | ATTTTAACATATAAGGTACCACAGTCATAG |
| SEQ ID NO: 13 | Nucleotide sequence of HGF-X7 | ATGTGGGTGACCAAACTCCTGCCAGCCCTGCTGCTGCA GCATGTCCTCCTGCATCTCCTCCTGCTCCCCATCGCCAT CCCCTATGCAGAGGGACAAAGGAAAAGAAGAAATACA ATTCATGAATTCAAAAAATCAGCAAAGACTACCCTAAT CAAAATAGATCCAGCACTGAAGATAAAAACCAAAAAA GTGAATACTGCAGACCAATGTGCTAATAGATGTACTAG GAATAAAGGACTTCCATTCACTTGCAAGGCTTTTGTTTT TGATAAAGCAAGAAAACAATGCCTCTGGTTCCCCTTCA ATAGCATGTCAAGTGGAGTGAAAAAAGAATTTGGCCAT GAATTTGACCTCTATGAAACAAAGACTACATTAGAAA CTGCATCATTGGTAAAGGACGCAGCTACAAGGGAACAG TATCTATCACTAAGAGTGGCATCAAATGTCAGCCCTGG AGTTCCATGATACCACACGAACACAGGTAAGAACAGTA TGAAGAAAAGAGATGAAGCCTCTGTCTTTTTTACATGTT AACAGTCTCATATTAGTCCTTCAGAATAATTCTACAATC CTAAAATAACTTAGCCAACTTGCTGAATTGTATTACGGC |

SEQUENCE LISTING:

```
AAGGTTTATATGAATTCATGACTGATATTTAGCAAATGA
TTAATTAATATGTTAATAAAATGTAGCCAAAACAATAT
CTTACCTTAATGCCTCAATTTGTAGATCTCGGTATTTGT
GGATCCTGGGTAGGAAACACATTTGAATGGTATTTACT
AAGATACTAAAATCCTTGGACTTCACTCTAATTTTAGTG
CCATTTAGAACTCAAGGTCTCAGTAAAAGTAGAAATAA
AGCCTGTTAACAAAACACAAACTGAATATTAAAAATGT
AACTGGATTTTCAAAGAAATGTTTACTGGTATTACCTGT
AGATGTATATTCTTTATTATGATCTTTTGTGTAAAGTCT
GGCAGACAAATGCAATATCTAATTGTTGAGTCCAATAT
CACAAGCAGTACAAAAGTATAAAAAAGACTTGGCCTTT
TCTAATGTGTTAAAATACTTTATGCTGGTAATAACACTA
AGAGTAGGGCACTAGAAATTTTAAGTGAAGATAATGTG
TTGCAGTTACTGCACTCAATGGCTTACTATTATAAACCA
AAACTGGGATCACTAAGCTCCAGTCAGTCAAAATGATC
AAAATTATTGAAGAGAATAAGCAATTCTGTTCTTTATTA
GGACACAGTAGATACAGACTACAAAGTGGAGTGTGCTT
AATAAGAGGTAGCATTTGTTAAGTGTCAATTACTCTATT
ATCCCTTGGAGCTTCTCAAAATAACCATATAAGGTGTA
AGATGTTAAAGGTTATGGTTACACTCAGTGCACAGGTA
AGCTAATAGGCTGAGAGAAGCTAAATTACTTACTGGGG
TCTCACAGTAAGAAAGTGAGCTGAAGTTTCAGCCCAGA
TTTAACTGGATTCTGGGCTCTTTATTCATGTTACTTCATG
AATCTGTTTCTCAATTGTGCAGAAAAAAGGGGGCTATTT
ATAAGAAAAGCAATAAACAAACAAGTAATGATCTCAA
ATAAGTAATGCAAGAAATAGTGAGATTTCAAAATCAGT
GGCAGCGATTTCTCAGTTCTGTCCTAAGTGGCCTTGCTC
AATCACCTGCTATCTTTTAGTGGAGCTTTGAAATTATGT
TTCAGACAACTTCGATTCAGTTCTAGAATGTTTGACTCA
GCAAATTCACAGGCTCATCTTTCTAACTTGATGGTGAAT
ATGGAAATTCAGCTAAATGGATGTTAATAAAATTCAAA
CGTTTTAAGGACAGATGGAAATGACAGAATTTTAAGGT
AAAATATATGAAGGAATATAAGATAAAGGATTTTTCTA
CCTTCAGCAAAAACATACCCACTAATTAGTAAAATTAA
TAGGCGAAAAAAAGTTGCATGCTCTTATACTGTAATGA
TTATCATTTTAAAACTAGCTTTTTGCCTTCGAGCTATCG
GGGTAAAGACCTACAGGAAAACTACTGTCGAAATCCTC
GAGGGGAAGAAGGGGGACCCTGGTGTTTCACAAGCAAT
CCAGAGGTACGCTACGAAGTCTGTGACATTCCTCAGTG
TTCAGAAGTTGAATGCATGACCTGCAATGGGGAGAGTT
ATCGAGGTCTCATGGATCATACAGAATCAGGCAAGATT
TGTCAGCGCTGGGATCATCAGACACCACACCGGCACAA
ATTCTTGCCTGAAAGATATCCCGACAAGGGCTTTGATG
ATAATTATTGCCGCAATCCCGATGGCCAGCCGAGGCCA
TGGTGCTATACTCTTGACCCTCACACCCGCTGGGAGTAC
TGTGCAATTAAAACATGCGCTGACAATACTATGAATGA
CACTGATGTTCCTTTGGAAACAACTGAATGCATCCAAG
GTCAAGGAGAAGGCTACAGGGGCACTGTCAATACCATT
TGGAATGGAATTCCATGTCAGCGTTGGGATTCTCAGTAT
CCTCACGAGCATGACATGACTCCTGAAAATTTCAAGTG
CAAGGACCTACGAGAAAATTACTGCCGAAATCCAGATG
GGTCTGAATCACCCTGGTGTTTTACCACTGATCCAAACA
TCCGAGTTGGCTACTGCTCCCAAATTCCAAACTGTGATA
TGTCACATGGACAAGATTGTTATCGTGGGAATGGCAAA
AATTATATGGGCAACTTATCCCAAACAAGATCTGGACT
AACATGTTCAATGTGGGACAAGAACATGGAAGACTTAC
ATCGTCATATCTTCTGGGAACCAGATGCAAGTAAGCTG
AATGAGAATTACTGCCGAAATCCAGATGATGATGCTCA
TGGACCCTGGTGCTACACGGGAAATCCACTCATTCCTTG
GGATTATTGCCCTATTTCTCGTTGTGAAGGTGATACCAC
ACCTACAATAGTCAATTTAGACCATCCCGTAATATCTTG
TGCCAAAACGAAACAATTGCGAGTTGTAAATGGGATTC
CAACACGAACAAACATAGGATGGATGGTTAGTTTGAGA
TACAGAAATAAACATATCTGCGGAGGATCATTGATAAA
GGAGAGTTGGGTTCTTACTGCACGACAGTGTTTCCCTTC
TCGAGACTTGAAAGATTATGAAGCTTGGCTTGGAATTC
ATGATGTCCACGGAAGAGGAGATGAGAAATGCAAACA
GGTTCTCAATGTTTCCCAGCTGGTATATGGCCCTGAAGG
ATCAGATCTGGTTTTAATGAAGCTTGCCAGGCCTGCTGT
CCTGGATGATTTTGTTAGTACGATTGATTTACCTAATTA
TGGATGCACAATTCCTGAAAAGACCAGTTGCAGTGTTT
ATGGCTGGGGCTACACTGGATTGATCAACTATGATGGC
CTATTACGAGTGGCACATCTCTATATAATGGGAAATGA
GAAATGCAGCCAGCATCATCGAGGGAAGGTGACTCTGA
ATGAGTCTGAAATATGTGCTGGGGCTGAAAAGATTGGA
TCAGGACCATGTGAGGGGGATTATGGTGGCCCACTTGT
TTGTGAGCAACATAAAATGAGAATGGTTCTTGGTGTCA
```

| SEQUENCE LISTING: | |
|---|---|
| | TTGTTCCTGGTCGTGGATGTGCCATTCCAAATCGTCCTG<br>GTATTTTGTCCGAGTAGCATATTATGCAAAATGGATAC<br>ACAAAATTATTTTAACATATAAGGTACCACAGTCATAG |
| SEQ ID NO: 14 | Nucleotide sequence of HGF-X8 | ATGTGGGTGACCAAACTCCTGCCAGCCCTGCTGCTGCA<br>GCATGTCCTCCTGCATCTCCTCCTGCTCCCCATCGCCAT<br>CCCCTATGCAGAGGGACAAAGGAAAAGAAGAAATACA<br>ATTCATGAATTCAAAAAATCAGCAAAGACTACCCTAAT<br>CAAAATAGATCCAGCACTGAAGATAAAAACCAAAAAA<br>GTGAATACTGCAGACCAATGTGCTAATAGATGTACTAG<br>GAATAAAGGACTTCCATTCACTTGCAAGGCTTTTGTTTT<br>TGATAAAGCAAGAAAACAATGCCTCTGGTTCCCCTTCA<br>ATAGCATGTCAAGTGGAGTGAAAAAAGAATTTGGCCAT<br>GAATTTGACCTCTATGAAAACAAAGACTACATTAGAAA<br>CTGCATCATTGGTAAAGGACGCAGCTACAAGGGAACAG<br>TATCTATCACTAAGAGTGGCATCAAATGTCAGCCCTGG<br>AGTTCCATGATACCACACGAACACAGGTAAGAACAGTA<br>TGAAGAAAAGAGATGAAGCCTCTGTCTTTTTTACATGTT<br>AACAGTCTCATATTAGTCCTTCAGAATAATTCTACAATC<br>CTAAAATAACTTAGCCAACTTGCTGAATTGTATTACGGC<br>AAGGTTTATATGAATTCATGACTGATATTTAGCAAATGA<br>TTAATTAATATGTTAATAAAATGTAGCCAAAACAATAT<br>CTTACCTTAATGCCTCAATTTGTAGATCTCGGTATTTGT<br>GGATCCTTATGTTTCAGACAACTTCGATTCAGTTCTAGA<br>ATGTTTGACTCAGCAAATTCACAGGCTCATCTTTCTAAC<br>TTGATGGTGAATATGGAAATTCAGCTAAATGGATGTTA<br>ATAAAATTCAAACGTTTTAAGGACAGATGGAAATGACA<br>GAATTTTAAGGTAAAATATATGAAGGAATATAAGATAA<br>AGGATTTTTCTACCTTCAGCAAAAACATACCCACTAATT<br>AGTAAAATTAATAGGCGAAAAAAAGTTGCATGCTCTTA<br>TACTGTAATGATTATCATTTTAAAACTAGCTTTTTGCCTT<br>CGAGCTATCGGGGTAAAGACCTACAGGAAAACTACTGT<br>CGAAATCCTCGAGGGGAAGAAGGGGGACCCTGGTGTTT<br>CACAAGCAATCCAGAGGTACGCTACGAAGTCTGTGACA<br>TTCCTCAGTGTTCAGAAGTTGAATGCATGACCTGCAATG<br>GGGAGAGTTATCGAGGTCTCATGGATCATACAGAATCA<br>GGCAAGATTTGTCAGCGCTGGGATCATCAGACACCACA<br>CCGGCACAAATTCTTGCCTGAAAGATATCCCGACAAGG<br>GCTTTGATGATAATTATTGCCGCAATCCCGATGGCCAGC<br>CGAGGCCATGGTGCTATACTCTTGACCCTCACACCCGCT<br>GGGAGTACTGTGCAATTAAAACATGCGCTGACAATACT<br>ATGAATGACACTGATGTTCCTTTGGAAACAACTGAATG<br>CATCCAAGGTCAAGGAGAAGGCTACAGGGGCACTGTCA<br>ATACCATTTGGAATGGAATTCCATGTCAGCGTTGGGATT<br>CTCAGTATCCTCACGAGCATGACATGACTCCTGAAAATT<br>TCAAGTGCAAGGACCTACGAGAAAATTACTGCCGAAAT<br>CCAGATGGGTCTGAATCACCCTGGTGTTTTACCACTGAT<br>CCAAACATCCGAGTTGGCTACTGCTCCCAAATTCCAAA<br>CTGTGATATGTCACATGGACAAGATTGTTATCGTGGGA<br>ATGGCAAAAATTATATGGGCAACTTATCCCAAACAAGA<br>TCTGGACTAACATGTTCAATGTGGGACAAGAACATGGA<br>AGACTTACATCGTCATATCTTCTGGGAACCAGATGCAA<br>GTAAGCTGAATGAGAATTACTGCCGAAATCCAGATGAT<br>GATGCTCATGGACCCTGGTGCTACACGGGAAATCCACT<br>CATTCCTTGGGATTATTGCCCTATTTCTCGTTGTGAAGG<br>TGATACCACACCTACAATAGTCAATTTAGACCATCCCGT<br>AATATCTTGTGCCAAAACGAAACAATTGCGAGTTGTAA<br>ATGGGATTCCAACACGAACAAACATAGGATGGATGGTT<br>AGTTTGAGATACAGAAATAAACATATCTGCGGAGGATC<br>ATTGATAAAGGAGAGTTGGGTTCTTACTGCACGACAGT<br>GTTTCCCTTCTCGAGACTTGAAAGATTATGAAGCTTGGC<br>TTGGAATTCATGATGTCCACGGAAGAGGAGATGAGAAA<br>TGCAAACAGGTTCTCAATGTTTCCCAGCTGGTATATGGC<br>CCTGAAGGATCAGATCTGGTTTTAATGAAGCTTGCCAG<br>GCCTGCTGTCCTGGATGATTTTGTTAGTACGATTGATTT<br>ACCTAATTATGGATGCACAATTCCTGAAAAGACCAGTT<br>GCAGTGTTTATGGCTGGGGCTACACTGGATTGATCAACT<br>ATGATGGCCTATTACGAGTGGCACATCTCTATATAATGG<br>GAAATGAGAAATGCAGCCAGCATCATCGAGGGAAGGT<br>GACTCTGAATGAGTCTGAAATATGTGCTGGGGCTGAAA<br>AGATTGGATCAGGACCATGTGAGGGGGATTATGGTGGC<br>CCACTTGTTTGTGAGCAACATAAAATGAGAATGGTTCTT<br>GGTGTCATTGTTCCTGGTCGTGGATGTGCCATTCCAAAT<br>CGTCCTGGTATTTTGTCCGAGTAGCATATTATGCAAAA<br>TGGATACACAAAATTATTTTAACATATAAGGTACCACA<br>GTCATAG |

SEQUENCE LISTING:

| SEQ ID NO: 15 | Nucleotide sequence of pTx | CAGGGTCGGAACAGGAGAGCGCACGAGGGAGCTTCCAGGGG
GAAACGCCTGGTATCTTTATAGTCCTGTCGGGTTTCGCCACCT
CTGACTTGAGCGTCGATTTTTGTGATGCTCGTCAGGGGGGCG
GAGCCTATGGAAAAACGCCAGCAACGCGGCCTTTTTACGGTT
CCTGGCCTTTTGCTGGCCTTTTGCTCACATGCGCGTTGACATT
GATTATTGACTAGTTATTAATAGTAATCAATTACGGGGTCAT
TAGTTCATAGCCCATATATGGAGTTCCGCGTTACATAACTTA
CGGTAAATGGCCCGCCTGGCTGACCGCCCAACGACCCCCGCC
CATTGACGTCAATAATGACGTATGTTCCCATAGTAACGCCAA
TAGGGACTTTCCATTGACGTCAATGGGTGGAGTATTTACGGT
AAACTGCCCACTTGGCAGTACATCAAGTGTATCATATGCCAA
GTCCGCCCCCTATTGACGTCAATGACGGTAAATGGCCCGCCT
GGCATTATGCCCAGTACATGACCTTACGGGACTTTCCTACTT
GGCAGTACATCTACGTATTAGTCATCGCTATTACCATGGTGA
TGCGGTTTTGGCAGTACACCAATGGGCGTGGATAGCGGTTTG
ACTCACGGGGATTTCCAAGTCTCCACCCCATTGACGTCAATG
GGAGTTTGTTTTGGCACCAAAATCAACGGGACTTTCCAAAAT
GTCGTAATAACCCCGCCCCGTTGACGCAAATGGGCGGTAGGC
GTGTACGGTGGGAGGTCTATATAAGCAGAGCTCGTTTAGTGA
ACCGTCAGATCGCCTGGAGACGCCATCCACGCTGTTTTGACC
TCCATAGAAGACACCGGGACCGATCCAGCCTCCGCGGCCGG
GAACGGTGCATTGGAACGCGGATTCCCCGTGCCAAGAGTGA
CGTAAGTACCGCCTATAGACTCTATAGGCACACCCCTTTGGC
TCTTATGCATGCTATACTGTTTTTGGCTTGGGGCCTATACACC
CCCGCTTCCTTATGCTATAGGTGATGGTATAGCTTAGCCTATA
GGTGTGGGTTATTGACCATTATTGACCACTCCCCTATTGGTG
ACGATACTTTCCATTACTAATCCATAACATGGCTCTAGACTT
AAGGCAGCGGCAGAAGAAGATGTAGGCAGCTGAGTTGTTGT
ATTCTGATAAGAGTCAGAGGTAACTCCCGTTGCGGTGCTGTT
AACGGTGGAGGGCAGTGTAGTCTGAGCAGTACTCGTTGCTGC
CGCGCGCGCCACCAGACATAATAGCTGACAGACTAACAGAC
TGTTCCTTTCCATGGGTCTTTTCTGCAGTCACCGTCCTTGACA
CGAAGCTTATCGATGTCGACCTCGAGTCTAGAGGGCCCGTTT
AAACCCGCTGATCAGCCTCGACTGTGCCTTCTAGTTGCCAGC
CATCTGTTGTTTGCCCCTCCCCCGTGCCTTCCTTGACCCTGGA
AGGTGCCACTCCCACTGTCCTTTCCTAATAAAATGAGGAAAT
TGCATCGCATTGTCTGAGTAGGTGTCATTCTATTCTGGGGGG
TGGGGTGGGGCAGGACAGCAAGGGGGAGGATTGGGAAGAC
AATAGCAGGCATGCTGGGGAGTCGAAATTCAGAAGAACTCG
TCAAGAAGGCGATAGAAGGCGATGCGCTGCGAATCGGGAGC
GGCGATACCGTAAAGCACGAGGAAGCGGTCAGCCCATTCGC
CGCCAAGCTCTTCAGCAATATCACGGGTAGCCAACGCTATGT
CCTGATAGCGGTCCGCCACACCCAGCCGGCCACAGTCGATGA
ATCCAGAAAAGCGGCCATTTTCCACCATGATATTCGGCAAGC
AGGCATCGCCATGGGTCACGACGAGATCCTCGCCGTCGGGC
ATGCTCGCCTTGAGCCTGGCGAACAGTTCGGCTGGCGCGAGC
CCCTGATGCTCTTCGTCCAGATCATCCTGATCGACAAGACCG
GCTTCCATCCGAGTACGTGCTCGCTCGATGCGATGTTTCGCTT
GGTGGTCGAATGGGCAGGTAGCCGGATCAAGCGTATGCAGC
CGCCGCATTGCATCAGCCATGATGGATACTTTCTCGGCAGGA
GCAAGGTGAGATGACAGGAGATCCTGCCCCGGCACTTCGCC
CAATAGCAGCCAGTCCCTTCCCGCTTCAGTGACAACGTCGAG
CACAGCTGCGCAAGGAACGCCCGTCGTGGCCAGCCACGATA
GCCGCGCTGCCTCGTCTTGCAGTTCATTCAGGGCACCGGACA
GGTCGGTCTTGACAAAAAGAACCGGGCGCCCCTGCGCTGAC
AGCCGGAACACGGCGGCATCAGAGCAGCCGATTGTCTGTTGT
GCCCAGTCATAGCCGAATAGCCTCTCCACCCAAGCGGCCGGA
GAACCTGCGTGCAATCCATCTTGTTCAATCATGCGAAACGAT
CCTCATCCTGTCTCTTGATCAGATCTTGATCCCCTGCGCCATC
AGATCCTTGGCGGCAAGAAAGCCATCCAGTTTACTTTGCAGG
GCTTCCCAACCTTACCAGAGGGCGCCCCAGCTGGCAATTCCG
GTTCGCTTGCTGCGTCAGACCCCGTAGAAAAGATCAAAGGAT
CTTCTTGAGATCCTTTTTTTCTGCGCGTAATCTGCTGCTTGCA
AACAAAAAAACCACCGCTACCAGCGGTGGTTTGTTTGCCGGA
TCAAGAGCTACCAACTCTTTTTCCGAAGGTAACTGGCTTCAG
CAGAGCGCAGATACCAAATACTGTTCTTCTAGTGTAGCCGTA
GTTAGGCCACCACTTCAAGAACTCTGTAGCACCGCCTACATA
CCTCGCTCTGCTAATCCTGTTACCAGTGGCTGCTGCCAGTGG
CGATAAGTCGTGTCTTACCGGGTTGGACTCAAGACGATAGTT
ACCGGATAAGGCGCAGCGGTCGGGCTGAACGGGGGGTTCGT
GCACACAGCCCAGCTTGGAGCGAACGACCTACACCGAACTG
AGATACCTACAGCGTGAGCTATGAGAAAGCGCCACGCTTCCC
GAAGGGAGAAAGGCGGACAGGTATCCGGTAAGCGGCAGGGT
CGGAACAGGAGAGCGCACGAGGGAGCTTCCAGGGGGAAAC |

| SEQUENCE LISTING: | |
|---|---|
| | GCCTGGTATCTTTATAGTCCTGTCGGGTTTCGCCACCTCTGAC<br>TTGAGCGTCGATTTTTGTGATGCTCGTCAGGGGGCGGAGCC<br>TATGGAAAAACGCCAGCAACGCGGCCTTTTTACGGTTCCTGG<br>CCTTTTGCTGGCCTTTTGCTCACATG |
| SEQ ID<br>NO: 16 | Nucleotide<br>sequence of<br>pTx-IGF-1X10 | CAGGGTCGGAACAGGAGAGCGCACGAGGGAGCTTCCAGGGG<br>GAAACGCCTGGTATCTTTATAGTCCTGTCGGGTTTCGCCACCT<br>CTGACTTGAGCGTCGATTTTTGTGATGCTCGTCAGGGGGCG<br>GAGCCTATGGAAAAACGCCAGCAACGCGGCCTTTTTACGGTT<br>CCTGGCCTTTTGCTGGCCTTTTGCTCACATGCGCGTTGACATT<br>GATTATTGACTAGTTATTAATAGTAATCAATTACGGGGTCAT<br>TAGTTCATAGCCCATATATGGAGTTCCGCGTTACATAACTTA<br>CGGTAAATGGCCCGCCTGGCTGACCGCCCAACGACCCCCGCC<br>CATTGACGTCAATAATGACGTATGTTCCCATAGTAACGCCAA<br>TAGGGACTTTCCATTGACGTCAATGGGTGGAGTATTTACGGT<br>AAACTGCCCACTTGGCAGTACATCAAGTGTATCATATGCCAA<br>GTCCGCCCCCTATTGACGTCAATGACGGTAAATGGCCCGCCT<br>GGCATTATGCCCAGTACATGACCTTACGGGACTTTCCTACTT<br>GGCAGTACATCTACGTATTAGTCATCGCTATTACCATGGTGA<br>TGCGGTTTTGGCAGTACACCAATGGGCGTGGATAGCGGTTTG<br>ACTCACGGGGATTTCCAAGTCTCCACCCCATTGACGTCAATG<br>GGAGTTTGTTTTGGCACCAAAATCAACGGGACTTTCCAAAAT<br>GTCGTAATAACCCCGCCCCGTTGACGCAAATGGGCGGTAGGC<br>GTGTACGGTGGGAGGTCTATATAAGCAGAGCTCGTTTAGTGA<br>ACCGTCAGATCGCCTGGAGACGCCATCCACGCTGTTTTGACC<br>TCCATAGAAGACACCGGGACCGATCCAGCCTCCGCGGCCGG<br>GAACGGTGCATTGGAACGCGGATTCCCCGTGCCAAGAGTGA<br>CGTAAGTACCGCCTATAGACTCTATAGGCACACCCCTTTGGC<br>TCTTATGCATGCTATACTGTTTTTGGCTTGGGGCCTATACACC<br>CCCGCTTCCTTATGCTATAGGTGATGGTATAGCTTAGCCTATA<br>GGTGTGGGTTATTGACCATTATTGACCACTCCCCTATTGGTG<br>ACGATACTTTCCATTACTAATCCATAACATGGCTCTAGACTT<br>AAGGCAGCGGCAGAAGAAGATGTAGGCAGCTGAGTTGTTGT<br>ATTCTGATAAGAGTCAGAGGTAACTCCCGTTGCGGTGCTGTT<br>AACGGTGGAGGGCAGTGTAGTCTGAGCAGTACTCGTTGCTGC<br>CGCGCGCGCCACCAGACATAATAGCTGACAGACTAACAGAC<br>TGTTCCTTTCCATGGGTCTTTTCTGCAGTCACCGTCCTTGACA<br>CGAAGCTTATCGATATGGGAAAAATCAGCAGTCTTCCAACCC<br>AATTATTTAAGTGCTGCTTTTGTGATTTCTTGAAGGTGAAGAT<br>GCACACCATGTCCTCCTCGCATCTCTTCTACCTGGCGCTGTGC<br>CTGCTCACCTTCACCAGCTCTGCCACGGCTGGACCGGAGACG<br>CTCTGCGGGGCTGAGCTGGTGGATGCTCTTCAGTTCGTGTGT<br>GGGAGACAGGGGCTTTTATTTCAACAAGCCCACAGGGTATGGC<br>TCCAGCAGTCGGAGGGCGCCTCAGACAGGCATCGTGGATGA<br>GTGCTGCTTCCGGAGCTGTGATCTAAGGAGGCTGGAGATGTA<br>TTGCGCACCCCTCAAGCCTGCCAAGTCAGCTCGCTCTGTCCG<br>TGCCCAGCGCCACACCGACATGCCCAAGACCCAGAAGGTAA<br>GCCCACCTGGGTGGGATCCAGCCATCCTCAAGTGGTCTCTCT<br>CTTGTGCATGTGGGTGGGCCAAGCAGAAATCCTGCCCCATAG<br>TCTCCTGGCTTACAAGTCAGAAAAGCTCCTTTGCACCAAAGG<br>GATGGATTACATCCCCATCTCTTTGCTAAACAAACATGGGCT<br>TTGGTGTCAGACAAAAGTGAAGTCCTGGCTTTCTCACACACC<br>AGCTTAGAGAGAAAAGACTTTTAGGTGAATGTGGCAGGAAA<br>GCGTGCTTGCTGGGCAAAGGCAGATTCATTCTTTCTCTTCCC<br>AGTATCAGCCCCCATCTACCAACAAGAACACGAAGTCTCAG<br>AGAAGGAAAGGAAGTACATTTGAAGAACGCAAGTAGCTTTT<br>TCTCCTTTATTTATAGGAAGTACATTTGAAGAACGCAAGTAG<br>AGGGAGTGCAGGAAACAAGAACTACAGGATGTAGGTCGACC<br>TCGAGTCTAGAGGGCCCGTTTAAACCCGCTGATCAGCCTCGA<br>CTGTGCCTTCTAGTTGCCAGCCATCTGTTGTTTGCCCCTCCCC<br>CGTGCCTTCCTTGACCCTGGAAGGTGCCACTCCCACTGTCCTT<br>TCCTAATAAAATGAGGAAATTGCATCGCATTGTCTGAGTAGG<br>TGTCATTCTATTCTGGGGGGTGGGGTGGGGCAGGACAGCAA<br>GGGGGAGGATTGGGAAGACAATAGCAGGCATGCTGGGGAGT<br>CGAAATTCAGAAGAACTCGTCAAGAAGGCGATAGAAGGCGA<br>TGCGCTGCGAATCGGGAGCGGCGATACCGTAAAGCACGAGG<br>AAGCGGTCAGCCCATTCGCCGCCAAGCTCTTCAGCAATATCA<br>CGGGTAGCCAACGCTATGTCCTGATAGCGGTCCGCCACACCC<br>AGCCGGCCACAGTCGATGAATCAGAAAAGCGGCCATTTTCC<br>ACCATGATATTCGGCAAGCAGGCATCGCCATGGGTCACGAC<br>GAGATCCTCGCCGTCGGGCATGCTCGCCTTGAGCCTGGCGA<br>CAGTTCGGCTGGCGCGAGCCCCTGATGCTCTTCGTCCAGATC<br>ATCCTGATCGACAAGACCGGCTTCCATCCGAGTACGTGCTCG<br>CTCGATGCGATGTTTCGCTTGGTGGTCGAATGGGCAGGTAGC<br>CGGATCAAGCGTATGCAGCCGCCGCATTGCATCAGCCATGAT<br>GGATACTTTCTCGGCAGGAGCAAGGTGAGATGACAGGAGAT<br>CCTGCCCCGGCACTTCGCCCAATAGCAGCCAGTCCCTTCCCG |

-continued

SEQUENCE LISTING:

```
CTTCAGTGACAACGTCGAGCACAGCTGCGCAAGGAACGCCC
GTCGTGGCCAGCCACGATAGCCGCGCTGCCTCGTCTTGCAGT
TCATTCAGGGCACCGGACAGGTCGGTCTTGACAAAAAGAAC
CGGGCGCCCCTGCGCTGACAGCCGGAACACGGCGGCATCAG
AGCAGCCGATTGTCTGTTGTGCCCAGTCATAGCCGAATAGCC
TCTCCACCCAAGCGGCCGGAGAACCTGCGTGCAATCCATCTT
GTTCAATCATGCGAAACGATCCTCATCCTGTCTCTTGATCAG
ATCTTGATCCCCTGCGCCATCAGATCCTTGGCGGCAAGAAAG
CCATCCAGTTTACTTTGCAGGGCTTCCCAACCTTACCAGAGG
GCGCCCCAGCTGGCAATTCCGGTTCGCTTGCTGCGTCAGACC
CCGTAGAAAAGATCAAAGGATCTTCTTGAGATCCTTTTTTTCT
GCGCGTAATCTGCTGCTTGCAAACAAAAAAACCACCGCTACC
AGCGGTGGTTTGTTTGCCGGATCAAGAGCTACCAACTCTTTT
TCCGAAGGTAACTGGCTTCAGCAGAGCGCAGATACCAAATA
CTGTTCTTCTAGTGTAGCCGTAGTTAGGCCACCACTTCAAGA
ACTCTGTAGCACCGCCTACATACCTCGCTCTGCTAATCCTGTT
ACCAGTGGCTGCTGCCAGTGGCGATAAGTCGTGTCTTACCGG
GTTGGACTCAAGACGATAGTTACCGGATAAGGCGCAGCGGT
CGGGCTGAACGGGGGTTCGTGCACACAGCCCAGCTTGGAG
CGAACGACCTACACCGAACTGAGATACCTACAGCGTGAGCT
ATGAGAAAGCGCCACGCTTCCCGAAGGGAGAAAGGCGGACA
GGTATCCGGTAAGCGGCAGGGTCGGAACAGGAGAGCGCACG
AGGGAGCTTCCAGGGGAAACGCCTGGTATCTTTATAGTCCT
GTCGGGTTTCGCCACCTCTGACTTGAGCGTCGATTTTTGTGAT
GCTCGTCAGGGGGGCGGAGCCTATGGAAAAACGCCAGCAAC
GCGGCCTTTTTACGGTTCCTGGCCTTTTGCTGGCCTTTTGCTC
ACATG
```

| SEQ ID NO: 17 | F primer of the first primer pair (pTx) | AGCTGGCAATTCCGGTTCGCTTGCTGCGTCAGACCCCGTA |
|---|---|---|
| SEQ ID NO: 18 | R primer of the first primer pair (pTx) | TACGGGGTCTGACGCAGCAAGCGAACCGGAATTGCCAGCT |
| SEQ ID NO: 19 | F primer of the second primer pair (pTx) | CTAATCCATAACATGGCTCTAGACTTAAGGCAGCGGCAGA |
| SEQ ID NO: 20 | R primer of the second primer pair (pTx) | TCTGCCGCTGCCTTAAGTCTAGAGCCATGTTATGGATTAG |

SEQ ID NO. 21  IGF-1X6
```
ATGGGAAAAATCAGCAGTCTTCCAACCCAATTATTTAAGTGC
TGCTTTTGTGATTTCTTGAAGGTGAAGATGCACACCATGTCCT
CCTCGCATCTCTTCTACCTGGCGCTGTGCCTGCTCACCTTCAC
CAGCTCTGCCACGGCTGGACCGGAGACGCTCTGCGGGGCTG
AGCTGGTGGATGCTCTTCAGTTCGTGTGTGGAGACAGGGGCT
TTTATTTCAACAAGCCCACAGGGTATGGCTCCAGCAGTCGGA
GGGCGCCTCAGACAGGCATCGTGGATGAGTGCTGCTTCCGGA
GCTGTGATCTAAGGAGGCTGGAGATGTATTGCGCACCCCTCA
AGCCTGCCAAGTCAGCTCGCTCTGTCCGTGCCCAGCGCCACA
CCGACATGCCCAAGACCCAGAAGGTAAGCCCACCTGGGTGG
GATCCAGCCATCCTCAAGTGGTCTCTCTCTTGTGCATGTGGGT
GGGCCAAGCAGAAATCCTGCCCCATAGTCTCCTGGCTTACAA
GTCAGAAAAGCTCCTTTGCACCCAAAGGGATGGATTACATCCC
CATCTCTTTGGTCACTCTGCATTGCAAATTTCCCCTCCCACCG
CTATGGACGATGTGATGATTGGAAGATGTTACAAAACAGTG
GCTAAACAAACATGGGCTTTGGTGTCAGACAAAAGTGAAGT
CCTGGCTTTCTCACACACCAGCTTAGAGAGAAAAGACTTTTA
GGTGAATGTGGCAGGAAAGCGTGCTTGCTGGGGCAAAGGCA
GATTCATTCTTTCTCTTCCCAGTATCAGCCCCCATCTACCAAC
AAGAACACGAAGTCTCAGAGAAGGAAAGGAAGTACATTTGA
AGAACGCAAGTAGCTTTTTCTCCTTTATTTATAGGAAGTACA
TTTGAAGAACGCAAGTAGAGGGAGTGCAGGAAACAAGAACT
ACAGGATGTAG
```

SEQ ID NO. 22  IGF-1X10
```
ATGGGAAAAATCAGCAGTCTTCCAACCCAATTATTTAAGTGC
TGCTTTTGTGATTTCTTGAAGGTGAAGATGCACACCATGTCCT
CCTCGCATCTCTTCTACCTGGCGCTGTGCCTGCTCACCTTCAC
CAGCTCTGCCACGGCTGGACCGGAGACGCTCTGCGGGGCTG
AGCTGGTGGATGCTCTTCAGTTCGTGTGTGGAGACAGGGGCT
TTTATTTCAACAAGCCCACAGGGTATGGCTCCAGCAGTCGGA
GGGCGCCTCAGACAGGCATCGTGGATGAGTGCTGCTTCCGGA
GCTGTGATCTAAGGAGGCTGGAGATGTATTGCGCACCCCTCA
AGCCTGCCAAGTCAGCTCGCTCTGTCCGTGCCCAGCGCCACA
```

| | | |
|---|---|---|
| | SEQUENCE LISTING: | |
| | | CCGACATGCCCAAGACCCAGAAGGTAAGCCCACCTGGGTGG<br>GATCCAGCCATCCTCAAGTGGTCTCTCTCTTGTGCATGTGGGT<br>GGGCCAAGCAGAAATCCTGCCCCATAGTCTCCTGGCTTACAA<br>GTCAGAAAAGCTCCTTTGCACCAAAGGGATGGATTACATCCC<br>CATCTCTTTGCTAAACAAACATGGGCTTTGGTGTCAGACAAA<br>AGTGAAGTCCTGGCTTTCTCACACACCAGCTTAGAGAGAAAA<br>GACTTTTAGGTGAATGTGGCAGGAAAGCGTGCTTGCTGGGGC<br>AAAGGCAGATTCATTCTTTCTCTTCCCAGTATCAGCCCCCATC<br>TACCAACAAGAACACGAAGTCTCAGAGAAGGAAAGGAAGTA<br>CATTTGAAGAACGCAAGTAGCTTTTTCTCCTTTATTTATAGGA<br>AGTACATTTGAAGAACGCAAGTAGAGGGAGTGCAGGAAACA<br>AGAACTACAGGATGTAG |
| SEQ ID<br>NO. 23 | aa sequence of<br>Class I IGF-1Ea | MGKISSLPTQLFKCCFCDFLKVKMHTMSSSHLFYLALCLLTFTS<br>SATAGPETLCGAELVDALQFVCGDRGFYFNKPTGYGSSSRRAP<br>QTGIVDECCFRSCDLRRLEMYCAPLKPAKSARSVRAQRHTDMP<br>KTQKEVHLKNASRGSAGNKNYRM |
| SEQ ID<br>NO. 24 | nucleotide<br>sequence of<br>Class I IGF-1Ea | ATGGGAAAAATCAGCAGTCTTCCAACCCAATTATTTAAGTGC<br>TGCTTTTGTGATTTCTTGAAGGTGAAGATGCACACCATGTCCT<br>CCTCGCATCTCTTCTACCTGGCGCTGTGCCTGCTCACCTTCAC<br>CAGCTCTGCCACGGCTGGACCGGAGACGCTCTGCGGGGCTG<br>AGCTGGTGGATGCTCTTCAGTTCGTGTGTGGAGACAGGGGCT<br>TTTATTTCAACAAGCCCACAGGGTATGGCTCCAGCAGTCGGA<br>GGGCGCCTCAGACAGGCATCGTGGATGAGTGCTGCTTCCGGA<br>GCTGTGATCTAAGGAGGCTGGAGATGTATTGCGCACCCCTCA<br>AGCCTGCCAAGTCAGCTCGCTCTGTCCGTGCCCAGCGCCACA<br>CCGACATGCCCAAGACCCAGAAGGAAGTACATTTGAAGAAC<br>GCAAGTAGAGGGAGTGCAGGAAACAAGAACTACAGGATGTA<br>G |
| SEQ ID<br>NO. 25 | aa sequence of<br>Class I IGF-1Ec | MGKISSLPTQLFKCCFCDFLKVKMHTMSSSHLFYLALCLLTFTS<br>SATAGPETLCGAELVDALQFVCGDRGFYFNKPTGYGSSSRRAP<br>QTGIVDECCFRSCDLRRLEMYCAPLKPAKSARSVRAQRHTDMP<br>KTQKYQPPSTNKNTKSQRRKGSTFEERK |
| SEQ ID<br>NO. 26 | nucleotide<br>sequence of<br>Class I IGF-1Ec | ATGGGAAAAATCAGCAGTCTTCCAACCCAATTATTTAAGTGC<br>TGCTTTTGTGATTTCTTGAAGGTGAAGATGCACACCATGTCCT<br>CCTCGCATCTCTTCTACCTGGCGCTGTGCCTGCTCACCTTCAC<br>CAGCTCTGCCACGGCTGGACCGGAGACGCTCTGCGGGGCTG<br>AGCTGGTGGATGCTCTTCAGTTCGTGTGTGGAGACAGGGGCT<br>TTTATTTCAACAAGCCCACAGGGTATGGCTCCAGCAGTCGGA<br>GGGCGCCTCAGACAGGCATCGTGGATGAGTGCTGCTTCCGGA<br>GCTGTGATCTAAGGAGGCTGGAGATGTATTGCGCACCCCTCA<br>AGCCTGCCAAGTCAGCTCGCTCTGTCCGTGCCCAGCGCCACA<br>CCGACATGCCCAAGACCCAGAAGTATCAGCCCCCATCTACCA<br>ACAAGAACACGAAGTCTCAGAGAAGGAAAGGAAGTACATTT<br>GAAGAACGCAAGTAG |
| SEQ ID<br>NO. 27 | aa sequence of<br>Class II IGF-<br>1Ea | MITPTVKMHTMSSSHLFYLALCLLTFTSSATAGPETLCGAELVD<br>ALQFVCGDRGFYFNKPTGYGSSSRRAPQTGIVDECCFRSCDLRR<br>LEMYCAPLKPAKSARSVRAQRHTDMPKTQKEVHLKNASRGSA<br>GNKNYRM |
| SEQ ID<br>NO. 28 | nucleotide<br>sequence of<br>Class II IGF-<br>1Ea | ATGATTACACCTACAGTGAAGATGCACACCATGTCCTCCTCG<br>CATCTCTTCTACCTGGCGCTGTGCCTGCTCACCTTCACCAGCT<br>CTGCCACGGCTGGACCGGAGACGCTCTGCGGGGCTGAGCTG<br>GTGGATGCTCTTCAGTTCGTGTGTGGAGACAGGGGCTTTTAT<br>TTCAACAAGCCCACAGGGTATGGCTCCAGCAGTCGGAGGGC<br>GCCTCAGACAGGCATCGTGGATGAGTGCTGCTTCCGGAGCTG<br>TGATCTAAGGAGGCTGGAGATGTATTGCGCACCCCTCAAGCC<br>TGCCAAGTCAGCTCGCTCTGTCCGTGCCCAGCGCCACACCGA<br>CATGCCCAAGACCCAGAAGGAAGTACATTTGAAGAACGCAA<br>GTAGAGGGAGTGCAGGAAACAAGAACTACAGGATGTAG |
| SEQ ID<br>NO. 29 | aa sequence of<br>Class I IGF-1Eb | MGKISSLPTQLFKCCFCDFLKVKMHTMSSSHLFYLALCLLTFTS<br>SATAGPETLCGAELVDALQFVCGDRGFYFNKPTGYGSSSRRAP<br>QTGIVDECCFRSCDLRRLEMYCAPLKPAKSARSVRAQRHTDMP<br>KTQKYQPPSTNKNTKSQRRKGWPKTHPGGEQKEGTEASLQIRG<br>KKKEQRREIGSRNAECRGKKGK |
| SEQ ID<br>NO. 30 | nucleotide<br>sequence of<br>Class I IGF-1Eb | ATGGGAAAAATCAGCAGTCTTCCAACCCAATTATTTAAGTGC<br>TGCTTTTGTGATTTCTTGAAGGTGAAGATGCACACCATGTCCT<br>CCTCGCATCTCTTCTACCTGGCGCTGTGCCTGCTCACCTTCAC<br>CAGCTCTGCCACGGCTGGACCGGAGACGCTCTGCGGGGCTG<br>AGCTGGTGGATGCTCTTCAGTTCGTGTGTGGAGACAGGGGCT<br>TTTATTTCAACAAGCCCACAGGGTATGGCTCCAGCAGTCGGA |

SEQUENCE LISTING:

|  |  |  |
|---|---|---|
|  |  | GGGCGCCTCAGACAGGCATCGTGGATGAGTGCTGCTTCCGGA<br>GCTGTGATCTAAGGAGGCTGGAGATGTATTGCGCACCCCTCA<br>AGCCTGCCAAGTCAGCTCGCTCTGTCCGTGCCCAGCGCCACA<br>CCGACATGCCCAAGACCCAGAAGTATCAGCCCCCATCTACCA<br>ACAAGAACACGAAGTCTCAGAGAAGGAAAGGTTGGCCAAAG<br>ACACATCCAGGAGGGGAACAGAAGGAGGGGACAGAAGCAA<br>GTCTGCAGATCAGAGGAAAGAAGAAAGAGCAGAGGAGGGA<br>GATTGGAAGTAGAAATGCTGAATGCAGAGGCAAAAAAGGAA<br>AATGA |
| SEQ ID<br>NO. 31 | IGF-1 (exon 1,<br>3, and 4) | ATGGGAAAAATCAGCAGTCTTCCAACCCAATTATTTAAGTGC<br>TGCTTTTGTGATTTCTTGAAGGTGAAGATGCACACCATGTCCT<br>CCTCGCATCTCTTCTACCTGGCGCTGTGCCTGCTCACCTTCAC<br>CAGCTCTGCCACGGCTGGACCGGAGACGCTCTGCGGGCTG<br>AGCTGGTGGATGCTCTTCAGTTCGTGTGTGGAGACAGGGGCT<br>TTTATTTCAACAAGCCCACAGGGTATGGCTCCAGCAGTCGGA<br>GGGCGCCTCAGACAGGCATCGTGGATGAGTGCTGCTTCCGGA<br>GCTGTGATCTAAGGAGGCTGGAGATGTATTGCGCACCCCTCA<br>AGCCTGCCAAGTCAGCTCGCTCTGTCCGTGCCCAGCGCCACA<br>CCGACATGCCCAAGACCCAGAAG |
| SEQ ID<br>NO. 32 | IGF-1 (intron 4) | GTAAGCCCACCTGGGTGGGATCCAGCCATCCTCAAGTGGTCT<br>CTCTCTTGTGCATGTGGGTGGGCCAAGCAGAAATCCTGCCCC<br>ATAGTCTCCTGGCTTACAAGTCAGAAAAGCTCCTTTGCACCA<br>AAGGGATGGATTACATCCCCATCTCTTTGGTCACTCTGCATT<br>GCAAATTTCCCCTCCCACCGCTATGGACGATGTGATGATTGG<br>AAGATGTTACAAAACAGTGGCTAAACAAACATGGGCTTTGG<br>TGTCAGACAAAAGTGAAGTCCTGGCTTTCTCACACACCAGCT<br>TAGAGCCCTTGGCAAATAATGTGATGTACCCAAGCCTCAGTT<br>TCATCAGTAACATTGGGATAATAATAATATCTACCACATCAG<br>TTTGTTGTCAAAATTAAGTAGCTCATGCATATACTTTGAGAT<br>GCTTTTCACATGCCTGCATAAAGTAATTGTTGGACCATCGTT<br>AATGTCTGCCATAATTGCACTTAATAACAAAGCTTGTAACCT<br>TTCAAGTTCTGAGATTCTACAATCTTCCAAAGAAAATAAAG<br>GCTAATGGGAACTATTCAAAATTCATATTCAGTAGCAAGCAT<br>AATTAAACATGAAACATTAAAAATAGAAATTTCTGTTTGGCT<br>ATAAGAATGCCTAGACATTTGTAATGATCAAAATCTGCAGGC<br>ATCATTTTCTAAGAGCTAGACTGTAAACAAACCTCAGAGGTA<br>CCAACTATGCCATCAGTAGTACATAAAACATCTGATGCACAT<br>TTAGTCACTTGATCGATTTCTCTTGAATGAGTGAACGAATGA<br>ACAAATGAATATAAGAGATTAAAATTTTAGCCATTAAGTAGA<br>AAGAATAAGAACTAAAGAGAAGGTAAAGGAGGAAAAAGAG<br>AAGGCAAGGAAGTTGAGTAAGGGAAGAAATAGCTCTCGTTT<br>AAGTATTTTGGGGACTCTGTTGAAAAAAGAAATGCCAACATG<br>TGGTTTTAATCTTTGGAGCTAGAACTAATAATATTGTGCAAA<br>AGCACAAGATGAGAGATCAAGAAGTTCACCATGACACCTTC<br>GCTGCTTCCTGGTCTTAAACCTCAGCTGAGGCTGGAAGAGGA<br>CCATGGTGGCTTATTGGAGATGTGACCCCAGGGAGCCCCTCT<br>GAAGGATGGAAGGGGACTGGGCAAGACCCAACACACACAG<br>AACACAGTAGCCACTGGCCAGGCAGGAAGCAAGGATCTCAG<br>AAAAGACTTTTAGGTGAATGTGGCAGGAAAGCGTGCTTGCTG<br>GGGCAAAGGCAGATTCATTCTTTCTCTTCCCAGGTGACCCAG<br>CGCCTCTTGGTTTCTAACTGGGGAGGGGGTAGGTGTCAAGAG<br>ATGAGTCCCAAAGTTCTGGAATGGTGGGTCTTGTGACTGAGG<br>TCTAGACCCCTCTCCAGCATGAGTGCTGTCTCCTGCATCATAT<br>GGAGCCTGGGCATTCTGAGCTCATTCAAAGGGACACCATGG<br>GAACCACTTGTTCTCAATGCAATTATTTTTGTGATGTTTACAG |
| SEQ ID<br>NO. 33 | IGF-1 (exon 5<br>and 6-1) | TATCAGCCCCCATCTACCAACAAGAACACGAAGTCTCAGAG<br>AAGGAAAGGAAGTACATTTGAAGAACGCAAGTAG |
| SEQ ID<br>NO. 34 | IGF-1 (intron 5) | AGGACAGGAGGATTAAACAGACAGAGGCAAGGATGATGAG<br>AGAGGAGCAGACAGCAAGAATGAAAAGCAGAAAATACAAT<br>AGAGGAAATGAAGAAAAGTAGGCCTGCTGGAGCTAGATGAT<br>GATGTGATGGAAATAGAAGTAACCTTTTAGAGAATCTCGCTA<br>AGAAACATGGAGAAAACGGAAAAGAAAAATGTAATGCCCTA<br>GAAAGCGCAAAGAAAGACAGTGGCAAAAATGAAAAAAAAA<br>AATAAAAATTATAAAAGAGGCAAAAAAAGACACACTATTCT<br>CTGCCTCTAAAACACAATTAAATAAAAGAATTTAAATAAAA<br>ATTAAGGCTTCTATATGCATTTTTAAATTTTGTATGAATCTGT<br>TATGGAAGAATTGCCTATGTCAATATATGTTCAGAGTTAAAT<br>ATTAGCCCCAAATGCTCAGCAAGACTGAATTGTGTCATAGAA<br>GTTCCCAGATTCCCTTTTCCCGCAATGTCATTGGAGGCTGCAT<br>TTCTTAGTCAAGTCCAGGGTTTAGGCCAAAGGGCATCCGGTA<br>TTGCCTAAAACCCTGTGAGGTCTGTGAGGTAACTTTTGAGAA<br>GAGGTCACTGCACTCTTCATCTTTTTTGCACTTTGGAATCAGA<br>TATAAAAGATGTATAAGTTTGCTAGGGCTGCCATAACAAAGT |

SEQUENCE LISTING:

ATCATAGGCTAGGTAGTTTAAACCACAGAAATTGATTTTTTC
ATAGTTCTGGGAGTTGAAAGTCCAAAATCAAAGTATCAGCCC
TTGCAAGGGCCTTAGAGAAGGCTCTGTCATGGGCTCCTCCCC
TCGGCTTGTAGGTGGCCTCCTTCTTCTCCCCCTGTGTCTTCAC
TTCATCTTCCCTCCATACATATCTCTGTGTCTAAACATCCTCT
GTGTGAAACAACACCAGCCAGGTTGGATTTGGGCCCACCCCA
CTGACCTCATTTTAACTTAATTATCTCTGTAAAGACTCTGTCT
CCAAATACAGTCATATTTTGACGTACTGGGAGTTAGGGCTTC
AACACATGAATTTGGACACAATTCAGCCAGTGACAGAAGAC
TTCTGATCTCTGATGATAACCACTGCATTTTGATTACAGCTCC
TAGAAAACACTCCCCTCCACCACCCCACCACAGATCTATTTT
TATATCTGAAACCCTGAGTTTCTGCTCCATGAGAACCCCAGG
AACATACTATGTTAGATCTGGAAGAAGCCTCAGAAATCCCCT
TATTTTGAAGACTAGGACACTGAGATCCAGAAGTGGGTAAA
GATGTGCTTGGGTTCTAAGCTGCTCTTCTTTTGGCCAGGAGA
CAACAGCACATAATCAAAGTGGGTCAACTAAGAAAGAATTC
CAGAAGGAAAAGAGAGGGCAGAAATGAAGGGAGAGAATGA
GAGCAAAAGTGCTGGATTTCCCTGAGGGTGAAGAAAAGTTA
AATAGAATCACAGAATTCAGATTTTAGAGATCTTCTCCTTCA
GATCCCTTGGTTTAATCAGTAGGATTGGGGTCTTCATAGATA
ATAAAGCAAAAACTCTCGCCATCCTCCAAGTTGTGAATTAGA
AGAGCTGAGAAAGGGTACAAGACGGAAGTTCTCTACCAAAC
AAATGGTGACATTTTGGGGTAAGAATATGACTAACCCAGAA
GTGAAGCATTTCATCCAAGTAGTCTATTTTGAAGATGTCATG
GTATAAAGGAACCTCCTTTCTGCCTGGTCCTCCATGCCTCTGC
CATGCTTTTTACTCCAGGATCACCCTTTCTAGTGGTTCACTGA
AAACCCAGGATTACTTAAATATGATGGACATGTTCACGGCTC
AATCCAGGAGGAAAAGGTCGAACTGAAAGCATGCCAAAGCC
CCACATGGGAGCCAAGCCACTGCTGCTGTGGTTGCAAAGTGG
ATCCTGGCTTATCAGAGCAGAGAGAAGCCAGGCTCGTGCCTT
AGCCCAAGTGGCCAGTCACCTTATTCAGGAGATACTAAGTTC
TCCAGCTAAGACATCCATGCTTTGGGACCAGCTGCAGACAGA
AGCCAATTCCTACTACAACCATCACCTTAGAGTAGCATATAG
ACACAGATGGCTCTTCAAAGGACCACAGTTCCATGGAATAAC
TAAGAATTCATGTCCTGTGGAAAGGTTTGAATAAACTATAAT
TATACCCAATCATAAATTTCATTCAAGAAGAACTAAAGCAAA
GGCAAAGACAGAGAGAAGAAGGAAGGAAGGAGGGAGGGAG
GGAGGGAAGGAAGGAAGGAAGGAAGGAAGGAAGGAAGGA
AGGAAGGAAGGAAGGAAAGGGAAGGAAGAACAAAAA
GACTTTCTAGTTAAAGAATGCTTAACTAGCAAACTATGTACT
ATAAGACAGTTCTTTTCGGAATGAGTTTTATCAACTCTAAAG
CAATTATCTTGAATGCCTACATGTGATTACTGAATAATATGA
ACCAAGAAAACAGAAAGAATCTATATTATCTTTCCATTTCCT
TCTTTCCAGTATCAATACCCAAGCCTCTAGTGATACATGGCA
TATAATGTTGGATGGATGGATGGATGGATGGATGGATGGAT
GGATGGATGGATGGATGAATGGATGGTTGGATGGACAAATG
AGTAACATAGGCTGATGAATAGTGGTAGAAAGACACACCAT
AAAAACAAGTGGCACTTCTGAGATGAAATGATTCCTATTCTC
CTACACAAGACAGTGAGGCAAGTACAGAGTAAAAAAGGAAA
GGCATAGGAGCTATGCTTATACAAGTATTGTATGTTTGGAAT
TTCCTTCGCTGGCCAAATTGAAATTGTTCAAGGACCTATTGCT
ACAGGTGGCAACTGGCTAAGAATTTCATAGTGAATATTATAC
ACCTATTACTCCCCTTAATGTTTCTTTGAAGTAAGCAGAATAT
TAATAATCATTTAAAATTCCAGTGTTTCAACTTCAATTGTTTC
CTAGGGCAAATTGATAATTGTGTGTAAAACTAATTGGAATAT
GTATGGAATAATCATCCTGAAATAAAATTGGTGAAAAGTATT
TGTTATTGGGCATCTACAATGTGCAAACCTCTGTACTAGGCA
TGAACAAGAGTTATAAGCATTGGAGAGGCTAAAATATAGTC
CTTAAGGCTGGGCACAGTGGCTCATGCCTGTAATCCTAGCAC
TTTGGGAGGCCAAGGCGGGCAGATTGCCTGAGCTCAGGAGT
TCAAGACCAGCCTGGGCAACATAGCGAAACCCCATCTCTACT
AAAAATACAAAAAAATTACCTGGGCATGGTGGCACGCACCT
GTAATCCCAGCTACTCAGGAGGCTGAGGCATGAGAATTCCTT
GAACCTGGGAGGCAGAGGTTGCAGCGAGCCGAGATCCTGCC
GCTGCATCCCAGCTTGGGTGACAGAGTGAGACTCTGTCTCAA
AAAAAAATTAAATAATAAATAAATAGTAAAATACAGTCATT
AAGAGTACAAAATGTAGATTCAGACTACCTGGGTTCAAATCT
TGGCTCTTACTTGCATTGTGGCTTTGGGCAGATCATGTAACTT
ATGTGTGCCTCAGTTTCCTCATCTGTTAAATAGGGGCAACAA
CTGAATCTACCTTATTCAGTTGTTGTGAGGGTTTATTGAGATT
GTGTGTGTGTATGTGTGTGAGTGTAGTGTGTGCATGTGTGTG
TCTGTGCAAGGAGTGGGAGGTGTATATTCAGAGACACATATT
ACAGCACTTAAAATGGTATCTAGCACTTAGTAAGCATTATTC
AAGTTTTAGTTAACATTATTTTACTTACCTCTGAAAATTGGAG
CTATGTGAAAAGAAGTTGGTCTCCTGAAGTAGAAGCCAGTC
TTGTGTCACCAAAAACTTCAAGCCCAAGCTTGCCAACGCTTT
TCCATGATGTGGTAGTAGAGTTTCAAGCATGTGGTAGGATAA

-continued

SEQUENCE LISTING:

```
GAGAACTCAATGACCTAAGAACCATTCCAACCCAGAGAACC
CCTGGTTCTATGAATAATTCCAACTTAAATAGGTAGCTTGGC
TCTCCCAAGTGAGAGCCATTGCTTCTGTTTCCGGGTCATATA
ATGAACTTTCAGAAAACCACCATTTTTCTCAACCAGTTAAAA
TTAAGTGTAATACGTGCTTTCATTTCATGGTGCCTGGGGAAA
ATTTAATTGTAGTATGAACTCCAGTTATTGGTAGTCTTAAGTA
AAATTGCCAAAATAAATAGAAATGCAGGATATTTCTGGGCTC
ACACAGCTTCCGGGACACTTTAGTTTCTTGGGCTGCCAATCC
AGTGCCTTTCACAAGCATTTGATCTTTTTTCAAACATCTCTTG
AAAACAAACAAAACCTCACACAGCTTCTAATGTGTGCACTGT
TCGAATGTAAGGGTGGAAAAGGAGGCAAAGAAATGAGCTCC
CAAAGAGCAATTCCCCTTCTCTCGCCTCCATCCCTTGACGAC
CTCCCTCCCACTAAAGGGAAACATTGTTTTCTTAGGTAATAA
ATTCTGCAATTTCTCAAGTCCATTAACATCCACTGGGCAAGA
TGAGATCTATTCTTTTTATTTGCCCATAGGAAAAGAATAGTG
CTTTTTTGCAATATTCACTAGATAACACAGAGTTGACTTTTAA
TCCAAGGGCAACATTGATAGTCTCTAGTTAAAGGGGAAGCCT
TCAGGAGCAATGAAAAGATTAATAGTTTTAGATGAAGCAGA
ATCCAAATCCCTTTTTATGAGTTTTGAAATATCCAGTTTGTAT
GCTCACCTCAATACTTAAAGCCCAGTTACTGATTCCTTTGGCC
TAAGCAAGACAGGTCAATTTTTAAAGAGGGAGTAGCTGAGG
TTAGCAAAAATTCTCCAGGTCCACAAAACTTCCAGACCTGCA
AGGTGAAAATCAGCTTTTCTGTCATCCCTAAAGGCCTAACTG
GAATCAGAACTTTTCCCTGATGCCCACATATTTGGAGGTCCT
TTTTTAATGGGACTCCTTAATGCCTTTAGTGCCATCCCATTTT
CATCCAGTGTCCAAAAGAAATGATTTAAAAATATAAACGTAT
GTTTAAATTCCAGAAGAGAGAAATGGAGATTGAGAACAATA
GGGAAATGATGAGAGCTATGGGAAAAGAGGTTTATGAGTCC
ATGTCTGATTCTTCCAGAGAGCCCCTAAGAAAGTTCTTATCA
TACCAGGAACTCAATTATAACTTTCATTGCCTATTGTTAGATG
AGTAACAGGAGCTAGAAAACATTTTGGAAATTCCCATCTTTA
TTTTTTTAACTAATATGATTATAGTTTTAAGAACCATTGGTCA
AGAAGCTAACTTTTTAAAAAGTGGAAGTATGATGGTTAGAA
ATAAGAATGCTAAAGGTGCATCAAGCTGATTTTAATTCTAAA
TGTCCTTGGCAGCAATTTAGAATCTGTAATAAACTACACCAA
ACAGTTTTGAGGGGAAGGGGATTAGTTTCTCCCCTTCCTTCG
TGTGTGTGTGTGCGCGTGTGTGTGTGCACCTTTGTGTTCTA
GCATTGTTGCACCCATTACAGAGCTGGGGGGAACTATTTTCC
AAAATTATAGGTGAGAACAGTTTCTTGGATTGTCTTTCAGTG
AAGGTAAATTCCTCTGTAAAAACTAACCATCATTCAGTAAAA
ACTGCAGGATTCCTTTGTCTTCTCAAAAGCCTGTTTCTCATCC
TAAATTAAAAATTATTCAGGAAATAGAGAGGACATTATTGG
AGGGGTGGAAATAAGTTGGTTTTCTTTTTATTGTATCTTTTGA
GGATCCAGGGACTTCTACCATTTCCCATCTAACATACAGAGA
AGGATTCTCTAGGTCCCTGTCTATAGACTGCAGTAACTTTCCT
ATAGAACCAATTTGCAATTTTAGAAATTTCTAGGTCTAATTA
TTGACCCATTACAACCAAAGGTCAATGCATCCAGCCAATCTT
CCTTCTATCATCCCCTGCCCTTACTTCTATTAGGGACTGGGAT
TACAGGCAAAACCCATCAAATGCCTCTTCTACCACTTTCCCA
TTTCTTAACCATTAGCCTCTAACTTCCTCTATTCAGTTTCTCAT
ATGCTTTCATGCCCATTGGGTCAGATAAAGGAACATTCATTT
ATTTGAGTAGGCATCTGTTATGATCACTCCGGAAAAAGATG
ACAATGGGTTACCTTGTCCTCCTGGGCTTCTCTAACTGACATG
GTCAAAATGCCCATATGAAGATAAGATGTTAAGAGCAAGAT
TTATGAAAAGCTGAGTATGATGGCAGCTCTTGTCTCATAAAA
TAACTCGAAAGTTCCCAGTGAAAGACCAAGAAATTTTACATC
AAACCCAAACCGGCCAAATGGTCCAAGCTTCCAAGCTGGGA
TCCATGGCTAAAGTTTCTACAAAATTCTGGGTACAATGTATA
AACATTCACTTGGGGCTTTCTGTCTAGCCAGCACCAAGAGGT
CAAGTAATCAAGGACCAACTAGCCCTGCCATCTGTGAAAATA
TGTGCTATTTTCACGGCTTTAGTTCACAATTATGGCAAGACA
AAAGTTCCAAATAATTAGGAGCAAGACCATGGCAGGTTGAC
GGTTGAGTAAGGTTCTCAATCAGCCGACAATTGTAGAGTTGG
GGATGTGCAATGTTTATGTCATGGTGTAAGTATGTGGCATGC
TTGACTAGCTTGTGAGGCACTGGAAGACTAGAAGGAATGAA
AAATATGAATGAATCAATAAATGCATAGTATAATTACTGTTA
TTTTGTCAGTATTGTTTTACCTAGGTCACTATTGAATGCTCTG
ATTTGTCTCTTTATAAATAATAATATGTTTTCTTCTTCAAAAG
AACACTAGGATGAAGGTAGAGGTGCTTTTGGCACAATGCCA
CAATTCTGATTTTTTAAAACTGTATGCATGCATAAAATGTTC
TTGAGCCATTCTCTGCCTTGGAATAGCACTGGCTGGCATTCT
GCATGTTTACTTTTATATGCTGAAGGCCCCCATCAACCTCAA
ACAGAGGCAAATCAATTTAACTTCTCATAGTGTTATTTTGTTC
ATCCTAAAAGTTCAAGAGAGCCTTCCAAACTTCCAAAATTTC
TCTCAATTCAGTGAGGAGGAAAATTCAGAACACAGCATTTGA
ATGTTCTGCCCAGATTTGTCACACACACAAGGAATGAGTGAA
AGAGGGCAACACCCTTTCCTCCTAACCCTGTGAACTCATCAC
```

SEQUENCE LISTING:

```
TATTGCATTGAAATGACACCAAAAGGTAAAAACCCTAGGCCT
CACATCTCCCAAGAACACTGCAATAGGAGTTACTGCATACAC
CAGTTTAAGTAACTCTAGCATAAATTGTATGTCAGATGAAAC
AATGGCATTTTGGAGGCTTAAGAGAAAAAGAATAATCAAAT
CCAGTTTTTAGGTACTAATGTGCTGAATCTTTAGCACATAGC
AGCAAAATTGCTAGAATCTGGTGTTTCACTTTTTAAAATACC
ACATTTGAACCTTTCAGCAATTCCAAAATCAACTCCCTCTGC
GAAAGATAATAAGCTTAAACATTTTTTAAATTTAAAAATGTA
ACACAAACAAACAGCTAAGCAAACAAGCTGCCCATAAAATC
AACAGTCTGGGGAGCCCTGATCCTGAAGTATTTTACAACATC
CTTCATGACTATTAAAGGCAACATAAACACCTCTTGTCAGCA
AGGGAAACTACCCTTGGCATTTTTTTTCTTTGTTCCCCAGGC
TTTTAAACCATTTTGATAGAGATTTTTTACATCACAGGCAGA
AATATTTGAAATAGAGTCAGGTGGTAGTCTTTAAAAGAGTAA
GAAAGTTGCTAAGTCAAGATAATCTTGGAATAAAGTCCTCTG
ATTCCTGGGGATTCCTAGGGATGCCCCAGTCACTAGAAAACA
GAGCTGTAAGTCCACTCTCCCAGCACTCAACGGAGCTCCGGA
AACCAAGGAGCTAGCTACTGTTTCCCCACATTCAGCCAGAGA
AAGGGCAGCACTCTAGCATGCAAACTGCTTTGACAATAGTAA
CAATTAAAAAGTAAATTAAAAAGAATCATAATAGCTGATATT
GATTAGGTACTTGCCCTGTGGCAAGAGCTATAGGGAATCACC
TCATTTAATCTTCACATGAAGCTTGCAGAGTGAGTACCACAA
TTATCACTATTGTATAGACAGGAAAACTCAGGCTGAGTATGG
CTAAGTGTCTTGCCAACGTCTTGGGCTAACAAGCGGTCAAGC
AGAATCCAAACCCGAGATAGATAGACCACAGTGTGCTAATC
AAGCACTGCACTCTCCTGCATTTCTTAGTTGATATTTACCA
TATACAATCTGTCACTTGTATGAGATGGCAGGGGGTTCTGTG
CTATTTGTCCTTGTAGAGAATACCACAGGAAGAAAGTAAGCA
GCCATGCAATATTTGCTGTTGACCTGAACTCCATTCCATCATT
CCTGCAGGAAATTCGCATCCATTAAATGAGCATTTCCTGGTT
TGCCACTTTGCTCAAACACTTTGCTTGGATCTGGAGAGGATA
TAGAAGTGAAGGAAATATGCTACCTGCTCTCAAGGAACTTAT
GTTTTAGTGGAGAGACAAACATGCAGAATTTACTCTACAGAA
CATCAATGCTTGAGCAAATGTAGACCCAGAGAGGGCTCTTAC
AGCACACAAGCCAGAACAGACTGATGGTGCTAACAATTAGG
TTCAAGGTTTTTCTAAACAGTAGACTCTCCTGCATACAACTAT
ACCGCATGCCAGGTAAATGACTGAGGGTTATTACATCCAATT
ATAACACCACTGTGATGTAGGTGCTCTTACCCCACACTTTCA
TTTTACAGAAGAGGAAATTGAGGACAGCACAATGTAGTGAT
TATCAAAGGTCACACGACTACTGTGTGGGAGAGCTAGGATTT
AAACCAGATGCATAAGATGAGGTCCTCCAAGAAACAGAAGA
TGAGAAGGTGTTAAATGAGCAGGGGTTTTATTAGGGGGAATT
AATGTGTGAACAGAAATAGGGGAGGATAGGCAAAGCCATCA
GATTGCAAGGCAAGCCTAACCCCAAGGGAAGGAGAGAGAGA
GAGTAGATTGGTTGGAAACATTTTTGGTGGGTCTATGGTCTA
AGGAAAGTTCAGCAAAGTCATCATGGAGTTTTTGAGCCAAA
GTTGGGCAATACAGTTGCCCAACAAATTTCTGTGTTTCTCAG
AAATAGGTCTGCCTCAATGTCCCCACCATACTTGGTCACTGG
CTCTTGGGAGGGGCCTGCCCTGTTCCAATCCACTAGAGCCAA
AGAAGAGCCGTTGTACTGGCAGGGGGTGGGGAATTCCTAC
AACCACATAAAAAGTGGGGTGAGGTTTCCAGAAAAAAACGT
GATGCTGGGCTAACCAAAACTGTGTCCAGTAAGTACATATCC
CTCACTCTGTTAAAGAAGCAGCCACATAAACAAGGAGTACA
CGTTTCTCAAAATGTGCACCTTGTTCTTTGGTTTTGAAGTCAC
ATCCCAAAGTGCTGAGTAGATCGCATGACCCTCGCTTTGCCT
GGCTGCCAGAGAGGAAAGGCTGATCCAACTCTCCTGGAATTT
GAACTTGTGATTCCCTGAAGTAAAGAGATATCAAAGTTGATA
CTGAGACATCTAAATCATCCTCCACCATTTCACATGTCCCCA
GGCCAAGCCAGCAAAATTGCTATAGCACATCCCTTTCAACAG
GTAAAGGGCTGATATCTGAGCCCTCTTTCCAATCATCCACTG
CTCTTTTCTTCTCATTTTGCCCTTTTTGGGAGCAGGTCAATGC
TGAGTTAGTACTTTATGCTGTACAATAAGCTGCTGATATTCC
ATGCTGGACAGAATTTTCCCAGTATTTTTATAGAGTGCCAG
GCTTTTCCTAGACTTCATGTCATACAATACTTAACTTGTTTGG
AGTGGGTGGAGATGGAAACATAGTCTATTGAAAACATCACT
GCTTCCTCCCTGAAGTTTAAAGAGCCTATTTTTATCCTTTTAG
ATTCTATCTCTCAGGCAAAATCTCATAAAGATAAGTGGGGAG
GAAAAAAGGGGGTTATAATACCTAGGGAGTTTGCTTTTGCT
AATTGAATACTGTGCTCCTAGACTTCTATAAATACCATTACA
AATGGGTCCCAGCTTGTGGTAATACTCACCCTCCTCATTGAG
TCTTCTGTCCCATGGCACAGCCTTTCCCTCCAAACTAGCATCT
ACCCCCATCTGGAAGCATGGGCAGCTCATGATATTATCAACT
ATTGCTATTGGAAAGTGATTTGGACTTGAAAGCACTAGATAT
TTTTTACCTCTTGGGGAGGCAGTTTAGCAGAGTGGTTAACTG
GTGAGCTCCAGAATCAGAAGGAATAGGTCCAAATTCCAACC
ACTATTACATCTCCATCATAAGAAATTAGGCAAGTTGTTTAT
CCTAAGTTTCAGATTCCTTAAAGATAAAACAGTCAAGACAGT
```

-continued

SEQUENCE LISTING:

```
AGTACTTATCCCTGAGAGAAGTATAGGAAACAAGAAAATAT
ATGCAATTTACATACATACTACAATCCCCAGCACATGACAAA
TGTTCAAGTAATGGGAACTGTTATTATTTTAGCCCTTTGTCTA
TCAGTTTGTTCCTCTGTGACCTCAAGCACATTACTAAATGTTA
GCGAGCTTCAGCTTGTACGTGGGACTGACAGGAATAACACC
GCATCACCTCATGTGGTGATTGTAAGGATTCAGTGATATTAT
TTTGTAAACTGTAAAGCCTTTGCAAATGTTAAGCAAGATTAT
TATTATTGCCGTTGTTATTAGTCCTCAGTGATCTTTTTTTTTT
TTTTTTTTTTTTTTTTTTTTTTTTGGAGACAGAGTTTTACT
CTGTCGCCAAGGCTGGAATGCAGTGGCACAATCTCAGCTCAC
TGCAACCTCCGCCTCCTGGGTTCAAGCAATTTTCCTGCCTCAG
CCTCCTGAGTAGCTGAAACTACAGGCACACGCCACCACACCA
GGCTAATTTTTTGTATTTTTAGTAGAGACGGGGTTTCACCATG
TTGGCCAGGCTGGTCTCCAGCTCCTGACCTCAAGTGATCTGC
CCACCTCGGCCTCCCAAAGTGCTGGGATTACAGGTGTGAGCC
ACCACACCTGGCACAGTAATCTTAATTGAAAAGTCTGTGGAT
AGCTTTCCAAAGGAAAGCTTGGAGCTTGGATAAGAACCAAG
AGATAATGGGAGAAGGTGAATGGCCTCTTCAGGGCCTTTCT
AGCACCCTAAATATGCGTGTCTGTCCATAATGGGTAATCATA
TATATCACAAATCAAACCCTCCACAAACTTATTTCCTAATGT
GTTTGTTAACCTTTCCTTCTAAAGGGTAAACTTCTTTAACCAA
CCCCAGTGAGCTGGAGGATCAATGTTTTCTTAATAGTCTTAC
CTTCGTTGGTGTCAATAGGAAACAGTATTTACTCACTACTGTT
TTCCTTTTAAAAATCTGTCTAGTTGCATACTAGAAACAGTTTC
AGCTGGTTTGTTTGTATTGGACAAGCTGCTGAAGTGAAAAGT
TTTTGCTTGACTGAATGTGAGACAGTTTCATAACTCTTCAAG
AAGTGCACCAAAGGTGGGTGCCAGCTCTGATGACGGCTGCTT
CTAACATGCCTCCACTTGCCGCCCATTGTCAAGGGTGGCTGG
CGTAATTAAGTTAAGACAATGAGCAAAGCAACAGATGCAAC
TGAGACCTAGTCCCTGAGTGCTTTTGTTTTGTCACTGTCATTG
TCTGCAACAAAGAAGTCACATGTGACAGCCTGGGAAGAGAG
CCAAATGCAAACCAGACGATATCCCAGCTGGTTTGAATGGCC
TCCACCGTGCACGTGTGTGCATGGGAATCATGCTACTTGGTA
CAGCATCTGCTTCACTCAAGTGAGTTTCAGCCCATGGCTTTG
CTGTGATGCTGAGACAGACCCAGAAGAAACAGACCAGGGAA
TCCCTCCGCTCAGACTTTACACTTTATACCTTGTGCTTTGAGA
GAAAAGAAAAAGAATCTCTCTATTGGAGACAAAAAATAGGA
TGTATGTGGTTGGTCAATCTAACCTCAATTCTTTTTGCTATAG
CCCCCCGCTAATTTAAAGAGTGAAGCATAGATGGTATCTTAA
TGTTTTCTTGTAGAAATTTGGGATTAATTTGGCTTGAGAGGA
AGAATGGAGATTAAACGCTTTATGAGGCTTTCTTTTAATTTGT
TCCCATTTCATTCCTGAATATTTTCTTAGTTTGGGCATTGCAG
ATGTTTAAAGAACTTCTTATTTTGAGCTGGTATGCCTCTTAAA
CAGAAAAACAAAAGGTAAAATTCAAATTAGTGTGTTTCTCCG
CCTGTTAATTAATTTGGTTAGTAGTTAGGCAGAGAGATGGCA
TCCTTAATAATATCTATTTTGCGGGTTTGATCAGCTACAGACC
ATCAACAGTGTTGATTGAGAATTGAACAAAAACATTTCAAGG
AGTTTGGGAACATTAGGGATGCTATTCTGTGGCCCCATGTGT
CCTTCTCTCATTTTTCTAGAGAACTCCTATAAGAAAGCAGAA
CACGGCCAGGCATGATGGCTCATGCCTGTAATCCCAGCACTT
CAGGAGGCTGAGGCAGGCAGATCACCTGAGGTCAGGAGTTC
AAGACCAGCCTGGCCAACATGGTGAAACCCTATCTCTATTAA
AAATACAAAAAATTAGCTGGGCATGATGGCGCGTGCCTGTA
ATCCCAGCTACTTGGGAGGCTGAGGCAGGAGAATCACTTGA
ACTGGGAGGCAAAGGTTGCAGTGAGCCTAGATCACACCACT
GCACTCCAGCCTGGGTGACAGAGTGAGACTCCAACTCAAAA
AAAAGAAAGAAAGAAAGAAAGCAGAACCCAATGGAA
GATTAAGAACACACATTTAGCTTACGCCTGTAATACCAGCAC
TTTGGGAGGCCAAGGCGGGTGGATCACAAGGTCAGAAGTTC
GAGACCAACCTGGCCAATATGGTGAAACCCCATCTCTACTAA
AAAGTACAAAAATTAGCCATGCATGGTGGCAGGCGTCTGTA
ATCCCAGCTACTACAGAGGCTGAGGCAGGAGAATCACTTGA
ACCCGGGAGGCAGAGGTTGCAGTGAGCTGAGAACGCGCCAC
TGCACTCCAGCCTGGGTGACAGAGCGAGACTCCATCTCAAAA
AAAAAAAACAACAAAAAAAAACAAAACACAAGTTTACTGGG
AACTTAGCAGTAGATGCTTTGCACCACAACAAATGTATCTTA
AGTGGTCTTTTGTGATATTTGAGGGAAAGTGCCAGAATTTAA
AACAAATGGCATTTCAAGTTATTCTATACAAATGCCCAGTTT
CTTTCTACCATCTTTTTTTCCTTTTTGCAGTGGTCACTGAGCTA
TTTTAGTGAATGTTTTTACACAATGATGCCATCTTCCTTCTAC
TCAGTCAGTACAAGATGTTGACCATCGACTCATAAAACACTA
GCTACCTTTCATGAAGGACTTGGTGATAACTCTCATGTTCCA
AGTAGAACCGGAAAACATGTGTAAGAAAACCTGCCGATCCC
TATGGGCCTTGGCCAATAGGTATTATTCCCAAGGGGTGGCAG
TTTATCTTTTTCCCCAGCCTTCATATTAAAACCTCTCACCTTCT
CCAGGTCTCAGGTCTGTGTAATCTCAAATGTGCTTTAGCTCCT
CACAATATTGTAACTGTGTGGGTGTTCATTACCTTAGCCAGA
```

| SEQUENCE LISTING: | |
|---|---|
| | AGACAGTTTACAGATTCCAGGTCTCATGGAGAGAACTTTTGT<br>TTTTGGTTATGAACCTCACTGTATACCAATAATTATCCATTAC<br>ATCCTTCTGTAGAGGGCTCTCTGGCTAGAGATAAAACCAAAA<br>AAAGAAGTACCTCAGGTTTATGCATATAAATGCCAGTTCCTC<br>CTTGATTTTATTTCAAAACTCCTGTCTACATACTTTGCAATTT<br>AAATACATTCAAGGATAAAGTAATAACTGTAGGAAAAGTAT<br>TATAATATAATGACTTAGTTCTGCACATCACAAGGGGGTCCC<br>TCATACTCATTCATTCATTTCACTCATTTTACAGATATTTATT<br>GAGCACCTGCAATAACCTGCACACTGCTCTAGACACTGGGAC<br>TATAACAGTAAACAGACAGATACATCTCTGGTCTCACAGGGC<br>TTCTATTCTAAGCAAAACTCAATATCCAGGCCGGGTGCAGTG<br>GCTCATGCCTGGAATGCCAGCACTTTGGGAGACCAAGGCCA<br>GGCAGATCACCTGAGCCCACTAGTTGAAGACCAGCCTGGGC<br>AATATAGCAAAACCCCGTCTCTACAAAAAAAAAAAAAAAAA<br>AAAAAAAAAAATTGTCAAGGCATGGTGGCATGCGCCTGTGG<br>TCCCAGCTACTTAGGAGGCTGAGGCAGGAGGATTGTGTAAG<br>CCTGGGAGGCAGAGGTTGCAGTGACCTGAGATGGCACCACC<br>ACACTCCAGCCTGGGCAACAGAGTGAGACCCTGTCCAAAA<br>AAAAAAACCCTCACTATCCTTAAGATAACATCATTGCTTGTT<br>GATGAGTGAATGTTAACACCAAATTAGGAACCCAGGACTTTT<br>AGTCTTGGCATGGTTACTTTCCAATAAAGATGACAATACTAA<br>GAAGAGAAAAATGATTTAATAATGATAATAGTGGCTAATAC<br>TTATGTAGTGCTTACCATGTGCCAGGTCTATTGTAAGTACTTT<br>TATATATATTAATTATTTAATCTTTGATCCTATAAGGTAGATA<br>TTATTGTTACCCTAGTTTATAGATGAAGAAACGGAAACACAA<br>GAGATTGCCACTCATACAAGTTTACACAGCCAGAAAATAGA<br>AAAGCTACGAGTTGAGCTCAGCCCAGTATGTCTATGATTTTA<br>CAGACTCAAAATTAATTATAAGATTTCCTAATCTTCGATTTCT<br>GAAACTCTGCCTTGCTCTAGAGGAAAACAAGAAAAACAATG<br>AAAAATAAATGTCTCTTTTTTACAAAAATTAAAACAGAACAA<br>ACTGCAATAAAACAACAGAGGATGAATCCAGAATGTGATTG<br>ATTTTTTTTCTTACTAGGAAAGGATCTAGAGGCCAGAAGGCT<br>GGATTTTTCAGGATCTCCTTTCAATCAATGAATCTGTGATAG<br>AAGCAGATGAATCAAATCTCATCTTTGTGTGATTATAAAGCT<br>GTCTGTGGTATTCACGCCACCAGGGGTACATAGAAGATGCCT<br>GAGTGAGGTTTGGCAAAAGTACTAAGGGCCTGTCCACCTATA<br>CATGCCCTTCTCAGGAAAACCAAGGTTCAAGCTCTCTATTAG<br>CTCAACTGGTAAGGCGTAAGACATGGAAGGTTGAGGCCCAA<br>TGTTAGAAATAGATGGATACATAAAACTTCATCAAGTTAATG<br>TCACTTTTTCTCCTTTATTTATAG |
| SEQ ID NO. 35 | IGF-1<br>(exon 6-2) | GAAGTACATTTGAAGAACGCAAGTAGAGGGAGTGCAGGAAA<br>CAAGAACTACAGGATGTAG |
| SEQ ID NO: 36 | SDF-1α | ATGAACGCCAAGGTCGTGGTCGTGCTGGTCCTCGTGCT<br>GACCGCGCTCTGCCTCAGCGACGGGAAGCCCGTCAGCC<br>TGAGCTACAGATGCCCATGCCGATTCTTCGAAAGCCAT<br>GTTGCCAGAGCCAACGTCAAGCATCTCAAAATTCTCAA<br>CACTCCAAACTGTGCCCTTCAGATTGTAGCCCGGCTGAA<br>GAACAACAACAGACAAGTGTGCATTGACCCGAAGCTAA<br>AGTGGATTCAGGAGTACCTGGAGAAAGCTTTAAACAAG<br>TAA |

What is claimed is:

1. A lyophilized pharmaceutical composition comprising plasmid DNA, wherein the lyophilized pharmaceutical composition is obtained by lyophilizing a liquid composition that comprises, prior to lyophilization:

a. DNA of a first plasmid, wherein the first plasmid is selected from the group consisting of VM202, pTx-HGF-X7, pTx-IGF-1Ec, pTx-IGF-1Ea, pTx-IGF-1X6, pTx-IGF-1X10, and pCK-SDF-1α;

b. potassium phosphate buffer with pH in the range from 7.0 to 9.0;

c. mannitol at a concentration in the range from 2% to 3% (w/v);

d. sucrose at a concentration of about 1.0% (w/v); and e. NaCl at a concentration in the range from 0.1% to 0.6% (w/v).

2. The lyophilized pharmaceutical composition of claim 1, wherein the first plasmid is VM202, optionally wherein the composition further comprises DNA of a second plasmid, wherein the second plasmid is selected from the group consisting of pTx-HGF-X7, pTx-IGF-1Ec, pTx-IGF-1Ea, pTx-IGF-1X6, pTx-IGF-1X10, and pCK-SDF-1α.

3. The lyophilized pharmaceutical composition of claim 1, wherein at least 90%, 95%, 97%, or 98% of the plasmid DNA in the liquid composition is supercoiled.

4. The lyophilized pharmaceutical composition of claim 1, wherein at least 90%, 95%, 97%, or 98% of the plasmid DNA remains supercoiled 30 minutes after reconstitution of the lyophilized pharmaceutical composition.

5. The lyophilized pharmaceutical composition of claim 1, wherein at least 90% or 95% of the plasmid DNA remains supercoiled after storage at 25° C. for 3 to 7 days following reconstitution of the lyophilized pharmaceutical composition.

6. The lyophilized pharmaceutical composition of claim 1, wherein at least 80% of the plasmid DNA remains supercoiled 30 minutes after reconstitution of the lyophilized pharmaceutical composition, wherein the lyophilized pharmaceutical composition had been stored at 40° C. for 10 weeks before reconstitution.

7. The lyophilized pharmaceutical composition of claim 1, wherein the lyophilized pharmaceutical composition comprises supercoiled DNA in an amount of at least 90% or 95% of a total amount of supercoiled DNA in the liquid composition.

8. The lyophilized pharmaceutical composition of claim 1, wherein the liquid composition comprises the first plasmid at a concentration in the range from 0.1 to 1 mg/ml.

9. The lyophilized pharmaceutical composition of claim 1, wherein the liquid composition comprises potassium phosphate at a concentration in the range from 5 mM to 15 mM.

10. The lyophilized pharmaceutical composition of claim 1, wherein the liquid composition comprises potassium phosphate buffer with pH in the range from 7.0 to 8.0, or pH 8.0.

11. The lyophilized pharmaceutical composition of claim 1, wherein the liquid composition comprises mannitol at a concentration of 2% (w/v).

12. The lyophilized pharmaceutical composition of claim 1, wherein the liquid composition comprises sucrose at a concentration of 1.0% (w/v).

13. The lyophilized pharmaceutical composition of claim 1, wherein the liquid composition comprises NaCl at a concentration in the range from 0.4% to 0.5% (w/v), or at a concentration of 0.45% (w/v).

14. A lyophilized pharmaceutical composition comprising plasmid DNA, wherein the pharmaceutical composition is obtained by lyophilizing a liquid composition that comprises, prior to lyophilization:

a. DNA of a first plasmid at a concentration of 0.5 mg/ml, wherein the first plasmid is selected from the group consisting of VM202, pTx-HGF-X7, pTx-IGF-1Ec, pTx-IGF-1Ea, pTx-IGF-1X6, pTx-IGF-1X10, and pCK-SDF-1α;

b. 10 mM potassium phosphate buffer of pH 8.0;

c. mannitol at a concentration of 2% (w/v);

d. sucrose at a concentration of 1.0% (w/v); and e. NaCl at a concentration of 0.45% (w/v), wherein at least 95% of the plasmid DNA in the liquid composition is supercoiled, and at least 90% of the plasmid DNA remains supercoiled after storage at 25° C. for 7 days following reconstitution of the lyophilized pharmaceutical composition.

15. A reconstituted composition produced by dissolving the lyophilized pharmaceutical composition of claim 14 in water.

16. The reconstituted composition of claim 15, wherein light absorbance of the reconstituted composition at 450 nm is less than 0.002, wherein the light absorbance is measured on the day of reconstitution or after storage of the lyophilized pharmaceutical composition for 10 weeks.

17. A lyophilized pharmaceutical composition comprising plasmid DNA in a unit dose, wherein the pharmaceutical composition is obtained by lyophilizing a liquid composition that comprises, prior to lyophilization:

a. DNA of a first plasmid at a concentration of 0.5 mg/ml, wherein the first plasmid is selected from the group consisting of VM202, pTx-HGF-X7, pTx-IGF-1Ec, pTx-IGF-1Ea, pTx-IGF-1X6, pTx-IGF-1X10, and pCK-SDF-1α;

b. 10 mM potassium phosphate buffer of pH 8.0;

c. mannitol at a concentration of 2% (w/v);

d. sucrose at a concentration of 1.0% (w/v); and e. NaCl at a concentration of 0.45% (w/v), wherein the lyophilized pharmaceutical composition is in a vial and the vial contains 2.5 mg of plasmid DNA in total.

18. A reconstituted composition produced by dissolving the lyophilized pharmaceutical composition of claim 17 in water.

* * * * *

SEQUENCE LISTING

<160> NUMBER OF SEQ ID NOS: 36

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

```
Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
```

-continued

```
              465                 470                 475                 480
Asp His Pro Val Ile Ser Cys Ala Lys Thr Lys Gln Leu Arg Val Val
                    485                 490                 495

Asn Gly Ile Pro Thr Arg Thr Asn Ile Gly Trp Met Val Ser Leu Arg
                500                 505                 510

Tyr Arg Asn Lys His Ile Cys Gly Ser Leu Ile Lys Glu Ser Trp
                515                 520                 525

Val Leu Thr Ala Arg Gln Cys Phe Pro Ser Arg Asp Leu Lys Asp Tyr
            530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
                595                 600                 605

Lys Thr Ser Cys Ser Val Tyr Gly Trp Gly Tyr Thr Gly Leu Ile Asn
        610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 2
<211> LENGTH: 723
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110
```

```
Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
            195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
    275                 280                 285

Asn Asp Thr Asp Val Pro Leu Glu Thr Thr Glu Cys Ile Gln Gly Gln
    290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
            355                 360                 365

Val Gly Tyr Cys Ser Gln Ile Pro Asn Cys Asp Met Ser His Gly Gln
    370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Ala His Gly Pro Trp Cys Tyr
    435                 440                 445

Thr Gly Asn Pro Leu Ile Pro Trp Asp Tyr Cys Pro Ile Ser Arg Cys
450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
    515                 520                 525

Gln Cys Phe Pro Ser Arg Asp Leu Lys Asp Tyr Glu Ala Trp Leu Gly
```

```
                530              535              540
Ile His Asp Val His Gly Arg Gly Asp Glu Lys Cys Lys Gln Val Leu
545              550              555              560

Asn Val Ser Gln Leu Val Tyr Gly Pro Glu Gly Ser Asp Leu Val Leu
                 565              570              575

Met Lys Leu Ala Arg Pro Ala Val Leu Asp Asp Phe Val Ser Thr Ile
                 580              585              590

Asp Leu Pro Asn Tyr Gly Cys Thr Ile Pro Glu Lys Thr Ser Cys Ser
                 595              600              605

Val Tyr Gly Trp Gly Tyr Thr Gly Leu Ile Asn Tyr Asp Gly Leu Leu
                 610              615              620

Arg Val Ala His Leu Tyr Ile Met Gly Asn Glu Lys Cys Ser Gln His
625              630              635              640

His Arg Gly Lys Val Thr Leu Asn Glu Ser Glu Ile Cys Ala Gly Ala
                 645              650              655

Glu Lys Ile Gly Ser Gly Pro Cys Glu Gly Asp Tyr Gly Gly Pro Leu
                 660              665              670

Val Cys Glu Gln His Lys Met Arg Met Val Leu Gly Val Ile Val Pro
                 675              680              685

Gly Arg Gly Cys Ala Ile Pro Asn Arg Pro Gly Ile Phe Val Arg Val
                 690              695              700

Ala Tyr Tyr Ala Lys Trp Ile His Lys Ile Ile Leu Thr Tyr Lys Val
705              710              715              720

Pro Gln Ser

<210> SEQ ID NO 3
<211> LENGTH: 482
<212> TYPE: DNA
<213> ORGANISM: Homo sapiens

<400> SEQUENCE: 3
atgtgggtga ccaaactcct gccagccctg ctgctgcagc atgtcctcct gcatctcctc     60
ctgctcccca tcgccatccc ctatgcagag ggacaaagga aagaagaaa tacaattcat    120 gaattcaaaa atcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgtttttgat aaagcaagaa acaatgcct ctggttcccc    300 ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta gagtggcat caaatgtcag ccctggagtt ccatgatacc acacgaacac    480
ag                                                                   482

<210> SEQ ID NO 4
<211> LENGTH: 1675
<212> TYPE: DNA
<213> ORGANISM: Homo sapiens

<400> SEQUENCE: 4
cctacaggaa aactactgtc gaaatcctcg aggggaagaa gggggaccct ggtgtttcac     60
aagcaatcca gaggtacgct acgaagtctg tgacattcct cagtgttcag aagttgaatg    120
catgaccctg caatggggaga gttatcgagg tctcatggat catacagaat caggcaagat    180
ttgtcagcgc tgggatcatc agacaccaca ccggcacaaa ttcttgcctg aaagatatcc    240
```

```
cgacaagggc tttgatgata attattgccg caatcccgat ggccagccga ggccatggtg      300
ctatactctt gaccctcaca cccgctggga gtactgtgca attaaaacat gcgctgacaa      360
tactatgaat gacactgatg ttcctttgga acaactgaa tgcatccaag gtcaaggaga       420
aggctacagg ggcactgtca ataccatttg gaatggaatt ccatgtcagc gttgggattc      480
tcagtatcct cacgagcatg acatgactcc tgaaaatttc aagtgcaagg acctacgaga     540
aaattactgc cgaaatccag atgggtctga atcaccctgg tgttttacca ctgatccaaa     600
catccgagtt ggctactgct cccaaattcc aaactgtgat atgtcacatg acaagattg      660 ttatcgtggg aatggcaaaa attatatggg caacttatcc caaacaagat ctggactaac     720
atgttcaatg tgggacaaga acatggaaga cttacatcgt catatcttct gggaaccaga    780
tgcaagtaag ctgaatgaga attactgccg aaatccagat gatgatgctc atggaccctg    840
gtgctacacg ggaaatccac tcattccttg ggattattgc cctatttctc gttgtgaagg    900
tgataccaca cctacaatag tcaatttaga ccatcccgta atatcttgtg ccaaaacgaa    960
acaattgcga gttgtaaatg ggattccaac acgaacaaac ataggatgga tggttagttt   1020
gagatacaga aataaacata tctgcggagg atcattgata aaggagagtt gggttcttac   1080
tgcacgacag tgtttcccctt ctcgagactt gaaagattat gaagcttggc ttggaattca   1140
tgatgtccac ggaagaggag atgagaaatg caaacaggtt ctcaatgttt cccagctggt   1200
atatggccct gaaggatcag atctggtttt aatgaagctt gccaggcctg ctgtcctgga   1260
tgattttgtt agtacgattg atttacctaa ttatggatgc acaattcctg aaaagaccag   1320
ttgcagtgtt tatggctggg gctacactgg attgatcaac tatgatggcc tattacgagt   1380
ggcacatctc tatataatgg gaaatgagaa atgcagccag catcatcgag ggaaggtgac   1440
tctgaatgag tctgaaatat gtgctggggc tgaaaagatt ggatcaggac catgtgaggg   1500
ggattatggt ggcccacttg tttgtgagca acataaaatg gaatggttc ttggtgtcat    1560 tgttcctggt cgtggatgtg ccattccaaa tcgtcctggt attttttgtcc gagtagcata   1620 ttatgcaaaa tggatacaca aaattatttt aacatataag gtaccacagt catag          1675
```

<210> SEQ ID NO 5
<211> LENGTH: 3756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
cgcgttgaca ttgattattg actagttatt aatagtaatc aattacgggg tcattagttc      60
atagcccata tatggagttc cgcgttacat aacttacggt aaatggcccg cctggctgac     120
cgcccaacga ccccccgccca ttgacgtcaa taatgacgta tgttcccata gtaacgccaa    180
tagggacttt ccattgacgt caatgggtgg agtatttacg gtaaactgcc cacttggcag     240
tacatcaagt gtatcatatg ccaagtccgc ccctattga cgtcaatgac ggtaaatggc     300
ccgcctggca ttatgcccag tacatgacct tacgggactt tcctacttgg cagtacatct     360
acgtattagt catcgctatt accatggtga tgcggttttg gcagtacacc aatgggcgtg    420
gatagcggtt tgactcacgg ggatttccaa gtctccaccc cattgacgtc aatgggagtt    480
tgttttggca ccaaaatcaa cgggactttc caaaatgtcg taataacccc gccccgttga    540
cgcaaatggg cggtaggcgt gtacggtggg aggtctatat aagcagagct cgtttagtga    600
```

```
accgtcagat cgcctggaga cgccatccac gctgttttga cctccataga agacaccggg    660
accgatccag cctccgcggc cgggaacggt gcattggaac gcggattccc cgtgccaaga    720
gtgacgtaag taccgcctat agactctata ggcacacccc tttggctctt atgcatgcta    780
tactgttttt ggcttggggc ctatacaccc ccgcttcctt atgctatagg tgatggtata    840
gcttagccta taggtgtggg ttattgacca ttattgacca ctcccctatt ggtgacgata    900 cttccatta ctaatccata acatggctct tgccacaac tatctctatt ggctatatgc    960
caatactctg tccttcagag actgacacgg actctgtatt tttacaggat ggggtcccat   1020
ttattattta caaattcaca tatacaacaa cgccgtcccc cgtgcccgca gttttatta   1080 aacatagcgt gggatctcca cgcgaatctc gggtacgtgt tccggacatg ggctcttctc   1140
cggtagcggc ggagcttcca catccgagcc ctggtcccat gcctccagcg gctcatggtc   1200
gctcggcagc tccttgctcc taacagtgga ggccagactt aggcacagca caatgcccac   1260
caccaccagt gtgccgcaca aggccgtggc ggtagggtat gtgtctgaaa atgagctcgg   1320
agattgggct cgcaccgctg acgcagatgg aagacttaag gcagcggcag aagaagatgc   1380
aggcagctga gttgttgtat tctgataaga gtcagaggta actcccgttg cggtgctgtt   1440
aacggtggag ggcagtgtag tctgagcagt actcgttgct gccgcgcgcg ccaccagaca   1500
taatagctga cagactaaca gactgttcct ttccatgggt cttttctgca gtcaccgtcc   1560
ttgacacgaa gcttggtacc gagctcggat ccactagtcc agtgtggtgg aattctgcag   1620
atatccagca cagtggcggc cgctcgagtc tagagggccc gtttaaaccc gctgatcagc   1680
ctcgactgtg ccttctagtt gccagccatc tgttgtttgc ccctcccccg tgccttcctt   1740
gaccctggaa ggtgccactc ccactgtcct ttcctaataa aatgaggaaa ttgcatcgca   1800
ttgtctgagt aggtgtcatt ctattctggg ggtggggtg gggcaggaca gcaaggggga   1860
ggattgggaa gacaatagca ggcatgctgg ggagtcgaaa ttcagaagaa ctcgtcaaga   1920
aggcgataga aggcgatgcg ctgcgaatcg ggagcggcga taccgtaaag cacgaggaag   1980
cggtcagccc attcgccgcc aagctcttca gcaatatcac gggtagccaa cgctatgtcc   2040
tgatagcggt ccgccacacc cagccggcca cagtcgatga atccagaaaa gcggccattt   2100
tccaccatga tattcggcaa gcaggcatcg ccatgggtca cgacgagatc ctcgccgtcg   2160
ggcatgctcg ccttgagcct ggcgaacagt tcggctggcg cgagccctg atgctcttcg   2220 tccagatcat cctgatcgac aagaccggct tccatccgag tacgtgctcg ctcgatgcga   2280
tgtttcgctt ggtggtcgaa tgggcaggta gccggatcaa gcgtatgcag ccgccgcatt   2340
gcatcagcca tgatggatac tttctcggca ggagcaaggt gagatgacag gagatcctgc   2400
cccggcactt cgcccaatag cagccagtcc cttcccgctt cagtgacaac gtcgagcaca   2460
gctgcgcaag gaacgcccgt cgtggccagc cacgatagcc gcgctgcctc gtcttgcagt   2520
tcattcaggg caccggacag gtcggtcttg acaaaaagaa ccgggcgccc ctgcgctgac   2580
agccggaaca cggcggcatc agagcagccg attgtctgtt gtgcccagtc atagccgaat   2640
agcctctcca cccaagcggc cggagaacct gcgtgcaatc catcttgttc aatcatgcga   2700
aacgatcctc atcctgtctc ttgatcagat cttgatcccc tgcgccatca gatccttggc   2760
ggcaagaaag ccatccagtt tactttgcag ggcttcccaa ccttaccaga gggcgcccca   2820
gctggcaatt ccggttcgct tgctgtccat aaaaccgccc agtctagcta tcgccatgta   2880
agcccactgc aagctacctg ctttctcttt gcgcttgcgt tttcccttgt ccagatagcc   2940
cagtagctga cattcatccg gggtcagcac cgtttctgcg gactggcttt ctacgtgaaa   3000
```

```
aggatctagg tgaagatcct ttttgataat ctcatgacca aaatcccttta acgtgagttt    3060 tcgttccact gagcgtcaga ccccgtagaa aagatcaaag gatcttcttg agatcctttt    3120
tttctgcgcg taatctgctg cttgcaaaca aaaaaccac cgctaccagc ggtggtttgt     3180
ttgccggatc aagagctacc aactcttttt ccgaaggtaa ctggcttcag cagagcgcag    3240
ataccaaata ctgttcttct agtgtagccg tagttaggcc accacttcaa gaactctgta    3300
gcaccgccta catcctcgc tctgctaatc ctgttaccag tggctgctgc cagtggcgat     3360
aagtcgtgtc ttaccgggtt ggactcaaga cgatagttac cggataaggc gcagcggtcg    3420
ggctgaacgg ggggttcgtg cacacagccc agcttggagc gaacgaccta caccgaactg    3480
agatacctac agcgtgagct atgagaaagc gccacgcttc ccgaagggag aaaggcggac    3540
aggtatccgg taagcggcag ggtcggaaca ggagagcgca cgagggagct ccaggggga    3600 aacgcctggt atctttatag tcctgtcggg tttcgccacc tctgacttga gcgtcgattt    3660
ttgtgatgct cgtcagggg gcggagccta tggaaaaacg ccagcaacgc ggcctttta    3720 cggttcctgg ccttttgctg gccttttgct cacatg                              3756
```

<210> SEQ ID NO 6
<211> LENGTH: 4956
<212> TYPE: DNA
<213> ORGANISM: Homo sapiens

<400> SEQUENCE: 6

```
gtaagaacag tatgaagaaa agagatgaag cctctgtctt ttttacatgt taacagtctc      60
atattagtcc ttcagaataa ttctacaatc ctaaaataac ttagccaact tgctgaattg     120
tattacggca aggtttatat gaattcatga ctgatattta gcaaatgatt aattaatatg     180
ttaataaaat gtagccaaaa caatatctta ccttaatgcc tcaatttgta gatctcggta    240
tttgtgaaat aataacgtaa acttcgttta aaaggattct tcttcctgtc tttgagaaag    300
tacggcactg tgcaggggga gaggttgatt gtgaaaaatc agaggtagat gagaatctta    360
ctgagggctg agggttcttt aaccttggtg gatctcaaca ttggttgcac attaaaatca    420
cctgctgcaa gcccttgacg aatcttactt agaagatgac aacacagaac aattaaatca    480
gaatctctgg ggagaatagg gcaccagtat ttttgagct cccaccatga ttccaaagtg     540
cagccaaatt tgagaaccac tgctaaaagc tcaagcttca gattgaccag cttttccatc    600
tcacctatcg cctaaagacc aaattggata atgtgttca ttacgacaga tgggtactat    660
ttaaagatga gtaaacacaa tatacttagg ctcgtcagac tgagagtttt aatcatcact    720
gaggaaaaac atagatatct aatactgact ggagtattag tcaaggctta tttcacacac   780
aattttatca gaaaccaaag tagtttaaaa cagctctccc cttattagta atgcattgga    840
gggtttactt taccatgtac cttgctgagc actgtacctt gttaatctca tttacttgta    900
atgagaacca cacagcggt agttttattg gttctatttt acctacatga caaaactgaa    960
gcataaaaac acttagtaag ttttcagtgt catgcacaac taggaagtga catggccaga   1020
atataagccc agtcaccatc actctataac ctgcgctttt aacaacttca gggcatgaca   1080
catttggccg gtcagtagaa cccatgctgt gatttgtttt tgcagtggtg gtgatgactg    1140
ccttgttgaa tccactttt attctattcc attttgggga cacaattctg caagatgatt    1200
cttcattagg aaacagagat gagttattga ccaacacaga aagaaaaaga gtttgttgct   1260
ccacactggg attaaaccta tgatcttggc ctaattaaca ctagctagta agtgtccaag  1320
```

```
ctgatcatct ctacaacatt tcaataacag aaaacaacaa ttttcaaaat tagttactta    1380
caattatgta gaaatgcctc taaaacacag tattttcctt atattacaaa aacaaaaatt    1440
ataattggtt ttgtcctctt ttgagagttt gcatggtgtt actccctgca tagtgaagaa    1500
aacattttat ttaagtagat ggatctaagt ttttcatgaa caaaggaatg acatttgaaa    1560
tcaatcctac cctagtccag gagaatgcat tagattaacc tagtagaggt cttatttcac    1620
cctgagtttt ctatgatcgt gattctctgc tggaggagta attgtgaaat agatctctct    1680
gggaactggc ttcctagtcc aatcagctct tttaccaatg aacacttcct tgtgatatag    1740
atgtttatgg ccgagaggat ccagtatatt aataaaatcc cttttgtat tcaatgaggg     1800
aaacacataa ttttcatcaa ttagcagctt attggaatat ctgcatgatg gtttaacact    1860
tttaagtgtt gactaaagat taattttaca gaaaatagaa aaagaaatat gtttctgtct    1920
ggaggaatga tttattgttg acccctaaat tgaaatattt tactagtggc ttaatggaaa    1980
gatgatgaaa gatgatgaaa ttaatgtaga agcttaacta gaaaatcagg tgacctgata    2040
tctacatctg tatccttcat tggccaccca gcattcatta atgaatcaga tgatggaata    2100
gatcaagttt cctaggaaca cagtgaatat taaaagaaaa caaagggagc ctagcaccta    2160
gaagacctag tttatatttc aaagtatatt tggatgtaac ccaattttaa acatttcctc    2220
acttgtctct cttaaagcct tgccaacagc aaggacagag aaccaaaaat agtgtatata    2280
tgaataaatg cttattacag aatctgctga ctggcacatg ctttgtgtgt aatgggttct    2340
cataaacact tgttgaatga acacacataa gtgaaagagc atggctaggc ttcatcccctt   2400
ggtcaaatat ggggtgctaa agaaaagcag gggaaataca ttgggacact aacaaaaaaa    2460
aacagttaat ttaggtaaaa gataaaatac accacagaat gaagaaaaga gatgacccag    2520
actgctcttt aaccttcatg tcctagagag gttttgata tgaattgcat tcagaattgt     2580
ggaaaggagc ccatctttttc tcttcatttt gattttatta actccaatgg gggaatttta    2640
ttcgtgtttt ggccatatct acttttgatt tctacattat tctctcttcc tttctacctg    2700
tatttgtcct aataaattgt tgacttatta attcactact tcctcacagc ttttttttgg    2760
ctttacaaat ccactggaaa ggtatatggg tgtatcactt tgtgtatttc ggtgtgcatg    2820
tgtagagggg acaaaaatcc tctctcaaac tataaatatt gagtatttgt gtattgaaca    2880
tttgctataa ctactaggtt tcttaaataa tcttaatata taaaatgata tagaaaaagg    2940
gaaattatag ttcgtattat tcatctaagt gaagagatta aaacccaggg agtaaataaa    3000
ttgtctaagg actaaggttg tatactattt aggtgataga tatggggcaa ccgtatgggt    3060
tttatgatta acaaataaac ttctcaccac tctaccatat caacttttcc ataaaagaga    3120
gctatagtat tctttgctta aataaatttg attagtgcat gacttcttga aaacatataa    3180
agcaaaagtc acatttgatt ctatcagaaa agtgagtaag ccatggccca aacaaaagat    3240
gcattaaaat attctggaat gatggagcta aaagtaagaa aaatgacttt ttaaaaaagt    3300
ttactgttag gaattgtgaa attatgctga attttagttg cattataatt tttgtcagtc    3360
atacggtctg acaacctgtc ttatttctat ttccccatat gaggaatgct agttaagtat    3420
ggatattaac tattactact tagatgcatt gaagttgcat aatatggata atacttcact    3480
ggttccctga aaatgtttag ttagtaataa gtctcttaca ctatttgttt tgtccaataa    3540
tttatatttt ctgaagactt aactctagaa tacactcatg tcaaaatgaa agaatttcat    3600
tgcaaaatat tgcttggtac atgacgcata cctgtatttg ttttgtgtca caacatgaaa    3660
aatgatggtt tattagaagt ttcattgggt aggaaacaca tttgaatggt atttactaag    3720
```

```
atactaaaat ccttggactt cactctaatt ttagtgccat ttagaactca aggtctcagt    3780
aaaagtagaa ataaagcctg ttaacaaaac acaaactgaa tattaaaaat gtaactggat    3840
tttcaaagaa atgtttactg gtattacctg tagatgtata ttctttatta tgatcttttg    3900
tgtaaagtct ggcagacaaa tgcaatatct aattgttgag tccaatatca caagcagtac    3960
aaaagtataa aaaagacttg gccttttcta atgtgttaaa atactttatg ctggtaataa    4020
cactaagagt agggcactag aaattttaag tgaagataat gtgttgcagt tactgcactc    4080
aatggcttac tattataaac caaaactggg atcactaagc tccagtcagt caaaatgatc    4140
aaaattattg aagagaataa gcaattctgt tctttattag gacacagtag atacagacta    4200
caaagtggag tgtgcttaat aagaggtagc atttgttaag tgtcaattac tctattatcc    4260
cttggagctt ctcaaaataa ccatataagg tgtaagatgt taaaggttat ggttacactc    4320
agtgcacagg taagctaata ggctgagaga agctaaatta cttactgggg tctcacagta    4380
agaaagtgag ctgaagtttc agcccagatt taactggatt ctgggctctt tattcatgtt    4440
acttcatgaa tctgtttctc aattgtgcag aaaaagggg gctatttata agaaaagcaa    4500
taaacaaaca agtaatgatc tcaaataagt aatgcaagaa atagtgagat ttcaaaatca    4560
gtggcagcga tttctcagtt ctgtcctaag tggccttgct caatcacctg ctatctttta    4620
gtggagcttt gaattatgt ttcagacaac ttcgattcag ttctagaatg tttgactcag     4680
caaattcaca ggctcatctt tctaacttga tggtgaatat ggaaattcag ctaaatggat    4740
gttaataaaa ttcaaacgtt ttaaggacag atggaaatga cagaattta aggtaaaata    4800 tatgaaggaa tataagataa aggattttc taccttcagc aaaaacatac ccactaatta    4860
gtaaaattaa taggcgaaaa aaagttgcat gctcttatac tgtaatgatt atcattttaa    4920
aactagcttt ttgccttcga gctatcgggg taaaga                             4956
```

<210> SEQ ID NO 7
<211> LENGTH: 7113
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 7

```
atgtgggtga ccaaactcct gccagccctg ctgctgcagc atgtcctcct gcatctcctc     60
ctgctcccca tcgccatccc ctatgcagag ggacaaagga aaagaagaa tacaattcat    120 gaattcaaaa aatcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgttttttgat aaagcaagaa acaatgcct ctggttcccc    300 ttcaatagca tgtcaagtgg agtgaaaaaa gaatttggcc atgaatttga cctctatgaa    360
aacaaagact acattagaaa ctgcatcatt ggtaaaggca gcagctacaa gggaacagta    420
tctatcacta gagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa acaatatct taccttaatg cctcaatttg tagatctcgg    720
tatttgtgaa ataataacgt aaacttcgtt taaaaggatt cttcttcctg tctttgagaa    780
```

```
agtacggcac tgtgcagggg gagaggttga ttgtgaaaaa tcagaggtag atgagaatct    840
tactgagggc tgagggttct ttaaccttgg tggatctcaa cattggttgc acattaaaat    900
cacctgctgc aagcccttga cgaatcttac ttagaagatg acaacacaga acaattaaat    960
cagaatctct ggggagaata gggcaccagt atttttgag ctcccaccat gattccaaag    1020
tgcagccaaa tttgagaacc actgctaaaa gctcaagctt cagattgacc agcttttcca    1080
tctcacctat cgcctaaaga ccaaattgga taaatgtgtt cattacgaca gatgggtact    1140
atttaaagat gagtaaacac aatatactta ggctcgtcag actgagagtt ttaatcatca    1200
ctgaggaaaa acatagatat ctaatactga ctggagtatt agtcaaggct tatttcacac    1260
acaattttat cagaaaccaa agtagtttaa aacagctctc cccttattag taatgcattg    1320
gagggtttac tttaccatgt accttgctga gcactgtacc ttgttaatct catttacttg    1380
taatgagaac cacacagcgg gtagttttat tggttctatt ttacctacat gacaaaactg    1440
aagcataaaa acacttagta agttttcagt gtcatgcaca actaggaagt gacatggcca    1500
gaatataagc ccagtcacca tcactctata acctgcgctt ttaacaactt cagggcatga    1560
cacatttggc cggtcagtag aacccatgct gtgatttgtt tttgcagtgg tggtgatgac    1620
tgccttgttg aatccacttt ttattctatt ccattttggg gacacaattc tgcaagatga    1680
ttcttcatta ggaaacagag atgagttatt gaccaacaca gaaagaaaaa gagtttgttg    1740
ctccacactg ggattaaacc tatgatcttg gcctaattaa cactagctag taagtgtcca    1800
agctgatcat ctctcaaaca tttcaataac agaaaacaac aattttcaaa attagttact    1860
tacaattatg tagaaatgcc tctaaaacac agtatttttcc ttatattaca aaaacaaaaa    1920
ttataattgg ttttgtcctc ttttgagagt ttgcatggtg ttactccctg catagtgaag    1980
aaaacatttt atttaagtag atggatctaa gttttttcatg aacaaaggaa tgacatttga    2040
aatcaatcct accctagtcc aggagaatgc attagattaa cctagtagag gtcttatttc    2100
accctgagtt ttctatgatc gtgattctct gctggaggag taattgtgaa atagatctct    2160
ctgggaactg gcttcctagt ccaatcagct cttttaccaa tgaacacttc cttgtgatat    2220
agatgtttat ggccgagagg atccagtata ttaataaaat ccctttttgt attcaatgag    2280
ggaaacacat aattttcatc aattagcagc ttattggaat atctgcatga tggtttaaca    2340
cttttaagtg ttgactaaag attaattttta cagaaaatag aaaaagaaat atgtttctgt    2400
ctggaggaat gatttattgt tgaccoctaa attgaaatat tttactagtg gcttaatgga    2460
aagatgatga aagatgatga aattaatgta gaagcttaac tagaaaatca ggtgacctga    2520
tatctacatc tgtatccttc attggccacc cagcattcat taatgaatca gatgatggaa    2580
tagatcaagt ttcctaggaa cacagtgaat attaaaagaa aacaagggga gcctagcacc    2640
tagaagacct agtttatatt tcaaagtata tttggatgta acccaatttt aaacatttcc    2700
tcacttgtct ctcttaaagc cttgccaaca gcaaggacag agaaccaaaa atagtgtata    2760
tatgaataaa tgcttattac agaatctgct gactggcaca tgctttgtgt gtaatgggtt    2820
ctcataaaca cttgttgaat gaacacacat aagtgaaaga gcatggctag gcttcatccc    2880
ttggtcaaat atggggtgct aaagaaaagc agggaaata cattgggaca ctaacaaaaa    2940
aaaacagtta atttaggtaa aagataaaat acaccacaga atgaagaaaa gagatgaccc    3000
agactgctct ttaaccttca tgtcctagag aggttttttga tatgaattgc attcagaatt    3060
gtggaaagga gcccatcttt tctcttcatt ttgattttat taactccaat gggggaattt    3120
```

```
tattcgtgtt ttggccatat ctactttga tttctacatt attctctctt cctttctacc    3180
tgtatttgtc ctaataaatt gttgacttat taattcacta cttcctcaca gctttttttt    3240
ggctttacaa atccactgga aaggtatatg ggtgtatcac tttgtgtatt tcggtgtgca    3300
tgtgtagagg ggacaaaaat cctctctcaa actataaata ttgagtattt gtgtattgaa    3360
catttgctat aactactagg tttcttaaat aatcttaata tataaaatga tatagaaaaa    3420
gggaaattat agttcgtatt attcatctaa gtgaagagat taaaacccag ggagtaaata    3480
aattgtctaa ggactaaggt tgtatactat ttaggtgata gatatggggc aaccgtatgg    3540
gttttatgat taacaaataa acttctcacc actctaccat atcaactttt ccataaaaga    3600
gagctatagt attctttgct taaataaatt tgattagtgc atgacttctt gaaaacatat    3660
aaagcaaaag tcacatttga ttctatcaga aaagtgagta agccatggcc caaacaaaag    3720
atgcattaaa atattctgga atgatggagc taaaagtaag aaaaatgact ttttaaaaaa    3780
gtttactgtt aggaattgtg aaattatgct gaattttagt tgcattataa tttttgtcag    3840
tcatacggtc tgacaacctg tcttatttct atttccccat atgaggaatg ctagttaagt    3900
atggatatta actattacta cttagatgca ttgaagttgc ataatatgga taatacttca    3960
ctggttccct gaaaatgttt agttagtaat aagtctctta cactatttgt tttgtccaat    4020
aatttatatt ttctgaagac ttaactctag aatacactca tgtcaaaatg aaagaatttc    4080
attgcaaaat attgcttggt acatgacgca tacctgtatt tgttttgtgt cacaacatga    4140
aaaatgatgg tttattagaa gtttcattgg gtaggaaaca catttgaatg gtatttacta    4200
agatactaaa atccttggac ttcactctaa ttttagtgcc atttagaact caaggtctca    4260
gtaaaagtag aaataaagcc tgttaacaaa acacaaactg aatattaaaa atgtaactgg    4320
attttcaaag aaatgtttac tggtattacc tgtagatgta tattctttat tatgatcttt    4380
tgtgtaaagt ctggcagaca aatgcaatat ctaattgttg agtccaatat cacaagcagt    4440
acaaaagtat aaaaaagact tggccttttc taatgtgtta aaatacttta tgctggtaat    4500
aacactaaga gtagggcact agaaattta agtgaagata atgtgttgca gttactgcac    4560
tcaatggctt actattataa accaaaactg ggatcactaa gctccagtca gtcaaaatga    4620
tcaaaattat tgaagagaat aagcaattct gttctttatt aggacacagt agatacagac    4680
tacaaagtgg agtgtgctta ataagaggta gcatttgtta agtgtcaatt actctattat    4740
cccttggagc ttctcaaaat aaccatataa ggtgtaagat gttaaaggtt atggttacac    4800
tcagtgcaca ggtaagctaa taggctgaga gaagctaaat tacttactgg ggtctcacag    4860
taagaaagtg agctgaagtt tcagcccaga tttaactgga ttctgggctc tttattcatg    4920
ttacttcatg aatctgtttc tcaattgtgc agaaaaaagg gggctattta taagaaaagc    4980
aataaacaaa caagtaatga tctcaaataa gtaatgcaag aaatagtgag atttcaaaat    5040
cagtggcagc gatttctcag ttctgtccta agtggccttg ctcaatcacc tgctatcttt    5100
tagtggagct ttgaaattat gtttcagaca acttcgattc agttctagaa tgtttgactc    5160
agcaaattca caggctcatc tttctaactt gatggtgaat atggaaattc agctaaatgg    5220
atgttaataa aattcaaacg ttttaaggac agatggaaat gacagaattt taaggtaaaa    5280
tatatgaagg aatataagat aaaggatttt tctaccttca gcaaaacat acccactaat    5340
tagtaaaatt aataggcgaa aaaagttgc atgctcttat actgtaatga ttatcatttt    5400
aaaactagct ttttgccttc gagctatcgg ggtaaagacc tacaggaaaa ctactgtcga    5460
aatcctcgag gggaagaagg gggaccctgg tgtttcacaa gcaatccaga ggtacgctac    5520
```

```
gaagtctgtg acattcctca gtgttcagaa gtttgaatgca tgacctgcaa tggggagagt    5580
tatcgaggtc tcatggatca tacagaatca ggcaagattt gtcagcgctg ggatcatcag    5640
acaccacacc ggcacaaatt cttgcctgaa agatatcccg acaagggctt tgatgataat    5700
tattgccgca atcccgatgg ccagccgagg ccatggtgct atactcttga ccctcacacc    5760 cgctggagt actgtgcaat taaaacatgc gctgacaata ctatgaatga cactgatgtt    5820
cctttggaaa caactgaatg catccaaggt caaggagaag gctacagggg cactgtcaat    5880
accatttgga atggaattcc atgtcagcgt tgggattctc agtatcctca cgagcatgac    5940
atgactcctg aaaatttcaa gtgcaaggac ctacagaaaa attactgccg aaatccagat    6000
gggtctgaat caccctggtg ttttaccact gatccaaaca tccgagttgg ctactgctcc    6060
caaattccaa actgtgatat gtcacatgga caagattgtt atcgtgggaa tggcaaaaat    6120
tatatgggca acttatccca acaagatct ggactaacat gttcaatgtg gacaagaac     6180 atggaagact acatcgtca tatcttctgg gaaccagatg caagtaagct gaatgagaat    6240
tactgccgaa atccagatga tgatgctcat ggaccctggt gctacacggg aaatccactc    6300
attccttggg attattgccc tatttctcgt tgtgaaggtg ataccacacc tacaatagtc    6360
aatttagacc atcccgtaat atcttgtgcc aaaacgaaac aattgcgagt tgtaaatggg    6420
attccaacac gaacaaacat aggatggatg gttagtttga gatacagaaa taaacatatc    6480
tgcggaggat cattgataaa ggagagttgg gttcttactg cacgacagtg tttcccttct    6540
cgagacttga agattatga agcttggctt ggaattcatg atgtccacgg aagaggagat    6600
gagaaatgca acaggttct caatgtttcc cagctggtat atggccctga aggatcagat    6660
ctggttttaa tgaagcttgc caggcctgct gtcctggatg attttgttag tacgattgat    6720
ttacctaatt atggatgcac aattcctgaa aagaccagtt gcagtgttta tggctggggc    6780
tacactggat tgatcaacta tgatggccta ttacgagtgg cacatctcta tataatggga    6840
aatgagaaat gcagccagca tcatcgaggg aaggtgactc tgaatgagtc tgaaatatgt    6900
gctggggctg aaaagattgg atcaggacca tgtgagggg attatggtgg cccacttgtt    6960
tgtgagcaac ataaaatgag aatggttctt ggtgtcattg ttcctggtcg tggatgtgcc    7020
attccaaatc gtcctggtat ttttgtccga gtagcatatt atgcaaaatg gatacacaaa    7080 attatttaa catataaggt accacagtca tag                                   7113
```

<210> SEQ ID NO 8
<211> LENGTH: 6190
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
atgtgggtga ccaaactcct gccagccctg ctgctgcagc atgtcctcct gcatctcctc     60
ctgctcccca tcgccatccc ctatgcagag ggacaaagga aagaagaaa tacaattcat    120 gaattcaaaa atcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgtttttgat aaagcaagaa acaatgcct ctggttcccc    300 ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
```

```
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa acaatatct taccttaatg cctcaatttg tagatctcgg     720
tatttgtgaa ataataacgt aaacttcgtt taaaaggatt cttcttcctg tctttgagaa    780
agtacggcac tgtgcagggg gagaggttga ttgtgaaaaa tcagaggtag atgagaatct    840
tactgagggc tgagggttct ttaaccttgg tggatctcaa cattggttgc acattaaaat    900
cacctgctgc aagcccttga cgaatcttac ttagaagatg acaacacaga acaattaaat    960
cagaatctct ggggagaata gggcaccagt attttttgag ctcccaccat gattccaaag   1020
tgcagccaaa tttgagaacc actgctaaaa gctcaagctt cagattgacc agcttttcca   1080
tctcacctat cgcctaaaga ccaaattgga taaatgtgtt cattacgaca gatgggtact   1140
atttaaagat gagtaaacac aatatactta ggctcgtcag actgagagtt ttaatcatca   1200
ctgaggaaaa acatagatat ctaatactga ctggagtatt agtcaaggct tatttcacac   1260
acaattttat cagaaaccaa agtagtttaa aacagctctc cccttattag taatgcattg   1320
gagggtttac tttaccatgt accttgctga gcactgtacc ttgttaatct catttacttg   1380
taatgagaac cacacagcgg gtagttttat tggttctatt ttacctacat gacaaaactg   1440
aagcataaaa acacttagta agttttcagt gtcatgcaca actaggaagt gacatggcca   1500
gaatataagc ccagtcacca tcactctata acctgcgctt ttaacaactt cagggcatga   1560
cacatttggc cggtcagtag aacccatgct gtgatttgtt tttgcagtgg tggtgatgac   1620
tgccttgttg aatccacttt ttattctatt ccattttggg gacacaattc tgcaagatga   1680
ttcttcatta ggaaacagag atgagttatt gaccaacaca gaaagaaaaa gagtttgttg   1740
ctccacactg ggattaaacc tatgatcttg gcctaattaa cactagctag taagtgtcca   1800
agctgatcat ctctacaaca tttcaataac agaaaacaac aattttcaaa attagttact   1860
tacaattatg tagaaatgcc tctaaaacac agtattttcc ttatattaca aaacaaaaa    1920 ttataattgg ttttgtcctc ttttgagagt ttgcatggtg ttactccctg catagtgaag   1980
aaaacatttt atttaagtag atggatctaa gttttcatg aacaaggaa tgacatttga     2040 aatcaatcct accctagtcc aggagaatgc attagattaa cctagtagag gtcttatttc   2100
accctgagtt ttctatgatc gtgattctct gctggaggag taattgtgaa atagatctct   2160
ctgggaactg gcttcctagt ccaatcagct cttttaccaa tgaacacttc cttgtgatat   2220
agatgtttat ggccgagagg atctcttcct ttctacctgt atttgtccta ataaattgtt   2280
gacttattaa ttcactactt cctcacagct ttttttggc tttacaaatc cactggaaag    2340
gtatatgggt gtatcacttt gtgtatttcg gtgtgcatgt gtagagggga caaaaatcct   2400
ctctcaaact ataaatattg agtatttgtg tattgaacat ttgctataac tactaggttt   2460
cttaaataat cttaatatat aaatgatat agaaaaaggg aaattatagt tcgtattatt     2520
catctaagtg aagagattaa aacccaggga gtaaataaat tgtctaagga ctaaggttgt   2580
atactattta ggtgatagat atggggcaac cgtatggtt ttatgattaa caaataaact     2640
tctcaccact ctaccatatc aacttttcca taaaagagag ctatagtatt ctttgcttaa   2700
ataaatttga ttagtgcatg acttcttgaa aacatataaa gcaaagtca catttgattc     2760
```

```
tatcagaaaa gtgagtaagc catggcccaa acaaagatg cattaaaata ttctggaatg    2820
atggagctaa aagtaagaaa aatgactttt taaaaaagtt tactgttagg aattgtgaaa    2880
ttatgctgaa ttttagttgc attataattt ttgtcagtca tacggtctga caacctgtct    2940
tatttctatt tccccatatg aggaatgcta gttaagtatg gatattaact attactactt    3000
agatgcattg aagttgcata atatggataa tacttcactg gttccctgaa aatgtttagt    3060
tagtaataag tctcttacac tatttgtttt gtccaataat ttatattttc tgaagactta    3120
actctagaat acactcatgt caaaatgaaa gaatttcatt gcaaaatatt gcttggtaca    3180
tgacgcatac ctgtatttgt tttgtgtcac aacatgaaaa atgatggttt attagaagtt    3240
tcattgggta ggaaacacat ttgaatggta tttactaaga tactaaaatc cttggacttc    3300
actctaattt tagtgccatt tagaactcaa ggtctcagta aaagtagaaa taagcctgt     3360 taacaaaaca caaactgaat attaaaaatg taactggatt ttcaaagaaa tgtttactgg    3420
tattacctgt agatgtatat tctttattat gatcttttgt gtaaagtctg gcagacaaat    3480
gcaatatcta attgttgagt ccaatatcac aagcagtaca aaagtataaa aaagacttgg    3540
ccttttctaa tgtgttaaaa tactttatgc tggtaataac actaagagta gggcactaga    3600
aattttaagt gaagataatg tgttgcagtt actgcactca atggcttact attataaacc    3660
aaaactggga tcactaagct ccagtcagtc aaaatgatca aaattattga agagaataag    3720
caattctgtt ctttattagg acacagtaga tacagactac aaagtggagt gtgcttaata    3780
agaggtagca tttgttaagt gtcaattact ctattatccc ttggagcttc tcaaaataac    3840
catataaggt gtaagatgtt aaaggttatg gttacactca gtgcacaggt aagctaatag    3900
gctgagagaa gctaaattac ttactggggt ctcacagtaa aaagtgagc tgaagtttca    3960 gcccagattt aactggattc tgggctcttt attcatgtta cttcatgaat ctgtttctca    4020
attgtgcaga aaaaggggg ctatttataa gaaaagcaat aaacaaacaa gtaatgatct    4080
caaataagta atgcaagaaa tagtgagatt tcaaaatcag tggcagcgat ttctcagttc    4140
tgtcctaagt ggccttgctc aatcacctgc tatcttttag tggagctttg aaattatgtt    4200
tcagacaact tcgattcagt tctagaatgt ttgactcagc aaattcacag gctcatcttt    4260
ctaacttgat ggtgaatatg gaaattcagc taaatggatg ttaataaaat tcaaacgttt    4320
taaggacaga tggaaatgac agaatttta ggtaaaatat atgaaggaat ataagataaa    4380 ggattttttct accttcagca aaaacatacc cactaattag taaaattaat aggcgaaaaa    4440
aagttgcatg ctcttatact gtaatgatta tcattttaaa actagctttt tgccttcgag    4500 ctatcgggt aaagacctac aggaaaacta ctgtcgaaat cctcgagggg aagaagggg     4560 accctggtgt ttcacaagca atccagaggt acgctacgaa gtctgtgaca ttcctcagtg    4620
ttcagaagtt gaatgcatga cctgcaatgg ggagagttat cgaggtctca tggatcatac    4680
agaatcaggc aagatttgtc agcgctggga tcatcagaca ccacaccggc acaaattctt    4740
gcctgaaaga tatcccgaca agggctttga tgataattat tgccgcaatc ccgatggcca    4800
gccgaggcca tggtgctata ctcttgaccc tcacacccgc tgggagtact gtgcaattaa    4860
aacatgcgct gacaatacta tgaatgacac tgatgttcct ttggaaacaa ctgaatgcat    4920
ccaaggtcaa ggagaaggct acaggggcac tgtcaatacc atttggaatg gaattccatg    4980
tcagcgttgg gattctcagt atcctcacga gcatgacatg actcctgaaa atttcaagtg    5040
caaggaccta cgagaaaatt actgccgaaa tccagatggg tctgaatcac cctggtgttt    5100
taccactgat ccaaacatcc gagttggcta ctgctcccaa attccaaact gtgatatgtc    5160
```

```
acatggacaa gattgttatc gtgggaatgg caaaaattat atgggcaact tatcccaaac    5220
aagatctgga ctaacatgtt caatgtggga caagaacatg gaagacttac atcgtcatat    5280
cttctgggaa ccagatgcaa gtaagctgaa tgagaattac tgccgaaatc cagatgatga    5340
tgctcatgga ccctggtgct acacgggaaa tccactcatt ccttgggatt attgccctat    5400
ttctcgttgt gaaggtgata ccacacctac aatagtcaat ttagaccatc ccgtaatatc    5460
ttgtgccaaa acgaaacaat tgcgagttgt aaatgggatt ccaacacgaa caaacatagg    5520
atggatggtt agtttgagat acagaaataa acatatctgc ggaggatcat tgataaagga    5580
gagttgggtt cttactgcac gacagtgttt cccttctcga gacttgaaag attatgaagc    5640
ttggcttgga attcatgatg tccacggaag aggagatgag aaatgcaaac aggttctcaa    5700
tgtttcccag ctggtatatg gccctgaagg atcagatctg gttttaatga agcttgccag    5760
gcctgctgtc ctggatgatt ttgttagtac gattgattta cctaattatg gatgcacaat    5820
tcctgaaaag accagttgca gtgtttatgg ctggggctac actggattga tcaactatga    5880
tggcctatta cgagtggcac atctctatat aatgggaaat gagaaatgca gccagcatca    5940
tcgagggaag gtgactctga atgagtctga aatatgtgct ggggctgaaa agattggatc    6000
aggaccatgt gagggggatt atggtggccc acttgtttgt gagcaacata aaatgagaat    6060
ggttcttggt gtcattgttc ctggtcgtgg atgtgccatt ccaaatcgtc ctggtatttt    6120
tgtccgagta gcatattatg caaatggat acacaaaatt attttaacat ataaggtacc    6180
acagtcatag                                                         6190
```

<210> SEQ ID NO 9
<211> LENGTH: 5190
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttttgat aaagcaagaa aacaatgcct ctggttcccc     300
ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta gagtggcat caaatgtcag ccctggagtt ccatgatacc acacgaacac     480
aggtaagaac agtatgaaga aaagagatga agcctctgtc ttttttacat gttaacagtc     540
tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct taccttaatg cctcaatttg tagatctcgg     720
tatttgtgaa ataataacgt aaacttcgtt taaaaggatt cttcttcctg tctttgagaa     780
agtacggcac tgtgcagggg gagaggttga ttgtgaaaaa tcagaggtag atgagaatct     840
tactgagggc tgagggttct ttaaccttgg tggatctcaa cattggttgc acattaaaat     900
cacctgctgc aagcccttga cgaatcttac ttagaagatg acaacacaga acaattaaat     960
```

```
cagaatctct ggggagaata gggcaccagt attttttgag ctcccaccat gattccaaag    1020
tgcagccaaa tttgagaacc actgctaaaa gctcaagctt cagattgacc agcttttcca    1080
tctcacctat cgcctaaaga ccaaattgga taaatgtgtt cattacgaca gatgggtact    1140
atttaaagat gagtaaacac aatatactta ggctcgtcag actgagagtt ttaatcatca    1200
ctgaggaaaa acatagatat ctaatactga ctggagtatt agtcaaggct tatttcacac    1260
acaattttat cagaaaccaa agtagtttaa aacagctctc cccttattag taatgcattg    1320
gagggtttac tttaccatgt accttgctga gcactgtacc ttgttaatct catttacttg    1380
taatgagaac cacacagcgg gtagttttat tggttctatt ttacctacat gacaaaactg    1440
aagcataaaa acacttagta agttttcagt gtcatgcaca actaggaagt gacatggcca    1500
gaatataagc ccagtcacca tcactctata acctgcgctt ttaacaactt cagggcatga    1560
cacatttggc cggtcagtag aacccatgct gtgatttgtt tttgcagtgg tggtgatgac    1620
tgccttgttg aatccacttt ttattctatt ccattttggg gacacaattc tgcaagatga    1680
ttcttcatta ggaaacagag atgagttatt gaccaacaca gaaagaaaaa gagtttgttg    1740
ctccacactg ggattaaacc tatgatcttg gcctaattaa cactagctag taagtgtcca    1800
agctgatcat ctctacaaca tttcaataac agaaaacaac aattttcaaa attagttact    1860
tacaattatg tagaaatgcc tctaaaacac agtattttcc ttatattaca aaaacaaaaa    1920
ttataattgg ttttgtcctc ttttgagagt ttgcatggtg ttactccctg catagtgaag    1980
aaaacatttt atttaagtag atggatctaa gttttttcatg aacaaaggaa tgacatttga    2040
aatcaatcct accctagtcc aggagaatgc attagattaa cctagtagag gtcttatttc    2100
accctgagtt ttctatgatc gtgattctct gctggaggag taattgtgaa atagatctct    2160
ctgggaactg gcttcctagt ccaatcagct ctttttaccaa tgaacacttc cttgtgatat    2220
agatgtttat ggccgagagg atcctgggta ggaaacacat ttgaatggta tttactaaga    2280
tactaaaatc cttggacttc actctaattt tagtgccatt tagaactcaa ggtctcagta    2340
aaagtagaaa taaagcctgt taacaaaaca caaactgaat attaaaaatg taactggatt    2400
ttcaaagaaa tgtttactgg tattacctgt agatgtatat tctttattat gatcttttgt    2460
gtaaagtctg gcagacaaat gcaatatcta attgttgagt ccaatatcac aagcagtaca    2520
aaagtataaa aaagacttgg cctttttctaa tgtgttaaaa tacttttatgc tggtaataac    2580 actaagagta gggcactaga aatttttaagt gaagataatg tgttgcagtt actgcactca    2640
atggcttact attataaacc aaaactggga tcactaagct ccagtcagtc aaaatgatca    2700
aaattattga agagaataag caattctgtt ctttattagg acacagtaga tacagactac    2760
aaagtggagt gtgcttaata agaggtagca tttgttaagt gtcaattact ctattatccc    2820
ttggagcttc tcaaaataac catataaggt gtaagatgtt aaaggttatg gttacactca    2880
gtgcacaggt aagctaatag gctgagagaa gctaaattac ttactggggt ctcacagtaa    2940
gaaagtgagc tgaagtttca gcccagattt aactggattc tgggctcttt attcatgtta    3000
cttcatgaat ctgtttctca attgtgcaga aaaaggggg ctatttataa gaaaagcaat    3060
aaacaaacaa gtaatgatct caaataagta atgcaagaaa tagtgagatt tcaaaatcag    3120
tggcagcgat ttctcagttc tgtcctaagt ggccttgctc aatcacctgc tatcttttag    3180
tggagctttg aaattatgtt tcagacaact tcgattcagt tctagaatgt ttgactcagc    3240
aaattcacag gctcatcttt ctaacttgat ggtgaatatg gaaattcagc taaatggatg    3300
```

| | |
|---|---|
| ttaataaaat tcaaacgttt taaggacaga tggaaatgac agaattttaa ggtaaaatat | 3360 |
| atgaaggaat ataagataaa ggattttct accttcagca aaaacatacc cactaattag | 3420 |
| taaaattaat aggcgaaaaa aagttgcatg ctcttatact gtaatgatta tcattttaaa | 3480 |
| actagctttt tgccttcgag ctatcggggt aaagacctac aggaaaacta ctgtcgaaat | 3540 |
| cctcgagggg aagaaggggg accctggtgt ttcacaagca atccagaggt acgctacgaa | 3600 |
| gtctgtgaca ttcctcagtg ttcagaagtt gaatgcatga cctgcaatgg ggagagttat | 3660 |
| cgaggtctca tggatcatac agaatcaggc aagatttgtc agcgctggga tcatcagaca | 3720 |
| ccacaccggc acaaattctt gcctgaaaga tatcccgaca agggctttga tgataattat | 3780 |
| tgccgcaatc ccgatggcca gccgaggcca tggtgctata ctcttgaccc tcacacccgc | 3840 |
| tgggagtact gtgcaattaa acatgcgct gacaatacta tgaatgacac tgatgttcct | 3900 |
| ttggaaacaa ctgaatgcat ccaaggtcaa ggagaaggct acaggggcac tgtcaatacc | 3960 |
| atttggaatg gaattccatg tcagcgttgg gattctcagt atcctcacga gcatgacatg | 4020 |
| actcctgaaa atttcaagtg caaggaccta cgagaaaatt actgccgaaa tccagatggg | 4080 |
| tctgaatcac cctggtgttt taccactgat ccaaacatcc gagttggcta ctgctcccaa | 4140 |
| attccaaact gtgatatgtc acatggacaa gattgttatc gtgggaatgg caaaaattat | 4200 |
| atgggcaact tatcccaaac aagatctgga ctaacatgtt caatgtggga caagaacatg | 4260 |
| gaagacttac atcgtcatat cttctgggaa ccagatgcaa gtaagctgaa tgagaattac | 4320 |
| tgccgaaatc cagatgatga tgctcatgga ccctggtgct acacgggaaa tccactcatt | 4380 |
| ccttgggatt attgccctat ttctcgttgt gaaggtgata ccacacctac aatagtcaat | 4440 |
| ttagaccatc ccgtaatatc ttgtgccaaa acgaaacaat tgcgagttgt aaatgggatt | 4500 |
| ccaacacgaa caaacatagg atggatggtt agtttgagat acagaaataa acatatctgc | 4560 |
| ggaggatcat tgataaagga gagttgggtt cttactgcac gacagtgttt cccttctcga | 4620 |
| gacttgaaag attatgaagc ttggcttgga attcatgatg tccacggaag aggagatgag | 4680 |
| aaatgcaaac aggttctcaa tgtttcccag ctggtatatg gccctgaagg atcagatctg | 4740 |
| gttttaatga agcttgccag gcctgctgtc tggatgatt tgttagtac gattgattta | 4800 |
| cctaattatg gatgcacaat tcctgaaaag accagttgca gtgtttatgg ctggggctac | 4860 |
| actggattga tcaactatga tggcctatta cgagtggcac atctctatat aatgggaaat | 4920 |
| gagaaatgca gccagcatca tcgagggaag gtgactctga atgagtctga aatatgtgct | 4980 |
| ggggctgaaa agattggatc aggaccatgt gaggggatt atggtggccc acttgtttgt | 5040 |
| gagcaacata aaatgagaat ggttcttggt gtcattgttc ctggtcgtgg atgtgccatt | 5100 |
| ccaaatcgtc ctggtatttt tgtccgagta gcatattatg caaaatggat acacaaaatt | 5160 |
| attttaacat ataaggtacc acagtcatag | 5190 |

<210> SEQ ID NO 10
<211> LENGTH: 4241
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | |
|---|---|
| atgtgggtga ccaaactcct gccagccctg ctgctgcagc atgtcctcct gcatctcctc | 60 |
| ctgctccca tcgccatccc ctatgcagag ggacaaagga aagaagaaa tacaattcat | 120 |

```
gaattcaaaa aatcagcaaa gactacccta atcaaaatag atccagcact gaagataaaa        180
accaaaaaag tgaatactgc agaccaatgt gctaatagat gtactaggaa taaaggactt        240
ccattcactt gcaaggcttt tgtttttgat aaagcaagaa acaatgcct ctggttcccc         300 ttcaatagca tgtcaagtgg agtgaaaaaa gaatttggcc atgaatttga cctctatgaa        360
aacaaagact acattagaaa ctgcatcatt ggtaaaggac gcagctacaa gggaacagta       420
tctatcacta gagtggcat caaatgtcag ccctggagtt ccatgatacc acacgaacac         480
aggtaagaac agtatgaaga aaagagatga agcctctgtc ttttttacat gttaacagtc       540
tcatattagt ccttcagaat aattctacaa tcctaaaata acttagccaa cttgctgaat       600
tgtattacgg caaggtttat atgaattcat gactgatatt tagcaaatga ttaattaata      660
tgttaataaa atgtagccaa aacaatatct taccttaatg cctcaatttg tagatctcgg      720
tatttgtgaa ataataacgt aaacttcgtt taaaaggatt cttcttcctg tctttgagaa      780
agtacggcac tgtgcagggg gagaggttga ttgtgaaaaa tcagaggtag atgagaatct      840
tactgagggc tgagggttct ttaaccttgg tggatctcaa cattggttgc acattaaaat       900
cacctgctgc aagcccttga cgaatcttac ttagaagatg acaacacaga acaattaaat       960
cagaatctct ggggagaata gggcaccagt attttttgag ctcccaccat gattccaaag      1020
tgcagccaaa tttgagaacc actgctaaaa gctcaagctt cagattgacc agcttttcca      1080
tctcacctat cgcctaaaga ccaaattgga taaatgtgtt cattacgaca gatgggtact      1140
atttaaagat gagtaaacac aatatactta ggctcgtcag actgagagtt ttaatcatca      1200
ctgaggaaaa acatagatat ctaatactga ctggagtatt agtcaaggct tatttcacac      1260
acaattttat cagaaaccaa agtagtttaa aacagctctc cccttattag taatgcattg      1320
gagggtttac tttaccatgt accttgctga gcactgtacc ttgttaatct catttacttg      1380
taatgagaac cacacagcgg gtagttttat tggttctatt ttacctacat gacaaaactg      1440
aagcataaaa acacttagta agttttcagt gtcatgcaca actaggaagt gacatggcca      1500
gaatataagc ccagtcacca tcactctata acctgcgctt taacaactt cagggcatga       1560 cacatttggc cggtcagtag aacccatgct gtgatttgtt tttgcagtgg tggtgatgac      1620
tgccttgttg aatccacttt ttattctatt ccattttggg gacacaattc tgcaagatga      1680
ttcttcatta ggaaacagag atgagttatt gaccaacaca gaaagaaaaa gagtttgttg      1740
ctccacactg ggattaaacc tatgatcttg gcctaattaa cactagctag taagtgtcca      1800
agctgatcat ctctacaaca tttcaataac agaaaacaac aattttcaaa attagttact      1860
tacaattatg tagaaatgcc tctaaaacac agtattttcc ttatattaca aaaacaaaaa      1920
ttataattgg ttttgtcctc ttttgagagt ttgcatggtg ttactccctg catagtgaag      1980
aaaacatttt atttaagtag atggatctaa gttttttcatg aacaaggaa tgacatttga     2040 aatcaatcct accctagtcc aggagaatgc attagattaa cctagtagag gtcttatttc     2100
accctgagtt ttctatgatc gtgattctct gctggaggag taattgtgaa atagatctct     2160
ctgggaactg gcttcctagt ccaatcagct cttttaccaa tgaacacttc cttgtgatat      2220
agatgtttat ggccgagagg atccttatgt ttcagacaac ttcgattcag ttctagaatg     2280
tttgactcag caaattcaca ggctcatctt tctaacttga tggtgaatat ggaaattcag     2340
ctaaatggat gttaataaaa ttcaaacgtt ttaaggacag atggaaatga cagaatttta      2400
aggtaaaata tatgaaggaa tataagataa aggatttttc taccttcagc aaaaacatac    2460
ccactaatta gtaaaattaa taggcgaaaa aaagttgcat gctcttatac tgtaatgatt    2520
```

```
atcattttaa aactagcttt ttgccttcga gctatcgggg taaagaccta caggaaaact    2580
actgtcgaaa tcctcgaggg gaagaagggg gaccctggtg tttcacaagc aatccagagg    2640
tacgctacga agtctgtgac attcctcagt gttcagaagt tgaatgcatg acctgcaatg    2700
gggagagtta tcgaggtctc atggatcata cagaatcagg caagatttgt cagcgctggg    2760
atcatcagac accacaccgg cacaaattct tgcctgaaag atatcccgac aagggctttg    2820
atgataatta ttgccgcaat cccgatggcc agccgaggcc atggtgctat actcttgacc    2880
ctcacacccg ctgggagtac tgtgcaatta aaacatgcgc tgacaatact atgaatgaca    2940
ctgatgttcc tttggaaaca actgaatgca tccaaggtca aggagaaggc tacaggggca    3000
ctgtcaatac catttggaat ggaattccat gtcagcgttg ggattctcag tatcctcacg    3060
agcatgacat gactcctgaa aatttcaagt gcaaggacct acgagaaaat tactgccgaa    3120
atccagatgg gtctgaatca ccctggtgtt ttaccactga tccaaacatc cgagttggct    3180
actgctccca aattccaaac tgtgatatgt cacatggaca agattgttat cgtgggaatg    3240
gcaaaaatta tatgggcaac ttatcccaaa caagatctgg actaacatgt tcaatgtggg    3300
acaagaacat ggaagactta catcgtcata tcttctggga accagatgca agtaagctga    3360
atgagaatta ctgccgaaat ccagatgatg atgctcatgg accctggtgc tacacgggaa    3420
atccactcat tccttgggat tattgcccta tttctcgttg tgaaggtgat accacaccta    3480
caatagtcaa tttagaccat cccgtaatat cttgtgccaa aacgaaacaa ttgcgagttg    3540
taaatgggat tccaacacga acaaacatag gatggatggt tagtttgaga tacagaaata    3600
aacatatctg cggaggatca ttgataaagg agagttgggt tcttactgca cgacagtgtt    3660
tcccttctcg agacttgaaa gattatgaag cttggcttgg aattcatgat gtccacggaa    3720
gaggagatga gaaatgcaaa caggttctca atgtttccca gctggtatat ggccctgaag    3780
gatcagatct ggttttaatg aagcttgcca ggcctgctgt cctggatgat tttgttagta    3840
cgattgattt acctaattat ggatgcacaa ttcctgaaaa gaccagttgc agtgtttatg    3900
gctggggcta cactggattg atcaactatg atggcctatt acgagtggca catctctata    3960
taatgggaaa tgagaaatgc agccagcatc atcgagggaa ggtgactctg aatgagtctg    4020
aaatatgtgc tggggctgaa aagattggat caggaccatg tgaggggat tatggtggcc    4080 cacttgtttg tgagcaacat aaaatgagaa tggttcttgg tgtcattgtt cctggtcgtg    4140
gatgtgccat tccaaatcgt cctggtattt ttgtccgagt agcatattat gcaaaatgga    4200
tacacaaaat tattttaaca tataaggtac cacagtcata g                       4241
```

<210> SEQ ID NO 11
<211> LENGTH: 5602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgtgggtga ccaaactcct gccagccctg ctgctgcagc atgtcctcct gcatctcctc     60
ctgctcccca tcgccatccc ctatgcagag ggacaaagga aagaagaaa tacaattcat    120 gaattcaaaa aatcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgtttttgat aaagcaagaa aacaatgcct ctggttcccc    300
```

```
ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa acaatatct taccttaatg cctcaatttg tagatctcgg    720
tatttgtgga tccagtatat taataaaatc ccttttttgta ttcaatgagg gaaacacata    780
attttcatca attagcagct tattggaata tctgcatgat ggtttaacac ttttaagtgt    840
tgactaaaga ttaattttac agaaaataga aaagaaata tgtttctgtc tggaggaatg    900
atttattgtt gaccctaaa ttgaaatatt ttactagtgg cttaatggaa agatgatgaa    960
agatgatgaa attaatgtag aagcttaact agaaaatcag gtgacctgat atctacatct   1020
gtatccttca ttggccaccc agcattcatt aatgaatcag atgatggaat agatcaagtt   1080
tcctaggaac acagtgaata ttaaagaaa acaaagggag cctagcacct agaagaccta    1140
gtttatattt caagtatat ttggatgtaa cccaatttta acatttcct cacttgtctc     1200
tcttaaagcc ttgccaacag caaggacaga gaaccaaaaa tagtgtatat atgaataaat    1260
gcttattaca gaatctgctg actggcacat gctttgtgtg taatgggttc tcataaacac    1320
ttgttgaatg aacacacata agtgaaagag catggctagg cttcatccct tggtcaaata    1380
tggggtgcta agaaaagca ggggaaatac attgggacac taacaaaaa aaacagttaa    1440
tttaggtaaa agataaaata caccacagaa tgaagaaag agatgaccca gactgctctt    1500
taaccttcat gtcctagaga ggttttttgat atgaattgca ttcagaattg tggaaaggag   1560
cccatctttt ctcttcattt tgattttatt aactccaatg ggggaatttt attcgtgttt   1620
tggccatatc tactttttgat ttctacatta ttctctcttc ctttctacct gtatttgtcc   1680
taataaattg ttgacttatt aattcactac ttcctcacag cttttttttg gctttacaaa   1740
tccactggaa aggtatatgg gtgtatcact ttgtgtattt cggtgtgcat gtgtagaggg   1800
gacaaaaatc ctctctcaaa ctataaatat tgagtatttg tgtattgaac atttgctata   1860
actactaggt ttcttaaata atcttaatat ataaaatgat atagaaaaag ggaaattata   1920
gttcgtatta ttcatctaag tgaagagatt aaaacccagg gagtaaataa attgtctaag   1980
gactaaggtt gtatactatt taggtgatag atatggggca accgtatggg ttttatgatt   2040
aacaaataaa cttctcacca ctctaccata tcaacttttc cataaaagag agctatagta   2100
ttctttgctt aaataaattt gattagtgca tgacttcttg aaaacatata aagcaaaagt   2160
cacatttgat tctatcagaa aagtgagtaa gccatggccc aaacaaaaga tgcattaaaa   2220
tattctggaa tgatggagct aaaagtaaga aaaatgactt tttaaaaaag tttactgtta   2280
ggaattgtga aattatgctg aatttttagtt gcattataat ttttgtcagt catacggtct   2340
gacaacctgt cttatttcta tttccccata tgaggaatgc tagttaagta tggatattaa   2400
ctattactac ttagatgcat tgaagttgca taatatggat aatacttcac tggttccctg   2460
aaaatgttta gttagtaata agtctcttac actatttgtt ttgtccaata atttatattt   2520
tctgaagact taactctaga atacactcat gtcaaaatga aagaatttca ttgcaaaata   2580
ttgcttggta catgacgcat acctgtattt gttttgtgtc acaacatgaa aaatgatggt   2640
```

```
ttattagaag tttcattggg taggaaacac atttgaatgg tatttactaa gatactaaaa   2700
tccttggact tcactctaat tttagtgcca tttagaactc aaggtctcag taaaagtaga   2760
aataaagcct gttaacaaaa cacaaactga atattaaaaa tgtaactgga ttttcaaaga   2820
aatgtttact ggtattacct gtagatgtat attctttatt atgatctttt gtgtaaagtc   2880
tggcagacaa atgcaatatc taattgttga gtccaatatc acaagcagta caaaagtata   2940
aaaaagactt ggccttttct aatgtgttaa aatactttat gctggtaata acactaagag   3000
tagggcacta gaaattttaa gtgaagataa tgtgttgcag ttactgcact caatggctta   3060
ctattataaa ccaaaactgg gatcactaag ctccagtcag tcaaaatgat caaaattatt   3120
gaagagaata agcaattctg ttctttatta ggacacagta gatacagact acaaagtgga   3180
gtgtgcttaa taagaggtag catttgttaa gtgtcaatta ctctattatc ccttggagct   3240
tctcaaaata accatataag gtgtaagatg ttaaaggtta tggttacact cagtgcacag   3300
gtaagctaat aggctgagag aagctaaatt acttactggg gtctcacagt aagaaagtga   3360
gctgaagttt cagcccagat ttaactggat tctgggctct ttattcatgt tacttcatga   3420
atctgtttct caattgtgca gaaaaaaggg ggctatttat aagaaaagca ataaacaaac   3480
aagtaatgat ctcaaataag taatgcaaga aatagtgaga tttcaaaatc agtggcagcg   3540
atttctcagt tctgtcctaa gtggccttgc tcaatcacct gctatctttt agtggagctt   3600
tgaaattatg tttcagacaa cttcgattca gttctagaat gtttgactca gcaaattcac   3660
aggctcatct ttctaacttg atggtgaata tggaaattca gctaaatgga tgttaataaa   3720
attcaaacgt tttaaggaca gatggaaatg acagaatttt aaggtaaaat atatgaagga   3780
atataagata aaggattttt ctaccttcag caaaaacata cccactaatt agtaaaatta   3840
ataggcgaaa aaagttgca tgctcttata ctgtaatgat tatcatttta aaactagctt   3900
tttgccttcg agctatcggg gtaaagacct acaggaaaac tactgtcgaa atcctcgagg   3960
ggaagaaggg ggaccctggt gtttcacaag caatccagag gtacgctacg aagtctgtga   4020
cattcctcag tgttcagaag ttgaatgcat gacctgcaat ggggagagtt atcgaggtct   4080
catggatcat acagaatcag gcaagatttg tcagcgctgg gatcatcaga caccacaccg   4140
gcacaaattc ttgcctgaaa gatatcccga caagggcttt gatgataatt attgccgcaa   4200
tcccgatggc cagccgaggc catggtgcta tactcttgac cctcacaccc gctgggagta   4260
ctgtgcaatt aaaacatgcg ctgacaatac tatgaatgac actgatgttc ctttggaaac   4320
aactgaatgc atccaaggtc aaggagaagg ctacaggggc actgtcaata ccatttggaa   4380
tggaattcca tgtcagcgtt gggattctca gtatcctcac gagcatgaca tgactcctga   4440
aaatttcaag tgcaaggacc tacgagaaaa ttactgccga aatccagatg ggtctgaatc   4500
accctggtgt tttaccactg atccaaacat ccgagttggc tactgctccc aaattccaaa   4560
ctgtgatatg tcacatggac aagattgtta tcgtgggaat ggcaaaaatt atatgggcaa   4620
cttatcccaa acaagatctg gactaacatg ttcaatgtgg gacaagaaca tggaagactt   4680
acatcgtcat atcttctggg aaccagatgc aagtaagctg aatgagaatt actgccgaaa   4740
tccagatgat gatgctcatg gaccctggtg ctacacggga aatccactca ttccttggga   4800
ttattgccct atttctcgtt gtgaaggtga taccacacct acaatagtca atttagacca   4860
tcccgtaata tcttgtgcca aaacgaaaca attgcgagtt gtaaatggga ttccaacacg   4920
aacaaacata ggatggatgg ttagtttgag atacagaaat aaacatatct gcggaggatc   4980
attgataaag gagagttggg ttcttactgc acgacagtgt ttcccttctc gagacttgaa   5040
```

| | |
|---|---|
| agattatgaa gcttggcttg gaattcatga tgtccacgga agaggagatg agaaatgcaa | 5100 |
| acaggttctc aatgtttccc agctggtata tggccctgaa ggatcagatc tggtttaat | 5160 |
| gaagcttgcc aggcctgctg tcctggatga ttttgttagt acgattgatt tacctaatta | 5220 |
| tggatgcaca attcctgaaa agaccagttg cagtgtttat ggctggggct acactggatt | 5280 |
| gatcaactat gatggcctat tacgagtggc acatctctat ataatgggaa atgagaaatg | 5340 |
| cagccagcat catcgaggga aggtgactct gaatgagtct gaaatatgtg ctggggctga | 5400 |
| aaagattgga tcaggaccat gtgaggggga ttatggtggc ccacttgttt gtgagcaaca | 5460 |
| taaaatgaga atggttcttg gtgtcattgt tcctggtcgt ggatgtgcca ttccaaatcg | 5520 |
| tcctggtatt tttgtccgag tagcatatta tgcaaaatgg atacacaaaa ttattttaac | 5580 |
| atataaggta ccacagtcat ag | 5602 |

<210> SEQ ID NO 12
<211> LENGTH: 4679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgtttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta agagtggcat caaatgtcag ccctggagtt ccatgatacc acacgaacac | 480 |
| aggtaagaac agtatgaaga aaagagatga agcctctgtc tttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tctcttcctt tctacctgta tttgtcctaa taaattgttg acttattaat | 780 |
| tcactacttc ctcacagctt ttttttggct ttacaaatcc actggaaagg tatatgggtg | 840 |
| tatcactttg tgtatttcgg tgtgcatgtg tagaggggac aaaaatcctc tctcaaacta | 900 |
| taaatattga gtatttgtgt attgaacatt tgctataact actaggtttc ttaaataatc | 960 |
| ttaatatata aaatgatata gaaaaaggga aattatagtt cgtattattc atctaagtga | 1020 |
| agagattaaa acccagggag taaataaatt gtctaaggca taaggttgta tactatttag | 1080 |
| gtgatagata tggggcaacc gtatgggttt tatgattaac aaataaactt ctcaccactc | 1140 |
| taccatatca actttttccat aaaagagagc tatagtattc tttgcttaaa taaatttgat | 1200 |
| tagtgcatga cttcttgaaa acatataaag caaagtcac atttgattct atcagaaaag | 1260 |
| tgagtaagcc atggcccaaa caaagatgc attaaaatat tctggaatga tggagctaaa | 1320 |
| agtaagaaaa atgactttt aaaaagttt actgttagga attgtgaaat tatgctgaat | 1380 |
| tttagttgca ttataattt tgtcagtcat acggtctgac aacctgtctt atttctattt | 1440 |

```
ccccatatga ggaatgctag ttaagtatgg atattaacta ttactactta gatgcattga   1500
agttgcataa tatggataat acttcactgg ttccctgaaa atgtttagtt agtaataagt   1560
ctcttacact atttgttttg tccaataatt tatattttct gaagacttaa ctctagaata   1620
cactcatgtc aaaatgaaag aatttcattg caaaatattg cttggtacat gacgcatacc   1680
tgtatttgtt ttgtgtcaca acatgaaaaa tgatggttta ttagaagttt cattgggtag   1740
gaaacacatt tgaatggtat ttactaagat actaaaatcc ttggacttca ctctaatttt   1800
agtgccattt agaactcaag gtctcagtaa aagtagaaat aaagcctgtt aacaaaacac   1860
aaactgaata ttaaaaatgt aactggattt tcaaagaaat gtttactggt attacctgta   1920
gatgtatatt ctttattatg atcttttgtg taaagtctgg cagacaaatg caatatctaa   1980
ttgttgagtc caatatcaca agcagtacaa agtataaaa aagacttggc cttttctaat    2040
gtgttaaaat actttatgct ggtaataaca ctaagagtag ggcactagaa attttaagtg   2100
aagataatgt gttgcagtta ctgcactcaa tggcttacta ttataaacca aaactgggat   2160
cactaagctc cagtcagtca aaatgatcaa aattattgaa gagaataagc aattctgttc   2220
tttattagga cacagtagat acagactaca aagtggagtg tgcttaataa gaggtagcat   2280
ttgttaagtg tcaattactc tattatccct tggagcttct caaaataacc atataaggtg   2340
taagatgtta aaggttatgg ttacactcag tgcacaggta agctaatagg ctgagagaag   2400
ctaaattact tactggggtc tcacagtaag aaagtgagct gaagtttcag cccagattta   2460
actggattct gggctcttta ttcatgttac ttcatgaatc tgtttctcaa ttgtgcagaa   2520 aaaggggc tatttataag aaaagcaata acaaacaag taatgatctc aaataagtaa     2580
tgcaagaaat agtgagattt caaaatcagt ggcagcgatt tctcagttct gtcctaagtg   2640
gccttgctca atcacctgct atcttttagt ggagctttga aattatgttt cagacaactt   2700
cgattcagtt ctagaatgtt tgactcagca aattcacagg ctcatctttc taacttgatg   2760
gtgaatatgg aaattcagct aaatggatgt taataaaatt caaacgtttt aaggacagat   2820
ggaaatgaca gaattttaag gtaaaatata tgaaggaata taagataaag gatttttcta   2880
ccttcagcaa aaacataccc actaattagt aaaattaata ggcgaaaaaa agttgcatgc   2940
tcttatactg taatgattat cattttaaaa ctagcttttt gccttcgagc tatcgggta   3000 aagacctaca ggaaaactac tgtcgaaatc ctcgagggga agaaggggga ccctggtgtt   3060
tcacaagcaa tccagaggta cgctacgaag tctgtgacat tcctcagtgt tcagaagttg   3120
aatgcatgac ctgcaatggg gagagttatc gaggtctcat ggatcataca gaatcaggca   3180
agatttgtca gcgctgggat catcagacac cacaccggca caaattcttg cctgaaagat   3240
atcccgacaa gggctttgat gataattatt gccgcaatcc cgatggccag ccgaggccat   3300
ggtgctatac tcttgacccct cacacccgct gggagtactg tgcaattaaa acatgcgctg   3360
acaatactat gaatgacact gatgttcctt tggaaacaac tgaatgcatc caaggtcaag   3420
gagaaggcta caggggcact gtcaatacca tttggaatgg aattccatgt cagcgttggg   3480
attctcagta tcctcacgag catgacatga ctcctgaaaa tttcaagtgc aaggacctac   3540
gagaaaatta ctgccgaaat ccagatgggt ctgaatcacc ctggtgtttt accactgatc   3600
caaacatccg agttggctac tgctcccaaa ttccaaactg tgatatgtca catggacaag   3660
attgttatcg tgggaatggc aaaaattata tgggcaactt atcccaaaca agatctggac   3720
taacatgttc aatgtgggac aagaacatgg aagacttaca tcgtcatatc ttctgggaac   3780
```

| | |
|---|---:|
| cagatgcaag taagctgaat gagaattact gccgaaatcc agatgatgat gctcatggac | 3840 |
| cctggtgcta cacgggaaat ccactcattc cttgggatta ttgccctatt tctcgttgtg | 3900 |
| aaggtgatac cacacctaca atagtcaatt tagaccatcc cgtaatatct tgtgccaaaa | 3960 |
| cgaaacaatt gcgagttgta aatgggattc caacacgaac aaacatagga tggatggtta | 4020 |
| gtttgagata cagaaataaa catatctgcg gaggatcatt gataaaggag agttgggttc | 4080 |
| ttactgcacg acagtgtttc ccttctcgag acttgaaaga ttatgaagct tggcttggaa | 4140 |
| ttcatgatgt ccacggaaga ggagatgaga aatgcaaaca ggttctcaat gtttcccagc | 4200 |
| tggtatatgg ccctgaagga tcagatctgg ttttaatgaa gcttgccagg cctgctgtcc | 4260 |
| tggatgattt tgttagtacg attgatttac ctaattatgg atgcacaatt cctgaaaaga | 4320 |
| ccagttgcag tgtttatggc tggggctaca ctggattgat caactatgat ggcctattac | 4380 |
| gagtggcaca tctctatata tgggaaatg agaaatgcag ccagcatcat cgagggaagg | 4440 |
| tgactctgaa tgagtctgaa atatgtgctg gggctgaaaa gattggatca ggaccatgtg | 4500 |
| agggggatta tggtggccca cttgtttgtg agcaacataa aatgagaatg gttcttggtg | 4560 |
| tcattgttcc tggtcgtgga tgtgccattc caaatcgtcc tggtattttt gtccgagtag | 4620 |
| catattatgc aaaatggata cacaaaatta ttttaacata taaggtacca cagtcatag | 4679 |

<210> SEQ ID NO 13
<211> LENGTH: 3679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| | |
|---|---:|
| atgtgggtga ccaaactcct gccagccctg ctgctgcagc atgtcctcct gcatctcctc | 60 |
| ctgctcccca tcgccatccc ctatgcagag ggacaaagga aaagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgttttttgat aaagcaagaa aacaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc tttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tcctgggtag gaaacacatt tgaatggtat ttactaagat actaaaatcc | 780 |
| ttggacttca ctctaatttt agtgccattt agaactcaag gtctcagtaa aagtagaaat | 840 |
| aaagcctgtt aacaaaacac aaactgaata ttaaaaatgt aactggattt tcaaagaaat | 900 |
| gtttactggt attacctgta gatgtatatt ctttattatg atcttttgtg taaagtctgg | 960 |
| cagacaaatg caatatctaa ttgttgagtc caatatcaca agcagtacaa agtataaaa | 1020 |
| aagacttggc ctttttctaat gtgttaaaat actttatgct ggtaataaca ctaagagtag | 1080 |
| ggcactagaa attttaagtg aagataatgt gttgcagtta ctgcactcaa tggcttacta | 1140 |

```
ttataaacca aaactgggat cactaagctc cagtcagtca aaatgatcaa aattattgaa   1200
gagaataagc aattctgttc tttattagga cacagtagat acagactaca aagtggagtg   1260
tgcttaataa gaggtagcat tgttaagtg tcaattactc tattatccct tggagcttct    1320
caaaataacc atataaggtg taagatgtta aaggttatgg ttacactcag tgcacaggta    1380
agctaatagg ctgagagaag ctaaattact tactggggtc tcacagtaag aaagtgagct   1440
gaagtttcag cccagattta actggattct gggctcttta ttcatgttac ttcatgaatc   1500
tgtttctcaa ttgtgcagaa aaaggggggc tatttataag aaaagcaata aacaaacaag   1560
taatgatctc aaataagtaa tgcaagaaat agtgagattt caaaatcagt ggcagcgatt   1620
tctcagttct gtcctaagtg gccttgctca atcacctgct atcttttagt ggagctttga   1680
aattatgttt cagacaactt cgattcagtt ctagaatgtt tgactcagca aattcacagg   1740
ctcatctttc taacttgatg gtgaatatgg aaattcagct aaatggatgt taataaaatt   1800
caaacgtttt aaggacagat ggaaatgaca gaattttaag gtaaaatata tgaaggaata   1860
taagataaag gattttctca ccttcagcaa aaacataccc actaattagt aaaattaata   1920
ggcgaaaaaa agttgcatgc tcttatactg taatgattat cattttaaaa ctagcttttt   1980
gccttcgagc tatcgggta aagacctaca ggaaaactac tgtcgaaatc ctcgagggga    2040
agaaggggga ccctggtgtt tcacaagcaa tccagaggta cgctacgaag tctgtgacat   2100
tcctcagtgt tcagaagttg aatgcatgac ctgcaatggg gagagttatc gaggtctcat   2160
ggatcataca gaatcaggca agatttgtca gcgctgggat catcagacac cacaccggca   2220
caaattcttg cctgaaagat atcccgacaa gggctttgat gataattatt gccgcaatcc   2280
cgatggccag ccgaggccat ggtgctatac tcttgaccct cacacccgct gggagtactg   2340
tgcaattaaa acatgcgctg acaatactat gaatgacact gatgttcctt tggaaacaac   2400
tgaatgcatc caaggtcaag gagaaggcta caggggcact gtcaatacca tttggaatgg   2460
aattccatgt cagcgttggg attctcagta tcctcacgag catgacatga ctcctgaaaa   2520
tttcaagtgc aaggacctac gagaaaatta ctgccgaaat ccagatgggt ctgaatcacc   2580
ctggtgtttt accactgatc aaacatccg agttggctac tgctcccaaa ttccaaactg    2640
tgatatgtca catggacaag attgttatcg tgggaatggc aaaaattata tgggcaactt   2700
atcccaaaca agatctggac taacatgttc aatgtgggac aagaacatgg aagacttaca   2760
tcgtcatatc ttctgggaac cagatgcaag taagctgaat gagaattact gccgaaatcc   2820
agatgatgat gctcatggac cctggtgcta cacgggaaat ccactcattc cttgggatta   2880
ttgccctatt tctcgttgtg aaggtgatac cacacctaca atagtcaatt tagaccatcc   2940
cgtaatatct tgtgccaaaa cgaaacaatt gcgagttgta aatgggattc caacacgaac   3000
aaacatagga tggatggtta gtttgagata cagaaataaa catatctgcg gaggatcatt   3060
gataaaggag agtggggttc ttactgcacg acagtgtttc ccttctcgag acttgaaaga   3120
ttatgaagct tggcttggaa ttcatgatgt ccacggaaga ggagatgaga atgcaaaca    3180 ggttctcaat gtttcccagc tggtatatgg ccctgaagga tcagatctgg ttttaatgaa   3240
gcttgccagg cctgctgtcc tggatgattt tgttagtacg attgatttac ctaattatgg   3300
atgcacaatt cctgaaaaga ccagttgcag tgtttatggc tgggggctaca ctggattgat  3360 caactatgat ggcctattac gagtggcaca tctctatata tgggaaatg agaaatgcag    3420 ccagcatcat cgagggaagg tgactctgaa tgagtctgaa atatgtgctg ggctgaaaa    3480 gattggatca ggaccatgtg aggggggatta tggtggccca cttgtttgtg agcaacataa  3540
```

```
aatgagaatg gttcttggtg tcattgttcc tggtcgtgga tgtgccattc caaatcgtcc    3600
tggtattttt gtccgagtag catattatgc aaaatggata cacaaaatta ttttaacata    3660
taaggtacca cagtcatag                                                  3679
```

<210> SEQ ID NO 14
<211> LENGTH: 2730
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atgtgggtga ccaaactcct gccagccctg ctgctgcagc atgtcctcct gcatctcctc     60
ctgctcccca tcgccatccc ctatgcagag ggacaaagga aagaagaaa tacaattcat    120 gaattcaaaa aatcagcaaa gactaccta atcaaaatag atccagcact gaagataaaa    180
accaaaaaag tgaatactgc agaccaatgt gctaatagat gtactaggaa taaaggactt    240
ccattcactt gcaaggcttt tgttttttgat aaagcaagaa acaatgcct ctggttcccc    300 ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta gagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgga tccttatgtt tcagacaact tcgattcagt tctagaatgt ttgactcagc    780
aaattcacag gctcatcttt ctaacttgat ggtgaatatg gaaattcagc taaatggatg    840
ttaataaaat tcaacgtttt aaggacaga tggaaatgac agaattttaa ggtaaaatat    900
atgaaggaat ataagataaa ggattttct accttcagca aaaacatacc cactaattag    960
taaaattaat aggcgaaaaa aagttgcatg ctcttatact gtaatgatta tcatttttaaa   1020 actagctttt tgccttcgag ctatcggggt aaagacctac aggaaaacta ctgtcgaaat   1080
cctcgagggg aagaaggggg accctggtgt tcacaagca atccagaggt acgctacgaa   1140
gtctgtgaca ttcctcagtg ttcagaagtt gaatgcatga cctgcaatgg ggagagttat   1200
cgaggtctca tggatcatac agaatcaggc aagatttgtc agcgctggga tcatcagaca   1260
ccacaccggc acaaattctt gcctgaaaga tatcccgaca agggctttga tgataattat   1320
tgccgcaatc ccgatggcca gccgaggcca tggtgctata ctcttgaccc tcacacccgc   1380
tgggagtact gtgcaattaa acatgcgct gacaatacta tgaatgacac tgatgttcct   1440
ttggaaacaa ctgaatgcat ccaaggtcaa ggagaaggct acaggggcac tgtcaatacc   1500
atttggaatg gaattccatg tcagcgttgg gattctcagt atcctcacga gcatgacatg   1560
actcctgaaa atttcaagtg caaggaccta cgagaaaatt actgccgaaa tccagatggg   1620
tctgaatcac cctggtgttt taccactgat ccaaacatcc gagttggcta ctgctcccaa   1680
attccaaact gtgatatgtc acatggacaa gattgttatc gtgggaatgg caaaaattat   1740
atgggcaact atcccaaac aagatctgga ctaacatgtt caatgtggga caagaacatg   1800
gaagacttac atcgtcatat cttctgggaa ccagatgcaa gtaagctgaa tgagaattac   1860
```

| | |
|---|---|
| tgccgaaatc cagatgatga tgctcatgga ccctggtgct acacgggaaa tccactcatt | 1920 |
| ccttgggatt attgccctat ttctcgttgt gaaggtgata ccacacctac aatagtcaat | 1980 |
| ttagaccatc ccgtaatatc ttgtgccaaa acgaaacaat tgcgagttgt aaatgggatt | 2040 |
| ccaacacgaa caaacatagg atggatggtt agtttgagat acagaaataa acatatctgc | 2100 |
| ggaggatcat tgataaagga gagttgggtt cttactgcac acagtgtttt cccttctcga | 2160 |
| gacttgaaag attatgaagc ttggcttgga attcatgatg tccacggaag aggagatgag | 2220 |
| aaatgcaaac aggttctcaa tgtttcccag ctggtatatg ccctgaagg atcagatctg | 2280 |
| gttttaatga agcttgccag gcctgctgtc ctggatgatt ttgttagtac gattgattta | 2340 |
| cctaattatg gatgcacaat tcctgaaaag accagttgca gtgtttatgg ctggggctac | 2400 |
| actggattga tcaactatga tggcctatta cgagtggcac atctctatat aatgggaaat | 2460 |
| gagaaatgca gccagcatca tcgagggaag gtgactctga atgagtctga aatatgtgct | 2520 |
| ggggctgaaa agattggatc aggaccatg gaggggatt atggtggccc acttgtttgt | 2580 |
| gagcaacata aaatgagaat ggttcttggt gtcattgttc ctggtcgtgg atgtgccatt | 2640 |
| ccaaatcgtc ctggtatttt tgtccgagta gcatattatg caaaatggat acacaaaatt | 2700 |
| attttaacat ataaggtacc acagtcatag | 2730 |

<210> SEQ ID NO 15
<211> LENGTH: 3250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | |
|---|---|
| cagggtcgga acaggagagc gcacgaggga gcttccaggg ggaaacgcct ggtatctta | 60 |
| tagtcctgtc gggtttcgcc acctctgact tgagcgtcga tttttgtgat gctcgtcagg | 120 |
| ggggcggagc ctatggaaaa acgccagcaa cgcggccttt ttacggttcc tggcctttg | 180 |
| ctggcctttt gctcacatgc gcgttgacat tgattattga ctagttatta atagtaatca | 240 |
| attacgggt cattagttca tagcccatat atggagttcc gcgttacata acttacggta | 300 |
| aatggcccgc ctggctgacc gcccaacgac ccccgcccat tgacgtcaat aatgacgtat | 360 |
| gttcccatag taacgccaat agggactttc cattgacgtc aatgggtgga gtatttacgg | 420 |
| taaactgccc acttggcagt acatcaagtg tatcatatgc caagtccgcc cctattgac | 480 |
| gtcaatgacg gtaaatggcc cgcctggcat tatgcccagt acatgacctt acgggacttt | 540 |
| cctacttggc agtacatcta cgtattagtc atcgctatta ccatggtgat gcggttttgg | 600 |
| cagtacacca atgggcgtgg atagcggttt gactcacggg gatttccaag tctccacccc | 660 |
| attgacgtca atgggagttt gttttggcac caaaatcaac gggactttcc aaaatgtcgt | 720 |
| aataaccccg ccccgttgac gcaaatgggc ggtaggcgtg tacggtggga ggtctatata | 780 |
| agcagagctc gtttagtgaa ccgtcagatc gcctggagac gccatccacg ctgttttgac | 840 |
| ctccatagaa gacaccggga ccgatccagc ctccgcggcc gggaacggtg cattggaacg | 900 |
| cggattcccc gtgccaagag tgacgtaagt accgcctata gactctatag gcacacccct | 960 |
| ttggctctta tgcatgctat actgtttttg gcttggggcc tatacacccc gcttcctta | 1020 |
| tgctataggt gatggtatag cttagcctat aggtgtgggt tattgaccat tattgaccac | 1080 |
| tcccctattg gtgacgatac tttccattac taatccataa catggctcta gacttaaggc | 1140 |

```
agcggcagaa gaagatgtag gcagctgagt tgttgtattc tgataagagt cagaggtaac    1200
tcccgttgcg gtgctgttaa cggtggaggg cagtgtagtc tgagcagtac tcgttgctgc    1260
cgcgcgcgcc accagacata atagctgaca gactaacaga ctgttccttt ccatgggtct    1320
tttctgcagt caccgtcctt gacacgaagc ttatcgatgt cgacctcgag tctagagggc    1380
ccgtttaaac ccgctgatca gcctcgactg tgccttctag ttgccagcca tctgttgttt    1440
gcccctcccc cgtgccttcc ttgacccctgg aaggtgccac tcccactgtc ctttcctaat    1500
aaaatgagga aattgcatcg cattgtctga gtaggtgtca ttctattctg ggggtgggg    1560 tgggcagga cagcaagggg gaggattggg aagacaatag caggcatgct ggggagtcga    1620
aattcagaag aactcgtcaa gaaggcgata aaggcgatg cgctgcgaat cgggagcggc    1680
gataccgtaa agcacgagga agcggtcagc ccattcgccg ccaagctctt cagcaatatc    1740
acgggtagcc aacgctatgt cctgatagcg gtccgccaca cccagccggc cacagtcgat    1800
gaatccagaa aagcggccat tttccaccat gatattcggc aagcaggcat cgccatgggt    1860
cacgacgaga tcctcgccgt cgggcatgct cgccttgagc ctggcgaaca gttcggctgg    1920
cgcgagcccc tgatgctctt cgtccagatc atcctgatcg acaagaccgg cttccatccg    1980
agtacgtgct cgctcgatgc gatgtttcgc ttggtggtcg aatgggcagg tagccggatc    2040
aagcgtatgc agccgccgca ttgcatcagc catgatggat actttctcgg caggagcaag    2100
gtgagatgac aggagatcct gccccggcac ttcgcccaat agcagccagt cccttcccgc    2160
ttcagtgaca acgtcgagca cagctgcgca aggaacgccc gtcgtggcca gccacgatag    2220
ccgcgctgcc tcgtcttgca gttcattcag ggcaccggac aggtcggtct tgacaaaaag    2280
aaccgggcgc ccctgcgctg acagccggaa cacggcggca tcagcagc cgattgtctg    2340 ttgtgcccag tcatagccga atagcctctc cacccaagcg gccggagaac ctgcgtgcaa    2400
tccatcttgt tcaatcatgc gaaacgatcc tcatcctgtc tcttgatcag atcttgatcc    2460
cctgcgccat cagatccttg gcggcaagaa agccatccag tttactttgc agggcttccc    2520
aaccttacca gagggcgccc cagctggcaa ttccggttcg cttgctgcgt cagacccccgt    2580 agaaaagatc aaaggatctt cttgagatcc ttttttttctg cgcgtaatct gctgcttgca    2640
aacaaaaaaa ccaccgctac cagcggtggt ttgtttgccg gatcaagagc taccaactct    2700
ttttccgaag gtaactggct tcagcagagc gcagatacca atactgttc ttctagtgta    2760 gccgtagtta ggccaccact tcaagaactc tgtagcaccg cctacatacc tcgctctgct    2820
aatcctgtta ccagtggctg ctgccagtgg cgataagtcg tgtcttaccg ggttggactc    2880
aagacgatag ttaccggata aggcgcagcg gtcgggctga acggggggtt cgtgcacaca    2940
gcccagcttg gagcgaacga cctacaccga actgagatac ctacagcgtg agctatgaga    3000
aagcgccacg cttcccgaag ggagaaaggc ggacaggtat ccggtaagcg cagggtcgg    3060 aacaggagag cgcacgaggg agcttccagg gggaaacgcc tggtatcttt atagtcctgt    3120
cgggtttcgc cacctctgac ttgagcgtcg attttttgtga tgctcgtcag ggggggcggag    3180 cctatggaaa aacgccagca acgcggcctt tttacggttc ctggccttttt gctggccttt    3240 tgctcacatg                                                          3250
```

<210> SEQ ID NO 16
<211> LENGTH: 4108
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 16

```
cagggtcgga acaggagagc gcacgaggga gcttccaggg ggaaacgcct ggtatcttta      60
tagtcctgtc gggtttcgcc acctctgact tgagcgtcga ttttttgtgat gctcgtcagg     120
ggggcggagc ctatggaaaa acgccagcaa cgcggccttt ttacggttcc tggccttttg     180
ctggcctttt gctcacatgc gcgttgacat tgattattga ctagttatta atagtaatca     240
attacggggt cattagttca tagcccatat atggagttcc gcgttacata acttacggta     300
aatggcccgc ctggctgacc gcccaacgac ccccgcccat tgacgtcaat aatgacgtat     360
gttcccatag taacgccaat agggactttc cattgacgtc aatgggtgga gtatttacgg     420
taaactgccc acttggcagt acatcaagtg tatcatatgc caagtccgcc cctattgac      480
gtcaatgacg gtaaatggcc cgcctggcat tatgcccagt acatgacctt acgggacttt     540
cctacttggc agtacatcta cgtattagtc atcgctatta ccatggtgat gcggttttgg     600
cagtacacca atgggcgtgg atagcggttt gactcacggg gatttccaag tctccacccc     660
attgacgtca atgggagttt gttttggcac caaaatcaac gggactttcc aaaatgtcgt     720
aataaccccg ccccgttgac gcaaatgggc ggtaggcgtg tacggtggga ggtctatata     780
agcagagctc gtttagtgaa ccgtcagatc gcctggagac gccatccacg ctgttttgac     840
ctccatagaa gacaccggga ccgatccagc ctccgcggcc gggaacggtg cattggaacg     900
cggattcccc gtgccaagag tgacgtaagt accgcctata gactctatag cacaccccct     960
ttggctctta tgcatgctat actgtttttg gcttggggcc tatacacccc cgcttcctta    1020
tgctataggt gatggtatag cttagcctat aggtgtgggt tattgaccat tattgaccac    1080
tcccctattg gtgacgatac tttccattac taatccataa catggctcta gacttaaggc    1140
agcggcagaa gaagatgtag gcagctgagt tgttgtattc tgataagagt cagaggtaac    1200
tcccgttgcg gtgctgttaa cggtggaggg cagtgtagtc tgagcagtac tcgttgctgc    1260
cgcgcgcgcc accagacata atagctgaca gactaacaga ctgttccttt ccatgggtct    1320
tttctgcagt caccgtcctt gacacgaagc ttatcgatat gggaaaaatc agcagtcttc    1380
caacccaatt atttaagtgc tgcttttgtg atttcttgaa ggtgaagatg cacaccatgt    1440
cctcctcgca tctcttctac ctggcgctgt gcctgctcac cttcaccagc tctgccacgg    1500
ctggaccgga gacgctctgc ggggctgagc tggtggatgc tcttcagttc gtgtgtggag    1560
acaggggctt ttatttcaac aagcccacag ggtatggctc cagcagtcgg agggcgcctc    1620
agacaggcat cgtggatgag tgctgcttcc ggagctgtga tctaaggagg ctggagatgt    1680
attgcgcacc cctcaagcct gccaagtcag ctcgctctgt ccgtgcccag cgccacaccg    1740
acatgcccaa gacccagaag gtaagcccac ctgggtggga tccagccatc ctcaagtggt    1800
ctctctcttg tgcatgtggg tgggccaagc agaaatcctg ccccatagtc tcctggctta    1860
caagtcagaa aagctccttt gcaccaaagg gatggattac atccccatct ctttgctaaa    1920
caaacatggg ctttggtgtc agacaaaagt gaagtcctgg cttctctcaca caccagctta    1980
gagagaaaag acttttaggt gaatgtggca ggaaagcgtg cttgctgggg caaaggcaga    2040
ttcattcttt ctcttcccag tatcagcccc catctaccaa caagaacacg aagtctcaga    2100
gaaggaaagg aagtacattt gaagaacgca agtagctttt tctcctttat ttataggaag    2160
tacatttgaa gaacgcaagt agagggagtg caggaaacaa gaactacagg atgtaggtcg    2220
```

```
acctcgagtc tagagggccc gtttaaaccc gctgatcagc ctcgactgtg ccttctagtt    2280
gccagccatc tgttgtttgc ccctcccccg tgccttcctt gaccctggaa ggtgccactc    2340
ccactgtcct ttcctaataa aatgaggaaa ttgcatcgca ttgtctgagt aggtgtcatt    2400
ctattctggg gggtggggtg gggcaggaca gcaagggga ggattgggaa gacaatagca    2460
ggcatgctgg ggagtcgaaa ttcagaagaa ctcgtcaaga aggcgataga aggcgatgcg    2520
ctgcgaatcg ggagcggcga taccgtaaag cacgaggaag cggtcagccc attgccgcc    2580 aagctcttca gcaatatcac gggtagccaa cgctatgtcc tgatagcggt ccgccacacc    2640
cagccggcca cagtcgatga atccagaaaa gcggccattt tccaccatga tattcggcaa    2700
gcaggcatcg ccatgggtca cgacgagatc ctcgccgtcg gcatgctcg ccttgagcct    2760 ggcgaacagt tcggctggcg cgagcccctg atgctcttcg tccagatcat cctgatcgac    2820
aagaccggct tccatccgag tacgtgctcg ctcgatgcga tgtttcgctt ggtggtcgaa    2880
tgggcaggta gccggatcaa gcgtatgcag ccgccgcatt gcatcagcca tgatggatac    2940
tttctcggca ggagcaaggt gagatgacag gagatcctgc cccggcactt cgcccaatag    3000
cagccagtcc cttcccgctt cagtgacaac gtcgagcaca gctgcgcaag gaacgcccgt    3060
cgtggccagc cacgatagcc gcgctgcctc gtcttgcagt tcattcaggg caccggacag    3120
gtcggtcttg acaaaaagaa ccgggcgccc ctgcgctgac agccggaaca cggcggcatc    3180
agagcagccg attgtctgtt gtgcccagtc atagccgaat agcctctcca cccaagcggc    3240
cggagaacct gcgtgcaatc catcttgttc aatcatgcga aacgatcctc atcctgtctc    3300
ttgatcagat cttgatcccc tgcgccatca gatccttggc ggcaagaaag ccatccagtt    3360
tactttgcag ggcttcccaa ccttaccaga gggcgcccca gctggcaatt ccggttcgct    3420
tgctgcgtca gaccccgtag aaaagatcaa aggatcttct tgagatcctt ttttctgcg    3480 cgtaatctgc tgcttgcaaa caaaaaaacc accgctacca gcggtggttt gtttgccgga    3540
tcaagagcta ccaactcttt ttccgaaggt aactggcttc agcagagcgc agataccaaa    3600
tactgttctt ctagtgtagc cgtagttagg ccaccacttc aagaactctg tagcaccgcc    3660
tacatacctc gctctgctaa tcctgttacc agtggctgct gccagtggcg ataagtcgtg    3720
tcttaccggg ttggactcaa gacgatagtt accggataag gcgcagcggt cgggctgaac    3780
ggggggttcg tgcacacagc ccagcttgga gcgaacgacc tacaccgaac tgagatacct    3840
acagcgtgag ctatgagaaa gcgccacgct tcccgaaggg agaaaggcgg acaggtatcc    3900
ggtaagcggc agggtcggaa caggagagcg cacgagggag cttccagggg gaaacgcctg    3960
gtatctttat agtcctgtcg ggtttcgcca cctctgactt gagcgtcgat ttttgtgatg    4020
ctcgtcaggg gggcggagcc tatggaaaaa cgccagcaac gcggcctttt tacggttcct    4080
ggccttttgc tggccttttg ctcacatg                                       4108
```

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 17

```
agctggcaat tccggttcgc ttgctgcgtc agaccccgta                            40
```

<210> SEQ ID NO 18

```
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tacggggtct gacgcagcaa gcgaaccgga attgccagct                            40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctaatccata acatggctct agacttaagg cagcggcaga                            40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tctgccgctg ccttaagtct agagccatgt tatggattag                            40

<210> SEQ ID NO 21
<211> LENGTH: 933
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgggaaaaa tcagcagtct tccaacccaa ttatttaagt gctgcttttg tgatttcttg      60
aaggtgaaga tgcacaccat gtcctcctcg catctcttct acctggcgct gtgcctgctc     120
accttcacca gctctgccac ggctggaccg gagacgctct gcggggctga gctggtggat     180
gctcttcagt tcgtgtgtgg agacaggggc ttttatttca acaagcccac agggtatggc     240
tccagcagtc ggagggcgcc tcagacaggc atcgtggatg agtgctgctt ccggagctgt     300
gatctaagga ggctggagat gtattgcgca ccctcaagc ctgccaagtc agctcgctct     360
gtccgtgccc agcgccacac cgacatgccc aagacccaga aggtaagccc acctgggtgg     420
gatccagcca tcctcaagtg gtctctctct tgtgcatgtg ggtgggccaa gcagaaatcc     480
tgccccatag tctcctggct acaagtcag aaaagctcct ttgcaccaaa gggatggatt     540
acatccccat ctctttggtc actctgcatt gcaaatttcc cctcccaccg ctatggacga     600
tgtgatgatt ggaagatgtt acaaacagt ggctaaacaa acatgggctt tggtgtcaga     660
caaaagtgaa gtcctggctt tctcacacac cagcttagag agaaaagact tttaggtgaa     720
tgtggcagga aagcgtgctt gctggggcaa aggcagattc attctttctc ttcccagtat     780
cagcccccat ctaccaacaa gaacacgaag tctcagagaa ggaaaggaag tacatttgaa     840
gaacgcaagt agcttttttct cctttatttta taggaagtac atttgaagaa cgcaagtaga     900
gggagtgcag gaaacaagaa ctacaggatg tag                                   933
```

<210> SEQ ID NO 22
<211> LENGTH: 858
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

| | |
|---|---|
| atgggaaaaa tcagcagtct ccaacccaa ttatttaagt gctgcttttg tgatttcttg | 60 |
| aaggtgaaga tgcacaccat gtcctcctcg catctcttct acctggcgct gtgcctgctc | 120 |
| accttcacca gctctgccac ggctggaccg gagacgctct gcggggctga gctggtggat | 180 |
| gctcttcagt tcgtgtgtgg agacagggc ttttatttca acaagcccac agggtatggc | 240 |
| tccagcagtc ggagggcgcc tcagacaggc atcgtggatg agtgctgctt ccggagctgt | 300 |
| gatctaagga ggctggagat gtattgcgca ccctcaagc ctgccaagtc agctcgctct | 360 |
| gtccgtgccc agcgccacac cgacatgccc aagacccaga aggtaagccc acctgggtgg | 420 |
| gatccagcca tcctcaagtg gtctctctct tgtgcatgtg ggtgggccaa gcagaaatcc | 480 |
| tgccccatag tctcctggct acaagtcag aaaagctcct ttgcaccaaa gggatggatt | 540 |
| acatccccat ctctttgcta aacaaacatg gctttggtg tcagacaaaa gtgaagtcct | 600 |
| ggctttctca cacaccagct tagagagaaa agactttag gtgaatgtgg caggaaagcg | 660 |
| tgcttgctgg ggcaaaggca gattcattct ttctcttccc agtatcagcc cccatctacc | 720 |
| aacaagaaca cgaagtctca gagaaggaaa ggaagtacat ttgaagaacg caagtagctt | 780 |
| tttctccttt atttatagga agtacatttg aagaacgcaa gtagagggag tgcaggaaac | 840 |
| aagaactaca ggatgtag | 858 |

<210> SEQ ID NO 23
<211> LENGTH: 153
<212> TYPE: PRT
<213> ORGANISM: Homo sapiens

<400> SEQUENCE: 23

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 24
<211> LENGTH: 462
<212> TYPE: DNA
<213> ORGANISM: Homo sapiens

<400> SEQUENCE: 24

```
atgggaaaaa tcagcagtct tccaacccaa ttatttaagt gctgcttttg tgatttcttg      60
aaggtgaaga tgcacaccat gtcctcctcg catctcttct acctggcgct gtgcctgctc     120
accttcacca gctctgccac ggctggaccg gagacgctct gcggggctga gctggtggat     180
gctcttcagt tcgtgtgtgg agacaggggc ttttatttca acaagcccac agggtatggc     240
tccagcagtc ggagggcgcc tcagacaggc atcgtggatg agtgctgctt ccggagctgt     300
gatctaagga ggctggagat gtattgcgca cccctcaagc ctgccaagtc agctcgctct     360
gtccgtgccc agcgccacac cgacatgccc aagacccaga aggaagtaca tttgaagaac     420
gcaagtagag ggagtgcagg aaacaagaac tacaggatgt ag                        462
```

<210> SEQ ID NO 25
<211> LENGTH: 158
<212> TYPE: PRT
<213> ORGANISM: Homo sapiens

<400> SEQUENCE: 25

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Ser Thr Phe Glu Glu Arg Lys
145                 150                 155
```

<210> SEQ ID NO 26
<211> LENGTH: 477
<212> TYPE: DNA
<213> ORGANISM: Homo sapiens

<400> SEQUENCE: 26

```
atgggaaaaa tcagcagtct tccaacccaa ttatttaagt gctgcttttg tgatttcttg      60
aaggtgaaga tgcacaccat gtcctcctcg catctcttct acctggcgct gtgcctgctc     120
accttcacca gctctgccac ggctggaccg gagacgctct gcggggctga gctggtggat     180
gctcttcagt tcgtgtgtgg agacaggggc ttttatttca acaagcccac agggtatggc     240
```

```
tccagcagtc ggagggcgcc tcagacaggc atcgtggatg agtgctgctt ccggagctgt    300
gatctaagga ggctggagat gtattgcgca cccctcaagc ctgccaagtc agctcgctct    360
gtccgtgccc agcgccacac cgacatgccc aagacccaga agtatcagcc cccatctacc    420
aacaagaaca cgaagtctca gagaaggaaa ggaagtacat ttgaagaacg caagtag      477
```

<210> SEQ ID NO 27
<211> LENGTH: 137
<212> TYPE: PRT
<213> ORGANISM: Homo sapiens

<400> SEQUENCE: 27

```
Met Ile Thr Pro Thr Val Lys Met His Thr Met Ser Ser His Leu
1               5                  10                  15

Phe Tyr Leu Ala Leu Cys Leu Leu Thr Phe Thr Ser Ser Ala Thr Ala
                20                  25                  30

Gly Pro Glu Thr Leu Cys Gly Ala Glu Leu Val Asp Ala Leu Gln Phe
            35                  40                  45

Val Cys Gly Asp Arg Gly Phe Tyr Phe Asn Lys Pro Thr Gly Tyr Gly
    50                  55                  60

Ser Ser Ser Arg Arg Ala Pro Gln Thr Gly Ile Val Asp Glu Cys Cys
65                  70                  75                  80

Phe Arg Ser Cys Asp Leu Arg Arg Leu Glu Met Tyr Cys Ala Pro Leu
                85                  90                  95

Lys Pro Ala Lys Ser Ala Arg Ser Val Arg Ala Gln Arg His Thr Asp
            100                 105                 110

Met Pro Lys Thr Gln Lys Glu Val His Leu Lys Asn Ala Ser Arg Gly
        115                 120                 125

Ser Ala Gly Asn Lys Asn Tyr Arg Met
    130                 135
```

<210> SEQ ID NO 28
<211> LENGTH: 414
<212> TYPE: DNA
<213> ORGANISM: Homo sapiens

<400> SEQUENCE: 28

```
atgattacac ctacagtgaa gatgcacacc atgtcctcct cgcatctctt ctacctggcg    60
ctgtgcctgc tcaccttcac cagctctgcc acggctggac cggagacgct ctgcggggct    120
gagctggtgg atgctcttca gttcgtgtgt ggagacaggg gcttttattt caacaagccc    180
acagggtatg gctccagcag tcggagggcg cctcagacag gcatcgtgga tgagtgctgc    240
ttccggagct gtgatctaag gaggctggag atgtattgcg caccctcaa gcctgccaag    300 tcagctcgct ctgtccgtgc ccagcgccac accgacatgc ccaagaccca gaaggaagta    360
catttgaaga acgcaagtag agggagtgca ggaaacaaga actacaggat gtag         414
```

<210> SEQ ID NO 29
<211> LENGTH: 195
<212> TYPE: PRT
<213> ORGANISM: Homo sapiens

<400> SEQUENCE: 29

```
Met Gly Lys Ile Ser Ser Leu Pro Thr Gln Leu Phe Lys Cys Cys Phe
1               5                  10                  15

Cys Asp Phe Leu Lys Val Lys Met His Thr Met Ser Ser His Leu
                20                  25                  30
```

```
Phe Tyr Leu Ala Leu Cys Leu Leu Thr Phe Thr Ser Ser Ala Thr Ala
             35                  40                  45

Gly Pro Glu Thr Leu Cys Gly Ala Glu Leu Val Asp Ala Leu Gln Phe
 50                  55                  60

Val Cys Gly Asp Arg Gly Phe Tyr Phe Asn Lys Pro Thr Gly Tyr Gly
 65                  70                  75                  80

Ser Ser Ser Arg Arg Ala Pro Gln Thr Gly Ile Val Asp Glu Cys Cys
                 85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Tyr Gln Pro Pro Ser Thr Asn Lys Asn Thr
130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys
        195

<210> SEQ ID NO 30
<211> LENGTH: 588
<212> TYPE: DNA
<213> ORGANISM: Homo sapiens

<400> SEQUENCE: 30
atgggaaaaa tcagcagtct tccaacccaa ttatttaagt gctgcttttg tgatttcttg      60
aaggtgaaga tgcacaccat gtcctcctcg catctcttct acctggcgct gtgcctgctc    120
accttcacca gctctgccac ggctggaccg gagacgctct gcggggctga gctggtggat    180
gctcttcagt tcgtgtgtgg agacaggggc ttttatttca acaagcccac agggtatggc    240
tccagcagtc ggagggcgcc tcagacaggc atcgtggatg agtgctgctt ccggagctgt    300
gatctaagga gctggagat gtattgcgca cccctcaagc ctgccaagtc agctcgctct    360
gtccgtgccc agcgccacac cgacatgccc aagacccaga gtatcagcc ccatctacc    420 aacaagaaca cgaagtctca gagaaggaaa ggttggccaa agacacatcc aggaggggaa    480
cagaaggagg ggacagaagc aagtctgcag atcagaggaa agaagaaaga gcagaggagg    540
gagattggaa gtagaaatgc tgaatgcaga ggcaaaaaag gaaaatga                  588

<210> SEQ ID NO 31
<211> LENGTH: 402
<212> TYPE: DNA
<213> ORGANISM: Homo sapiens

<400> SEQUENCE: 31
atgggaaaaa tcagcagtct tccaacccaa ttatttaagt gctgcttttg tgatttcttg      60
aaggtgaaga tgcacaccat gtcctcctcg catctcttct acctggcgct gtgcctgctc    120
accttcacca gctctgccac ggctggaccg gagacgctct gcggggctga gctggtggat    180
gctcttcagt tcgtgtgtgg agacaggggc ttttatttca acaagcccac agggtatggc    240
tccagcagtc ggagggcgcc tcagacaggc atcgtggatg agtgctgctt ccggagctgt    300
```

```
gatctaagga ggctggagat gtattgcgca ccctcaagc ctgccaagtc agctcgctct    360
gtccgtgccc agcgccacac cgacatgccc aagacccaga ag                     402

<210> SEQ ID NO 32
<211> LENGTH: 1505
<212> TYPE: DNA
<213> ORGANISM: Homo sapiens

<400> SEQUENCE: 32
gtaagcccac ctgggtggga tccagccatc ctcaagtggt ctctctcttg tgcatgtggg    60
tgggccaagc agaaatcctg ccccatagtc tcctggctta caagtcagaa aagctccttt   120
gcaccaaagg gatggattac atccccatct ctttggtcac tctgcattgc aaatttcccc   180
tcccaccgct atggacgatg tgatgattgg aagatgttac aaaacagtgg ctaaacaaac   240
atgggctttg gtgtcagaca aaagtgaagt cctggctttc tcacacacca gcttagagcc   300
cttggcaaat aatgtgatgt acccaagcct cagtttcatc agtaacattg gataataat    360 aatatctacc acatcagttt gttgtcaaaa ttaagtagct catgcatata ctttgagatg   420
cttttcacat gcctgcataa agtaattgtt ggaccatcgt taatgtctgc cataattgca   480
cttaataaca agcttgtaa cctttcaagt tctgagattc tacaatcttc caagaaaat    540 aaaaggctaa tgggaactat tcaaaattca tattcagtag caagcataat taaacatgaa   600
acattaaaaa tagaaatttc tgtttggcta taagaatgcc tagacatttg taatgatcaa   660
aatctgcagg catcatttc taagagctag actgtaaaca aacctcagag gtaccaacta   720
tgccatcagt agtacataaa acatctgatg cacatttagt cacttgatcg atttctcttg   780
aatgagtgaa cgaatgaaca atgaatata agagattaaa atttttagcca ttaagtagaa   840 agaataagaa ctaaagagaa ggtaaaggag gaaaaagaga aggcaaggaa gttgagtaag   900
ggaagaaata gctctcgttt aagtattttg gggactctgt tgaaaaaaga aatgccaaca   960
tgtggtttta atctttggag ctagaactaa taatattgtg caaaagcaca agatgagaga  1020
tcaagaagtt caccatgaca ccttcgctgc ttcctggtct taaacctcag ctgaggctgg  1080
aagaggacca tggtggctta ttggagatgt gaccccaggg agcccctctg aaggatggaa  1140
ggggactggg caagacccaa cacacacaga acacagtagc cactggccag gcaggaagca  1200
aggatctcag aaaagacttt taggtgaatg tggcaggaaa gcgtgcttgc tggggcaaag  1260
gcagattcat tctttctctt cccaggtgac ccagcgcctc ttggtttcta actggggagg  1320
gggtaggtgt caagagatga gtcccaaagt tctggaatgg tgggtcttgt gactgaggtc  1380
tagacccctc tccagcatga gtgctgtctc ctgcatcata tggagcctgg gcattctgag  1440
ctcattcaaa gggacaccat gggaaccact tgttctcaat gcaattattt ttgtgatgtt  1500
tacag                                                              1505

<210> SEQ ID NO 33
<211> LENGTH: 75
<212> TYPE: DNA
<213> ORGANISM: Homo sapiens

<400> SEQUENCE: 33
tatcagcccc catctaccaa caagaacacg aagtctcaga gaaggaaagg aagtacattt    60
gaagaacgca agtag                                                    75

<210> SEQ ID NO 34
<211> LENGTH: 15250
```

```
<212> TYPE: DNA
<213> ORGANISM: Homo sapiens

<400> SEQUENCE: 34
aggacaggag gattaaacag acagaggcaa ggatgatgag agaggagcag acagcaagaa      60
tgaaaagcag aaaatacaat agaggaaatg aagaaaagta ggcctgctgg agctagatga     120
tgatgtgatg gaaatagaag taaccttta  gagaatctcg ctaagaaaca tggagaaaac     180
ggaaaagaaa aatgtaatgc cctagaaagc gcaaagaaag acagtggcaa aaatgaaaaa     240
aaaaaataaa aattataaaa gaggcaaaaa aagacacact attctctgcc tctaaaacac     300
aattaaataa aagaatttaa ataaaaatta aggcttctat atgcattttt aaattttgta     360
tgaatctgtt atggaagaat tgcctatgtc aatatatgtt cagagttaaa tattagcccc     420
aaatgctcag caagactgaa ttgtgtcata gaagttccca gattcccttt tcccgcaatg     480
tcattggagg ctgcatttct tagtcaagtc cagggtttag gccaaagggc atccggtatt     540
gcctaaaacc ctgtgaggtc tgtgaggtaa cttttgagaa gaggtcactg cactcttcat     600
cttttttgca ctttggaatc agatataaaa gatgtataag tttgctaggg ctgccataac     660
aaagtatcat aggctaggta gtttaaacca cagaaattga ttttttcata gttctgggag     720
ttgaaagtcc aaaatcaaag tatcagccct tgcaagggcc ttagagaagg ctctgtcatg     780
ggctcctccc ctcggcttgt aggtggcctc cttcttctcc ccctgtgtct tcacttcatc     840
ttccctccat acatatctct gtgtctaaac atcctctgtg tgaaacaaca ccagccaggt     900
tggatttggg cccaccccac tgacctcatt ttaacttaat tatctctgta aagactctgt     960
ctccaaatac agtcatattt tgacgtactg ggagttaggg cttcaacaca tgaatttgga    1020
cacaattcag ccagtgacag aagacttctg atctctgatg ataaccactg cattttgatt    1080
acagctccta gaaaacactc ccctccacca ccccaccaca gatctatttt tatatctgaa    1140
accctgagtt tctgctccat gagaacccca ggaacatact atgttagatc tggaagaagc    1200
ctcagaaatc cccttatttt gaagactagg acactgagat ccagaagtgg gtaaagatgt    1260
gcttgggttc taagctgctc ttcttttggc caggagacaa cagcacataa tcaaagtggg    1320
tcaactaaga aagaattcca gaaggaaaag agagggcaga aatgaaggga gagaatgaga    1380
gcaaaagtgc tggatttccc tgagggtgaa gaaaagttaa atagaatcac agaattcaga    1440
ttttagagat cttctccttc agatcccttg gtttaatcag taggattggg gtcttcatag    1500
ataataaagc aaaaactctc gccatcctcc aagttgtgaa ttagaagagc tgagaaaggg    1560
tacaagacga agttctcta  ccaaacaaat ggtgacattt tggggtaaga atatgactaa    1620
cccagaagtg aagcatttca tccaagtagt ctattttgaa gatgtcatgg tataaaggaa    1680
cctcctttct gcctggtcct ccatgcctct gccatgcttt ttactccagg atcaccctt     1740
ctagtggttc actgaaaacc caggattact taaatatgat ggacatgttc acggctcaat    1800
ccaggaggaa aaggtcgaac tgaaagcatg ccaaagcccc acatgggagc caagccactg    1860
ctgctgtggt tgcaaagtgg atcctggctt atcagagcag agagaagcca ggctcgtgcc    1920
ttagcccaag tggccagtca ccttattcag gagatactaa gttctccagc taagacatcc    1980
atgctttggg accagctgca gacagaagcc aattcctact acaaccatca ccttagagta    2040
gcatatagac acagatggct cttcaaagga ccacagttcc atggaataac taagaattca    2100
tgtcctgtgg aaaggtttga ataaactata attatacca  atcataaatt tcattcaaga    2160
agaactaaag caaaggcaaa gacagagaga agaaggaagg aaggagggag ggagggaggg    2220
```

```
aaggaaggaa ggaaggaagg aaggaaggaa ggaaggaagg aaggaaggaa ggaaagggaa      2280
ggaagaacaa aaagactttc tagttaaaga atgcttaact agcaaactat gtactataag      2340
acagttcttt tcggaatgag ttttatcaac tctaaagcaa ttatcttgaa tgcctacatg      2400
tgattactga ataatatgaa ccaagaaaac agaaagaatc tatattatct ttccatttcc      2460
ttctttccag tatcaatacc caagcctcta gtgatacatg gcatataatg ttggatggat      2520
ggatggatgg atggatggat ggatggatgg atggatggat gaatggatgg ttggatggac      2580
aaatgagtaa cataggctga tgaatagtgg tagaaagaca caccataaaa acaagtggca      2640
cttctgagat gaaatgattc ctattctcct acacaagaca gtgaggcaag tacagagtaa      2700
aaaaggaaag gcataggagc tatgcttata caagtattgt atgtttggaa tttccttcgc      2760
tggccaaatt gaaattgttc aaggacctat tgctacaggt ggcaactggc taagaatttc      2820
atagtgaata ttatacacct attactcccc ttaatgtttc tttgaagtaa gcagaatatt      2880
aataatcatt taaaattcca gtgtttcaac ttcaattgtt tcctagggca aattgataat      2940
tgtgtgtaaa actaattgga atatgtatgg aataatcatc ctgaaataaa attggtgaaa      3000
agtatttgtt attgggcatc tacaatgtgc aaacctctgt actaggcatg aacaagagtt      3060
ataagcattg gagaggctaa aatatagtcc ttaaggctgg gcacagtggc tcatgcctgt      3120
aatcctagca ctttgggagg ccaaggcggg cagattgcct gagctcagga gttcaagacc      3180
agcctgggca acatagcgaa accccatctc tactaaaaat acaaaaaaat tacctgggca      3240
tggtggcacg cacctgtaat cccagctact caggaggctg aggcatgaga attccttgaa      3300
cctgggaggc agaggttgca gcgagccgag atcctgccgc tgcatcccag cttgggtgac      3360
agagtgagac tctgtctcaa aaaaaaatta aataataaat aaatagtaaa atacagtcat      3420
taagagtaca aaatgtagat tcagactacc tgggttcaaa tcttggctct tacttgcatt      3480
gtggctttgg gcagatcatg taacttatgt gtgcctcagt ttcctcatct gttaaatagg      3540
ggcaacaact gaatctacct tattcagttg ttgtgagggt ttattgagat tgtgtgtgtg      3600
tatgtgtgtg agtgtagtgt gtgcatgtgt gtgtctgtgc aaggagtggg aggtgtatat      3660
tcagagacac atattacagc acttaaaatg gtatctagca cttagtaagc attattcaag      3720
ttttagttaa cattattttta cttacctctg aaaattggag ctatgtgaaa aagaagttgg      3780
tctcctgaag tagaagccag tcttgtgtca ccaaaaactt caagcccaag cttgccaacg      3840
cttttccatg atgtggtagt agagtttcaa gcatgtggta ggataagaga actcaatgac      3900
ctaagaacca ttccaaccca gagaacccct ggttctatga ataattccaa cttaaatagg      3960
tagcttggct ctcccaagtg agagccattg cttctgtttc cgggtcatat aatgaacttt      4020
cagaaaacca ccattttttct caaccagtta aaattaagtg taatacgtgc tttcatttca      4080
tggtgcctgg ggaaaattta attgtagtat gaactccagt tattggtagt cttaagtaaa      4140
attgccaaaa taaatagaaa tgcaggatat ttctgggctc acacagcttc cgggacactt      4200
tagtttcttg ggctgccaat ccagtgcctt tcacaagcat ttgatctttt ttcaaacatc      4260
tcttgaaaac aaacaaaacc tcacacagct tctaatgtgt gcactgttcg aatgtaaggg      4320
tggaaaagga ggcaaagaaa tgagctccca aagagcaatt ccccttctct cgcctccatc      4380
ccttgacgac ctccctccca ctaaagggaa acattgtttt cttaggtaat aaattctgca      4440
atttctcaag tccattaaca tccactgggc aagatgagat ctattctttt tatttgccca      4500
taggaaaaga atagtgcttt tttgcaatat tcactagata acacagagtt gacttttaat      4560
ccaagggcaa cattgatagt ctctagttaa aggggaagcc ttcaggagca atgaaaagat      4620
```

-continued

```
taatagtttt agatgaagca gaatccaaat ccctttttat gagttttgaa atatccagtt    4680
tgtatgctca cctcaatact taaagcccag ttactgattc ctttggccta agcaagacag    4740 gtcaatttt aaagagggag tagctgaggt tagcaaaaat tctccaggtc cacaaaactt    4800
ccagacctgc aaggtgaaaa tcagcttttc tgtcatccct aaaggcctaa ctggaatcag    4860
aacttttccc tgatgcccac atatttggag gtccttttt aatgggactc cttaatgcct    4920
ttagtgccat cccattttca tccagtgtcc aaaagaaatg atttaaaaat ataaacgtat    4980
gtttaaattc cagaagagag aaatggagat tgagaacaat agggaaatga tgagagctat    5040
gggaaaagag gtttatgagt ccatgtctga ttcttccaga gagcccctaa gaaagttctt    5100
atcataccag gaactcaatt ataactttca ttgcctattg ttagatgagt aacaggagct    5160
agaaaacatt ttggaaattc ccatctttat tttttaact aatatgatta tagttttaag    5220
aaccattggt caagaagcta acttttaaa aagtggaagt atgatggtta gaaataagaa    5280
tgctaaaggt gcatcaagct gattttaatt ctaaatgtcc ttggcagcaa tttagaatct    5340
gtaataaact acaccaaaca gttttgaggg gaaggggatt agtttctccc cttccttcgt    5400
gtgtgtgtgt gcgcgtgtgt gtgtgtgcac cttgtgttc tagcattgtt gcacccatta    5460
cagagctggg gggaactatt ttccaaaatt ataggtgaga acagtttctt ggattgtctt    5520
tcagtgaagg taaattcctc tgtaaaaact aaccatcatt cagtaaaaac tgcaggattc    5580
ctttgtcttc tcaaaagcct gtttctcatc ctaaattaaa aattattcag gaaatagaga    5640
ggacattatt ggagggggtgg aaataagttg gttttctttt tattgtatct tttgaggatc    5700
cagggacttc taccatttcc catctaacat acagagaagg attctctagg tccctgtcta    5760
tagactgcag taacttttct atagaaccaa tttgcaattt tagaaatttc taggtctaat    5820
tattgaccca ttacaaccaa aggtcaatgc atccagccaa tcttccttct atcatcccct    5880
gcccttactt ctattaggga ctgggattac aggcaaaacc catcaaatgc ctcttctacc    5940
actttcccat ttcttaacca ttagcctcta acttcctcta ttcagtttct catatgcttt    6000
catgcccatt gggtcagata aaggaacatt catttatttg agtaggcatc tgttatgatc    6060
actccggaaa aaagatgaca atgggttacc ttgtcctcct gggcttctct aactgacatg    6120
gtcaaaatgc ccatatgaag ataagatgtt aagagcaaga tttatgaaaa gctgagtatg    6180
atggcagctc ttgtctcata aaataactcg aaagttccca gtgaaagacc aagaaatttt    6240
acatcaaacc caaaccggcc aaatggtcca agcttccaag ctgggatcca tggctaaagt    6300
ttctacaaaa ttctgggtac aatgtataaa cattcacttg gggctttctg tctagccagc    6360
accaagaggt caagtaatca aggaccaact agccctgcca tctgtgaaaa tatgtgctat    6420
tttcacggct ttagttcaca attatggcaa gacaaaagtt ccaaataatt aggagcaaga    6480
ccatggcagg ttgacggttg agtaaggttc tcaatcagcc gacaattgta gagttgggga    6540
tgtgcaatgt ttatgtcatg gtgtaagtat gtggcatgct tgactagctt gtgaggcact    6600
ggaagactag aaggaatgaa aaatatgaat gaatcaataa atgcatagta taattactgt    6660 tatttttgtca gtattgtttt acctaggtca ctattgaatg ctctgatttg tctctttata    6720
aataataata tgttttcttc ttcaaaagaa cactaggatg aaggtagagg tgcttttggc    6780
acaatgccac aattctgatt tttttaaaac tgtatgcatg cataaaatgt tcttgagcca    6840
ttctctgcct tggaatagca ctggctggca ttctgcatgt ttacttttat atgctgaagg    6900
cccccatcaa cctcaaacag aggcaaatca atttaacttc tcatagtgtt attttgttca    6960
```

```
tcctaaaagt tcaagagagc cttccaaact tccaaatttt ctctcaattc agtgaggagg    7020
aaaattcaga acacagcatt tgaatgttct gcccagattt gtcacacaca caaggaatga    7080
gtgaaagagg gcaacaccct ttcctcctaa ccctgtgaac tcatcactat tgcattgaaa    7140
tgacaccaaa aggtaaaaac cctaggcctc acatctccca agaacactgc aataggagtt    7200
actgcataca ccagtttaag taactctagc ataaattgta tgtcagatga aacaatggca    7260
ttttggaggc ttaagagaaa aagaataatc aaatccagtt tttaggtact aatgtgctga    7320
atctttagca catagcagca aaattgctag aatctggtgt ttcactttt aaaataccac    7380 atttgaacct ttcagcaatt ccaaaatcaa ctccctctgc gaaagataat aagcttaaac    7440
attttttaaa tttaaaaatg taacacaaac aaacagctaa gcaaacaagc tgcccataaa    7500
atcaacagtc tggggagccc tgatcctgaa gtattttaca acatccttca tgactattaa    7560
aggcaacata aacacctctt gtcagcaagg gaaactaccc ttggcatttt ttttctttg    7620 ttccccaggc ttttaaacca ttttgataga gattttttac atcacaggca gaaatatttg    7680
aaatagagtc aggtggtagt ctttaaaaga gtaagaaagt tgctaagtca agataatctt    7740
ggaataaagt cctctgattc ctggggattc ctagggatgc cccagtcact agaaaacaga    7800
gctgtaagtc cactctccca gcactcaacg gagctccgga aaccaaggag ctagctactg    7860
tttccccaca ttcagccaga gaaagggcag cactctagca tgcaaactgc tttgacaata    7920
gtaacaatta aaaagtaaat taaaaagaat cataatagct gatattgatt aggtacttgc    7980
cctgtggcaa gagctatagg gaatcacctc atttaatctt cacatgaagc ttgcagagtg    8040
agtaccacaa ttatcactat tgtatagaca ggaaaactca ggctgagtat ggctaagtgt    8100
cttgccaacg tcttgggcta acaagcggtc aagcagaatc caaacccgag atagatagac    8160
cacagtgtgc taatcaagca ctgcactctc tcctgcattt cttagttgat atttaccata    8220
tacaatctgt cacttgtatg agatggcagg gggttctgtg ctatttgtcc ttgtagagaa    8280
taccacagga agaaagtaag cagccatgca atatttgctg ttgacctgaa ctccattcca    8340
tcattcctgc aggaaattcg catccattaa atgagcattt cctggtttgc cactttgctc    8400
aaacactttg cttggatctg gagaggatat agaagtgaag gaaatatgct acctgctctc    8460
aaggaactta tgttttagtg gagagacaaa catgcagaat ttactctaca gaacatcaat    8520
gcttgagcaa atgtagaccc agagagggct cttacagcac acaagccaga acagactgat    8580
ggtgctaaca attaggttca aggttttttct aaacagtaga ctctcctgca tacaactata    8640
ccgcatgcca ggtaaatgac tgagggttat tacatccaat tataacacca ctgtgatgta    8700
ggtgctctta ccccacactt tcattttaca gaagaggaaa ttgaggacag cacaatgtag    8760
tgattatcaa aggtcacacg actactgtgt gggagagcta ggatttaaac cagatgcata    8820
agatgaggtc ctccaagaaa cagaagatga gaaggtgtta aatgagcagg ggtttatta    8880 gggggaatta atgtgtgaac agaaatagg gaggatagg caaagccatca gattgcaagg    8940 caagcctaac cccaagggaa ggagagagag agagtagatt ggttggaaac atttttggtg    9000
ggtctatggt ctaaggaaag ttcagcaaag tcatcatgga gtttttgagc caaagttggg    9060
caatacagtt gcccaacaaa tttctgtgtt tctcagaaat aggtctgcct caatgtcccc    9120
accatacttg gtcactggct cttgggaggg gcctgccctg ttccaatcca ctagagccaa    9180
agaagagccg ttgtactggc aggggggtggg ggaattccta caaccacata aaaagtgggg    9240 tgaggttttcc agaaaaaaac gtgatgctgg gctaaccaaa actgtgtcca gtaagtacat    9300
atccctcact ctgttaaaga agcagccaca taaacaagga gtacacgttt ctcaaaatgt    9360
```

```
gcaccttgtt ctttggtttt gaagtcacat cccaaagtgc tgagtagatc gcatgaccct  9420
cgctttgcct ggctgccaga gaggaaaggc tgatccaact ctcctggaat ttgaacttgt  9480
gattccctga agtaaagaga tatcaaagtt gatactgaga catctaaatc atcctccacc  9540
atttcacatg tccccaggcc aagccagcaa aattgctata gcacatccct ttcaacaggt  9600
aaagggctga tatctgagcc ctcttccaa tcatccactg ctcttttctt ctcattttgc   9660
ccttttggg agcaggtcaa tgctgagtta gtacttatg ctgtacaata agctgctgat    9720
attccatgct ggacagaatt ttcccagtat ttttatagaa gtgccaggct tttcctagac   9780
ttcatgtcat acaatactta acttgtttgg agtgggtgga gatggaaaca tagtctattg   9840
aaaacatcac tgcttcctcc ctgaagttta aagagcctat ttttatcctt ttagattcta   9900
tctctcaggc aaaatctcat aaagataagt ggggaggaaa aaaagggggt tataatacct   9960
agggagtttg cttttgctaa ttgaatactg tgctcctaga cttctataaa taccattaca  10020
aatgggtccc agcttgtggt aatactcacc ctcctcattg agtcttctgt cccatggcac  10080
agcctttccc tccaaactag catctacccc catctggaag catgggcagc tcatgatatt  10140
atcaactatt gctattggaa agtgatttgg acttgaaagc actagatatt ttttacctct  10200
tggggaggca gtttagcaga gtggttaact ggtgagctcc agaatcagaa ggaataggtc   10260
caaattccaa ccactattac atctccatca taagaaatta ggcaagttgt ttatcctaag  10320
tttcagattc cttaaagata aaacagtcaa gacagtagta cttatccctg agagaagtat  10380
aggaaacaag aaaatatatg caatttacat acatactaca atccccagca catgacaaat  10440
gttcaagtaa tgggaactgt tattatttta gcccttgtc tatcagtttg ttcctctgtg   10500
acctcaagca cattactaaa tgttagcgag cttcagcttg tacgtgggac tgacaggaat  10560
aacaccgcat cacctcatgt ggtgattgta aggattcagt gatattattt tgtaaactgt  10620
aaagcctttg caaatgttaa gcaagattat tattattgcc gttgttatta gtcctcagtg  10680
atctttttt ttttttttt ttttttttt tttttttttt ttggagacag agttttactc    10740
tgtcgccaag gctggaatgc agtggcacaa tctcagctca ctgcaacctc cgcctcctgg  10800
gttcaagcaa ttttcctgcc tcagcctcct gagtagctga actacaggc acacgccacc    10860
acaccaggct aatttttgt atttttagta gagacggggt ttcaccatgt tggccaggct  10920
ggtctccagc tcctgacctc aagtgatctg cccacctcgg cctcccaaag tgctgggatt  10980
acaggtgtga gccaccacac ctggcacagt aatcttaatt gaaaagtctg tggatagctt  11040
tccaaaggaa agcttggagc ttggataaga accaagagat aatgggagaa ggtgaatggc  11100
ctcttcaggg cctttctag cacctaaat atgcgtgtct gtccataatg ggtaatcata    11160
tatatcacaa atcaaaccct ccacaaactt atttcctaat gtgtttgtta acctttcctt  11220
ctaaagggta aacttcttta accaaccca gtgagctgga ggatcaatgt tttcttaata    11280
gtcttacctt cgttggtgtc aataggaaac agtatttact cactactgtt ttccttttaa   11340
aaatctgtct agttgcatac tagaaacagt ttcagctggt ttgtttgtat tggacaagct  11400
gctgaagtga aaagtttttg cttgactgaa tgtgagacag tttcataact cttcaagaag   11460
tgcaccaaag gtgggtgcca gctctgatga cggctgcttc taacatgcct ccacttgccg   11520
cccattgtca agggtggctg gcgtaattaa gttaagacaa tgagcaaagc aacagatgca  11580
actgagacct agtccctgag tgcttttgtt ttgtcactgt cattgtctgc aacaaagaag  11640
tcacatgtga cagcctggga agagagccaa atgcaaacca gacgatatcc cagctggttt  11700
```

```
gaatggcctc caccgtgcac gtgtgtgcat gggaatcatg ctacttggta cagcatctgc    11760
ttcactcaag tgagtttcag cccatggctt tgctgtgatg ctgagacaga cccagaagaa    11820
acagaccagg gaatccctcc gctcagactt tacactttat accttgtgct tgagagaaa     11880 agaaaaagaa tctctctatt ggagacaaaa aataggatgt atgtggttgg tcaatctaac    11940
ctcaattctt tttgctatag ccccccgcta atttaaagag tgaagcatag atggtatctt    12000
aatgttttct tgtagaaatt tgggattaat ttggcttgag aggaagaatg gagattaaac    12060
gctttatgag gctttctttt aatttgttcc catttcattc ctgaatattt tcttagtttg    12120
ggcattgcag atgtttaaag aacttcttat tttgagctgg tatgcctctt aaacagaaaa    12180
acaaaaggta aaattcaaat tagtgtgttt ctccgcctgt taattaattt ggttagtagt    12240
taggcagaga gatggcatcc ttaataatat ctattttgcg ggtttgatca gctacagacc    12300
atcaacagtg ttgattgaga attgaacaaa aacatttcaa ggagtttggg aacattaggg    12360
atgctattct gtggcccat gtgtccttct ctcattttc tagagaactc ctataagaaa      12420
gcagaacacg gccaggcatg atggctcatg cctgtaatcc cagcacttca ggaggctgag    12480
gcaggcagat cacctgaggt caggagttca agaccagcct ggccaacatg gtgaaaccct    12540
atctctatta aaaatacaaa aaattagctg gcatgatgg cgcgtgcctg taatcccagc     12600
tacttgggag gctgaggcag gagaatcact tgaactggga ggcaaaggtt gcagtgagcc    12660
tagatcacac cactgcactc cagcctgggt gacagagtga gactccaact caaaaaaaag    12720
aaagaaagaa agaaagaaag cagaacccaa tggaagatta agaacacaca tttagcttac    12780
gcctgtaata ccagcacttt gggaggccaa ggcgggtgga tcacaaggtc agaagttcga    12840
gaccaacctg gccaatatgg tgaaacccca tctctactaa aaagtacaaa aattagccat    12900
gcatggtggc aggcgtctgt aatcccagct actacagagg ctgaggcagg agaatcactt    12960
gaacccggga ggcagaggtt gcagtgagct gagaacgcgc cactgcactc cagcctgggt    13020
gacagagcga gactccatct caaaaaaaaa aacaacaaa aaaaaacaaa acacaagttt     13080
actgggaact tagcagtaga tgctttgcac cacaacaaat gtatcttaag tggtcttttg    13140
tgatatttga gggaaagtgc cagaatttaa aacaaatggc atttcaagtt attctataca    13200
aatgcccagt ttcttttctac catcttttttt tccttttgc agtggtcact gagctatttt    13260
agtgaatgtt tttacacaat gatgccatct tccttctact cagtcagtac aagatgttga    13320
ccatcgactc ataaaacact agctaccttt catgaaggac ttggtgataa ctctcatgtt    13380
ccaagtagaa ccggaaaaca tgtgtaagaa aacctgccga tccctatggg ccttggccaa    13440
taggtattat tcccaagggg tggcagttta tcttttttccc cagccttcat attaaaacct    13500
ctcaccttct ccaggtctca ggtctgtgta atctcaaatg tgctttagct cctcacaata    13560
ttgtaactgt gtgggtgttc attaccttag ccagaagaca gtttacagat tccaggtctc    13620
atggagagaa cttttgtttt tggttatgaa cctcactgta taccaataat tatccattac    13680
atccttctgt agagggctct ctggctagag ataaaaccaa aaaagaagt acctcaggtt     13740 tatgcatata aatgccagtt cctccttgat tttatttcaa aactcctgtc tacatacttt    13800
gcaatttaaa tacattcaag gataaagtaa taactgtagg aaaagtatta taatataatg    13860
acttagttct gcacatcaca aggggtccc tcatactcat tcattcattt cactcatttt     13920
acagatattt attgagcacc tgcaataacc tgcacactgc tctagacact gggactataa    13980
cagtaaacag acagatacat ctctggtctc acagggcttc tattctaagc aaaactcaat    14040
atccaggccg ggtgcagtgg ctcatgcctg gaatgccagc actttgggag accaaggcca    14100
```

```
ggcagatcac ctgagcccac tagttgaaga ccagcctggg caatatagca aaacccccgtc    14160 tctacaaaaa aaaaaaaaaa aaaaaaaaaa aaattgtcaa ggcatggtgg catgcgcctg    14220
tggtcccagc tacttaggag gctgaggcag gaggattgtg taagcctggg aggcagaggt    14280
tgcagtgacc tgagatggca ccaccacact ccagcctggg caacagagtg agaccctgtc    14340
caaaaaaaaa aaaccctcac tatccttaag ataacatcat tgcttgttga tgagtgaatg    14400
ttaacaccaa attaggaacc caggactttt agtcttggca tggttacttt ccaataaaga    14460
tgacaatact aagaagagaa aaatgattta ataatgataa tagtggctaa tacttatgta    14520
gtgcttacca tgtgccaggt ctattgtaag tactttttata tatattaatt atttaatctt    14580
tgatcctata aggtagatat tattgttacc ctagtttata gatgaagaaa cggaaacaca    14640
agagattgcc actcatacaa gtttacacag ccagaaaata gaaaagctac gagttgagct    14700
cagcccagta tgtctatgat tttacagact caaaattaat tataagattt cctaatcttc    14760
gatttctgaa actctgcctt gctctagagg aaaacaagaa aaacaatgaa aaataaatgt    14820 ctcttttttta caaaaattaa aacagaacaa actgcaataa aacaacagag gatgaatcca    14880
gaatgtgatt gatttttttt cttactagga aaggatctag aggccagaag gctggatttt    14940
tcaggatctc ctttcaatca atgaatctgt gatagaagca gatgaatcaa atctcatctt    15000
tgtgtgatta taaagctgtc tgtggtattc acgccaccag gggtacatag aagatgcctg    15060
agtgaggttt ggcaaaagta ctaagggcct gtccacctat acatgccctt ctcaggaaaa    15120
ccaaggttca agctctctat tagctcaact ggtaaggcgt aagacatgga aggttgaggc    15180
ccaatgttag aaatagatgg atacataaaa cttcatcaag ttaatgtcac tttttctcct    15240
ttatttatag                                                           15250

<210> SEQ ID NO 35
<211> LENGTH: 60
<212> TYPE: DNA
<213> ORGANISM: Homo sapiens

<400> SEQUENCE: 35
gaagtacatt tgaagaacgc aagtagaggg agtgcaggaa acaagaacta caggatgtag     60

<210> SEQ ID NO 36
<211> LENGTH: 270
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atgaacgcca aggtcgtggt cgtgctggtc ctcgtgctga ccgcgctctg cctcagcgac     60
gggaagcccg tcagcctgag ctacagatgc ccatgccgat tcttcgaaag ccatgttgcc    120
agagccaacg tcaagcatct caaaattctc aacactccaa actgtgccct tcagattgta    180
gcccggctga gaacaacaa cagacaagtg tgcattgacc cgaagctaaa gtggattcag    240
gagtacctgg agaaagcttt aaacaagtaa                                    270
```